US012753418B2

(12) United States Patent
Down et al.

(10) Patent No.: US 12,753,418 B2
(45) Date of Patent: Oct. 6, 2026

(54) COMPOSITIONS AND METHODS FOR THE TREATMENT OF HEMOPHILIA

(71) Applicant: Poseida Therapeutics, Inc., San Diego, CA (US)

(72) Inventors: Julian David Down, San Diego, CA (US); Xinggang Liu, San Diego, CA (US); Jingjing Jiang, San Diego, CA (US)

(73) Assignee: Poseida Therapeutics, Inc., San Diego, CA (US)

( * ) Notice: Subject to any disclaimer, the term of this patent is extended or adjusted under 35 U.S.C. 154(b) by 451 days.

(21) Appl. No.: 18/279,434

(22) PCT Filed: Mar. 4, 2022

(86) PCT No.: PCT/US2022/018976

§ 371 (c)(1),
(2) Date: Aug. 30, 2023

(87) PCT Pub. No.: WO2022/187671

PCT Pub. Date: Sep. 9, 2022

(65) Prior Publication Data

US 2024/0182921 A1 Jun. 6, 2024

Related U.S. Application Data

(60) Provisional application No. 63/156,657, filed on Mar. 4, 2021.

(51) Int. Cl.

| | |
|---|---|
| ***C12N 15/86*** | (2006.01) |
| ***A61K 48/00*** | (2006.01) |
| ***A61P 7/04*** | (2006.01) |

(52) U.S. Cl.

CPC .......... *C12N 15/86* (2013.01); *A61K 48/0066* (2013.01); *A61P 7/04* (2018.01); *C12N 2750/14143* (2013.01); *C12N 2800/90* (2013.01)

(58) Field of Classification Search

CPC ................ C12N 15/86; C12N 2800/90; A61K 48/0058; A61K 48/0066

See application file for complete search history.

(56) References Cited

U.S. PATENT DOCUMENTS

| | | | |
|---|---|---|---|
| 12,540,335 | B2 | 2/2026 | Jiang et al. |
| 2025/0381300 | A1 | 12/2025 | Nitzahn et al. |

FOREIGN PATENT DOCUMENTS

| | | | |
|---|---|---|---|
| EP | 2911687 | A1 | 9/2015 |
| WO | 2015139093 | A1 | 9/2015 |
| WO | 2021178707 | A1 | 9/2021 |

OTHER PUBLICATIONS

Bire et al: "Optimization of the piggyBac Transposon Using mRNA and Insulators: Toward a More Reliable Gene Delivery System", PLOS ONE, vo. 8, No. 12, Dec. 3, 2013 (Dec. 3, 2013), e82559, 1-10.

Siew et al: "Prevention of Cholestatic Liver Disease and Reduced Tumorigenicity in a Murine Model of PFIC Type 3 Using Hybrid AAV-piggyBac Gene Therapy" Hepatology, John Wiley & Sons, Inc, US, vol. 70, No. 6, Jun. 26, 2019 (Jun. 26, 2019), pp. 2047-2061.

*Primary Examiner* — Fereydoun G Sajjadi
*Assistant Examiner* — Qinhua Gu
(74) *Attorney, Agent, or Firm* — Leason Ellis LLP; Brian M. Gummow; Maha M. Saber

(57) ABSTRACT

The present disclosure is directed to compositions and methods for the treatment of hemophilia. The compositions and methods can comprise an adeno-associated virus (AAV) piggyBac polynucleotide comprising a transgene. The transgene may comprise ornithine Factor VIII (FVIII) or Factor IX (FIX).

15 Claims, 9 Drawing Sheets

Specification includes a Sequence Listing.

| Exemplary Combinations | Promoter | Transgene Sequence | polyA sequence |
|---|---|---|---|
| #1 | ApoEhAAT | FVIII sequence | SV40 polyA |
| #2 | TTR | FVIII sequence | SV40 polyA |
| #3 | HLP | FVIII sequence | SV40 polyA |
| #4 | TTRm | FVIII sequence | SV40 polyA |
| #5 | TTRm | FIX sequence | SV40 polyA |
| #6 | HLP | FVIII sequence | SV40 polyA |

| Exemplary Combinations | Promoter | 1st Transgene Sequence | Self-cleaving peptide sequence | 2nd Transgene Sequence | polyA sequence |
|---|---|---|---|---|---|
| #1 | HLP | FVIII sequence | T2A | nLuciferase | SV40 polyA |
| #2 | TTRm | FVIII sequence | T2A | nLuciferase | SV40 polyA |
| #3 | HLP | FIX sequence | T2A | nLuciferase | SV40 polyA |
| #4 | TTRm | FIX sequence | T2A | nLuciferase | SV40 polyA |
| #5 | TTRm | FIX sequence | GSG-T2A | nLuciferase | SV40 polyA |

SEQUENCE LISTING

```
<160> NUMBER OF SEQ ID NOS: 80

<210> SEQ ID NO 1
<211> LENGTH: 63
<212> TYPE: DNA
<213> ORGANISM: Artificial Sequence
<220> FEATURE:
<223> OTHER INFORMATION: Synthetic Sequence

<400> SEQUENCE: 1

ccctagaaag ataatcatat tgtgacgtac gttaaagata atcatgcgta aaattgacgc     60

atg                                                                   63


<210> SEQ ID NO 2
<211> LENGTH: 35
<212> TYPE: DNA
<213> ORGANISM: Artificial Sequence
<220> FEATURE:
<223> OTHER INFORMATION: Synthetic Sequence

<400> SEQUENCE: 2

catgcgtcaa ttttacgcag actatctttc taggg                                35


<210> SEQ ID NO 3
<211> LENGTH: 175
<212> TYPE: DNA
<213> ORGANISM: Artificial Sequence
<220> FEATURE:
<223> OTHER INFORMATION: Synthetic Sequence

<400> SEQUENCE: 3

tgttttatcg gtctgtatat cgaggtttat ttattaattt gaatagatat taagttttat     60

tatatttaca cttacatact aataataaat tcaacaaaca atttatttat gtttatttat    120
```

ttattaaaaa aaaacaaaaa ctcaaaattt cttctataaa gtaacaaaac tttta 175

<210> SEQ ID NO 4
<211> LENGTH: 274
<212> TYPE: DNA
<213> ORGANISM: Artificial Sequence
<220> FEATURE:
<223> OTHER INFORMATION: Synthetic Sequence

<400> SEQUENCE: 4
gatatctata acaagaaaat atatatataa taagttatca cgtaagtaga acatgaaata 60
acaatataat tatcgtatga gttaaatctt aaaagtcacg taaaagataa tcatgcgtca 120
ttttgactca cgcggtcgtt atagttcaaa atcagtgaca cttaccgcat tgacaagcac 180
gcctcacggg agctccaagc ggcgactgag atgtcctaaa tgcacagcga cggattcgcg 240
ctatttagaa agagagagca atatttcaag aatg 274

<210> SEQ ID NO 5
<211> LENGTH: 232
<212> TYPE: DNA
<213> ORGANISM: Artificial Sequence
<220> FEATURE:
<223> OTHER INFORMATION: Synthetic Sequence

<400> SEQUENCE: 5
gagggacagc cccccccaa agcccccagg gatgtaatta cgtccctccc ccgctagggg 60
gcagcagcga gccgcccggg gctccgctcc ggtccggcgc tccccccgca tccccgagcc 120
ggcagcgtgc ggggacagcc cgggcacggg gaaggtggca cgggatcgct ttcctctgaa 180
cgcttctcgc tgctctttga gcctgcagac acctgggggg atacggggaa aa 232

<210> SEQ ID NO 6
<211> LENGTH: 231
<212> TYPE: DNA
<213> ORGANISM: Artificial Sequence
<220> FEATURE:
<223> OTHER INFORMATION: Synthetic Sequence

<400> SEQUENCE: 6
ttttccccgt atcccccag gtgtctgcag gctcaaagag cagcgagaag cgttcagagg 60
aaagcgatcc cgtgccacct tccccgtgcc cgggctgtcc ccgcacgctg ccggctcggg 120
gatgcggggg gagcgccgga ccggagcgga gccccgggcg gctcgctgct gccccctagc 180
gggggaggga cgtaattaca tccctggggg ctttgggggg gggctgtccc t 231

<210> SEQ ID NO 7
<211> LENGTH: 727
<212> TYPE: DNA
<213> ORGANISM: Artificial Sequence
<220> FEATURE:
<223> OTHER INFORMATION: Synthetic Sequence

<400> SEQUENCE: 7
aggctcagag gcacacagga gtttctgggc tcaccctgcc cccttccaac ccctcagttc 60
ccatcctcca gcagctgttt gtgtgctgcc tctgaagtcc acactgaaca aacttcagcc 120
tactcatgtc cctaaaatgg gcaaacattg caagcagcaa acagcaaaca cacagccctc 180
cctgcctgct gaccttggag ctggggcaga ggtcagagac ctctctgggc ccatgccacc 240
tccaacatcc actcgacccc ttggaatttc ggtggagagg agcagaggtt gtcctggcgt 300
ggtttaggta gtgtgagagg ggtacccggg gatcttgcta ccagtggaac agccactaag 360
gattctgcag tgagagcaga gggccagcta agtggtactc tcccagagac tgtctgactc 420
acgccacccc ctccaccttg gacacaggac gctgtggttt ctgagccagg tacaatgact 480
cctttcggta agtgcagtgg aagctgtaca ctgcccaggc aaagcgtccg ggcagcgtag 540
gcgggcgact cagatcccag ccagtggact tagcccctgt ttgctcctcc gataactggg 600
gtgaccttgg ttaatattca ccagcagcct cccccgttgc cctctggat ccactgctta 660 aatacggacg aggacagggc cctgtctcct cagcttcagg caccaccact gacctgggac 720
agtgaat 727

<210> SEQ ID NO 8
<211> LENGTH: 689
<212> TYPE: DNA
<213> ORGANISM: Artificial Sequence
<220> FEATURE:
<223> OTHER INFORMATION: Synthetic Sequence

<400> SEQUENCE: 8
cgaaccatgg gaattgtacc gcgggggagg ctgctggtga atattaacca aggtcacccc 60
agttatcgga ggagcaaaca ggggctaagt ccaccggggg aggctgctgg tgaatattaa 120
ccaaggtcac cccagttatc ggaggagcaa acaggggcta agtccaccgg gggaggctgc 180
tggtgaatat taaccaaggt caccccagtt atcggaggag caaacagggg ctaagtccac 240
ggatcccact gggaggatgt tgagtaagat ggaaaactac tgatgaccct tgcagagaca 300
gagtattagg acatgtttga acaggggccg ggcgatcagc aggtagctct agaggatccc 360
cgtctgtctg cacatttcgt agagcgagtg ttccgatact ctaatctccc taggcaaggt 420
tcatatttgt gtaggttact tattctcctt ttgttgacta agtcaataat cagaatcagc 480
aggtttggag tcagcttggc agggatcagc agcctgggtt ggaaggaggg ggtataaaag 540
ccccttcacc aggagaagcc gtcacacaga tccacaagct cctgaagagg taagggttta 600
agggatggtt ggttggtggg gtattaatgt ttaattacct ggagcacctg cctgaaatca 660
ctttttttca ggttggacgc gtcgccacc 689

<210> SEQ ID NO 9
<211> LENGTH: 689
<212> TYPE: DNA
<213> ORGANISM: Artificial Sequence
<220> FEATURE:
<223> OTHER INFORMATION: Synthetic Sequence

<400> SEQUENCE: 9
cgaaccatgg gaattgtacc gcgggggagg ctgctggtga atattaacca aggtcacccc 60
agttatcgga ggagcaaaca ggggctaagt ccaccggggg aggctgctgg tgaatattaa 120
ccaaggtcac cccagttatc ggaggagcaa acaggggcta agtccaccgg gggaggctgc 180
tggtgaatat taaccaaggt caccccagtt atcggaggag caaacagggg ctaagtccac 240
ggatcccact gggaggatgt tgagtaagat ggaaaactac tgatgaccct tgcagagaca 300
gagtattagg acatgtttga acaggggccg ggcgatcagc aggtagctct agaggatccc 360
cgtctgtctg cacatttcgt agagcgagtg ttccgatact ctaatctccc taggcaaggt 420
tcatatttgt gtaggttact tattctcctt ttgttgacta agtcaataat cagaatcagc 480
aggtttggag tcagcttggc agggatcagc agcctgggtt ggaaggaggg ggtataaaag 540
ccccttcacc aggagaagcc gtcacacaga tccacaagct cctgaagagg taagggttta 600
agggatggtt ggttggtggg gtattaatgt ttaattacct ggagcacctg cctgaaatca 660 cttttttca ggttggacgc gtcgctagc 689

<210> SEQ ID NO 10
<211> LENGTH: 252
<212> TYPE: DNA
<213> ORGANISM: Artificial Sequence
<220> FEATURE:
<223> OTHER INFORMATION: Synthetic Sequence

<400> SEQUENCE: 10
tgtttgctgc ttgcaatgtt tgcccatttt agggtggaca caggacgctg tggtttctga 60
gccagggggc gactcagatc ccagccagtg gacttagccc ctgtttgctc ctccgataac 120
tggggtgacc ttggttaata ttcaccagca gcctcccccg ttgcccctct ggatccactg 180
cttaaatacg gacgaggaca gggccctgtc tcctcagctt caggcaccac cactgacctg 240
ggacagtgaa tc 252

<210> SEQ ID NO 11
<211> LENGTH: 341
<212> TYPE: DNA
<213> ORGANISM: Artificial Sequence
<220> FEATURE:
<223> OTHER INFORMATION: Synthetic Sequence

<400> SEQUENCE: 11
gtctgtctgc acatttcgta gagcgagtgt tccgatactc taatctccct aggcaaggtt 60
catattgact taggttactt attctccttt tgttgactaa gtcaataatc agaatcagca 120
ggtttggagt cagcttggca gggatcagca gcctgggttg gaaggagggg gtataaaagc 180
cccttcacca ggagaagccg tcacacagat ccacaagctc ctgctagcag gtaagtgccg 240
tgtgtggttc ccgcgggcct ggcctcttta cgggttatgg cccttgcgtg ccttgaatta 300
ctgacactga catccacttt ttctttttct ccacaggaat t 341

<210> SEQ ID NO 12
<211> LENGTH: 336
<212> TYPE: DNA
<213> ORGANISM: Artificial Sequence
<220> FEATURE:
<223> OTHER INFORMATION: Synthetic Sequence

<400> SEQUENCE: 12
gtctgtctgc acatttcgta gagcgagtgt tccgatactc taatctccct aggcaaggtt 60
catattgact taggttactt attctccttt tgttgactaa gtcaataatc agaatcagca 120
ggtttggagt cagcttggca gggatcagca gcctgggttg gaaggagggg gtataaaagc 180
cccttcacca ggagaagccg tcacacagat ccacaagctc ctgctagcag gtaagtgccg 240
tgtgtggttc ccgcgggcct ggcctcttta cgggttatgg cccttgcgtg ccttgaatta 300
ctgacactga catccacttt ttctttttct ccacag 336

<210> SEQ ID NO 13
<211> LENGTH: 4371
<212> TYPE: DNA
<213> ORGANISM: Artificial Sequence
<220> FEATURE:
<223> OTHER INFORMATION: Synthetic Sequence

<400> SEQUENCE: 13

```
atgcagattg agctgagcac ctgcttcttc ctgtgcctgc tgaggttctg cttctctgcc     60
accaggagat actacctggg ggctgtggag ctgagctggg actacatgca gtctgacctg    120
ggggagctgc ctgtggatgc caggttcccc cccagagtgc ccaagagctt ccccttcaac    180
acctctgtgg tgtacaagaa gaccctgttt gtggagttca ctgaccacct gttcaacatt    240
gccaagccca ggccccctg gatgggcctg ctgggcccca ccatccaggc tgaggtgtat     300
gacactgtgg tgatcaccct gaagaacatg gccagccacc ctgtgagcct gcatgctgtg    360
ggggtgagct actggaaggc ctctgagggg gctgagtatg atgaccagac cagccagagg    420
gagaaggagg atgacaaggt gttccctggg ggcagccaca cctatgtgtg gcaggtgctg    480
aaggagaatg gccccatggc ctctgacccc ctgtgcctga cctacagcta cctgagccat    540
gtggacctgg tgaaggacct gaactctggc ctgattgggg ccctgctggt gtgcagggag    600
ggcagcctgg ccaaggagaa gacccagacc ctgcacaagt tcatcctgct gtttgctgtg    660
tttgatgagg gcaagagctg gcactctgaa accaagaaca gcctgatgca ggacagggat    720
gctgcctctg ccagggcctg gcccaagatg cacactgtga atggctatgt gaacaggagc    780
ctgcctggcc tgattggctg ccacaggaag tctgtgtact ggcatgtgat tggcatgggc    840
accacccctg aggtgcacag catcttcctg gagggccaca ccttcctggt caggaaccac    900
aggcaggcca gcctggagat cagccccatc accttcctga ctgcccagac cctgctgatg    960
gacctgggcc agttcctgct gttctgccac atcagcagcc accagcatga tggcatggag   1020
gcctatgtga aggtggacag ctgccctgag gagccccagc tgaggatgaa gaacaatgag   1080
gaggctgagg actatgatga tgacctgact gactctgaga tggatgtggt gaggtttgat   1140
gatgacaaca gccccagctt catccagatc aggtctgtgg ccaagaagca ccccaagacc   1200
tgggtgcact acattgctgc tgaggaggag gactgggact atgccccccct ggtgctggcc  1260
cctgatgaca ggagctacaa gagccagtac ctgaacaatg gcccccagag gattggcagg   1320
aagtacaaga aggtcaggtt catggcctac actgatgaaa ccttcaagac cagggaggcc   1380
atccagcatg agtctggcat cctgggcccc ctgctgtatg gggaggtggg ggacaccctg   1440
ctgatcatct tcaagaacca ggccagcagg ccctacaaca tctaccccca tggcatcact   1500
gatgtgaggc ccctgtacag caggaggctg cccaaggggg tgaagcacct gaaggacttc   1560
cccatcctgc ctggggagat cttcaagtac aagtggactg tgactgtgga ggatggcccc   1620
accaagtctg accccaggtg cctgaccaga tactacagca gctttgtgaa catggagagg   1680
gacctggcct ctggcctgat tggcccccctg ctgatctgct acaaggagtc tgtggaccag  1740
aggggcaacc agatcatgtc tgacaagagg aatgtgatcc tgttctctgt gtttgatgag   1800
aacaggagct ggtacctgac tgagaacatc cagaggttcc tgcccaaccc tgctggggtg   1860
cagctggagg accctgagtt ccaggccagc aacatcatgc acagcatcaa tggctatgtg   1920
tttgacagcc tgcagctgtc tgtgtgcctg catgaggtgg cctactggta catcctgagc   1980
attggggccc agactgactt cctgtctgtg ttcttctctg gctacacctt caagcacaag   2040
atggtgtatg aggacaccct gaccctgttc cccttctctg ggagactgt gttcatgagc    2100
atggagaacc ctggcctgtg gattctgggc tgccacaact ctgacttcag gaacaggggc   2160
atgactgccc tgctgaaagt ctccagctgt gacaagaaca ctggggacta ctatgaggac   2220
agctatgagg acatctctgc ctacctgctg agcaagaaca atgccattga gcccaggagc   2280
ttcagccaga accccccagt gctgaagagg caccagaggg agatcaccag gaccaccctg   2340
cagtctgacc aggaggagat tgactatgat gacaccatct ctgtggagat gaagaaggag   2400
```

```
gactttgaca tctacgacga ggacgagaac cagagcccca ggagcttcca gaagaagacc   2460
aggcactact tcattgctgc tgtggagagg ctgtgggact atggcatgag cagcagcccc   2520
catgtgctga ggaacagggc ccagtctggc tctgtgcccc agttcaagaa ggtggtgttc   2580
caggagttca ctgatggcag cttcacccag cccctgtaca gaggggagct gaatgagcac   2640
ctgggcctgc tgggccccta catcagggct gaggtggagg acaacatcat ggtgaccttc   2700
aggaaccagg ccagcaggcc ctacagcttc tacagcagcc tgatcagcta tgaggaggac   2760
cagaggcagg ggctgagcc  caggaagaac tttgtgaagc ccaatgaaac caagacctac   2820
ttctggaagg tgcagcacca catggccccc accaaggatg agtttgactg caaggcctgg   2880
gcctacttct ctgatgtgga cctggagaag gatgtgcact ctggcctgat tggcccccctg  2940
ctggtgtgcc acaccaacac cctgaaccct gcccatggca ggcaggtgac tgtgcaggag   3000
tttgccctgt tcttcaccat ctttgatgaa accaagagct ggtacttcac tgagaacatg   3060
gagaggaact gcagggcccc ctgcaacatc cagatggagg accccacctt caaggagaac   3120
tacaggttcc atgccatcaa tggctacatc atggacaccc tgcctggcct ggtgatggcc   3180
caggaccaga ggatcaggtg gtacctgctg agcatgggca gcaatgagaa catccacagc   3240
atccacttct ctggccatgt gttcactgtg aggaagaagg aggagtacaa gatggccctg   3300
tacaacctgt accctggggt gtttgagact gtggagatgc tgcccagcaa ggctggcatc   3360
tggagggtgg agtgcctgat tggggagcac ctgcatgctg gcatgagcac cctgttcctg   3420
gtgtacagca acaagtgcca gaccccccctg ggcatggcct ctggccacat cagggacttc   3480
cagatcactg cctctggcca gtatggccag tgggccccca agctggccag gctgcactac   3540
tctggcagca tcaatgcctg gagcaccaag gagcccttca gctggatcaa ggtggacctg   3600
ctggccccca tgatcatcca tggcatcaag acccaggggg ccaggcagaa gttcagcagc   3660
ctgtacatca gccagttcat catcatgtac agcctggatg gcaagaagtg gcagacctac   3720
aggggcaaca gcactggcac cctgatggtg ttctttggca atgtggacag ctctggcatc   3780
aagcacaaca tcttcaaccc ccccatcatt gccagataca tcaggctgca ccccacccac   3840
tacagcatca ggagcaccct gaggatggag ctgatgggct gtgacctgaa cagctgcagc   3900
atgcccctgg gcatggagag caaggccatc tctgatgccc agatcactgc cagcagctac   3960
ttcaccaaca tgtttgccac ctggagcccc agcaaggcca ggctgcacct gcagggcagg   4020
agcaatgcct ggaggcccca ggtcaacaac cccaaggagt ggctgcaggt ggacttccag   4080
aagaccatga aggtgactgg ggtgaccacc caggggtga agagcctgct gaccagcatg    4140
tatgtgaagg agttcctgat cagcagcagc caggatggcc accagtggac cctgttcttc   4200
cagaatggca aggtgaaggt gttccagggc aaccaggaca gcttcacccc tgtggtgaac   4260
agcctggacc cccccctgct gaccagatac ctgaggattc acccccagag ctgggtgcac   4320
cagattgccc tgaggatgga ggtgctgggc tgtgaggccc aggacctgta c            4371
```

<210> SEQ ID NO 14
<211> LENGTH: 192
<212> TYPE: DNA
<213> ORGANISM: Artificial Sequence
<220> FEATURE:
<223> OTHER INFORMATION: Synthetic Sequence

<400> SEQUENCE: 14

```
cagacatgat aagatacatt gatgagtttg gacaaaccac aactagaatg cagtgaaaaa     60
```

aatgctttat ttgtgaaatt tgtgatgcta ttgctttatt tgtaaccatt ataagctgca 120
ataaacaagt taacaacaac aattgcattc attttatgtt tcaggttcag ggggaggtgt 180
gggaggtttt tt 192

<210> SEQ ID NO 15
<211> LENGTH: 54
<212> TYPE: DNA
<213> ORGANISM: Artificial Sequence
<220> FEATURE:
<223> OTHER INFORMATION: Synthetic Sequence

<400> SEQUENCE: 15
gaaggacggg gaagcctgct tacatgcgga gatgtggagg agaatcctgg tccc 54

<210> SEQ ID NO 16
<211> LENGTH: 513
<212> TYPE: DNA
<213> ORGANISM: Artificial Sequence
<220> FEATURE:
<223> OTHER INFORMATION: Synthetic Sequence

<400> SEQUENCE: 16
atggtcttta ccctggaaga tttcgtcggc gactggcggc agacagccgg ctataatctg 60
gaccaggtgc tggaacaagg cggagtgtcc agcctgttcc agaatctggg agtgtccgtg 120
acacccatcc agcggattgt gctgtctggc gagaacggcc tgaagatcga catccacgtg 180
atcatccctt acgagggcct gagcggcgat cagatgggac agatcgagaa gattttcaag 240
gtggtgtacc ccgtggacga ccaccacttc aaagtgatcc tgcactacgg caccctggtc 300
atcgatggcg tgacccctaa catgatcgac tacttcggca gaccctacga gggaatcgcc 360
gtgttcgacg gcaagaaaat caccgtgacc ggcacactgt ggaacgggaa caagatcatc 420
gacgagcggc tgatcaaccc cgatggcagc ctgctgttca gagtgaccat taacggcgtg 480
acaggctggc ggctgtgcga aaggattctg gcc 513

<210> SEQ ID NO 17
<211> LENGTH: 130
<212> TYPE: DNA
<213> ORGANISM: Artificial Sequence
<220> FEATURE:
<223> OTHER INFORMATION: Synthetic Sequence

<400> SEQUENCE: 17
cctgcaggca gctgcgcgct cgctcgctca ctgaggccgc ccgggcgtcg ggcgaccttt 60
ggtcgcccgg cctcagtgag cgagcgagcg cgcagagagg gagtggccaa ctccatcact 120
aggggttcct 130

<210> SEQ ID NO 18
<211> LENGTH: 141
<212> TYPE: DNA
<213> ORGANISM: Artificial Sequence
<220> FEATURE:
<223> OTHER INFORMATION: Synthetic Sequence

<400> SEQUENCE: 18
aggaacccct agtgatggag ttggccactc cctctctgcg cgctcgctcg ctcactgagg 60
ccgggcgacc aaaggtcgcc cgacgcccgg gctttgcccg ggcggcctca gtgagcgagc 120
gagcgcgcag ctgcctgcag g 141

<210> SEQ ID NO 19
<211> LENGTH: 213
<212> TYPE: DNA
<213> ORGANISM: Artificial Sequence
<220> FEATURE:
<223> OTHER INFORMATION: Synthetic Sequence

<400> SEQUENCE: 19
cgtacgttaa agataatcat gcgtaaaatt gacgcatgtg ttttatcggt ctgtatatcg 60
aggtttattt attaatttga atagatatta agttttatta tatttacact tacatactaa 120
taataaattc aacaaacaat ttatttatgt ttatttattt attaaaaaaa aacaaaaact 180
caaaatttct tctataaagt aacaaaactt tta 213

<210> SEQ ID NO 20
<211> LENGTH: 232
<212> TYPE: DNA
<213> ORGANISM: Artificial Sequence
<220> FEATURE:
<223> OTHER INFORMATION: Synthetic Sequence

<400> SEQUENCE: 20
ttttccccgt atccccccag gtgtctgcag gctcaaagag cagcgagaag cgttcagagg 60
aaagcgatcc cgtgccacct tccccgtgcc cgggctgtcc ccgcacgctg ccggctcggg 120
gatgcggggg gagcgccgga ccggagcgga gccccgggcg gctcgctgct gccccctagc 180
gggggaggga cgtaattaca tccctggggg ctttgggggg gggctgtccc tc 232

<210> SEQ ID NO 21
<211> LENGTH: 309
<212> TYPE: DNA
<213> ORGANISM: Artificial Sequence
<220> FEATURE:
<223> OTHER INFORMATION: Synthetic Sequence

<400> SEQUENCE: 21
gatatctata acaagaaaat atatatataa taagttatca cgtaagtaga acatgaaata 60
acaatataat tatcgtatga gttaaatctt aaaagtcacg taaaagataa tcatgcgtca 120
ttttgactca cgcggtcgtt atagttcaaa atcagtgaca cttaccgcat tgacaagcac 180
gcctcacggg agctccaagc ggcgactgag atgtcctaaa tgcacagcga cggattcgcg 240
ctatttagaa agagagagca atatttcaag aatgcatgcg tcaattttac gcagactatc 300
tttctaggg 309

<210> SEQ ID NO 22
<211> LENGTH: 122
<212> TYPE: DNA
<213> ORGANISM: Artificial Sequence
<220> FEATURE:
<223> OTHER INFORMATION: Synthetic Sequence

<400> SEQUENCE: 22
taagatacat tgatgagttt ggacaaacca caactagaat gcagtgaaaa aaatgcttta 60
tttgtgaaat ttgtgatgct attgctttat ttgtaaccat tataagctgc aataaacaag 120
tt 122

<210> SEQ ID NO 23
<211> LENGTH: 1383
<212> TYPE: DNA
<213> ORGANISM: Artificial Sequence
<220> FEATURE:

<223> OTHER INFORMATION: Synthetic Sequence

<400> SEQUENCE: 23
atgcagcgcg tgaacatgat tatggccgag tctcccggcc tgatcaccat ctgtctgctg 60
ggctatctgc tgagcgccga gtgcaccgtg tttctggatc acgagaacgc caacaagatc 120
ctgaacagac ccaagcggta caacagcggc aaactggaag agttcgtgca gggtaacctg 180
gaacgcgagt gcatggaaga gaagtgcagc ttcgaagagg ccagagaggt gttcgagaac 240
accgagagaa ccaccgagtt ctggaagcag tacgtggacg gcgatcagtg cgagagcaac 300
ccttgtctga atggcggcag ctgcaaggat gacatcaaca gctacgagtg ctggtgcccc 360
ttcggcttcg agggcaagaa ttgcgagctg gatgtgacct gcaacatcaa gaacggcaga 420
tgcgagcagt tctgcaagaa cagcgccgac aacaaggtcg tgtgctcctg cacagagggc 480
tacagactgg ccgagaatca gaagtcctgc gagcccgctg tgccctttcc atgtggcaga 540
gtgtctgtgt cccagaccag caagctgacc agagccgaga cagtgttccc cgatgtggac 600
tacgtgaaca gcaccgaggc cgagacaatc ctggacaaca tcacccagag cacccagtcc 660
ttcaacgact tcaccagagt cgtcggcggc gaggatgcta agcctggaca gtttccttgg 720
caagtggtgc tgaacggcaa ggtggacgct ttttgtggcg gctccatcgt gaacgagaag 780
tggatcgtga ccgccgctca ctgtgtggaa accggcgtga agattacagt ggtggccggg 840
gagcacaaca tcgaggaaac agagcacacc gagcagaaac ggaacgtgat cagaatcatc 900
cctcaccaca actacaacgc cgccatcaac aagtacaacc acgacattgc cctgctcgag 960
ctggacgaac ccctggtcct gaactcttac gtgaccccta tctgtatcgc cgacaaagag 1020
tacaccaaca tctttctgaa gttcggcagc ggctacgtgt ccggctgggg aagagttttc 1080
cacaagggca gatcagccct ggtgctgcag tacctgagag tgcccctggt ggatagagcc 1140
acatgcctgc tgagcaccaa gttcaccatc tacaacaaca tgttctgcgc cggcttccac 1200
gaaggcggca gagattcttg tcagggcgat tctggcggcc ctcacgtgac agaagtcgag 1260
ggcacatctt ttctgaccgg catcatcagc tggggcgaag agtgtgccat gaaggggaag 1320
tacggcatct ataccaaggt gtccagatac gtgaactgga tcaaagaaaa gaccaagctc 1380
acc 1383

<210> SEQ ID NO 24
<211> LENGTH: 63
<212> TYPE: DNA
<213> ORGANISM: Artificial Sequence
<220> FEATURE:
<223> OTHER INFORMATION: Synthetic Sequence

<400> SEQUENCE: 24
ggatccggag aaggacgggg aagcctgctt acatgcggag atgtggagga gaatcctggt 60
ccc 63

<210> SEQ ID NO 25
<211> LENGTH: 628
<212> TYPE: DNA
<213> ORGANISM: Artificial Sequence
<220> FEATURE:
<223> OTHER INFORMATION: Synthetic Sequence

<400> SEQUENCE: 25
atggtcttta ccctggaaga tttcgtcggc gactggcggc agacagccgg ctataatctg 60
gaccaggtgc tggaacaagg cggagtgtcc agcctgttcc agaatctggg agtgtccgtg 120
acacccatcc agcggattgt gctgtctggc gagaacggcc tgaagatcga catccacgtg 180
atcatccctt acgagggcct gagcggcgat cagatgggac agatcgagaa gattttcaag 240
gtggtgtacc ccgtggacga ccaccacttc aaagtgatcc tgcactacgg caccctggtc 300
atcgatggcg tgacccctaa catgatcgac tacttcggca gaccctacga gggaatcgcc 360
gtgttcgacg gcaagaaaat caccgtgacc ggcacactgt ggaacgggaa caagatcatc 420
gacgagcggc tgatcaaccc cgatggcagc ctgctgttca gagtgaccat taacggcgtg 480
acaggctggc ggctgtgcga aaggattctg gcctgatgat ctagagatct catatgcctt 540
taattaaaca ctagttctat agtgtcacct aaattccctt tagtgagggt taatggccgt 600
aggccgccag aattgggtcc agacatga 628

<210> SEQ ID NO 26
<211> LENGTH: 1457
<212> TYPE: PRT
<213> ORGANISM: Artificial Sequence
<220> FEATURE:
<223> OTHER INFORMATION: Synthetic Sequence

<400> SEQUENCE: 26

Met Gln Ile Glu Leu Ser Thr Cys Phe Phe Leu Cys Leu Leu Arg Phe
1 5 10 15

Cys Phe Ser Ala Thr Arg Arg Tyr Tyr Leu Gly Ala Val Glu Leu Ser
20 25 30

Trp Asp Tyr Met Gln Ser Asp Leu Gly Glu Leu Pro Val Asp Ala Arg
35 40 45

Phe Pro Pro Arg Val Pro Lys Ser Phe Pro Phe Asn Thr Ser Val Val
50 55 60

Tyr Lys Lys Thr Leu Phe Val Glu Phe Thr Asp His Leu Phe Asn Ile
65 70 75 80

Ala Lys Pro Arg Pro Pro Trp Met Gly Leu Leu Gly Pro Thr Ile Gln
85 90 95

Ala Glu Val Tyr Asp Thr Val Val Ile Thr Leu Lys Asn Met Ala Ser
100 105 110

His Pro Val Ser Leu His Ala Val Gly Val Ser Tyr Trp Lys Ala Ser
115 120 125

Glu Gly Ala Glu Tyr Asp Asp Gln Thr Ser Gln Arg Glu Lys Glu Asp
130 135 140

Asp Lys Val Phe Pro Gly Gly Ser His Thr Tyr Val Trp Gln Val Leu
145 150 155 160

Lys Glu Asn Gly Pro Met Ala Ser Asp Pro Leu Cys Leu Thr Tyr Ser
165 170 175

Tyr Leu Ser His Val Asp Leu Val Lys Asp Leu Asn Ser Gly Leu Ile
180 185 190

Gly Ala Leu Leu Val Cys Arg Glu Gly Ser Leu Ala Lys Glu Lys Thr
195 200 205

Gln Thr Leu His Lys Phe Ile Leu Leu Phe Ala Val Phe Asp Glu Gly
210 215 220

Lys Ser Trp His Ser Glu Thr Lys Asn Ser Leu Met Gln Asp Arg Asp
225 230 235 240

Ala Ala Ser Ala Arg Ala Trp Pro Lys Met His Thr Val Asn Gly Tyr
245 250 255

Val Asn Arg Ser Leu Pro Gly Leu Ile Gly Cys His Arg Lys Ser Val
260 265 270

```
Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685
```

```
Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Pro Pro Val Leu
        755                 760                 765

Lys Arg His Gln Arg Glu Ile Thr Arg Thr Thr Leu Gln Ser Asp Gln
    770                 775                 780

Glu Glu Ile Asp Tyr Asp Asp Thr Ile Ser Val Glu Met Lys Lys Glu
785                 790                 795                 800

Asp Phe Asp Ile Tyr Asp Glu Asp Glu Asn Gln Ser Pro Arg Ser Phe
                805                 810                 815

Gln Lys Lys Thr Arg His Tyr Phe Ile Ala Ala Val Glu Arg Leu Trp
            820                 825                 830

Asp Tyr Gly Met Ser Ser Ser Pro His Val Leu Arg Asn Arg Ala Gln
        835                 840                 845

Ser Gly Ser Val Pro Gln Phe Lys Lys Val Val Phe Gln Glu Phe Thr
    850                 855                 860

Asp Gly Ser Phe Thr Gln Pro Leu Tyr Arg Gly Glu Leu Asn Glu His
865                 870                 875                 880

Leu Gly Leu Leu Gly Pro Tyr Ile Arg Ala Glu Val Glu Asp Asn Ile
                885                 890                 895

Met Val Thr Phe Arg Asn Gln Ala Ser Arg Pro Tyr Ser Phe Tyr Ser
            900                 905                 910

Ser Leu Ile Ser Tyr Glu Glu Asp Gln Arg Gln Gly Ala Glu Pro Arg
        915                 920                 925

Lys Asn Phe Val Lys Pro Asn Glu Thr Lys Thr Tyr Phe Trp Lys Val
    930                 935                 940

Gln His His Met Ala Pro Thr Lys Asp Glu Phe Asp Cys Lys Ala Trp
945                 950                 955                 960

Ala Tyr Phe Ser Asp Val Asp Leu Glu Lys Asp Val His Ser Gly Leu
                965                 970                 975

Ile Gly Pro Leu Leu Val Cys His Thr Asn Thr Leu Asn Pro Ala His
            980                 985                 990

Gly Arg Gln Val Thr Val Gln Glu  Phe Ala Leu Phe Phe  Thr Ile Phe
        995                 1000                1005

Asp Glu  Thr Lys Ser Trp Tyr  Phe Thr Glu Asn Met  Glu Arg Asn
    1010                1015                1020

Cys Arg  Ala Pro Cys Asn Ile  Gln Met Glu Asp Pro  Thr Phe Lys
    1025                1030                1035

Glu Asn  Tyr Arg Phe His Ala  Ile Asn Gly Tyr Ile  Met Asp Thr
    1040                1045                1050

Leu Pro  Gly Leu Val Met Ala  Gln Asp Gln Arg Ile  Arg Trp Tyr
    1055                1060                1065

Leu Leu  Ser Met Gly Ser Asn  Glu Asn Ile His Ser  Ile His Phe
    1070                1075                1080

Ser Gly  His Val Phe Thr Val  Arg Lys Lys Glu Glu  Tyr Lys Met
    1085                1090                1095

Ala Leu  Tyr Asn Leu Tyr Pro  Gly Val Phe Glu Thr  Val Glu Met
```

```
    1100                1105                1110

Leu Pro  Ser Lys Ala Gly Ile  Trp Arg Val Glu Cys  Leu Ile Gly
    1115                1120                1125

Glu His  Leu His Ala Gly Met  Ser Thr Leu Phe Leu  Val Tyr Ser
    1130                1135                1140

Asn Lys  Cys Gln Thr Pro Leu  Gly Met Ala Ser Gly  His Ile Arg
    1145                1150                1155

Asp Phe  Gln Ile Thr Ala Ser  Gly Gln Tyr Gly Gln  Trp Ala Pro
    1160                1165                1170

Lys Leu  Ala Arg Leu His Tyr  Ser Gly Ser Ile Asn  Ala Trp Ser
    1175                1180                1185

Thr Lys  Glu Pro Phe Ser Trp  Ile Lys Val Asp Leu  Leu Ala Pro
    1190                1195                1200

Met Ile  Ile His Gly Ile Lys  Thr Gln Gly Ala Arg  Gln Lys Phe
    1205                1210                1215

Ser Ser  Leu Tyr Ile Ser Gln  Phe Ile Ile Met Tyr  Ser Leu Asp
    1220                1225                1230

Gly Lys  Lys Trp Gln Thr Tyr  Arg Gly Asn Ser Thr  Gly Thr Leu
    1235                1240                1245

Met Val  Phe Phe Gly Asn Val  Asp Ser Ser Gly Ile  Lys His Asn
    1250                1255                1260

Ile Phe  Asn Pro Pro Ile Ile  Ala Arg Tyr Ile Arg  Leu His Pro
    1265                1270                1275

Thr His  Tyr Ser Ile Arg Ser  Thr Leu Arg Met Glu  Leu Met Gly
    1280                1285                1290

Cys Asp  Leu Asn Ser Cys Ser  Met Pro Leu Gly Met  Glu Ser Lys
    1295                1300                1305

Ala Ile  Ser Asp Ala Gln Ile  Thr Ala Ser Ser Tyr  Phe Thr Asn
    1310                1315                1320

Met Phe  Ala Thr Trp Ser Pro  Ser Lys Ala Arg Leu  His Leu Gln
    1325                1330                1335

Gly Arg  Ser Asn Ala Trp Arg  Pro Gln Val Asn Asn  Pro Lys Glu
    1340                1345                1350

Trp Leu  Gln Val Asp Phe Gln  Lys Thr Met Lys Val  Thr Gly Val
    1355                1360                1365

Thr Thr  Gln Gly Val Lys Ser  Leu Leu Thr Ser Met  Tyr Val Lys
    1370                1375                1380

Glu Phe  Leu Ile Ser Ser Ser  Gln Asp Gly His Gln  Trp Thr Leu
    1385                1390                1395

Phe Phe  Gln Asn Gly Lys Val  Lys Val Phe Gln Gly  Asn Gln Asp
    1400                1405                1410

Ser Phe  Thr Pro Val Val Asn  Ser Leu Asp Pro Pro  Leu Leu Thr
    1415                1420                1425

Arg Tyr  Leu Arg Ile His Pro  Gln Ser Trp Val His  Gln Ile Ala
    1430                1435                1440

Leu Arg  Met Glu Val Leu Gly  Cys Glu Ala Gln Asp  Leu Tyr
    1445                1450                1455
```

<210> SEQ ID NO 27
<211> LENGTH: 461
<212> TYPE: PRT
<213> ORGANISM: Artificial Sequence
<220> FEATURE:
<223> OTHER INFORMATION: Synthetic Sequence

<400> SEQUENCE: 27

Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Thr Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
        275                 280                 285

His Thr Glu Gln Lys Arg Asn Val Ile Arg Ile Ile Pro His His Asn
    290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335

Ala Asp Lys Glu Tyr Thr Asn Ile Phe Leu Lys Phe Gly Ser Gly Tyr
            340                 345                 350

Val Ser Gly Trp Gly Arg Val Phe His Lys Gly Arg Ser Ala Leu Val
        355                 360                 365

Leu Gln Tyr Leu Arg Val Pro Leu Val Asp Arg Ala Thr Cys Leu Leu
    370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
                405                 410                 415

```
Thr Glu Val Glu Gly Thr Ser Phe Leu Thr Gly Ile Ile Ser Trp Gly
            420                 425                 430

Glu Glu Cys Ala Met Lys Gly Lys Tyr Gly Ile Tyr Thr Lys Val Ser
        435                 440                 445

Arg Tyr Val Asn Trp Ile Lys Glu Lys Thr Lys Leu Thr
    450                 455                 460


<210> SEQ ID NO 28
<211> LENGTH: 1045
<212> TYPE: DNA
<213> ORGANISM: Artificial Sequence
<220> FEATURE:
<223> OTHER INFORMATION: Synthetic Sequence

<400> SEQUENCE: 28

tttcctggac tacttcagac gaacttcgta gggcgcataa gtctcgacca cgcaatgacg     60

cagcgatgct tgaaaaaaac accgctttca aggcggctgg acgaagaccg caagacaccc    120

tccacctcac ctagcctgta tctctgcaat agcctaatta cttcggaatc tcctgtcgta    180

attccttaga taaacggcaa ttaggtgaca ctctaaatct gtgtggaacc ggcttccaaa    240

cactctacca cctctattag tgacacagag agaatccttg agtggcttct aggtatattg    300

aacaacttca tcacgaattg agcagtgatc atggttctac gtatcaacca atattaacca    360

ctgtgctctg tagcattgct aaatcgggct gtctgtttca ccatagatcg tgaggccatg    420

cccacgggca ttagaactta gcctgtttag cgataatccc aacaatgagc tgggatatga    480

cgagaagtat ttagcaacct tttcgtgatc ggctacgtaa aacctcatat tacggcatgt    540

acctgatcat tgacctcagg ccatacgcat gtgggagaat agagggaata gcacgatata    600

ctgcctccct tatcttcctc aggttgaggc gcaatgatta tcactgctac gggcacagtg    660

ttactatcgg gatcagggac tgtgtctgta cccggttcta ccacgccgta gctcccacat    720

tgtcgccgtc acgtcgttag ggccagcctg cgcttggtac gtgatcgagg agtatcgtct    780

tgtgcacaca aacaaaatag actgggtccc aagcgcactt agacaaggca ttgtactact    840

caagtgttgg atgtgaggaa tgatacaatc gaaccccgtc gttcggtcaa caatttggct    900

agagctgtgt tgatacacag cggacgggag ttacggggac agtcctccga gctggccagc    960

aagatgcagc tgacgcctgc accggaagta atccggaggc cggccaggcc tcctgcgagg   1020

gggcgcctcg agaccttgcg gccgc                                         1045


<210> SEQ ID NO 29
<211> LENGTH: 6724
<212> TYPE: DNA
<213> ORGANISM: Artificial Sequence
<220> FEATURE:
<223> OTHER INFORMATION: Synthetic Sequence

<400> SEQUENCE: 29

ttaaccctag aaagataatc atattgtgac gtacgttaaa gataatcatg cgtaaaattg     60

acgcatgtgt tttatcggtc tgtatatcga ggtttattta ttaatttgaa tagatattaa    120

gttttattat atttacactt acatactaat aataaattca acaaacaatt tatttatgtt    180

tatttattta ttaaaaaaaa acaaaaactc aaaatttctt ctataaagta acaaaacttt    240

tatcgaatac ctgcagcccg ggggatgcag agggacagcc ccccccaaa gcccccaggg    300

atgtaattac gtccctcccc cgctaggggg cagcagcgag ccgcccgggg ctccgctccg    360

gtccggcgct ccccccgcat ccccgagccg gcagcgtgcg gggacagccc gggcacgggg    420
```

aaggtggcac gggatcgctt tcctctgaac gcttctcgct gctctttgag cctgcagaca 480
cctgggggga tacggggaaa agttgactgt gcctttcgat cgaaccatgg gaattaacca 540
ggctcagagg cacacaggag tttctgggct caccctgccc ccttccaacc cctcagttcc 600
catcctccag cagctgtttg tgtgctgcct ctgaagtcca cactgaacaa acttcagcct 660
actcatgtcc ctaaaatggg caaacattgc aagcagcaaa cagcaaacac acagccctcc 720
ctgcctgctg accttggagc tggggcagag gtcagagacc tctctgggcc catgccacct 780
ccaacatcca ctcgacccct tggaatttcg gtggagagga gcagaggttg tcctggcgtg 840
gtttaggtag tgtgagaggg gtacccgggg atcttgctac cagtggaaca gccactaagg 900
attctgcagt gagagcagag ggccagctaa gtggtactct cccagagact gtctgactca 960
cgccaccccc tccaccttgg acacaggacg ctgtggtttc tgagccaggt acaatgactc 1020
ctttcggtaa gtgcagtgga agctgtacac tgcccaggca aagcgtccgg gcagcgtagg 1080
cgggcgactc agatcccagc cagtggactt agcccctgtt tgctcctccg ataactgggg 1140
tgaccttggt taatattcac cagcagcctc ccccgttgcc cctctggatc cactgcttaa 1200
atacggacga ggacagggcc ctgtctcctc agcttcaggc accaccactg acctgggaca 1260
gtgaatccgc ggtctagaaa gaggtaaggg tttaagggat ggttggttgg tggggtatta 1320
atgtttaatt acctggagca cctgcctgaa atcacttttt ttcaggttgg acgcgtcgct 1380
agcatgcaga ttgagctgag cacctgcttc ttcctgtgcc tgctgaggtt ctgcttctct 1440
gccaccagga gatactacct gggggctgtg gagctgagct gggactacat gcagtctgac 1500
ctgggggagc tgcctgtgga tgccaggttc ccccccagag tgcccaagag cttccccttc 1560
aacacctctg tggtgtacaa gaagaccctg tttgtggagt tcactgacca cctgttcaac 1620
attgccaagc ccaggccccc ctggatgggc ctgctgggcc ccaccatcca ggctgaggtg 1680
tatgacactg tggtgatcac cctgaagaac atggccagcc accctgtgag cctgcatgct 1740
gtgggggtga gctactggaa ggcctctgag gggctgagt atgatgacca gaccagccag 1800
agggagaagg aggatgacaa ggtgttccct gggggcagcc acacctatgt gtggcaggtg 1860
ctgaaggaga atggccccat ggcctctgac cccctgtgcc tgacctacag ctacctgagc 1920
catgtggacc tggtgaagga cctgaactct ggcctgattg ggccctgct ggtgtgcagg 1980
gagggcagcc tggccaagga gaagacccag accctgcaca agttcatcct gctgtttgct 2040
gtgtttgatg agggcaagag ctggcactct gaaaccaaga acagcctgat gcaggacagg 2100
gatgctgcct ctgccagggc ctggcccaag atgcacactg tgaatggcta tgtgaacagg 2160
agcctgcctg gcctgattgg ctgccacagg aagtctgtgt actggcatgt gattggcatg 2220
ggcaccaccc ctgaggtgca cagcatcttc ctggagggcc acaccttcct ggtcaggaac 2280
cacaggcagg ccagcctgga gatcagcccc atcaccttcc tgactgccca gaccctgctg 2340
atggacctgg gccagttcct gctgttctgc cacatcagca gccaccagca tgatggcatg 2400
gaggcctatg tgaaggtgga cagctgccct gaggagcccc agctgaggat gaagaacaat 2460
gaggaggctg aggactatga tgatgacctg actgactctg agatggatgt ggtgaggttt 2520
gatgatgaca acagccccag cttcatccag atcaggtctg tggccaagaa gcaccccaag 2580
acctgggtgc actacattgc tgctgaggag gaggactggg actatgcccc cctggtgctg 2640
gcccctgatg acaggagcta caagagccag tacctgaaca atggccccca gaggattggc 2700
aggaagtaca agaaggtcag gttcatggcc tacactgatg aaaccttcaa gaccagggag 2760

-continued gccatccagc atgagtctgg catcctgggc cccctgctgt atggggaggt gggggacacc 2820
ctgctgatca tcttcaagaa ccaggccagc aggccctaca acatctaccc ccatggcatc 2880
actgatgtga ggcccctgta cagcaggagg ctgcccaagg gggtgaagca cctgaaggac 2940
ttccccatcc tgcctgggga gatcttcaag tacaagtgga ctgtgactgt ggaggatggc 3000
cccaccaagt ctgaccccag gtgcctgacc agatactaca gcagctttgt gaacatggag 3060
agggacctgg cctctggcct gattggcccc ctgctgatct gctacaagga gtctgtggac 3120
cagaggggca accagatcat gtctgacaag aggaatgtga tcctgttctc tgtgtttgat 3180
gagaacagga gctggtacct gactgagaac atccagaggt tcctgcccaa ccctgctggg 3240
gtgcagctgg aggaccctga gttccaggcc agcaacatca tgcacagcat caatggctat 3300
gtgtttgaca gcctgcagct gtctgtgtgc ctgcatgagg tggcctactg gtacatcctg 3360
agcattgggg cccagactga cttcctgtct gtgttcttct ctggctacac cttcaagcac 3420
aagatggtgt atgaggacac cctgaccctg ttccccttct ctggggagac tgtgttcatg 3480
agcatggaga accctggcct gtggattctg ggctgccaca actctgactt caggaacagg 3540
ggcatgactg ccctgctgaa agtctccagc tgtgacaaga acactgggga ctactatgag 3600
gacagctatg aggacatctc tgcctacctg ctgagcaaga acaatgccat tgagcccagg 3660
agcttcagcc agaacccccc agtgctgaag aggcaccaga gggagatcac caggaccacc 3720
ctgcagtctg accaggagga gattgactat gatgacacca tctctgtgga gatgaagaag 3780
gaggactttg acatctacga cgaggacgag aaccagagcc ccaggagctt ccagaagaag 3840
accaggcact acttcattgc tgctgtggag aggctgtggg actatggcat gagcagcagc 3900
ccccatgtgc tgaggaacag ggcccagtct ggctctgtgc cccagttcaa gaaggtggtg 3960
ttccaggagt tcactgatgg cagcttcacc cagcccctgt acagagggga gctgaatgag 4020
cacctgggcc tgctgggccc ctacatcagg gctgaggtgg aggacaacat catggtgacc 4080
ttcaggaacc aggccagcag gccctacagc ttctacagca gcctgatcag ctatgaggag 4140
gaccagaggc agggggctga gcccaggaag aactttgtga agcccaatga aaccaagacc 4200
tacttctgga aggtgcagca ccacatggcc cccaccaagg atgagtttga ctgcaaggcc 4260
tgggcctact tctctgatgt ggacctggag aaggatgtgc actctggcct gattggcccc 4320
ctgctggtgt gccacaccaa caccctgaac cctgcccatg gcaggcaggt gactgtgcag 4380
gagtttgccc tgttcttcac catctttgat gaaaccaaga gctggtactt cactgagaac 4440
atggagagga actgcagggc cccctgcaac atccagatgg aggaccccac cttcaaggag 4500
aactacaggt tccatgccat caatggctac atcatggaca ccctgcctgg cctggtgatg 4560
gcccaggacc agaggatcag gtggtacctg ctgagcatgg gcagcaatga gaacatccac 4620
agcatccact tctctggcca tgtgttcact gtgaggaaga aggaggagta caagatggcc 4680
ctgtacaacc tgtaccctgg ggtgtttgag actgtggaga tgctgcccag caaggctggc 4740
atctggaggg tggagtgcct gattggggag cacctgcatg ctggcatgag caccctgttc 4800
ctggtgtaca gcaacaagtg ccagaccccc ctgggcatgg cctctggcca catcagggac 4860
ttccagatca ctgcctctgg ccagtatggc cagtgggccc ccaagctggc caggctgcac 4920
tactctggca gcatcaatgc ctggagcacc aaggagccct tcagctggat caaggtggac 4980
ctgctggccc ccatgatcat ccatggcatc aagacccagg gggccaggca gaagttcagc 5040
agcctgtaca tcagccagtt catcatcatg tacagcctgg atggcaagaa gtggcagacc 5100
tacaggggca acagcactgg caccctgatg gtgttctttg gcaatgtgga cagctctggc 5160
atcaagcaca acatcttcaa cccccccatc attgccagat acatcaggct gcaccccacc 5220
cactacagca tcaggagcac cctgaggatg gagctgatgg gctgtgacct gaacagctgc 5280
agcatgcccc tgggcatgga gagcaaggcc atctctgatg cccagatcac tgccagcagc 5340
tacttcacca acatgtttgc cacctggagc cccagcaagg ccaggctgca cctgcagggc 5400
aggagcaatg cctggaggcc ccaggtcaac aaccccaagg agtggctgca ggtggacttc 5460
cagaagacca tgaaggtgac tggggtgacc acccaggggg tgaagagcct gctgaccagc 5520
atgtatgtga aggagttcct gatcagcagc agccaggatg gccaccagtg gaccctgttc 5580
ttccagaatg gcaaggtgaa ggtgttccag ggcaaccagg acagcttcac ccctgtggtg 5640
aacagcctgg accccccct gctgaccaga tacctgagga ttcaccccca gagctgggtg 5700
caccagattg ccctgaggat ggaggtgctg ggctgtgagg cccaggacct gtactgatga 5760
aacgttagat ctggtaccga tcacatatgc ctttaattaa acactagttc tatagtgtca 5820
cctaaattcc ctttagtgag ggttaatggc cgtaggccgc cagaattggg tccagacatg 5880
ataagataca ttgatgagtt tggacaaacc acaactagaa tgcagtgaaa aaaatgcttt 5940
atttgtgaaa tttgtgatgc tattgcttta tttgtaacca ttataagctg caataaacaa 6000
gttaacaaca acaattgcat tcattttatg tttcaggttc agggggaggt gtgggaggtt 6060
ttttcggact ctaggacctg cgcatgcgct tggcgtaatc atggtcatag ctgtttcctg 6120
ttttccccgt atcccccag gtgtctgcag gctcaaagag cagcgagaag cgttcagagg 6180
aaagcgatcc cgtgccacct tccccgtgcc cgggctgtcc ccgcacgctg ccggctcggg 6240
gatgcggggg gagcgccgga ccggagcgga gccccgggcg gctcgctgct gccccctagc 6300
gggggaggga cgtaattaca tccctggggg ctttgggggg gggctgtccc tctcaccgcg 6360
gtggagctcc agcttttgtt cgaattgggg cccccctcg agggtatcga tgatatctat 6420
aacaagaaaa tatatatata ataagttatc acgtaagtag aacatgaaat aacaatataa 6480
ttatcgtatg agttaaatct taaaagtcac gtaaaagata atcatgcgtc attttgactc 6540
acgcggtcgt tatagttcaa aatcagtgac acttaccgca ttgacaagca cgcctcacgg 6600
gagctccaag cggcgactga gatgtcctaa atgcacagcg acggattcgc gctatttaga 6660
aagagagagc aatatttcaa gaatgcatgc gtcaatttta cgcagactat ctttctaggg 6720
ttaa 6724

<210> SEQ ID NO 30
<211> LENGTH: 6550
<212> TYPE: DNA
<213> ORGANISM: Artificial Sequence
<220> FEATURE:
<223> OTHER INFORMATION: Synthetic Sequence

<400> SEQUENCE: 30
ttaaccctag aaagataatc atattgtgac gtacgttaaa gataatcatg cgtaaaattg 60
acgcatgtgt tttatcggtc tgtatatcga ggtttattta ttaatttgaa tagatattaa 120
gttttattat atttacactt acatactaat aataaattca acaaacaatt tatttatgtt 180
tatttattta ttaaaaaaaa acaaaaaactc aaaatttctt ctataaagta acaaaacttt 240
tatcgaatac ctgcagcccg ggggatgcag agggacagcc cccccccaaa gcccccaggg 300
atgtaattac gtccctcccc cgctaggggg cagcagcgag ccgcccgggg ctccgctccg 360
gtccggcgct cccccgcat ccccgagccg gcagcgtgcg gggacagccc gggcacgggg 420

-continued

```
aaggtggcac gggatcgctt tcctctgaac gcttctcgct gctctttgag cctgcagaca    480
cctgggggga tacggggaaa agttgactgt gcctttcgat cgaaccatgg gaattgtacc    540
gcgggggagg ctgctggtga atattaacca aggtcacccc agttatcgga ggagcaaaca    600
ggggctaagt ccaccggggg aggctgctgg tgaatattaa ccaaggtcac cccagttatc    660
ggaggagcaa acaggggcta agtccaccgg gggaggctgc tggtgaatat taaccaaggt    720
caccccagtt atcggaggag caaacagggg ctaagtccac ggatcccact gggaggatgt    780
tgagtaagat ggaaaactac tgatgaccct tgcagagaca gagtattagg acatgtttga    840
acaggggccg ggcgatcagc aggtagctct agaggatccc cgtctgtctg cacatttcgt    900
agagcgagtg ttccgatact ctaatctccc taggcaaggt tcatatttgt gtaggttact    960
tattctcctt ttgttgacta agtcaataat cagaatcagc aggtttggag tcagcttggc   1020
agggatcagc agcctgggtt ggaaggaggg ggtataaaag ccccttcacc aggagaagcc   1080
gtcacacaga tccacaagct cctgaagagg taagggttta agggatggtt ggttggtggg   1140
gtattaatgt ttaattacct ggagcacctg cctgaaatca ctttttttca ggttggacgc   1200
gtcgccacca tgcagattga gctgagcacc tgcttcttcc tgtgcctgct gaggttctgc   1260
ttctctgcca ccaggagata ctacctgggg gctgtggagc tgagctggga ctacatgcag   1320
tctgacctgg gggagctgcc tgtggatgcc aggttccccc ccagagtgcc caagagcttc   1380
cccttcaaca cctctgtggt gtacaagaag accctgtttg tggagttcac tgaccacctg   1440
ttcaacattg ccaagcccag gccccccctgg atgggcctgc tgggccccac catccaggct   1500
gaggtgtatg acactgtggt gatcaccctg aagaacatgg ccagccaccc tgtgagcctg   1560
catgctgtgg gggtgagcta ctggaaggcc tctgaggggg ctgagtatga tgaccagacc   1620
agccagaggg agaaggagga tgacaaggtg ttccctgggg gcagccacac ctatgtgtgg   1680
caggtgctga aggagaatgg ccccatggcc tctgaccccc tgtgcctgac ctacagctac   1740
ctgagccatg tggacctggt gaaggacctg aactctggcc tgattggggc cctgctggtg   1800
tgcagggagg gcagcctggc caaggagaag acccagaccc tgcacaagtt catcctgctg   1860
tttgctgtgt ttgatgaggg caagagctgg cactctgaaa ccaagaacag cctgatgcag   1920
gacagggatg ctgcctctgc cagggcctgg cccaagatgc acactgtgaa tggctatgtg   1980
aacaggagcc tgcctggcct gattggctgc cacaggaagt ctgtgtactg gcatgtgatt   2040
ggcatgggca ccacccctga ggtgcacagc atcttcctgg agggccacac cttcctggtc   2100
aggaaccaca ggcaggccag cctggagatc agccccatca ccttcctgac tgcccagacc   2160
ctgctgatgg acctgggcca gttcctgctg ttctgccaca tcagcagcca ccagcatgat   2220
ggcatggagg cctatgtgaa ggtggacagc tgccctgagg agccccagct gaggatgaag   2280
aacaatgagg aggctgagga ctatgatgat gacctgactg actctgagat ggatgtggtg   2340
aggtttgatg atgacaacag ccccagcttc atccagatca ggtctgtggc caagaagcac   2400
cccaagacct gggtgcacta cattgctgct gaggaggagg actgggacta tgcccccctg   2460
gtgctggccc ctgatgacag gagctacaag agccagtacc tgaacaatgg cccccagagg   2520
attggcagga agtacaagaa ggtcaggttc atggcctaca ctgatgaaac cttcaagacc   2580
agggaggcca tccagcatga gtctggcatc ctgggccccc tgctgtatgg ggaggtgggg   2640
gacaccctgc tgatcatctt caagaaccag gccagcaggc cctacaacat ctacccccat   2700
ggcatcactg atgtgaggcc cctgtacagc aggaggctgc ccaagggggt gaagcacctg   2760
aaggacttcc ccatcctgcc tggggagatc ttcaagtaca agtggactgt gactgtggag   2820
```

gatggcccca ccaagtctga ccccaggtgc ctgaccagat actacagcag ctttgtgaac 2880
atggagaggg acctggcctc tggcctgatt ggcccctgc tgatctgcta caaggagtct 2940
gtggaccaga ggggcaacca gatcatgtct gacaagagga atgtgatcct gttctctgtg 3000
tttgatgaga acaggagctg gtacctgact gagaacatcc agaggttcct gcccaaccct 3060
gctggggtgc agctggagga ccctgagttc caggccagca acatcatgca cagcatcaat 3120
ggctatgtgt ttgacagcct gcagctgtct gtgtgcctgc atgaggtggc ctactggtac 3180
atcctgagca ttggggccca gactgacttc ctgtctgtgt tcttctctgg ctacaccttc 3240
aagcacaaga tggtgtatga ggacaccctg accctgttcc ccttctctgg ggagactgtg 3300
ttcatgagca tggagaaccc tggcctgtgg attctgggct gccacaactc tgacttcagg 3360
aacaggggca tgactgccct gctgaaagtc tccagctgtg acaagaacac tggggactac 3420
tatgaggaca gctatgagga catctctgcc tacctgctga gcaagaacaa tgccattgag 3480
cccaggagct tcagccagaa cccccagtg ctgaagaggc accagaggga gatcaccagg 3540
accaccctgc agtctgacca ggaggagatt gactatgatg acaccatctc tgtggagatg 3600
aagaaggagg actttgacat ctacgacgag gacgagaacc agagccccag gagcttccag 3660
aagaagacca ggcactactt cattgctgct gtggagaggc tgtgggacta tggcatgagc 3720
agcagcccc atgtgctgag gaacagggcc cagtctggct ctgtgcccca gttcaagaag 3780
gtggtgttcc aggagttcac tgatggcagc ttcacccagc ccctgtacag aggggagctg 3840
aatgagcacc tgggcctgct gggcccctac atcagggctg aggtggagga caacatcatg 3900
gtgaccttca ggaaccaggc cagcaggccc tacagcttct acagcagcct gatcagctat 3960
gaggaggacc agaggcaggg ggctgagccc aggaagaact ttgtgaagcc caatgaaacc 4020
aagacctact tctggaaggt gcagcaccac atggcccca ccaaggatga gtttgactgc 4080
aaggcctggg cctacttctc tgatgtggac ctggagaagg atgtgcactc tggcctgatt 4140
ggcccctgc tggtgtgcca caccaacacc ctgaaccctg cccatggcag gcaggtgact 4200
gtgcaggagt ttgccctgtt cttcaccatc tttgatgaaa ccaagagctg gtacttcact 4260
gagaacatgg agaggaactg cagggccccc tgcaacatcc agatggagga ccccaccttc 4320
aaggagaact acaggttcca tgccatcaat ggctacatca tggacaccct gcctggcctg 4380
gtgatggccc aggaccagag gatcaggtgg tacctgctga gcatgggcag caatgagaac 4440
atccacagca tccacttctc tggccatgtg ttcactgtga ggaagaagga ggagtacaag 4500
atggccctgt acaacctgta ccctggggtg tttgagactg tggagatgct gcccagcaag 4560
gctggcatct ggagggtgga gtgcctgatt ggggagcacc tgcatgctgg catgagcacc 4620
ctgttcctgg tgtacagcaa caagtgccag accccctgg gcatggcctc tggccacatc 4680
agggacttcc agatcactgc ctctggccag tatggccagt gggcccccaa gctggccagg 4740
ctgcactact ctggcagcat caatgcctgg agcaccaagg agcccttcag ctggatcaag 4800
gtggacctgc tggcccccat gatcatccat ggcatcaaga cccagggggc caggcagaag 4860
ttcagcagcc tgtacatcag ccagttcatc atcatgtaca gcctggatgg caagaagtgg 4920
cagacctaca ggggcaacag cactggcacc ctgatggtgt tctttggcaa tgtggacagc 4980
tctggcatca agcacaacat cttcaacccc cccatcattg ccagatacat caggctgcac 5040
cccacccact acagcatcag gagcaccctg aggatggagc tgatgggctg tgacctgaac 5100
agctgcagca tgcccctggg catggagagc aaggccatct ctgatgccca gatcactgcc 5160
agcagctact tcaccaacat gtttgccacc tggagcccca gcaaggccag gctgcacctg 5220
cagggcagga gcaatgcctg gaggccccag gtcaacaacc ccaaggagtg gctgcaggtg 5280
gacttccaga agaccatgaa ggtgactggg gtgaccaccc agggggtgaa gagcctgctg 5340
accagcatgt atgtgaagga gttcctgatc agcagcagcc aggatggcca ccagtggacc 5400
ctgttcttcc agaatggcaa ggtgaaggtg ttccagggca accaggacag cttcacccct 5460
gtggtgaaca gcctggaccc ccccctgctg accagatacc tgaggattca cccccagagc 5520
tgggtgcacc agattgccct gaggatggag gtgctgggct gtgaggccca ggacctgtac 5580
tgatgaaacg ttagatctgg taccgatcac atatgccttt aattaaacac tagttctata 5640
gtgtcaccta aattcccttt agtgagggtt aatggccgta ggccgccaga attgggtcca 5700
gacatgataa gatacattga tgagtttgga caaaccacaa ctagaatgca gtgaaaaaaa 5760
tgctttattt gtgaaatttg tgatgctatt gctttatttg taaccattat aagctgcaat 5820
aaacaagtta acaacaacaa ttgcattcat tttatgtttc aggttcaggg ggaggtgtgg 5880
gaggtttttt cggactctag gacctgcgca tgcgcttggc gtaatcatgg tcatagctgt 5940
ttcctgtttt ccccgtatcc ccccaggtgt ctgcaggctc aaagagcagc gagaagcgtt 6000
cagaggaaag cgatcccgtg ccaccttccc cgtgcccggg ctgtccccgc acgctgccgg 6060
ctcggggatg cggggggagc gccggaccgg agcggagccc cgggcggctc gctgctgccc 6120
cctagcgggg gagggacgta attacatccc tgggggcttt gggggggggc tgtccctctc 6180
accgcggtgg agctccagct tttgttcgaa ttggggcccc ccctcgaggg tatcgatgat 6240
atctataaca agaaaatata tatataataa gttatcacgt aagtagaaca tgaaataaca 6300
atataattat cgtatgagtt aaatcttaaa agtcacgtaa aagataatca tgcgtcattt 6360
tgactcacgc ggtcgttata gttcaaaatc agtgacactt accgcattga caagcacgcc 6420
tcacgggagc tccaagcggc gactgagatg tcctaaatgc acagcgacgg attcgcgcta 6480
tttagaaaga gagagcaata tttcaagaat gcatgcgtca attttacgca gactatcttt 6540
ctagggttaa 6550

<210> SEQ ID NO 31
<211> LENGTH: 6550
<212> TYPE: DNA
<213> ORGANISM: Artificial Sequence
<220> FEATURE:
<223> OTHER INFORMATION: Synthetic Sequence

<400> SEQUENCE: 31
ttaaccctag aaagataatc atattgtgac gtacgttaaa gataatcatg cgtaaaattg 60
acgcatgtgt tttatcggtc tgtatatcga ggtttattta ttaatttgaa tagatattaa 120
gttttattat atttacactt acatactaat aataaattca acaaacaatt tatttatgtt 180
tatttattta ttaaaaaaaa acaaaaactc aaaatttctt ctataaagta acaaaacttt 240
tatcgaatac ctgcagcccg ggggatgcag agggacagcc cccccccaaa gcccccaggg 300
atgtaattac gtccctcccc cgctaggggg cagcagcgag ccgcccgggg ctccgctccg 360
gtccggcgct ccccccgcat ccccgagccg gcagcgtgcg gggacagccc gggcacgggg 420
aaggtggcac gggatcgctt tcctctgaac gcttctcgct gctctttgag cctgcagaca 480
cctgggggga tacggggaaa agttgactgt gcctttcgat cgaaccatgg gaattgtacc 540
gcgggggagg ctgctggtga atattaacca aggtcacccc agttatcgga ggagcaaaca 600
ggggctaagt ccaccggggg aggctgctgg tgaatattaa ccaaggtcac cccagttatc 660
ggaggagcaa acaggggcta agtccaccgg gggaggctgc tggtgaatat taaccaaggt 720
caccccagtt atcggaggag caaacagggg ctaagtccac ggatccccact gggaggatgt 780
tgagtaagat ggaaaactac tgatgaccct tgcagagaca gagtattagg acatgtttga 840
acaggggccg ggcgatcagc aggtagctct agaggatccc cgtctgtctg cacatttcgt 900
agagcgagtg ttccgatact ctaatctccc taggcaaggt tcatatttgt gtaggttact 960
tattctcctt ttgttgacta agtcaataat cagaatcagc aggtttggag tcagcttggc 1020
agggatcagc agcctgggtt ggaaggaggg ggtataaaag cccttcacc aggagaagcc 1080
gtcacacaga tccacaagct cctgaagagg taagggttta agggatggtt ggttggtggg 1140
gtattaatgt ttaattacct ggagcacctg cctgaaatca cttttttca ggttggacgc 1200
gtcgctagca tgcagattga gctgagcacc tgcttcttcc tgtgcctgct gaggttctgc 1260
ttctctgcca ccaggagata ctacctgggg gctgtggagc tgagctggga ctacatgcag 1320
tctgacctgg gggagctgcc tgtggatgcc aggttccccc ccagagtgcc caagagcttc 1380
cccttcaaca cctctgtggt gtacaagaag accctgtttg tggagttcac tgaccacctg 1440
ttcaacattg ccaagcccag gcccccctgg atgggcctgc tgggccccac catccaggct 1500
gaggtgtatg acactgtggt gatcaccctg aagaacatgg ccagccaccc tgtgagcctg 1560
catgctgtgg gggtgagcta ctggaaggcc tctgaggggg ctgagtatga tgaccagacc 1620
agccagaggg agaaggagga tgacaaggtg ttccctgggg gcagccacac ctatgtgtgg 1680
caggtgctga aggagaatgg ccccatggcc tctgaccccc tgtgcctgac ctacagctac 1740
ctgagccatg tggacctggt gaaggacctg aactctggcc tgattggggc cctgctggtg 1800
tgcagggagg gcagcctggc caaggagaag acccagaccc tgcacaagtt catcctgctg 1860
tttgctgtgt ttgatgaggg caagagctgg cactctgaaa ccaagaacag cctgatgcag 1920
gacagggatg ctgcctctgc cagggcctgg cccaagatgc acactgtgaa tggctatgtg 1980
aacaggagcc tgcctggcct gattggctgc cacaggaagt ctgtgtactg gcatgtgatt 2040
ggcatgggca ccacccctga ggtgcacagc atcttcctgg agggccacac cttcctggtc 2100
aggaaccaca ggcaggccag cctggagatc agccccatca ccttcctgac tgcccagacc 2160
ctgctgatgg acctgggcca gttcctgctg ttctgccaca tcagcagcca ccagcatgat 2220
ggcatggagg cctatgtgaa ggtggacagc tgccctgagg agccccagct gaggatgaag 2280
aacaatgagg aggctgagga ctatgatgat gacctgactg actctgagat ggatgtggtg 2340
aggtttgatg atgacaacag ccccagcttc atccagatca ggtctgtggc caagaagcac 2400
cccaagacct gggtgcacta cattgctgct gaggaggagg actgggacta tgccccccctg 2460
gtgctggccc ctgatgacag gagctacaag agccagtacc tgaacaatgg cccccagagg 2520
attggcagga agtacaagaa ggtcaggttc atggcctaca ctgatgaaac cttcaagacc 2580
agggaggcca tccagcatga gtctggcatc ctgggccccc tgctgtatgg ggaggtgggg 2640
gacaccctgc tgatcatctt caagaaccag gccagcaggc cctacaacat ctacccccat 2700
ggcatcactg atgtgaggcc cctgtacagc aggaggctgc ccaagggggt gaagcacctg 2760
aaggacttcc ccatcctgcc tggggagatc ttcaagtaca agtggactgt gactgtggag 2820
gatggcccca ccaagtctga ccccaggtgc ctgaccagat actacagcag ctttgtgaac 2880
atggagaggg acctggcctc tggcctgatt ggcccccctgc tgatctgcta caaggagtct 2940
gtggaccaga ggggcaacca gatcatgtct gacaagagga atgtgatcct gttctctgtg 3000

-continued

```
tttgatgaga acaggagctg gtacctgact gagaacatcc agaggttcct gcccaaccct   3060
gctggggtgc agctggagga ccctgagttc caggccagca acatcatgca cagcatcaat   3120
ggctatgtgt ttgacagcct gcagctgtct gtgtgcctgc atgaggtggc ctactggtac   3180
atcctgagca ttggggccca gactgacttc ctgtctgtgt tcttctctgg ctacaccttc   3240
aagcacaaga tggtgtatga ggacaccctg accctgttcc ccttctctgg ggagactgtg   3300
ttcatgagca tggagaaccc tggcctgtgg attctgggct gccacaactc tgacttcagg   3360
aacaggggca tgactgccct gctgaaagtc tccagctgtg acaagaacac tggggactac   3420
tatgaggaca gctatgagga catctctgcc tacctgctga gcaagaacaa tgccattgag   3480
cccaggagct tcagccagaa ccccccagtg ctgaagaggc accagaggga gatcaccagg   3540
accaccctgc agtctgacca ggaggagatt gactatgatg acaccatctc tgtggagatg   3600
aagaaggagg actttgacat ctacgacgag gacgagaacc agagccccag gagcttccag   3660
aagaagacca ggcactactt cattgctgct gtggagaggc tgtgggacta tggcatgagc   3720
agcagccccc atgtgctgag gaacagggcc cagtctggct ctgtgcccca gttcaagaag   3780
gtggtgttcc aggagttcac tgatggcagc ttcacccagc ccctgtacag aggggagctg   3840
aatgagcacc tgggcctgct gggcccctac atcagggctg aggtggagga caacatcatg   3900
gtgaccttca ggaaccaggc cagcaggccc tacagcttct acagcagcct gatcagctat   3960
gaggaggacc agaggcaggg ggctgagccc aggaagaact ttgtgaagcc caatgaaacc   4020
aagacctact tctggaaggt gcagcaccac atggccccca ccaaggatga gtttgactgc   4080
aaggcctggg cctacttctc tgatgtggac ctggagaagg atgtgcactc tggcctgatt   4140
ggccccctgc tggtgtgcca caccaacacc ctgaaccctg cccatggcag gcaggtgact   4200
gtgcaggagt ttgccctgtt cttcaccatc tttgatgaaa ccaagagctg gtacttcact   4260
gagaacatgg agaggaactg cagggccccc tgcaacatcc agatggagga ccccaccttc   4320
aaggagaact acaggttcca tgccatcaat ggctacatca tggacaccct gcctggcctg   4380
gtgatggccc aggaccagag gatcaggtgg tacctgctga gcatgggcag caatgagaac   4440
atccacagca tccacttctc tggccatgtg ttcactgtga ggaagaagga ggagtacaag   4500
atggccctgt acaacctgta ccctggggtg tttgagactg tggagatgct gcccagcaag   4560
gctggcatct ggagggtgga gtgcctgatt ggggagcacc tgcatgctgg catgagcacc   4620
ctgttcctgg tgtacagcaa caagtgccag acccccctgg gcatggcctc tggccacatc   4680
agggacttcc agatcactgc ctctggccag tatggccagt gggcccccaa gctggccagg   4740
ctgcactact ctggcagcat caatgcctgg agcaccaagg agcccttcag ctggatcaag   4800
gtggacctgc tggcccccat gatcatccat ggcatcaaga cccagggggc caggcagaag   4860
ttcagcagcc tgtacatcag ccagttcatc atcatgtaca gcctggatgg caagaagtgg   4920
cagacctaca ggggcaacag cactggcacc ctgatggtgt tctttggcaa tgtggacagc   4980
tctggcatca agcacaacat cttcaacccc cccatcattg ccagatacat caggctgcac   5040
cccacccact acagcatcag gagcaccctg aggatggagc tgatgggctg tgacctgaac   5100
agctgcagca tgcccctggg catggagagc aaggccatct ctgatgccca gatcactgcc   5160
agcagctact tcaccaacat gtttgccacc tggagcccca gcaaggccag gctgcacctg   5220
cagggcagga gcaatgcctg gaggccccag gtcaacaacc ccaaggagtg gctgcaggtg   5280
gacttccaga agaccatgaa ggtgactggg gtgaccaccc agggggtgaa gagcctgctg   5340
accagcatgt atgtgaagga gttcctgatc agcagcagcc aggatggcca ccagtggacc   5400
```

ctgttcttcc agaatggcaa ggtgaaggtg ttccagggca accaggacag cttcacccct 5460
gtggtgaaca gcctggaccc ccccctgctg accagatacc tgaggattca cccccagagc 5520
tgggtgcacc agattgccct gaggatggag gtgctgggct gtgaggccca ggacctgtac 5580
tgatgaaacg ttagatctgg taccgatcac atatgccttt aattaaacac tagttctata 5640
gtgtcaccta aattcccttt agtgagggtt aatggccgta ggccgccaga attgggtcca 5700
gacatgataa gatacattga tgagtttgga caaaccacaa ctagaatgca gtgaaaaaaa 5760
tgctttattt gtgaaatttg tgatgctatt gctttatttg taaccattat aagctgcaat 5820
aaacaagtta acaacaacaa ttgcattcat tttatgtttc aggttcaggg ggaggtgtgg 5880
gaggtttttt cggactctag gacctgcgca tgcgcttggc gtaatcatgg tcatagctgt 5940
ttcctgtttt ccccgtatcc ccccaggtgt ctgcaggctc aaagagcagc gagaagcgtt 6000
cagaggaaag cgatcccgtg ccaccttccc cgtgcccggg ctgtccccgc acgctgccgg 6060
ctcggggatg cggggggagc gccggaccgg agcggagccc cgggcggctc gctgctgccc 6120
cctagcgggg gagggacgta attacatccc tgggggcttt gggggggggc tgtccctctc 6180
accgcggtgg agctccagct tttgttcgaa ttggggcccc ccctcgaggg tatcgatgat 6240
atctataaca agaaaatata tatataataa gttatcacgt aagtagaaca tgaaataaca 6300
atataattat cgtatgagtt aaatcttaaa agtcacgtaa aagataatca tgcgtcattt 6360
tgactcacgc ggtcgttata gttcaaaatc agtgacactt accgcattga caagcacgcc 6420
tcacgggagc tccaagcggc gactgagatg tcctaaatgc acagcgacgg attcgcgcta 6480
tttagaaaga gagagcaata tttcaagaat gcatgcgtca attttacgca gactatcttt 6540
ctagggttaa 6550

<210> SEQ ID NO 32
<211> LENGTH: 6172
<212> TYPE: DNA
<213> ORGANISM: Artificial Sequence
<220> FEATURE:
<223> OTHER INFORMATION: Synthetic Sequence

<400> SEQUENCE: 32
ttaaccctag aaagataatc atattgtgac gtacgttaaa gataatcatg cgtaaaattg 60
acgcatgtgt tttatcggtc tgtatatcga ggtttattta ttaatttgaa tagatattaa 120
gttttattat atttacactt acatactaat aataaattca acaaacaatt tatttatgtt 180
tatttattta ttaaaaaaaa acaaaaaactc aaaatttctt ctataaagta acaaaacttt 240
tatcgaatac ctgcagcccg ggggatgcag agggacagcc cccccccaaa gcccccaggg 300
atgtaattac gtccctcccc cgctaggggg cagcagcgag ccgcccgggg ctccgctccg 360
gtccggcgct ccccccgcat ccccgagccg gcagcgtgcg gggacagccc gggcacgggg 420
aaggtggcac gggatcgctt tcctctgaac gcttctcgct gctctttgag cctgcagaca 480
cctgggggga tacggggaaa agttgactgt gcctttcgat cgaactcgtc gactaggcgc 540
gtgtttgctg cttgcaatgt ttgcccattt tagggtggac acaggacgct gtggtttctg 600
agccaggggg cgactcagat cccagccagt ggacttagcc cctgtttgct cctccgataa 660
ctggggtgac cttggttaat attcaccagc agcctccccc gttgcccctc tggatccact 720
gcttaaatac ggacgaggac agggccctgt ctcctcagct tcaggcacca ccactgacct 780
gggacagtga atcgcaagaa ttctaatacg acgtctctga cctaggccac catgcagatt 840

-continued

```
gagctgagca cctgcttctt cctgtgcctg ctgaggttct gcttctctgc caccaggaga    900
tactacctgg gggctgtgga gctgagctgg gactacatgc agtctgacct gggggagctg    960
cctgtggatg ccaggttccc ccccagagtg cccaagagct tccccttcaa cacctctgtg   1020
gtgtacaaga agaccctgtt tgtggagttc actgaccacc tgttcaacat tgccaagccc   1080
aggccccccct ggatgggcct gctgggcccc accatccagg ctgaggtgta tgacactgtg  1140
gtgatcaccc tgaagaacat ggccagccac cctgtgagcc tgcatgctgt gggggtgagc   1200
tactggaagg cctctgaggg ggctgagtat gatgaccaga ccagccagag ggagaaggag   1260
gatgacaagg tgttccctgg gggcagccac acctatgtgt ggcaggtgct gaaggagaat   1320
ggccccatgg cctctgaccc cctgtgcctg acctacagct acctgagcca tgtggacctg   1380
gtgaaggacc tgaactctgg cctgattggg gccctgctgg tgtgcaggga gggcagcctg   1440
gccaaggaga agacccagac cctgcacaag ttcatcctgc tgtttgctgt gtttgatgag   1500
ggcaagagct ggcactctga aaccaagaac agcctgatgc aggacaggga tgctgcctct   1560
gccagggcct ggcccaagat gcacactgtg aatggctatg tgaacaggag cctgcctggc   1620
ctgattggct gccacaggaa gtctgtgtac tggcatgtga ttggcatggg caccacccct   1680
gaggtgcaca gcatcttcct ggagggccac accttcctgg tcaggaacca caggcaggcc   1740
agcctggaga tcagccccat caccttcctg actgcccaga ccctgctgat ggacctgggc   1800
cagttcctgc tgttctgcca catcagcagc caccagcatg atggcatgga ggcctatgtg   1860
aaggtggaca gctgccctga ggagccccag ctgaggatga agaacaatga ggaggctgag   1920
gactatgatg atgacctgac tgactctgag atggatgtgg tgaggtttga tgatgacaac   1980
agccccagct tcatccagat caggtctgtg gccaagaagc accccaagac ctgggtgcac   2040
tacattgctg ctgaggagga ggactgggac tatgcccccc tggtgctggc ccctgatgac   2100
aggagctaca agagccagta cctgaacaat ggcccccaga ggattggcag gaagtacaag   2160
aaggtcaggt tcatggccta cactgatgaa accttcaaga ccagggaggc catccagcat   2220
gagtctggca tcctgggccc cctgctgtat ggggaggtgg gggacaccct gctgatcatc   2280
ttcaagaacc aggccagcag gccctacaac atctaccccc atggcatcac tgatgtgagg   2340
cccctgtaca gcaggaggct gcccaagggg gtgaagcacc tgaaggactt ccccatcctg   2400
cctggggaga tcttcaagta caagtggact gtgactgtgg aggatggccc caccaagtct   2460
gaccccaggt gcctgaccag atactacagc agctttgtga acatggagag ggacctggcc   2520
tctggcctga ttggcccccct gctgatctgc tacaaggagt ctgtggacca gaggggcaac  2580
cagatcatgt ctgacaagag gaatgtgatc ctgttctctg tgtttgatga gaacaggagc   2640
tggtacctga ctgagaacat ccagaggttc ctgcccaacc ctgctggggt gcagctggag   2700
gaccctgagt tccaggccag caacatcatg cacagcatca atggctatgt gtttgacagc   2760
ctgcagctgt ctgtgtgcct gcatgaggtg gcctactggt acatcctgag cattggggcc   2820
cagactgact tcctgtctgt gttcttctct ggctacacct tcaagcacaa gatggtgtat   2880
gaggacaccc tgaccctgtt ccccttctct ggggagactg tgttcatgag catggagaac   2940
cctggcctgt ggattctggg ctgccacaac tctgacttca ggaacagggg catgactgcc   3000
ctgctgaaag tctccagctg tgacaagaac actggggact actatgagga cagctatgag   3060
gacatctctg cctacctgct gagcaagaac aatgccattg agcccaggag cttcagccag   3120
aaccccccag tgctgaagag gcaccagagg gagatcacca ggaccaccct gcagtctgac   3180
caggaggaga ttgactatga tgacaccatc tctgtggaga tgaagaagga ggactttgac   3240
```

atctacgacg aggacgagaa ccagagcccc aggagcttcc agaagaagac caggcactac 3300
ttcattgctg ctgtggagag gctgtgggac tatggcatga gcagcagccc ccatgtgctg 3360
aggaacaggg cccagtctgg ctctgtgccc cagttcaaga aggtggtgtt ccaggagttc 3420
actgatggca gcttcaccca gcccctgtac agaggggagc tgaatgagca cctgggcctg 3480
ctgggcccct acatcagggc tgaggtggag gacaacatca tggtgacctt caggaaccag 3540
gccagcaggc cctacagctt ctacagcagc ctgatcagct atgaggagga ccagaggcag 3600
ggggctgagc ccaggaagaa ctttgtgaag cccaatgaaa ccaagaccta cttctggaag 3660
gtgcagcacc acatggcccc caccaaggat gagtttgact gcaaggcctg ggcctacttc 3720
tctgatgtgg acctggagaa ggatgtgcac tctggcctga ttggccccct gctggtgtgc 3780
cacaccaaca ccctgaaccc tgcccatggc aggcaggtga ctgtgcagga gtttgccctg 3840
ttcttcacca tctttgatga aaccaagagc tggtacttca ctgagaacat ggagaggaac 3900
tgcagggccc cctgcaacat ccagatggag gaccccacct tcaaggagaa ctacaggttc 3960
catgccatca atggctacat catggacacc ctgcctggcc tggtgatggc ccaggaccag 4020
aggatcaggt ggtacctgct gagcatgggc agcaatgaga acatccacag catccacttc 4080
tctggccatg tgttcactgt gaggaagaag gaggagtaca agatggccct gtacaacctg 4140
taccctgggg tgtttgagac tgtggagatg ctgcccagca aggctggcat ctggagggtg 4200
gagtgcctga ttggggagca cctgcatgct ggcatgagca ccctgttcct ggtgtacagc 4260
aacaagtgcc agacccccct gggcatggcc tctggccaca tcagggactt ccagatcact 4320
gcctctggcc agtatggcca gtgggccccc aagctggcca ggctgcacta ctctggcagc 4380
atcaatgcct ggagcaccaa ggagcccttc agctggatca aggtggacct gctggccccc 4440
atgatcatcc atggcatcaa gacccagggg gccaggcaga agttcagcag cctgtacatc 4500
agccagttca tcatcatgta cagcctggat ggcaagaagt ggcagaccta caggggcaac 4560
agcactggca ccctgatggt gttctttggc aatgtggaca gctctggcat caagcacaac 4620
atcttcaacc cccccatcat tgccagatac atcaggctgc accccaccca ctacagcatc 4680
aggagcaccc tgaggatgga gctgatgggc tgtgacctga acagctgcag catgcccctg 4740
ggcatggaga gcaaggccat ctctgatgcc cagatcactg ccagcagcta cttcaccaac 4800
atgtttgcca cctggagccc cagcaaggcc aggctgcacc tgcagggcag gagcaatgcc 4860
tggaggcccc aggtcaacaa ccccaaggag tggctgcagg tggacttcca gaagaccatg 4920
aaggtgactg gggtgaccac ccagggggtg aagagcctgc tgaccagcat gtatgtgaag 4980
gagttcctga tcagcagcag ccaggatggc caccagtgga ccctgttctt ccagaatggc 5040
aaggtgaagg tgttccaggg caaccaggac agcttcaccc ctgtggtgaa cagcctggac 5100
ccccccctgc tgaccagata cctgaggatt cacccccaga gctgggtgca ccagattgcc 5160
ctgaggatgg aggtgctggg ctgtgaggcc caggacctgt actgatgaaa cgttagatct 5220
ggtaccgatc acatatgcct ttaattaaac actagttcta tagtgtcacc taaattccct 5280
ttagtgaggg ttaatggccg taggccgcca gaattgggtc cagacatgat aagatacatt 5340
gatgagtttg gacaaaccac aactagaatg cagtgaaaaa aatgctttat ttgtgaaatt 5400
tgtgatgcta ttgctttatt tgtaaccatt ataagctgca ataaacaagt taacaacaac 5460
aattgcattc attttatgtt tcaggttcag ggggaggtgt gggaggtttt ttcggactct 5520
aggacctgcg catgcgcttg gcgtaatcat ggtcatagct gtttcctgtt ttccccgtat 5580 cccccaggt gtctgcaggc tcaaagagca gcgagaagcg ttcagaggaa agcgatcccg 5640
tgccaccttc cccgtgcccg ggctgtcccc gcacgctgcc ggctcgggga tgcgggggga 5700
gcgccggacc ggagcggagc cccgggcggc tcgctgctgc cccctagcgg gggagggacg 5760
taattacatc cctgggggct ttgggggggg gctgtccctc tcaccgcggt ggagctccag 5820
cttttgttcg aattggggcc ccccctcgag ggtatcgatg atatctataa caagaaaata 5880
tatatataat aagttatcac gtaagtagaa catgaaataa caatataatt atcgtatgag 5940
ttaaatctta aaagtcacgt aaaagataat catgcgtcat tttgactcac gcggtcgtta 6000
tagttcaaaa tcagtgacac ttaccgcatt gacaagcacg cctcacggga gctccaagcg 6060
gcgactgaga tgtcctaaat gcacagcgac ggattcgcgc tatttagaaa gagagagcaa 6120
tatttcaaga atgcatgcgt caattttacg cagactatct ttctagggtt aa 6172

<210> SEQ ID NO 33
<211> LENGTH: 6234
<212> TYPE: DNA
<213> ORGANISM: Artificial Sequence
<220> FEATURE:
<223> OTHER INFORMATION: Synthetic Sequence

<400> SEQUENCE: 33
ttaaccctag aaagataatc atattgtgac gtacgttaaa gataatcatg cgtaaaattg 60
acgcatgtgt tttatcggtc tgtatatcga ggtttattta ttaatttgaa tagatattaa 120
gttttattat atttacactt acatactaat aataaattca acaaacaatt tatttatgtt 180
tatttattta ttaaaaaaaa acaaaaaactc aaaatttctt ctataaagta acaaaacttt 240
tatcgaatac ctgcagcccg ggggatgcag agggacagcc cccccccaaa gcccccaggg 300
atgtaattac gtccctcccc cgctaggggg cagcagcgag ccgcccgggg ctccgctccg 360
gtccggcgct ccccccgcat ccccgagccg gcagcgtgcg gggacagccc gggcacgggg 420
aaggtggcac gggatcgctt tcctctgaac gcttctcgct gctctttgag cctgcagaca 480
cctgggggga tacggggaaa agttgactgt gcctttcgat cgaactcgtc gactaggcgc 540
ggtctgtctg cacatttcgt agagcgagtg ttccgatact ctaatctccc taggcaaggt 600
tcatattgac ttaggttact tattctcctt ttgttgacta agtcaataat cagaatcagc 660
aggtttggag tcagcttggc agggatcagc agcctgggtt ggaaggaggg ggtataaaag 720
ccccttcacc aggagaagcc gtcacacaga tccacaagct cctgctagca ggtaagtgcc 780
gtgtgtggtt cccgcgggcc tggcctcttt acgggttatg gcccttgcgt gccttgaatt 840
actgacactg acatccactt tttctttttc tccacaggaa ttcctaggcc accatgcaga 900
ttgagctgag cacctgcttc ttcctgtgcc tgctgaggtt ctgcttctct gccaccagga 960
gatactacct gggggctgtg gagctgagct gggactacat gcagtctgac ctgggggagc 1020
tgcctgtgga tgccaggttc ccccccagag tgcccaagag cttccccttc aacacctctg 1080
tggtgtacaa gaagaccctg tttgtggagt tcactgacca cctgttcaac attgccaagc 1140
ccaggccccc ctggatgggc ctgctgggcc ccaccatcca ggctgaggtg tatgacactg 1200
tggtgatcac cctgaagaac atggccagcc accctgtgag cctgcatgct gtgggggtga 1260
gctactggaa ggcctctgag ggggctgagt atgatgacca gaccagccag agggagaagg 1320
aggatgacaa ggtgttccct gggggcagcc acacctatgt gtggcaggtg ctgaaggaga 1380
atggccccat ggcctctgac cccctgtgcc tgacctacag ctacctgagc catgtggacc 1440
tggtgaagga cctgaactct ggcctgattg ggccctgct ggtgtgcagg gagggcagcc 1500

-continued

```
tggccaagga gaagacccag accctgcaca agttcatcct gctgtttgct gtgtttgatg   1560
agggcaagag ctggcactct gaaaccaaga acagcctgat gcaggacagg gatgctgcct   1620
ctgccagggc ctggcccaag atgcacactg tgaatggcta tgtgaacagg agcctgcctg   1680
gcctgattgg ctgccacagg aagtctgtgt actggcatgt gattggcatg ggcaccaccc   1740
ctgaggtgca cagcatcttc ctggagggcc acaccttcct ggtcaggaac cacaggcagg   1800
ccagcctgga gatcagcccc atcaccttcc tgactgccca gaccctgctg atggacctgg   1860
gccagttcct gctgttctgc cacatcagca gccaccagca tgatggcatg gaggcctatg   1920
tgaaggtgga cagctgccct gaggagcccc agctgaggat gaagaacaat gaggaggctg   1980
aggactatga tgatgacctg actgactctg agatggatgt ggtgaggttt gatgatgaca   2040
acagccccag cttcatccag atcaggtctg tggccaagaa gcaccccaag acctgggtgc   2100
actacattgc tgctgaggag gaggactggg actatgcccc cctggtgctg gcccctgatg   2160
acaggagcta caagagccag tacctgaaca atggccccca gaggattggc aggaagtaca   2220
agaaggtcag gttcatggcc tacactgatg aaaccttcaa gaccagggag gccatccagc   2280
atgagtctgg catcctgggc cccctgctgt atggggaggt gggggacacc ctgctgatca   2340
tcttcaagaa ccaggccagc aggccctaca acatctaccc ccatggcatc actgatgtga   2400
ggcccctgta cagcaggagg ctgcccaagg gggtgaagca cctgaaggac ttccccatcc   2460
tgcctgggga gatcttcaag tacaagtgga ctgtgactgt ggaggatggc cccaccaagt   2520
ctgaccccag gtgcctgacc agatactaca gcagctttgt gaacatggag agggacctgg   2580
cctctggcct gattggcccc ctgctgatct gctacaagga gtctgtggac cagaggggca   2640
accagatcat gtctgacaag aggaatgtga tcctgttctc tgtgtttgat gagaacagga   2700
gctggtacct gactgagaac atccagaggt tcctgcccaa ccctgctggg gtgcagctgg   2760
aggaccctga gttccaggcc agcaacatca tgcacagcat caatggctat gtgtttgaca   2820
gcctgcagct gtctgtgtgc ctgcatgagg tggcctactg gtacatcctg agcattgggg   2880
cccagactga cttcctgtct gtgttcttct ctggctacac cttcaagcac aagatggtgt   2940
atgaggacac cctgaccctg ttccccttct ctggggagac tgtgttcatg agcatggaga   3000
accctggcct gtggattctg ggctgccaca actctgactt caggaacagg ggcatgactg   3060
ccctgctgaa agtctccagc tgtgacaaga acactgggga ctactatgag gacagctatg   3120
aggacatctc tgcctacctg ctgagcaaga acaatgccat tgagcccagg agcttcagcc   3180
agaacccccc agtgctgaag aggcaccaga gggagatcac caggaccacc ctgcagtctg   3240
accaggagga gattgactat gatgacacca tctctgtgga gatgaagaag gaggactttg   3300
acatctacga cgaggacgag aaccagagcc ccaggagctt ccagaagaag accaggcact   3360
acttcattgc tgctgtggag aggctgtggg actatggcat gagcagcagc cccccatgtgc  3420
tgaggaacag ggcccagtct ggctctgtgc cccagttcaa gaaggtggtg ttccaggagt   3480
tcactgatgg cagcttcacc cagcccctgt acagagggga gctgaatgag cacctgggcc   3540
tgctgggccc ctacatcagg gctgaggtgg aggacaacat catggtgacc ttcaggaacc   3600
aggccagcag gccctacagc ttctacagca gcctgatcag ctatgaggag gaccagaggc   3660
agggggctga gcccaggaag aactttgtga agcccaatga aaccaagacc tacttctgga   3720
aggtgcagca ccacatggcc cccaccaagg atgagtttga ctgcaaggcc tgggcctact   3780
tctctgatgt ggacctggag aaggatgtgc actctggcct gattggcccc ctgctggtgt   3840
```

```
gccacaccaa caccctgaac cctgcccatg gcaggcaggt gactgtgcag gagtttgccc   3900
tgttcttcac catctttgat gaaaccaaga gctggtactt cactgagaac atggagagga   3960
actgcagggc cccctgcaac atccagatgg aggaccccac cttcaaggag aactacaggt   4020
tccatgccat caatggctac atcatggaca ccctgcctgg cctggtgatg gcccaggacc   4080
agaggatcag gtggtacctg ctgagcatgg gcagcaatga gaacatccac agcatccact   4140
tctctggcca tgtgttcact gtgaggaaga aggaggagta caagatggcc ctgtacaacc   4200
tgtaccctgg ggtgtttgag actgtggaga tgctgcccag caaggctggc atctggaggg   4260
tggagtgcct gattggggag cacctgcatg ctggcatgag caccctgttc ctggtgtaca   4320
gcaacaagtg ccagaccccc ctgggcatgg cctctggcca catcagggac ttccagatca   4380
ctgcctctgg ccagtatggc cagtgggccc ccaagctggc caggctgcac tactctggca   4440
gcatcaatgc ctggagcacc aaggagccct tcagctggat caaggtggac ctgctggccc   4500
ccatgatcat ccatggcatc aagacccagg gggccaggca gaagttcagc agcctgtaca   4560
tcagccagtt catcatcatg tacagcctgg atggcaagaa gtggcagacc tacaggggca   4620
acagcactgg caccctgatg gtgttctttg gcaatgtgga cagctctggc atcaagcaca   4680
acatcttcaa cccccccatc attgccagat acatcaggct gcaccccacc cactacagca   4740
tcaggagcac cctgaggatg gagctgatgg gctgtgacct gaacagctgc agcatgcccc   4800
tgggcatgga gagcaaggcc atctctgatg cccagatcac tgccagcagc tacttcacca   4860
acatgtttgc cacctggagc cccagcaagg ccaggctgca cctgcagggc aggagcaatg   4920
cctggaggcc ccaggtcaac aaccccaagg agtggctgca ggtggacttc cagaagacca   4980
tgaaggtgac tggggtgacc acccaggggg tgaagagcct gctgaccagc atgtatgtga   5040
aggagttcct gatcagcagc agccaggatg gccaccagtg gaccctgttc ttccagaatg   5100
gcaaggtgaa ggtgttccag ggcaaccagg acagcttcac ccctgtggtg aacagcctgg   5160
acccccccct gctgaccaga tacctgagga ttcaccccca gagctgggtg caccagattg   5220
ccctgaggat ggaggtgctg ggctgtgagg cccaggacct gtactgatga aacgttagat   5280
ctggtaccga tcacatatgc ctttaattaa acactagttc tatagtgtca cctaaattcc   5340
ctttagtgag ggttaatggc cgtaggccgc cagaattggg tccagacatg ataagataca   5400
ttgatgagtt tggacaaacc acaactagaa tgcagtgaaa aaaatgcttt atttgtgaaa   5460
tttgtgatgc tattgcttta tttgtaacca ttataagctg caataaacaa gttaacaaca   5520
acaattgcat tcattttatg tttcaggttc agggggaggt gtgggaggtt ttttcggact   5580
ctaggacctg cgcatgcgct tggcgtaatc atggtcatag ctgtttcctg ttttccccgt   5640
atccccccag gtgtctgcag gctcaaagag cagcgagaag cgttcagagg aaagcgatcc   5700
cgtgccacct tccccgtgcc cgggctgtcc ccgcacgctg ccggctcggg gatgcggggg   5760
gagcgccgga ccggagcgga gccccgggcg gctcgctgct gccccctagc gggggaggga   5820
cgtaattaca tccctggggg ctttgggggg gggctgtccc tctcaccgcg gtggagctcc   5880
agcttttgtt cgaattgggg ccccccctcg agggtatcga tgatatctat aacaagaaaa   5940
tatatatata ataagttatc acgtaagtag aacatgaaat aacaatataa ttatcgtatg   6000
agttaaatct taaaagtcac gtaaaagata atcatgcgtc attttgactc acgcggtcgt   6060
tatagttcaa aatcagtgac acttaccgca ttgacaagca cgcctcacgg gagctccaag   6120
cggcgactga gatgtcctaa atgcacagcg acggattcgc gctatttaga aagagagagc   6180
aatatttcaa gaatgcatgc gtcaatttta cgcagactat ctttctaggg ttaa         6234
```

<210> SEQ ID NO 34
<211> LENGTH: 6748
<212> TYPE: DNA
<213> ORGANISM: Artificial Sequence
<220> FEATURE:
<223> OTHER INFORMATION: Synthetic Sequence

<400> SEQUENCE: 34
ttaaccctag aaagataatc atattgtgac gtacgttaaa gataatcatg cgtaaaattg 60
acgcatgtgt tttatcggtc tgtatatcga ggtttattta ttaatttgaa tagatattaa 120
gttttattat atttacactt acatactaat aataaattca acaaacaatt tatttatgtt 180
tatttattta ttaaaaaaaa acaaaaaactc aaaatttctt ctataaagta acaaaacttt 240
tatcgaatac ctgcagcccg ggggatgcag agggacagcc cccccccaaa gcccccaggg 300
atgtaattac gtccctcccc cgctaggggg cagcagcgag ccgcccgggg ctccgctccg 360
gtccggcgct ccccccgcat ccccgagccg gcagcgtgcg gggacagccc gggcacgggg 420
aaggtggcac gggatcgctt tcctctgaac gcttctcgct gctctttgag cctgcagaca 480
cctgggggga tacggggaaa agttgactgt gcctttcgat cgaactcgtc gactaggcgc 540
gtgtttgctg cttgcaatgt ttgcccattt tagggtggac acaggacgct gtggtttctg 600
agccaggggg cgactcagat cccagccagt ggacttagcc cctgtttgct cctccgataa 660
ctggggtgac cttggttaat attcaccagc agcctccccc gttgcccctc tggatccact 720
gcttaaatac ggacgaggac agggccctgt ctcctcagct tcaggcacca ccactgacct 780
gggacagtga atcgcaagaa ttctaatacg acgtctctga cctaggccac catgcagatt 840
gagctgagca cctgcttctt cctgtgcctg ctgaggttct gcttctctgc caccaggaga 900
tactacctgg gggctgtgga gctgagctgg gactacatgc agtctgacct gggggagctg 960
cctgtggatg ccaggttccc ccccagagtg cccaagagct tccccttcaa cacctctgtg 1020
gtgtacaaga agaccctgtt tgtggagttc actgaccacc tgttcaacat tgccaagccc 1080 aggccccccct ggatgggcct gctgggcccc accatccagg ctgaggtgta tgacactgtg 1140
gtgatcaccc tgaagaacat ggccagccac cctgtgagcc tgcatgctgt gggggtgagc 1200
tactggaagg cctctgaggg ggctgagtat gatgaccaga ccagccagag ggagaaggag 1260
gatgacaagg tgttccctgg gggcagccac acctatgtgt ggcaggtgct gaaggagaat 1320
ggccccatgg cctctgaccc cctgtgcctg acctacagct acctgagcca tgtggacctg 1380
gtgaaggacc tgaactctgg cctgattggg gccctgctgg tgtgcaggga gggcagcctg 1440
gccaaggaga agacccagac cctgcacaag ttcatcctgc tgtttgctgt gtttgatgag 1500
ggcaagagct ggcactctga aaccaagaac agcctgatgc aggacaggga tgctgcctct 1560
gccagggcct ggcccaagat gcacactgtg aatggctatg tgaacaggag cctgcctggc 1620
ctgattggct gccacaggaa gtctgtgtac tggcatgtga ttggcatggg caccacccct 1680
gaggtgcaca gcatcttcct ggagggccac accttcctgg tcaggaacca caggcaggcc 1740
agcctggaga tcagccccat caccttcctg actgcccaga ccctgctgat ggacctgggc 1800
cagttcctgc tgttctgcca catcagcagc caccagcatg atggcatgga ggcctatgtg 1860
aaggtggaca gctgccctga ggagccccag ctgaggatga agaacaatga ggaggctgag 1920
gactatgatg atgacctgac tgactctgag atggatgtgg tgaggtttga tgatgacaac 1980
agccccagct tcatccagat caggtctgtg gccaagaagc accccaagac ctgggtgcac 2040

```
tacattgctg ctgaggagga ggactgggac tatgcccccc tggtgctggc ccctgatgac   2100
aggagctaca agagccagta cctgaacaat ggcccccaga ggattggcag gaagtacaag   2160
aaggtcaggt tcatggccta cactgatgaa accttcaaga ccagggaggc catccagcat   2220
gagtctggca tcctgggccc cctgctgtat ggggaggtgg gggacaccct gctgatcatc   2280
ttcaagaacc aggccagcag gccctacaac atctaccccc atggcatcac tgatgtgagg   2340
cccctgtaca gcaggaggct gcccaagggg gtgaagcacc tgaaggactt ccccatcctg   2400
cctggggaga tcttcaagta caagtggact gtgactgtgg aggatggccc caccaagtct   2460
gaccccaggt gcctgaccag atactacagc agctttgtga acatggagag ggacctggcc   2520
tctggcctga ttggcccccct gctgatctgc tacaaggagt ctgtggacca gaggggcaac   2580
cagatcatgt ctgacaagag gaatgtgatc ctgttctctg tgtttgatga gaacaggagc   2640
tggtacctga ctgagaacat ccagaggttc ctgcccaacc ctgctggggt gcagctggag   2700
gaccctgagt tccaggccag caacatcatg cacagcatca atggctatgt gtttgacagc   2760
ctgcagctgt ctgtgtgcct gcatgaggtg gcctactggt acatcctgag cattggggcc   2820
cagactgact tcctgtctgt gttcttctct ggctacacct tcaagcacaa gatggtgtat   2880
gaggacaccc tgaccctgtt ccccttctct ggggagactg tgttcatgag catggagaac   2940
cctggcctgt ggattctggg ctgccacaac tctgacttca ggaacagggg catgactgcc   3000
ctgctgaaag tctccagctg tgacaagaac actggggact actatgagga cagctatgag   3060
gacatctctg cctacctgct gagcaagaac aatgccattg agcccaggag cttcagccag   3120
aacccccccag tgctgaagag gcaccagagg gagatcacca ggaccaccct gcagtctgac   3180
caggaggaga ttgactatga tgacaccatc tctgtggaga tgaagaagga ggactttgac   3240
atctacgacg aggacgagaa ccagagcccc aggagcttcc agaagaagac caggcactac   3300
ttcattgctg ctgtggagag gctgtgggac tatggcatga gcagcagccc ccatgtgctg   3360
aggaacaggg cccagtctgg ctctgtgccc cagttcaaga aggtggtgtt ccaggagttc   3420
actgatggca gcttcaccca gcccctgtac agaggggagc tgaatgagca cctgggcctg   3480
ctgggcccct acatcagggc tgaggtggag gacaacatca tggtgacctt caggaaccag   3540
gccagcaggc cctacagctt ctacagcagc ctgatcagct atgaggagga ccagaggcag   3600
ggggctgagc ccaggaagaa ctttgtgaag cccaatgaaa ccaagaccta cttctggaag   3660
gtgcagcacc acatggcccc caccaaggat gagtttgact gcaaggcctg ggcctacttc   3720
tctgatgtgg acctggagaa ggatgtgcac tctggcctga ttggcccccct gctggtgtgc   3780
cacaccaaca ccctgaaccc tgcccatggc aggcaggtga ctgtgcagga gtttgccctg   3840
ttcttcacca tctttgatga aaccaagagc tggtacttca ctgagaacat ggagaggaac   3900
tgcagggccc cctgcaacat ccagatggag gaccccacct tcaaggagaa ctacaggttc   3960
catgccatca atggctacat catggacacc ctgcctggcc tggtgatggc ccaggaccag   4020
aggatcaggt ggtacctgct gagcatgggc agcaatgaga acatccacag catccacttc   4080
tctggccatg tgttcactgt gaggaagaag gaggagtaca agatggccct gtacaacctg   4140
taccctgggg tgtttgagac tgtggagatg ctgcccagca aggctggcat ctggagggtg   4200
gagtgcctga ttggggagca cctgcatgct ggcatgagca ccctgttcct ggtgtacagc   4260
aacaagtgcc agaccccccct gggcatggcc tctggccaca tcagggactt ccagatcact   4320
gcctctggcc agtatggcca gtgggccccc aagctggcca ggctgcacta ctctggcagc   4380
atcaatgcct ggagcaccaa ggagcccttc agctggatca aggtggacct gctggccccc   4440
```

| | | | | | | |
|---|---|---|---|---|---|---|
| atgatcatcc | atggcatcaa | gacccagggg | gccaggcaga | agttcagcag | cctgtacatc | 4500 |
| agccagttca | tcatcatgta | cagcctggat | ggcaagaagt | ggcagaccta | caggggcaac | 4560 |
| agcactggca | ccctgatggt | gttctttggc | aatgtggaca | gctctggcat | caagcacaac | 4620 |
| atcttcaacc | cccccatcat | tgccagatac | atcaggctgc | accccaccca | ctacagcatc | 4680 |
| aggagcaccc | tgaggatgga | gctgatgggc | tgtgacctga | acagctgcag | catgcccctg | 4740 |
| ggcatggaga | gcaaggccat | ctctgatgcc | cagatcactg | ccagcagcta | cttcaccaac | 4800 |
| atgtttgcca | cctggagccc | cagcaaggcc | aggctgcacc | tgcagggcag | gagcaatgcc | 4860 |
| tggaggcccc | aggtcaacaa | ccccaaggag | tggctgcagg | tggacttcca | gaagaccatg | 4920 |
| aaggtgactg | gggtgaccac | ccaggggggtg | aagagcctgc | tgaccagcat | gtatgtgaag | 4980 |
| gagttcctga | tcagcagcag | ccaggatggc | caccagtgga | ccctgttctt | ccagaatggc | 5040 |
| aaggtgaagg | tgttccaggg | caaccaggac | agcttcaccc | ctgtggtgaa | cagcctggac | 5100 |
| cccccccctgc | tgaccagata | cctgaggatt | cacccccaga | gctgggtgca | ccagattgcc | 5160 |
| ctgaggatgg | aggtgctggg | ctgtgaggcc | caggacctgt | acggctccgg | agaaggacgg | 5220 |
| ggaagcctgc | ttacatgcgg | agatgtggag | gagaatcctg | gtcccatggt | ctttaccctg | 5280 |
| gaagatttcg | tcggcgactg | gcggcagaca | gccggctata | atctggacca | ggtgctggaa | 5340 |
| caaggcggag | tgtccagcct | gttccagaat | ctgggagtgt | ccgtgacacc | catccagcgg | 5400 |
| attgtgctgt | ctggcgagaa | cggcctgaag | atcgacatcc | acgtgatcat | cccttacgag | 5460 |
| ggcctgagcg | gcgatcagat | gggacagatc | gagaagattt | tcaaggtggt | gtaccccgtg | 5520 |
| gacgaccacc | acttcaaagt | gatcctgcac | tacggcaccc | tggtcatcga | tggcgtgacc | 5580 |
| cctaacatga | tcgactactt | cggcagaccc | tacgagggaa | tcgccgtgtt | cgacggcaag | 5640 |
| aaaatcaccg | tgaccggcac | actgtggaac | gggaacaaga | tcatcgacga | gcggctgatc | 5700 |
| aaccccgatg | gcagcctgct | gttcagagtg | accattaacg | gcgtgacagg | ctggcggctg | 5760 |
| tgcgaaagga | ttctggcctg | atgaaacgtt | agatctggta | ccgatcacat | atgcctttaa | 5820 |
| ttaaacacta | gttctatagt | gtcacctaaa | ttccctttag | tgagggttaa | tggccgtagg | 5880 |
| ccgccagaat | tgggtccaga | catgataaga | tacattgatg | agtttggaca | aaccacaact | 5940 |
| agaatgcagt | gaaaaaaatg | ctttatttgt | gaaatttgtg | atgctattgc | tttatttgta | 6000 |
| accattataa | gctgcaataa | acaagttaac | aacaacaatt | gcattcattt | tatgtttcag | 6060 |
| gttcaggggg | aggtgtggga | ggttttttcg | gactctagga | cctgcgcatg | cgcttggcgt | 6120 |
| aatcatggtc | atagctgttt | cctgttttcc | ccgtatcccc | ccaggtgtct | gcaggctcaa | 6180 |
| agagcagcga | gaagcgttca | gaggaaagcg | atcccgtgcc | accttccccg | tgcccgggct | 6240 |
| gtccccgcac | gctgccggct | cggggatgcg | gggggagcgc | cggaccggag | cggagccccg | 6300 |
| ggcggctcgc | tgctgccccc | tagcggggga | gggacgtaat | tacatccctg | ggggctttgg | 6360 |
| gggggggctg | tccctctcac | cgcggtggag | ctccagcttt | tgttcgaatt | ggggcccccc | 6420 |
| ctcgagggta | tcgatgatat | ctataacaag | aaaatatata | tataataagt | tatcacgtaa | 6480 |
| gtagaacatg | aaataacaat | ataattatcg | tatgagttaa | atcttaaaag | tcacgtaaaa | 6540 |
| gataatcatg | cgtcattttg | actcacgcgg | tcgttatagt | tcaaaatcag | tgacacttac | 6600 |
| cgcattgaca | agcacgcctc | acgggagctc | caagcggcga | ctgagatgtc | ctaaatgcac | 6660 |
| agcgacggat | tcgcgctatt | tagaaagaga | gagcaatatt | tcaagaatgc | atgcgtcaat | 6720 |
| tttacgcaga | ctatctttct | agggttaa | | | | 6748 |

<210> SEQ ID NO 35
<211> LENGTH: 6810
<212> TYPE: DNA
<213> ORGANISM: Artificial Sequence
<220> FEATURE:
<223> OTHER INFORMATION: Synthetic Sequence

<400> SEQUENCE: 35
ttaaccctag aaagataatc atattgtgac gtacgttaaa gataatcatg cgtaaaattg 60
acgcatgtgt tttatcggtc tgtatatcga ggtttattta ttaatttgaa tagatattaa 120
gttttattat atttacactt acatactaat aataaattca acaaacaatt tatttatgtt 180
tatttattta ttaaaaaaaa acaaaaaactc aaaatttctt ctataaagta acaaaacttt 240
tatcgaatac ctgcagcccg ggggatgcag agggacagcc cccccccaaa gcccccaggg 300
atgtaattac gtccctcccc cgctaggggg cagcagcgag ccgcccgggg ctccgctccg 360
gtccggcgct ccccccgcat ccccgagccg gcagcgtgcg gggacagccc gggcacgggg 420
aaggtggcac gggatcgctt tcctctgaac gcttctcgct gctctttgag cctgcagaca 480
cctgggggga tacggggaaa agttgactgt gcctttcgat cgaactcgtc gactaggcgc 540
ggtctgtctg cacatttcgt agagcgagtg ttccgatact ctaatctccc taggcaaggt 600
tcatattgac ttaggttact tattctcctt ttgttgacta agtcaataat cagaatcagc 660
aggtttggag tcagcttggc agggatcagc agcctgggtt ggaaggaggg ggtataaaag 720
ccccttcacc aggagaagcc gtcacacaga tccacaagct cctgctagca ggtaagtgcc 780
gtgtgtggtt cccgcgggcc tggcctcttt acgggttatg gcccttgcgt gccttgaatt 840
actgacactg acatccactt tttctttttc tccacaggaa ttcctaggcc accatgcaga 900
ttgagctgag cacctgcttc ttcctgtgcc tgctgaggtt ctgcttctct gccaccagga 960
gatactacct gggggctgtg gagctgagct gggactacat gcagtctgac ctgggggagc 1020
tgcctgtgga tgccaggttc ccccccagag tgcccaagag cttccccttc aacacctctg 1080
tggtgtacaa gaagaccctg tttgtggagt tcactgacca cctgttcaac attgccaagc 1140
ccaggccccc ctggatgggc ctgctgggcc ccaccatcca ggctgaggtg tatgacactg 1200
tggtgatcac cctgaagaac atggccagcc accctgtgag cctgcatgct gtgggggtga 1260
gctactggaa ggcctctgag ggggctgagt atgatgacca gaccagccag agggagaagg 1320
aggatgacaa ggtgttccct gggggcagcc acacctatgt gtggcaggtg ctgaaggaga 1380
atggccccat ggcctctgac cccctgtgcc tgacctacag ctacctgagc catgtggacc 1440
tggtgaagga cctgaactct ggcctgattg ggccctgct ggtgtgcagg gagggcagcc 1500
tggccaagga gaagacccag accctgcaca agttcatcct gctgtttgct gtgtttgatg 1560
agggcaagag ctggcactct gaaaccaaga acagcctgat gcaggacagg gatgctgcct 1620
ctgccagggc ctggcccaag atgcacactg tgaatggcta tgtgaacagg agcctgcctg 1680
gcctgattgg ctgccacagg aagtctgtgt actggcatgt gattggcatg ggcaccaccc 1740
ctgaggtgca cagcatcttc ctggagggcc acaccttcct ggtcaggaac cacaggcagg 1800
ccagcctgga gatcagcccc atcaccttcc tgactgccca gaccctgctg atggacctgg 1860
gccagttcct gctgttctgc cacatcagca gccaccagca tgatggcatg gaggcctatg 1920
tgaaggtgga cagctgccct gaggagcccc agctgaggat gaagaacaat gaggaggctg 1980
aggactatga tgatgacctg actgactctg agatggatgt ggtgaggttt gatgatgaca 2040
acagccccag cttcatccag atcaggtctg tggccaagaa gcaccccaag acctgggtgc 2100
actacattgc tgctgaggag gaggactggg actatgcccc cctggtgctg gcccctgatg 2160
acaggagcta caagagccag tacctgaaca atggccccca gaggattggc aggaagtaca 2220
agaaggtcag gttcatggcc tacactgatg aaaccttcaa gaccagggag gccatccagc 2280
atgagtctgg catcctgggc cccctgctgt atggggaggt gggggacacc ctgctgatca 2340
tcttcaagaa ccaggccagc aggccctaca acatctaccc ccatggcatc actgatgtga 2400
ggcccctgta cagcaggagg ctgcccaagg gggtgaagca cctgaaggac ttccccatcc 2460
tgcctgggga gatcttcaag tacaagtgga ctgtgactgt ggaggatggc cccaccaagt 2520
ctgaccccag gtgcctgacc agatactaca gcagctttgt gaacatggag agggacctgg 2580
cctctggcct gattggcccc ctgctgatct gctacaagga gtctgtggac cagaggggca 2640
accagatcat gtctgacaag aggaatgtga tcctgttctc tgtgtttgat gagaacagga 2700
gctggtacct gactgagaac atccagaggt tcctgcccaa ccctgctggg gtgcagctgg 2760
aggaccctga gttccaggcc agcaacatca tgcacagcat caatggctat gtgtttgaca 2820
gcctgcagct gtctgtgtgc ctgcatgagg tggcctactg gtacatcctg agcattgggg 2880
cccagactga cttcctgtct gtgttcttct ctggctacac cttcaagcac aagatggtgt 2940
atgaggacac cctgaccctg ttccccttct ctggggagac tgtgttcatg agcatggaga 3000
accctggcct gtggattctg ggctgccaca actctgactt caggaacagg ggcatgactg 3060
ccctgctgaa agtctccagc tgtgacaaga acactgggga ctactatgag gacagctatg 3120
aggacatctc tgcctacctg ctgagcaaga acaatgccat tgagcccagg agcttcagcc 3180
agaacccccc agtgctgaag aggcaccaga gggagatcac caggaccacc ctgcagtctg 3240
accaggagga gattgactat gatgacacca tctctgtgga gatgaagaag gaggactttg 3300
acatctacga cgaggacgag aaccagagcc ccaggagctt ccagaagaag accaggcact 3360
acttcattgc tgctgtggag aggctgtggg actatggcat gagcagcagc ccccatgtgc 3420
tgaggaacag ggcccagtct ggctctgtgc cccagttcaa gaaggtggtg ttccaggagt 3480
tcactgatgg cagcttcacc cagcccctgt acagagggga gctgaatgag cacctgggcc 3540
tgctgggccc ctacatcagg gctgaggtgg aggacaacat catggtgacc ttcaggaacc 3600
aggccagcag gccctacagc ttctacagca gcctgatcag ctatgaggag gaccagaggc 3660
agggggctga gcccaggaag aactttgtga agcccaatga aaccaagacc tacttctgga 3720
aggtgcagca ccacatggcc cccaccaagg atgagtttga ctgcaaggcc tgggcctact 3780
tctctgatgt ggacctggag aaggatgtgc actctggcct gattggcccc ctgctggtgt 3840
gccacaccaa caccctgaac cctgcccatg gcaggcaggt gactgtgcag gagtttgccc 3900
tgttcttcac catctttgat gaaaccaaga gctggtactt cactgagaac atggagagga 3960
actgcagggc cccctgcaac atccagatgg aggaccccac cttcaaggag aactacaggt 4020
tccatgccat caatggctac atcatggaca ccctgcctgg cctggtgatg gcccaggacc 4080
agaggatcag gtggtacctg ctgagcatgg gcagcaatga gaacatccac agcatccact 4140
tctctggcca tgtgttcact gtgaggaaga aggaggagta caagatggcc ctgtacaacc 4200
tgtaccctgg ggtgtttgag actgtggaga tgctgcccag caaggctggc atctggaggg 4260
tggagtgcct gattggggag cacctgcatg ctggcatgag caccctgttc ctggtgtaca 4320
gcaacaagtg ccagaccccc ctgggcatgg cctctggcca catcagggac ttccagatca 4380
ctgcctctgg ccagtatggc cagtgggccc ccaagctggc caggctgcac tactctggca 4440

```
gcatcaatgc ctggagcacc aaggagccct tcagctggat caaggtggac ctgctggccc   4500
ccatgatcat ccatggcatc aagacccagg gggccaggca gaagttcagc agcctgtaca   4560
tcagccagtt catcatcatg tacagcctgg atggcaagaa gtggcagacc tacaggggca   4620
acagcactgg caccctgatg gtgttctttg gcaatgtgga cagctctggc atcaagcaca   4680
acatcttcaa cccccccatc attgccagat acatcaggct gcaccccacc cactacagca   4740
tcaggagcac cctgaggatg gagctgatgg gctgtgacct gaacagctgc agcatgcccc   4800
tgggcatgga gagcaaggcc atctctgatg cccagatcac tgccagcagc tacttcacca   4860
acatgtttgc cacctggagc cccagcaagg ccaggctgca cctgcagggc aggagcaatg   4920
cctggaggcc ccaggtcaac aaccccaagg agtggctgca ggtggacttc cagaagacca   4980
tgaaggtgac tggggtgacc acccaggggg tgaagagcct gctgaccagc atgtatgtga   5040
aggagttcct gatcagcagc agccaggatg gccaccagtg gaccctgttc ttccagaatg   5100
gcaaggtgaa ggtgttccag ggcaaccagg acagcttcac ccctgtggtg aacagcctgg   5160
acccccccct gctgaccaga tacctgagga ttcaccccca gagctgggtg caccagattg   5220
ccctgaggat ggaggtgctg ggctgtgagg cccaggacct gtacggctcc ggagaaggac   5280
ggggaagcct gcttacatgc ggagatgtgg aggagaatcc tggtcccatg gtctttaccc   5340
tggaagattt cgtcggcgac tggcggcaga cagccggcta taatctggac caggtgctgg   5400
aacaaggcgg agtgtccagc ctgttccaga atctgggagt gtccgtgaca cccatccagc   5460
ggattgtgct gtctggcgag aacggcctga agatcgacat ccacgtgatc atcccttacg   5520
agggcctgag cggcgatcag atgggacaga tcgagaagat tttcaaggtg gtgtaccccg   5580
tggacgacca ccacttcaaa gtgatcctgc actacggcac cctggtcatc gatggcgtga   5640
cccctaacat gatcgactac ttcggcagac cctacgaggg aatcgccgtg ttcgacggca   5700
agaaaatcac cgtgaccggc acactgtgga acgggaacaa gatcatcgac gagcggctga   5760
tcaaccccga tggcagcctg ctgttcagag tgaccattaa cggcgtgaca ggctggcggc   5820
tgtgcgaaag gattctggcc tgatgaaacg ttagatctgg taccgatcac atatgccttt   5880
aattaaacac tagttctata gtgtcaccta aattcccttt agtgagggtt aatggccgta   5940
ggccgccaga attgggtcca gacatgataa gatacattga tgagtttgga caaaccacaa   6000
ctagaatgca gtgaaaaaaa tgctttattt gtgaaatttg tgatgctatt gctttatttg   6060
taaccattat aagctgcaat aaacaagtta acaacaacaa ttgcattcat tttatgtttc   6120
aggttcaggg ggaggtgtgg gaggtttttt cggactctag gacctgcgca tgcgcttggc   6180
gtaatcatgg tcatagctgt ttcctgtttt ccccgtatcc ccccaggtgt ctgcaggctc   6240
aaagagcagc gagaagcgtt cagaggaaag cgatcccgtg ccaccttccc cgtgcccggg   6300
ctgtccccgc acgctgccgg ctcggggatg cggggggagc gccggaccgg agcggagccc   6360
cgggcggctc gctgctgccc cctagcgggg gagggacgta attacatccc tgggggcttt   6420
gggggggggc tgtccctctc accgcggtgg agctccagct tttgttcgaa ttggggcccc   6480
ccctcgaggg tatcgatgat atctataaca agaaaatata tatataataa gttatcacgt   6540
aagtagaaca tgaaataaca atataattat cgtatgagtt aaatcttaaa agtcacgtaa   6600
aagataatca tgcgtcattt tgactcacgc ggtcgttata gttcaaaatc agtgacactt   6660
accgcattga caagcacgcc tcacgggagc tccaagcggc gactgagatg tcctaaatgc   6720
acagcgacgg attcgcgcta tttagaaaga gagagcaata tttcaagaat gcatgcgtca   6780
attttacgca gactatcttt ctagggttaa                                   6810
```

<210> SEQ ID NO 36
<211> LENGTH: 3246
<212> TYPE: DNA
<213> ORGANISM: Artificial Sequence
<220> FEATURE:
<223> OTHER INFORMATION: Synthetic Sequence

<400> SEQUENCE: 36
ttaaccctag aaagataatc atattgtgac gtacgttaaa gataatcatg cgtaaaattg 60
acgcatgtgt tttatcggtc tgtatatcga ggtttattta ttaatttgaa tagatattaa 120
gttttattat atttacactt acatactaat aataaattca acaaacaatt tatttatgtt 180
tatttattta ttaaaaaaaa acaaaaaactc aaaatttctt ctataaagta acaaaacttt 240
tatcgaatac ctgcagcccg ggggatgcag agggacagcc cccccccaaa gcccccaggg 300
atgtaattac gtccctcccc cgctaggggg cagcagcgag ccgcccgggg ctccgctccg 360
gtccggcgct ccccccgcat ccccgagccg gcagcgtgcg gggacagccc gggcacgggg 420
aaggtggcac gggatcgctt tcctctgaac gcttctcgct gctctttgag cctgcagaca 480
cctgggggga tacggggaaa agttgactgt gcctttcgat cgaactcgtc gactaggcgc 540
ggtctgtctg cacatttcgt agagcgagtg ttccgatact ctaatctccc taggcaaggt 600
tcatattgac ttaggttact tattctcctt ttgttgacta agtcaataat cagaatcagc 660
aggtttggag tcagcttggc agggatcagc agcctgggtt ggaaggaggg ggtataaaag 720
ccccttcacc aggagaagcc gtcacacaga tccacaagct cctgctagca ggtaagtgcc 780
gtgtgtggtt cccgcgggcc tggcctcttt acgggttatg gcccttgcgt gccttgaatt 840
actgacactg acatccactt tttctttttc tccacaggaa ttcctaggcc accatgcagc 900
gcgtgaacat gattatggcc gagtctcccg gcctgatcac catctgtctg ctgggctatc 960
tgctgagcgc cgagtgcacc gtgtttctgg atcacgagaa cgccaacaag atcctgaaca 1020
gacccaagcg gtacaacagc ggcaaactgg aagagttcgt gcagggtaac ctggaacgcg 1080
agtgcatgga agagaagtgc agcttcgaag aggccagaga ggtgttcgag aacaccgaga 1140
gaaccaccga gttctggaag cagtacgtgg acggcgatca gtgcgagagc aacccttgtc 1200
tgaatggcgg cagctgcaag gatgacatca acagctacga gtgctggtgc cccttcggct 1260
tcgagggcaa gaattgcgag ctggatgtga cctgcaacat caagaacggc agatgcgagc 1320
agttctgcaa gaacagcgcc gacaacaagg tcgtgtgctc ctgcacagag ggctacagac 1380
tggccgagaa tcagaagtcc tgcgagcccg ctgtgccctt tccatgtggc agagtgtctg 1440
tgtcccagac cagcaagctg accagagccg agacagtgtt ccccgatgtg gactacgtga 1500
acagcaccga ggccgagaca atcctggaca acatcaccca gagcacccag tccttcaacg 1560
acttcaccag agtcgtcggc ggcgaggatg ctaagcctgg acagtttcct tggcaagtgg 1620
tgctgaacgg caaggtggac gctttttgtg gcggctccat cgtgaacgag aagtggatcg 1680
tgaccgccgc tcactgtgtg gaaaccggcg tgaagattac agtggtggcc ggggagcaca 1740
acatcgagga aacagagcac accgagcaga aacggaacgt gatcagaatc atccctcacc 1800
acaactacaa cgccgccatc aacaagtaca accacgacat tgccctgctc gagctggacg 1860
aacccctggt cctgaactct tacgtgaccc ctatctgtat cgccgacaaa gagtacacca 1920
acatctttct gaagttcggc agcggctacg tgtccggctg gggaagagtt ttccacaagg 1980
gcagatcagc cctggtgctg cagtacctga gagtgcccct ggtggataga gccacatgcc 2040
tgctgagcac caagttcacc atctacaaca acatgttctg cgccggcttc cacgaaggcg 2100
gcagagattc ttgtcagggc gattctggcg gccctcacgt gacagaagtc gagggcacat 2160
cttttctgac cggcatcatc agctggggcg aagagtgtgc catgaagggg aagtacggca 2220
tctataccaa ggtgtccaga tacgtgaact ggatcaaaga aaagaccaag ctcacctgat 2280
gaaacgttag atctggtacc gatcacatat gcctttaatt aaacactagt tctatagtgt 2340
cacctaaatt ccctttagtg agggttaatg gccgtaggcc gccagaattg ggtccagaca 2400
tgataagata cattgatgag tttggacaaa ccacaactag aatgcagtga aaaaaatgct 2460
ttatttgtga aatttgtgat gctattgctt tatttgtaac cattataagc tgcaataaac 2520
aagttaacaa caacaattgc attcatttta tgtttcaggt tcagggggag gtgtgggagg 2580 tttttcgga ctctaggacc tgcgcatgcg cttggcgtaa tcatggtcat agctgtttcc 2640
tgttttcccc gtatccccc aggtgtctgc aggctcaaag agcagcgaga agcgttcaga 2700
ggaaagcgat cccgtgccac cttccccgtg cccgggctgt ccccgcacgc tgccggctcg 2760
gggatgcggg gggagcgccg gaccggagcg gagccccggg cggctcgctg ctgcccccta 2820
gcgggggagg gacgtaatta catccctggg ggctttgggg gggggctgtc cctctcaccg 2880
cggtggagct ccagcttttg ttcgaattgg ggccccccct cgagggtatc gatgatatct 2940
ataacaagaa aatatatata taataagtta tcacgtaagt agaacatgaa ataacaatat 3000
aattatcgta tgagttaaat cttaaaagtc acgtaaaaga taatcatgcg tcattttgac 3060
tcacgcggtc gttatagttc aaaatcagtg acacttaccg cattgacaag cacgcctcac 3120
gggagctcca agcggcgact gagatgtcct aaatgcacag cgacggattc gcgctattta 3180
gaaagagaga gcaatatttc aagaatgcat gcgtcaattt tacgcagact atctttctag 3240
ggttaa 3246

<210> SEQ ID NO 37
<211> LENGTH: 3184
<212> TYPE: DNA
<213> ORGANISM: Artificial Sequence
<220> FEATURE:
<223> OTHER INFORMATION: Synthetic Sequence

<400> SEQUENCE: 37
ttaaccctag aaagataatc atattgtgac gtacgttaaa gataatcatg cgtaaaattg 60
acgcatgtgt tttatcggtc tgtatatcga ggtttattta ttaatttgaa tagatattaa 120
gttttattat atttacactt acatactaat aataaattca acaaacaatt tatttatgtt 180
tatttattta ttaaaaaaaa acaaaaactc aaaatttctt ctataaagta acaaaacttt 240
tatcgaatac ctgcagcccg ggggatgcag agggacagcc cccccccaaa gcccccaggg 300
atgtaattac gtccctcccc cgctaggggg cagcagcgag ccgcccgggg ctccgctccg 360
gtccggcgct ccccccgcat ccccgagccg gcagcgtgcg gggacagccc gggcacgggg 420
aaggtggcac gggatcgctt tcctctgaac gcttctcgct gctctttgag cctgcagaca 480
cctgggggga tacggggaaa agttgactgt gcctttcgat cgaactcgtc gactaggcgc 540
gtgtttgctg cttgcaatgt ttgcccattt tagggtggac acaggacgct gtggtttctg 600
agccaggggg cgactcagat cccagccagt ggacttagcc cctgtttgct cctccgataa 660
ctggggtgac cttggttaat attcaccagc agcctccccc gttgcccctc tggatccact 720
gcttaaatac ggacgaggac agggccctgt ctcctcagct tcaggcacca ccactgacct 780
gggacagtga atcgcaagaa ttctaatacg acgtctctga cctaggccac catgcagcgc 840

```
gtgaacatga ttatggccga gtctcccggc ctgatcacca tctgtctgct gggctatctg    900
ctgagcgccg agtgcaccgt gtttctggat cacgagaacg ccaacaagat cctgaacaga    960
cccaagcggt acaacagcgg caaactggaa gagttcgtgc agggtaacct ggaacgcgag   1020
tgcatggaag agaagtgcag cttcgaagag gccagagagg tgttcgagaa caccgagaga   1080
accaccgagt tctggaagca gtacgtggac ggcgatcagt gcgagagcaa cccttgtctg   1140
aatggcggca gctgcaagga tgacatcaac agctacgagt gctggtgccc cttcggcttc   1200
gagggcaaga attgcgagct ggatgtgacc tgcaacatca agaacggcag atgcgagcag   1260
ttctgcaaga acagcgccga caacaaggtc gtgtgctcct gcacagaggg ctacagactg   1320
gccgagaatc agaagtcctg cgagcccgct gtgccctttc catgtggcag agtgtctgtg   1380
tcccagacca gcaagctgac cagagccgag acagtgttcc ccgatgtgga ctacgtgaac   1440
agcaccgagg ccgagacaat cctggacaac atcacccaga gcacccagtc cttcaacgac   1500
ttcaccagag tcgtcggcgg cgaggatgct aagcctggac agtttccttg gcaagtggtg   1560
ctgaacggca aggtggacgc tttttgtggc ggctccatcg tgaacgagaa gtggatcgtg   1620
accgccgctc actgtgtgga aaccggcgtg aagattacag tggtggccgg ggagcacaac   1680
atcgaggaaa cagagcacac cgagcagaaa cggaacgtga tcagaatcat ccctcaccac   1740
aactacaacg ccgccatcaa caagtacaac cacgacattg ccctgctcga gctggacgaa   1800
cccctggtcc tgaactctta cgtgacccct atctgtatcg ccgacaaaga gtacaccaac   1860
atctttctga agttcggcag cggctacgtg tccggctggg gaagagtttt ccacaagggc   1920
agatcagccc tggtgctgca gtacctgaga gtgcccctgg tggatagagc cacatgcctg   1980
ctgagcacca agttcaccat ctacaacaac atgttctgcg ccggcttcca cgaaggcggc   2040
agagattctt gtcagggcga ttctggcggc cctcacgtga cagaagtcga gggcacatct   2100
tttctgaccg gcatcatcag ctggggcgaa gagtgtgcca tgaaggggaa gtacggcatc   2160
tataccaagg tgtccagata cgtgaactgg atcaaagaaa agaccaagct cacctgatga   2220
aacgttagat ctggtaccga tcacatatgc ctttaattaa acactagttc tatagtgtca   2280
cctaaattcc ctttagtgag ggttaatggc cgtaggccgc cagaattggg tccagacatg   2340
ataagataca ttgatgagtt tggacaaacc acaactagaa tgcagtgaaa aaaatgcttt   2400
atttgtgaaa tttgtgatgc tattgcttta tttgtaacca ttataagctg caataaacaa   2460
gttaacaaca acaattgcat tcattttatg tttcaggttc agggggaggt gtgggaggtt   2520
ttttcggact ctaggacctg cgcatgcgct tggcgtaatc atggtcatag ctgtttcctg   2580
ttttccccgt atccccccag gtgtctgcag gctcaaagag cagcgagaag cgttcagagg   2640
aaagcgatcc cgtgccacct tccccgtgcc cgggctgtcc ccgcacgctg ccggctcggg   2700
gatgcggggg gagcgccgga ccggagcgga gccccgggcg gctcgctgct gccccctagc   2760
gggggaggga cgtaattaca tccctggggg ctttgggggg gggctgtccc tctcaccgcg   2820
gtggagctcc agcttttgtt cgaattgggg ccccccctcg agggtatcga tgatatctat   2880
aacaagaaaa tatatatata ataagttatc acgtaagtag aacatgaaat aacaatataa   2940
ttatcgtatg agttaaatct taaaagtcac gtaaaagata atcatgcgtc attttgactc   3000
acgcggtcgt tatagttcaa aatcagtgac acttaccgca ttgacaagca cgcctcacgg   3060
gagctccaag cggcgactga gatgtcctaa atgcacagcg acggattcgc gctatttaga   3120
aagagagagc aatatttcaa gaatgcatgc gtcaatttta cgcagactat ctttctaggg   3180
```

ttaa 3184

<210> SEQ ID NO 38
<211> LENGTH: 3760
<212> TYPE: DNA
<213> ORGANISM: Artificial Sequence
<220> FEATURE:
<223> OTHER INFORMATION: Synthetic Sequence

<400> SEQUENCE: 38
ttaaccctag aaagataatc atattgtgac gtacgttaaa gataatcatg cgtaaaattg 60
acgcatgtgt tttatcggtc tgtatatcga ggtttattta ttaatttgaa tagatattaa 120
gttttattat atttacactt acatactaat aataaattca acaaacaatt tatttatgtt 180
tatttattta ttaaaaaaaa acaaaaactc aaaatttctt ctataaagta acaaaacttt 240
tatcgaatac ctgcagcccg ggggatgcag agggacagcc cccccccaaa gcccccaggg 300
atgtaattac gtccctcccc cgctaggggg cagcagcgag ccgcccgggg ctccgctccg 360
gtccggcgct ccccccgcat ccccgagccg gcagcgtgcg gggacagccc gggcacgggg 420
aaggtggcac gggatcgctt tcctctgaac gcttctcgct gctctttgag cctgcagaca 480
cctgggggga tacggggaaa agttgactgt gcctttcgat cgaactcgtc gactaggcgc 540
gtgtttgctg cttgcaatgt ttgcccattt tagggtggac acaggacgct gtggtttctg 600
agccaggggg cgactcagat cccagccagt ggacttagcc cctgtttgct cctccgataa 660
ctggggtgac cttggttaat attcaccagc agcctccccc gttgcccctc tggatccact 720
gcttaaatac ggacgaggac agggccctgt ctcctcagct tcaggcacca ccactgacct 780
gggacagtga atcgcaagaa ttctaatacg acgtctctga cctaggccac catgcagcgc 840
gtgaacatga ttatggccga gtctcccggc ctgatcacca tctgtctgct gggctatctg 900
ctgagcgccg agtgcaccgt gtttctggat cacgagaacg ccaacaagat cctgaacaga 960
cccaagcggt acaacagcgg caaactggaa gagttcgtgc agggtaacct ggaacgcgag 1020
tgcatggaag agaagtgcag cttcgaagag gccagagagg tgttcgagaa caccgagaga 1080
accaccgagt tctggaagca gtacgtggac ggcgatcagt gcgagagcaa cccttgtctg 1140
aatggcggca gctgcaagga tgacatcaac agctacgagt gctggtgccc cttcggcttc 1200
gagggcaaga attgcgagct ggatgtgacc tgcaacatca agaacggcag atgcgagcag 1260
ttctgcaaga acagcgccga caacaaggtc gtgtgctcct gcacagaggg ctacagactg 1320
gccgagaatc agaagtcctg cgagcccgct gtgccctttc catgtggcag agtgtctgtg 1380
tcccagacca gcaagctgac cagagccgag acagtgttcc ccgatgtgga ctacgtgaac 1440
agcaccgagg ccgagacaat cctggacaac atcacccaga gcacccagtc cttcaacgac 1500
ttcaccagag tcgtcggcgg cgaggatgct aagcctggac agtttccttg gcaagtggtg 1560
ctgaacggca aggtggacgc tttttgtggc ggctccatcg tgaacgagaa gtggatcgtg 1620
accgccgctc actgtgtgga aaccggcgtg aagattacag tggtggccgg ggagcacaac 1680
atcgaggaaa cagagcacac cgagcagaaa cggaacgtga tcagaatcat ccctcaccac 1740
aactacaacg ccgccatcaa caagtacaac cacgacattg ccctgctcga gctggacgaa 1800
cccctggtcc tgaactctta cgtgacccct atctgtatcg ccgacaaaga gtacaccaac 1860
atctttctga agttcggcag cggctacgtg tccggctggg gaagagtttt ccacaagggc 1920
agatcagccc tggtgctgca gtacctgaga gtgcccctgg tggatagagc cacatgcctg 1980
ctgagcacca agttcaccat ctacaacaac atgttctgcg ccggcttcca cgaaggcggc 2040
agagattctt gtcagggcga ttctggcggc cctcacgtga cagaagtcga gggcacatct 2100
tttctgaccg gcatcatcag ctggggcgaa gagtgtgcca tgaaggggaa gtacggcatc 2160
tataccaagg tgtccagata cgtgaactgg atcaaagaaa agaccaagct caccggctcc 2220
ggagaaggac ggggaagcct gcttacatgc ggagatgtgg aggagaatcc tggtcccatg 2280
gtctttaccc tggaagattt cgtcggcgac tggcggcaga cagccggcta taatctggac 2340
caggtgctgg aacaaggcgg agtgtccagc ctgttccaga atctgggagt gtccgtgaca 2400
cccatccagc ggattgtgct gtctggcgag aacggcctga agatcgacat ccacgtgatc 2460
atcccttacg agggcctgag cggcgatcag atgggacaga tcgagaagat tttcaaggtg 2520
gtgtaccccg tggacgacca ccacttcaaa gtgatcctgc actacggcac cctggtcatc 2580
gatggcgtga cccctaacat gatcgactac ttcggcagac cctacgaggg aatcgccgtg 2640
ttcgacggca agaaaatcac cgtgaccggc acactgtgga acgggaacaa gatcatcgac 2700
gagcggctga tcaaccccga tggcagcctg ctgttcagag tgaccattaa cggcgtgaca 2760
ggctggcggc tgtgcgaaag gattctggcc tgatgaaacg ttagatctgg taccgatcac 2820
atatgccttt aattaaacac tagttctata gtgtcaccta aattcccttt agtgagggtt 2880
aatggccgta ggccgccaga attgggtcca gacatgataa gatacattga tgagtttgga 2940
caaaccacaa ctagaatgca gtgaaaaaaa tgctttattt gtgaaatttg tgatgctatt 3000
gctttatttg taaccattat aagctgcaat aaacaagtta acaacaacaa ttgcattcat 3060
tttatgtttc aggttcaggg ggaggtgtgg gaggtttttt cggactctag gacctgcgca 3120
tgcgcttggc gtaatcatgg tcatagctgt ttcctgtttt ccccgtatcc ccccaggtgt 3180
ctgcaggctc aaagagcagc gagaagcgtt cagaggaaag cgatcccgtg ccaccttccc 3240
cgtgcccggg ctgtccccgc acgctgccgg ctcggggatg cggggggagc gccggaccgg 3300
agcggagccc cgggcggctc gctgctgccc cctagcgggg gagggacgta attacatccc 3360
tgggggcttt gggggggggc tgtccctctc accgcggtgg agctccagct tttgttcgaa 3420
ttggggcccc ccctcgaggg tatcgatgat atctataaca agaaaatata tatataataa 3480
gttatcacgt aagtagaaca tgaaataaca atataattat cgtatgagtt aaatcttaaa 3540
agtcacgtaa aagataatca tgcgtcattt tgactcacgc ggtcgttata gttcaaaatc 3600
agtgacactt accgcattga caagcacgcc tcacgggagc tccaagcggc gactgagatg 3660
tcctaaatgc acagcgacgg attcgcgcta tttagaaaga gagagcaata tttcaagaat 3720
gcatgcgtca attttacgca gactatcttt ctagggttaa 3760

<210> SEQ ID NO 39
<211> LENGTH: 3822
<212> TYPE: DNA
<213> ORGANISM: Artificial Sequence
<220> FEATURE:
<223> OTHER INFORMATION: Synthetic Sequence

<400> SEQUENCE: 39
ttaaccctag aaagataatc atattgtgac gtacgttaaa gataatcatg cgtaaaattg 60
acgcatgtgt tttatcggtc tgtatatcga ggtttattta ttaatttgaa tagatattaa 120
gttttattat atttacactt acatactaat aataaattca acaaacaatt tatttatgtt 180
tatttattta ttaaaaaaaa acaaaaactc aaaatttctt ctataaagta acaaaacttt 240
tatcgaatac ctgcagcccg ggggatgcag agggacagcc cccccccaaa gcccccaggg 300

-continued

```
atgtaattac gtccctcccc cgctaggggg cagcagcgag ccgcccgggg ctccgctccg    360
gtccggcgct ccccccgcat ccccgagccg gcagcgtgcg gggacagccc gggcacgggg    420
aaggtggcac gggatcgctt tcctctgaac gcttctcgct gctctttgag cctgcagaca    480
cctgggggga tacggggaaa agttgactgt gcctttcgat cgaactcgtc gactaggcgc    540
ggtctgtctg cacatttcgt agagcgagtg ttccgatact ctaatctccc taggcaaggt    600
tcatattgac ttaggttact tattctcctt ttgttgacta agtcaataat cagaatcagc    660
aggtttggag tcagcttggc agggatcagc agcctgggtt ggaaggaggg ggtataaaag    720
ccccttcacc aggagaagcc gtcacacaga tccacaagct cctgctagca ggtaagtgcc    780
gtgtgtggtt cccgcgggcc tggcctcttt acgggttatg gcccttgcgt gccttgaatt    840
actgacactg acatccactt tttctttttc tccacaggaa ttcctaggcc accatgcagc    900
gcgtgaacat gattatggcc gagtctcccg gcctgatcac catctgtctg ctgggctatc    960
tgctgagcgc cgagtgcacc gtgtttctgg atcacgagaa cgccaacaag atcctgaaca   1020
gacccaagcg gtacaacagc ggcaaactgg aagagttcgt gcagggtaac ctggaacgcg   1080
agtgcatgga agagaagtgc agcttcgaag aggccagaga ggtgttcgag aacaccgaga   1140
gaaccaccga gttctggaag cagtacgtgg acggcgatca gtgcgagagc aacccttgtc   1200
tgaatggcgg cagctgcaag gatgacatca acagctacga gtgctggtgc cccttcggct   1260
tcgagggcaa gaattgcgag ctggatgtga cctgcaacat caagaacggc agatgcgagc   1320
agttctgcaa gaacagcgcc gacaacaagg tcgtgtgctc ctgcacagag ggctacagac   1380
tggccgagaa tcagaagtcc tgcgagcccg ctgtgccctt tccatgtggc agagtgtctg   1440
tgtcccagac cagcaagctg accagagccg agacagtgtt ccccgatgtg gactacgtga   1500
acagcaccga ggccgagaca atcctggaca acatcaccca gagcacccag tccttcaacg   1560
acttcaccag agtcgtcggc ggcgaggatg ctaagcctgg acagtttcct tggcaagtgg   1620
tgctgaacgg caaggtggac gctttttgtg gcggctccat cgtgaacgag aagtggatcg   1680
tgaccgccgc tcactgtgtg gaaaccggcg tgaagattac agtggtggcc ggggagcaca   1740
acatcgagga aacagagcac accgagcaga aacggaacgt gatcagaatc atccctcacc   1800
acaactacaa cgccgccatc aacaagtaca accacgacat tgccctgctc gagctggacg   1860
aacccctggt cctgaactct tacgtgaccc ctatctgtat cgccgacaaa gagtacacca   1920
acatctttct gaagttcggc agcggctacg tgtccggctg ggggaagagtt ttccacaagg   1980
gcagatcagc cctggtgctg cagtacctga gagtgcccct ggtggataga gccacatgcc   2040
tgctgagcac caagttcacc atctacaaca acatgttctg cgccggcttc cacgaaggcg   2100
gcagagattc ttgtcagggc gattctggcg gccctcacgt gacagaagtc gagggcacat   2160
cttttctgac cggcatcatc agctggggcg aagagtgtgc catgaagggg aagtacggca   2220
tctataccaa ggtgtccaga tacgtgaact ggatcaaaga aaagaccaag ctcaccggct   2280
ccggagaagg acggggaagc ctgcttacat gcggagatgt ggaggagaat cctggtccca   2340
tggtctttac cctggaagat ttcgtcggcg actggcggca gacagccggc tataatctgg   2400
accaggtgct ggaacaaggc ggagtgtcca gcctgttcca gaatctggga gtgtccgtga   2460
cacccatcca gcggattgtg ctgtctggcg agaacggcct gaagatcgac atccacgtga   2520
tcatccctta cgagggcctg agcggcgatc agatgggaca gatcgagaag attttcaagg   2580
tggtgtaccc cgtggacgac caccacttca aagtgatcct gcactacggc accctggtca   2640
tcgatggcgt gaccccctaac atgatcgact acttcggcag accctacgag ggaatcgccg   2700
```

tgttcgacgg caagaaaatc accgtgaccg gcacactgtg gaacgggaac aagatcatcg 2760
acgagcggct gatcaacccc gatggcagcc tgctgttcag agtgaccatt aacggcgtga 2820
caggctggcg gctgtgcgaa aggattctgg cctgatgaaa cgttagatct ggtaccgatc 2880
acatatgcct ttaattaaac actagttcta tagtgtcacc taaattccct ttagtgaggg 2940
ttaatggccg taggccgcca gaattgggtc cagacatgat aagatacatt gatgagtttg 3000
gacaaaccac aactagaatg cagtgaaaaa aatgctttat ttgtgaaatt tgtgatgcta 3060
ttgctttatt tgtaaccatt ataagctgca ataaacaagt taacaacaac aattgcattc 3120
attttatgtt tcaggttcag ggggaggtgt gggaggtttt ttcggactct aggacctgcg 3180
catgcgcttg gcgtaatcat ggtcatagct gtttcctgtt ttccccgtat ccccccaggt 3240
gtctgcaggc tcaaagagca gcgagaagcg ttcagaggaa agcgatcccg tgccaccttc 3300
cccgtgcccg ggctgtcccc gcacgctgcc ggctcgggga tgcgggggga gcgccggacc 3360
ggagcggagc cccgggcggc tcgctgctgc cccctagcgg gggagggacg taattacatc 3420
cctgggggct ttgggggggg gctgtccctc tcaccgcggt ggagctccag cttttgttcg 3480
aattggggcc ccccctcgag ggtatcgatg atatctataa caagaaaata tatatataat 3540
aagttatcac gtaagtagaa catgaaataa caatataatt atcgtatgag ttaaatctta 3600
aaagtcacgt aaaagataat catgcgtcat tttgactcac gcggtcgtta tagttcaaaa 3660
tcagtgacac ttaccgcatt gacaagcacg cctcacggga gctccaagcg gcgactgaga 3720
tgtcctaaat gcacagcgac ggattcgcgc tatttagaaa gagagagcaa tatttcaaga 3780
atgcatgcgt caattttacg cagactatct ttctagggtt aa 3822

<210> SEQ ID NO 40
<211> LENGTH: 4582
<212> TYPE: DNA
<213> ORGANISM: Artificial Sequence
<220> FEATURE:
<223> OTHER INFORMATION: Synthetic Sequence

<400> SEQUENCE: 40
cctgcaggca gctgcgcgct cgctcgctca ctgaggccgc ccgggcgtcg ggcgaccttt 60
ggtcgcccgg cctcagtgag cgagcgagcg cgcagagagg gagtggccaa ctccatcact 120
aggggttcct gcggccgcga agactcttaa ccctagaaag ataatcatat tgtgacgtac 180
gttaaagata atcatgcgta aaattgacgc atgtgtttta tcggtctgta tatcgaggtt 240
tatttattaa tttgaataga tattaagttt tattatattt acacttacat actaataata 300
aattcaacaa acaatttatt tatgtttatt tatttattaa aaaaaaacaa aaactcaaaa 360
tttcttctat aaagtaacaa aactttttatc aaatacctgc agcccggggg atgcagaggg 420
acagcccccc cccaaagccc ccagggatgt aattacgtcc ctcccccgct agggggcagc 480
agcgagccgc ccggggctcc gctccggtcc ggcgctcccc ccgcatcccc gagccggcag 540
cgtgcgggga cagcccgggc acggggaagg tggcacggga tcgctttcct ctgaacgctt 600
ctcgctgctc tttgagcctg cagacacctg gggggatacg gggaaaagtt gactgtgcct 660
ttcgatcgaa ctcgtcgact aggcgcggtc tgtctgcaca tttcgtagag cgagtgttcc 720
gatactctaa tctccctagg caaggttcat attgacttag gttacttatt ctccttttgt 780
tgactaagtc aataatcaga atcagcaggt ttggagtcag cttggcaggg atcagcagcc 840
tgggttggaa ggagggggta taaaagcccc ttcaccagga gaagccgtca cacagatcca 900
caagctcctg ctagcaggta agtgccgtgt gtggttcccg cgggcctggc ctctttacgg 960
gttatggccc ttgcgtgcct tgaattactg acactgacat ccactttttc tttttctcca 1020
caggaattcc taggccacca tgcagcgcgt gaacatgatt atggccgagt ctcccggcct 1080
gatcaccatc tgtctgctgg gctatctgct gagcgccgag tgcaccgtgt ttctggatca 1140
cgagaacgcc aacaagatcc tgaacagacc caagcggtac aacagcggca aactggaaga 1200
gttcgtgcag ggtaacctgg aacgcgagtg catggaagag aagtgcagct tcgaagaggc 1260
cagagaggtg ttcgagaaca ccgagagaac caccgagttc tggaagcagt acgtggacgg 1320
cgatcagtgc gagagcaacc cttgtctgaa tggcggcagc tgcaaggatg acatcaacag 1380
ctacgagtgc tggtgcccct tcggcttcga gggcaagaat tgcgagctgg atgtgacctg 1440
caacatcaag aacggcagat gcgagcagtt ctgcaagaac agcgccgaca acaaggtcgt 1500
gtgctcctgc acagagggct acagactggc cgagaatcag aagtcctgcg agcccgctgt 1560
gccctttcca tgtggcagag tgtctgtgtc ccagaccagc aagctgacca gagccgagac 1620
agtgttcccc gatgtggact acgtgaacag caccgaggcc gagacaatcc tggacaacat 1680
cacccagagc acccagtcct tcaacgactt caccagagtc gtcggcggcg aggatgctaa 1740
gcctggacag tttccttggc aagtggtgct gaacggcaag gtggacgctt tttgtggcgg 1800
ctccatcgtg aacgagaagt ggatcgtgac cgccgctcac tgtgtggaaa ccggcgtgaa 1860
gattacagtg gtggccgggg agcacaacat cgaggaaaca gagcacaccg agcagaaacg 1920
gaacgtgatc agaatcatcc ctcaccacaa ctacaacgcc gccatcaaca agtacaacca 1980
cgacattgcc ctgctcgagc tggacgaacc cctggtcctg aactcttacg tgacccctat 2040
ctgtatcgcc gacaaagagt acaccaacat ctttctgaag ttcggcagcg gctacgtgtc 2100
cggctgggga agagttttcc acaagggcag atcagccctg gtgctgcagt acctgagagt 2160
gcccctggtg gatagagcca catgcctgct gagcaccaag ttcaccatct acaacaacat 2220
gttctgcgcc ggcttccacg aaggcggcag agattcttgt cagggcgatt ctggcggccc 2280
tcacgtgaca gaagtcgagg gcacatcttt tctgaccggc atcatcagct ggggcgaaga 2340
gtgtgccatg aaggggaagt acggcatcta taccaaggtg tccagatacg tgaactggat 2400
caaagaaaag accaagctca cctaatgaag atctcatatg cctttaatta aacactagtt 2460
ctatagtgtc acctaaattc cctttagtga gggttaatgg ccgtaggccg ccagaattgg 2520
gtccagacat gataagatac attgatgagt ttggacaaac cacaactaga atgcagtgaa 2580
aaaaatgctt tatttgtgaa atttgtgatg ctattgcttt atttgtaacc attataagct 2640
gcaataaaca agttaacaac aacaattgca ttcattttat gtttcaggtt cagggggagg 2700
tgtgggaggt tttttcggac tctaggacct gcgcatgcgc ttggcgtaat catggtcata 2760
gctgtttcct gttttccccg tatcccccca ggtgtctgca ggctcaaaga gcagcgagaa 2820
gcgttcagag gaaagcgatc ccgtgccacc ttccccgtgc ccgggctgtc cccgcacgct 2880
gccggctcgg ggatgcgggg ggagcgccgg accggagcgg agccccgggc ggctcgctgc 2940
tgccccctag cgggggaggg acgtaattac atccctgggg gctttggggg ggggctgtcc 3000
ctctcaccgc ggtggagctc cagcttttgt tcgaattggg gccccccctc gagggtatcg 3060
atgatatcta taacaagaaa atatatatat aataagttat cacgtaagta gaacatgaaa 3120
taacaatata attatcgtat gagttaaatc ttaaaagtca cgtaaaagat aatcatgcgt 3180
cattttgact cacgcggtcg ttatagttca aaatcagtga cacttaccgc attgacaagc 3240
acgcctcacg ggagctccaa gcggcgactg agatgtccta aatgcacagc gacggattcg 3300
cgctatttag aaagagagag caatatttca agaatgcatg cgtcaatttt acgcagacta 3360
tctttctagg gttaatctag ctagccttaa gggcgctttc ctggactact tcagacgaac 3420
ttcgtagggc gcataagtct cgaccacgca atgacgcagc gatgcttgaa aaaaacaccg 3480
ctttcaaggc ggctggacga agaccgcaag acaccctcca cctcacctag cctgtatctc 3540
tgcaatagcc taattacttc ggaatctcct gtcgtaattc cttagataaa cggcaattag 3600
gtgacactct aaatctgtgt ggaaccggct tccaaacact ctaccacctc tattagtgac 3660
acagagagaa tccttgagtg gcttctaggt atattgaaca acttcatcac gaattgagca 3720
gtgatcatgg ttctacgtat caaccaatat taaccactgt gctctgtagc attgctaaat 3780
cgggctgtct gtttcaccat agatcgtgag gccatgccca cgggcattag aacttagcct 3840
gtttagcgat aatcccaaca atgagctggg atatgacgag aagtatttag caaccttttc 3900
gtgatcggct acgtaaaacc tcatattacg gcatgtacct gatcattgac ctcaggccat 3960
acgcatgtgg gagaatagag ggaatagcac gatatactgc ctcccttatc ttcctcaggt 4020
tgaggcgcaa tgattatcac tgctacgggc acagtgttac tatcgggatc agggactgtg 4080
tctgtacccg gttctaccac gccgtagctc ccacattgtc gccgtcacgt cgttagggcc 4140
agcctgcgct tggtacgtga tcgaggagta tcgtcttgtg cacacaaaca aaatagactg 4200
ggtcccaagc gcacttagac aaggcattgt actactcaag tgttggatgt gaggaatgat 4260
acaatcgaac cccgtcgttc ggtcaacaat ttggctagag ctgtgttgat acacagcgga 4320
cgggagttac ggggacagtc ctccgagctg gccagcaaga tgcagctgac gcctgcaccg 4380
gaagtaatcc ggaggccggc caggcctcct gcgagggggc gcctcgagac cttgcggccg 4440
caggaacccc tagtgatgga gttggccact ccctctctgc gcgctcgctc gctcactgag 4500
gccgggcgac caaaggtcgc ccgacgcccg ggctttgccc gggcggcctc agtgagcgag 4560
cgagcgcgca gctgcctgca gg 4582

<210> SEQ ID NO 41
<211> LENGTH: 4137
<212> TYPE: DNA
<213> ORGANISM: Artificial Sequence
<220> FEATURE:
<223> OTHER INFORMATION: Synthetic Sequence

<400> SEQUENCE: 41
cctgcaggca gctgcgcgct cgctcgctca ctgaggccgc ccgggcgtcg ggcgaccttt 60
ggtcgcccgg cctcagtgag cgagcgagcg cgcagagagg gagtggccaa ctccatcact 120
aggggttcct gcggccgcga agactcttaa ccctagaaag ataatcatat tgtgacgtac 180
gttaaagata atcatgcgta aaattgacgc atgtgtttta tcggtctgta tatcgaggtt 240
tatttattaa tttgaataga tattaagttt tattatattt acacttacat actaataata 300
aattcaacaa acaatttatt tatgtttatt tatttattaa aaaaaaacaa aaactcaaaa 360
tttcttctat aaagtaacaa aacttttatc gaatacctgc agcccggggg atgcagaggg 420
acagcccccc cccaaagccc ccagggatgt aattacgtcc ctcccccgct agggggcagc 480
agcgagccgc ccggggctcc gctccggtcc ggcgctcccc ccgcatcccc gagccggcag 540
cgtgcgggga cagcccgggc acggggaagg tggcacggga tcgctttcct ctgaacgctt 600
ctcgctgctc tttgagcctg cagacacctg gggggatacg ggaaaagtt gactgtgcct 660 ttcgatcgaa ctcgtcgact aggcgcggtc tgtctgcaca tttcgtagag cgagtgttcc 720

```
gatactctaa tctccctagg caaggttcat attgacttag gttacttatt ctccttttgt    780
tgactaagtc aataatcaga atcagcaggt ttggagtcag cttggcaggg atcagcagcc    840
tgggttggaa ggagggggta taaaagcccc ttcaccagga gaagccgtca cacagatcca    900
caagctcctg ctagcaggta agtgccgtgt gtggttcccg cgggcctggc ctctttacgg    960
gttatggccc ttgcgtgcct tgaattactg acactgacat ccactttttc tttttctcca   1020
caggaattcc taggccacca tgcagcgcgt gaacatgatt atggccgagt ctcccggcct   1080
gatcaccatc tgtctgctgg gctatctgct gagcgccgag tgcaccgtgt ttctggatca   1140
cgagaacgcc aacaagatcc tgaacagacc caagcggtac aacagcggca aactggaaga   1200
gttcgtgcag ggtaacctgg aacgcgagtg catggaagag aagtgcagct tcgaagaggc   1260
cagagaggtg ttcgagaaca ccgagagaac caccgagttc tggaagcagt acgtggacgg   1320
cgatcagtgc gagagcaacc cttgtctgaa tggcggcagc tgcaaggatg acatcaacag   1380
ctacgagtgc tggtgcccct tcggcttcga gggcaagaat tgcgagctgg atgtgacctg   1440
caacatcaag aacggcagat gcgagcagtt ctgcaagaac agcgccgaca acaaggtcgt   1500
gtgctcctgc acagagggct acagactggc cgagaatcag aagtcctgcg agcccgctgt   1560
gccctttcca tgtggcagag tgtctgtgtc ccagaccagc aagctgacca gagccgagac   1620
agtgttcccc gatgtggact acgtgaacag caccgaggcc gagacaatcc tggacaacat   1680
cacccagagc acccagtcct tcaacgactt caccagagtc gtcggcggcg aggatgctaa   1740
gcctggacag tttccttggc aagtggtgct gaacggcaag gtggacgctt tttgtggcgg   1800
ctccatcgtg aacgagaagt ggatcgtgac cgccgctcac tgtgtggaaa ccggcgtgaa   1860
gattacagtg gtggccgggg agcacaacat cgaggaaaca gagcacaccg agcagaaacg   1920
gaacgtgatc agaatcatcc ctcaccacaa ctacaacgcc gccatcaaca agtacaacca   1980
cgacattgcc ctgctcgagc tggacgaacc cctggtcctg aactcttacg tgacccctat   2040
ctgtatcgcc gacaaagagt acaccaacat ctttctgaag ttcggcagcg gctacgtgtc   2100
cggctgggga agagttttcc acaagggcag atcagccctg gtgctgcagt acctgagagt   2160
gcccctggtg gatagagcca catgcctgct gagcaccaag ttcaccatct acaacaacat   2220
gttctgcgcc ggcttccacg aaggcggcag agattcttgt cagggcgatt ctggcggccc   2280
tcacgtgaca gaagtcgagg gcacatcttt tctgaccggc atcatcagct ggggcgaaga   2340
gtgtgccatg aaggggaagt acggcatcta taccaaggtg tccagatacg tgaactggat   2400
caaagaaaag accaagctca ccggatccgg agaaggacgg ggaagcctgc ttacatgcgg   2460
agatgtggag gagaatcctg gtcccatggt ctttaccctg gaagatttcg tcggcgactg   2520
gcggcagaca gccggctata atctggacca ggtgctggaa caaggcggag tgtccagcct   2580
gttccagaat ctgggagtgt ccgtgacacc catccagcgg attgtgctgt ctggcgagaa   2640
cggcctgaag atcgacatcc acgtgatcat ccccttacgag ggcctgagcg gcgatcagat   2700
gggacagatc gagaagattt tcaaggtggt gtaccccgtg gacgaccacc acttcaaagt   2760
gatcctgcac tacggcaccc tggtcatcga tggcgtgacc cctaacatga tcgactactt   2820
cggcagaccc tacgagggaa tcgccgtgtt cgacggcaag aaaatcaccg tgaccggcac   2880
actgtggaac gggaacaaga tcatcgacga gcggctgatc aaccccgatg gcagcctgct   2940
gttcagagtg accattaacg gcgtgacagg ctggcggctg tgcgaaagga ttctggcctg   3000
atgatctaga gatctcatat gcctttaatt aaacactagt tctatagtgt cacctaaatt   3060
ccctttagtg agggttaatg gccgtaggcc gccagaattg ggtccagaca tgataagata   3120
```

cattgatgag tttggacaaa ccacaactag aatgcagtga aaaaaatgct ttatttgtga 3180
aatttgtgat gctattgctt tatttgtaac cattataagc tgcaataaac aagttaacaa 3240
caacaattgc attcatttta tgtttcaggt tcagggggag gtgtgggagg ttttttcgga 3300
ctctaggacc tgcgcatgcg cttggcgtaa tcatggtcat agctgtttcc tgttttcccc 3360
gtatcccccc aggtgtctgc aggctcaaag agcagcgaga agcgttcaga ggaaagcgat 3420
cccgtgccac cttccccgtg cccgggctgt ccccgcacgc tgccggctcg gggatgcggg 3480
gggagcgccg gaccggagcg gagccccggg cggctcgctg ctgcccccta gcgggggagg 3540
gacgtaatta catccctggg ggctttgggg gggggctgtc cctctcaccg cggtggagct 3600
ccagcttttg ttcgaattgg ggcccccccct cgagggtatc gatgatatct ataacaagaa 3660
aatatatata taataagtta tcacgtaagt agaacatgaa ataacaatat aattatcgta 3720
tgagttaaat cttaaaagtc acgtaaaaga taatcatgcg tcattttgac tcacgcggtc 3780
gttatagttc aaaatcagtg acacttaccg cattgacaag cacgcctcac gggagctcca 3840
agcggcgact gagatgtcct aaatgcacag cgacggattc gcgctattta gaaagagaga 3900
gcaatatttc aagaatgcat gcgtcaattt tacgcagact atctttctag ggttaatcta 3960
gctagcctta agggcgcctc gagaccttgc ggccgcagga acccctagtg atggagttgg 4020
ccactccctc tctgcgcgct cgctcgctca ctgaggccgg gcgaccaaag gtcgcccgac 4080
gcccgggctt tgcccgggcg gcctcagtga gcgagcgagc gcgcagctgc ctgcagg 4137

<210> SEQ ID NO 42
<211> LENGTH: 4651
<212> TYPE: DNA
<213> ORGANISM: Artificial Sequence
<220> FEATURE:
<223> OTHER INFORMATION: Synthetic Sequence

<400> SEQUENCE: 42
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc tatcgatggc gcgcctccag atatcataca ctcgagcaac 180
tttgtataga aaagttggcg cgtgtttgct gcttgcaatg tttgcccatt ttagggtgga 240
cacaggacgc tgtggtttct gagccagggg gcgactcaga tcccagccag tggacttagc 300
ccctgtttgc tcctccgata actggggtga ccttggttaa tattcaccag cagcctcccc 360
cgttgcccct ctggatccac tgcttaaata cggacgagga cagggccctg tctcctcagc 420
ttcaggcacc accactgacc tgggacagtg aatcgcaaga attcacgcgt caattgctcg 480
aggccaccat ggctcccaag aagaagcgga aagttggcgg cggaggcagc agcctggatg 540
atgagcatat tctgagcgcc ctgctgcaga gcgacgatga actcgtgggc gaagatagcg 600
acagcgaggt gtccgatcac gtgtccgagg atgacgtgca gtccgatacc gaggaagcct 660
tcatcgacga ggtgcacgaa gtgcagccta caagcagcgg cagcgagatc ctggacgagc 720
agaatgtgat cgagcagcca ggatctagcc tggccagcaa cagaatcctg acactgcccc 780
agagaaccat ccggggcaag aacaagcact gctggtccac cagcaagagc accagacggt 840
ctagagtgtc tgccctgaac atcgtgcgaa gccagagggg ccctaccaga atgtgccgga 900
acatctacga ccctctgctg tgcttcaagc tgttcttcac cgacgagatc atctccgaga 960
tcgtgaagtg gaccaacgcc gagatcagcc tgaagcggag agaatccatg accagcgcca 1020

-continued

```
ccttcagaga caccaacgag gacgagatct acgccttctt cggcatcctg gtcatgacag   1080
ccgtgcggaa ggacaaccac atgagcaccg acgacctgtt cgaccgcagc ctgtctatgg   1140
tgtacgtgtc cgtgatgagc cgggacagat tcgacttcct gatccggtgc ctgcggatgg   1200
acgacaagtc catcagaccc acactgcgcg agaacgacgt gttcacacct gtgcggaaga   1260
tctgggacct gttcatccac cagtgcatcc agaactacac ccctggcgct cacctgacca   1320
tcgacgaaca gctgctgggc ttcagaggca gatgcccctt cagagtgtac atccccaaca   1380
agccctctaa gtacggcatc aagatcctga tgatgtgcga cagcggcacc aagtacatga   1440
tcaacggcat gccctacctc ggcagaggca cccaaacaaa tggcgtgcca ctgggcgagt   1500
actacgtgaa agaactgagc aagcctgtgc acggcagctg cagaaacatc acctgtgaca   1560
actggtttac cagcattccc ctggccaaga acctgctgca agaaccctac aagctgacaa   1620
tcgtgggcac cgtgcggagc aacaagaggg aaattcccga ggtgctgaag aactctcgga   1680
gcagacctgt gggcaccagc atgttctgct tcgacggacc tctgacactg gtgtcctaca   1740
agcccaagcc tgccaagatg gtgtacctgc tgagcagctg tgacgaggac gccagcatca   1800
atgagagcac cggcaagccc cagatggtca tgtactacaa ccagaccaaa ggcggcgtgg   1860
acaccctgga tcagatgtgc agcgtgatga cctgcagcag aaagaccaac agatggccca   1920
tggctctgct gtacggcatg atcaatatcg cctgcatcaa cagcttcatc atctacagcc   1980
acaacgtgtc cagcaagggc gagaaggtgc agagccggaa gaaattcatg cggaacctgt   2040
acatgagcct gaccagcagc ttcatgagaa agcggctgga agcccctaca ctgaagagat   2100
acctgcggga caacatcagc aacatcctgc ctaaagaggt gcccggcacc agcgacgata   2160
gcacagagga acccgtgatg aagaagagga cctactgcac ctactgtccc agcaagatcc   2220
ggcggaaggc caacgccagc tgcaaaaagt gcaagaaagt gatctgccgc gagcacaaca   2280
tcgatatgtg ccagagctgc ttctgatgag atgcattcga agcggccgcg agctcaagct   2340
tgcaattccg ataacttgtt tattgcagct tataatggtt acaaataaag caatagcatc   2400
acaaatttca caaataaagc atttttttca ctgcattcta gttgtggttt gtccaaactc   2460
atcaatgtat cttatcatgt ctggcgctag cagcacaagt ttgtacaaaa aagcaggctc   2520
ctcgcaggag gcctggccgg cctccggatt acttccggtg caggcgtcag ctgcatcttg   2580
ctggccagct cggaggactg tccccgtaac tcccgtccgc tgtgtatcaa cacagctcta   2640
gccaaattgt tgaccgaacg acggggttcg attgtatcat tcctcacatc caacacttga   2700
gtagtacaat gccttgtcta agtgcgcttg ggacccagtc tattttgttt gtgtgcacaa   2760
gacgatactc ctcgatcacg taccaagcgc aggctggccc taacgacgtg gtattctcgt   2820
attggtgtgc cccagattgc ataaggcact catcacctgc gtttatgacg ctggacgcct   2880
gcgtatgttg caggactcct atgatgtcgc tagcctgatg cgttgttatg tgattgaggt   2940
ttagtacttg gcaatatcat tagatggaac taatacgcgg tctaatcgtt acaggtttcc   3000
gacgattgag aagtatcacc tgattctcgg gagcgacttg taactctact acacttattg   3060
atttggtact cctatgtgtt gctatcttga ctccgtaaat cgccgtgata cactctcttc   3120
gtttctcggc aatctatggc tctaaactat acacaggcat tctaagaata atctgacctg   3180
tccctgtagt actggtaggt tactaccagt acggcgacaa tgtgggagct acggcgtggt   3240
agaaccgggt acagacacag tccctgatcc cgatagtaac actgtgcccg tagcagtgat   3300
aatcattgcg cctcaacctg aggaagataa gggaggcagt atatcgtgct attccctcta   3360
ttctcccaca tgcgtatggc ctgaggtcaa tgatcaggta catgccgtaa tatgaggttt   3420
```

tacgtagccg atcacgaaaa ggttgctaaa tacttctcgt catatcccag ctcattgttg 3480
ggattatcgc taaacaggct aagttctaat gcccgtgggc atggcctcac gatctatggt 3540
gaaacagaca gcccgattta gcaatgctac agagcacagt ggttaatatt ggttgatacg 3600
tagaaccatg atcactgctc aattcgtgat gaagttgttc aatataccta gaagccactc 3660
aaggattctc tctgtgtcac taatagaggt ggtagagtgt ttggaagccg gttccacaca 3720
gatttagagt gtcacctaat tgccgtttat ctaaggaatt acgacaggag attccgaagt 3780
aattaggcta ttgcagagat acaggctagg tgaggtggag ggtgtcttgc ggtcttcgtc 3840
cagccgcctt gaaagcgggg tttttttcaa gcatcgctgc gtcattgcgt ggtcgagact 3900
tatgcgccct acgaagttcg tctgaagtag tccaggaaag acctactttg cagttatctt 3960
cgcattccca cactcaccac tacaactact cttccctcaa tttcccggtt agtttcgcta 4020
agctccgacc ttgggttact gtgttgcatc cgactcgctg cggctttcta gtacgctgta 4080
ctgtttcatt cttctgtagg tctggttccg taagtccgaa tttccaggcc gtggtctagt 4140
cctaattatt ttctgtcccg gtagctatat ttagccgagg gtttgtccat ttgcccggcg 4200
tagagcgccg cgtttgcgaa catttgcgcc cgtaatacgt agggacaccg tcgggtaatg 4260
gatggcaaaa gccgaaaacg gcgtcttccg gcgcttggat tcagcgctct tgagccataa 4320
accgcgttgc ttctttggtt aattcgtatt aatgatccta agcgccagct tattcgttaa 4380
gaggcactag gcgcgccgcg gcatgcgatc gccagcatgg ctacgaccca gctttcttgt 4440
acaaagtggt gatggccggc cgcttcgagt taattaatcc aaccggttac cgcctaggat 4500
cgatagatct aggaacccct agtgatggag ttggccactc cctctctgcg cgctcgctcg 4560
ctcactgagg ccgggcgacc aaaggtcgcc cgacgcccgg gctttgcccg ggcggcctca 4620
gtgagcgagc gagcgcgcag ctgcctgcag g 4651

<210> SEQ ID NO 43
<211> LENGTH: 7302
<212> TYPE: DNA
<213> ORGANISM: Artificial Sequence
<220> FEATURE:
<223> OTHER INFORMATION: Synthetic Sequence

<400> SEQUENCE: 43
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcaggcgcc 240
attcgccatt caggctgcgc aactgttggg aagggcgatc ggtgcgggcc tcttcgctat 300
tacgccagct ggcgaaaggg ggatgtgctg caaggcgatt aagttgggta acgccagggt 360
tttcccagtc acgacgttgt aaaacgacgg ccagtgaatt ggagatcggt acttcgcgaa 420
tgcgtcgaga tggtaccacc ggtactgcgc gctcgctcgc tcactgaggc cgcccgggca 480
aagcccgggc gtcgggcgac ctttggtcgc ccggcctcag tgagcgagcg agcgcgcaga 540
gagggagtgg ccaactccat cactaggggt tccttgtagt taatgattaa cccgccatgc 600
tacttatcta cgtagccatg ctctagctta agcctaggcg cgtgtttgct gcttgcaatg 660
tttgcccatt ttagggtgga cacaggacgc tgtggtttct gagccagggg gcgactcaga 720
tcccagccag tggacttagc ccctgtttgc tcctccgata actggggtga ccttggttaa 780

```
tattcaccag cagcctcccc cgttgcccct ctggatccac tgcttaaata cggatatccg    840
aggacagggc cctgtctcct cagcttcagg caccaccact gacctgggac agtgaatcgc    900
aagaattcac gcgtcaattg ctcgaggcca ccatggctcc caagaagaag cggaaagttg    960
gcggcggagg cagcagcctg gatgatgagc atattctgag cgccctgctg cagagcgacg   1020
atgaactcgt gggcgaagat agcgacagcg aggtgtccga tcacgtgtcc gaggatgacg   1080
tgcagtccga taccgaggaa gccttcatcg acgaggtgca cgaagtgcag cctacaagca   1140
gcggcagcga gatcctggac gagcagaatg tgatcgagca gccaggatct agcctggcca   1200
gcaacagaat cctgacactg ccccagagaa ccatccgggg caagaacaag cactgctggt   1260
ccaccagcaa gagcaccaga cggtctagag tgtctgccct gaacatcgtg cgaagccaga   1320
ggggccctac cagaatgtgc cggaacatct acgaccctct gctgtgcttc aagctgttct   1380
tcaccgacga gatcatctcc gagatcgtga agtggaccaa cgccgagatc agcctgaagc   1440
ggagagaatc catgaccagc gccaccttca gagacaccaa cgaggacgag atctacgcct   1500
tcttcggcat cctggtcatg acagccgtgc ggaaggacaa ccacatgagc accgacgacc   1560
tgttcgaccg cagcctgtct atggtgtacg tgtccgtgat gagccgggac agattcgact   1620
tcctgatccg gtgcctgcgg atggacgaca agtccatcag acccacactg cgcgagaacg   1680
acgtgttcac acctgtgcgg aagatctggg acctgttcat ccaccagtgc atccagaact   1740
acacccctgg cgctcacctg accatcgacg aacagctgct gggcttcaga ggcagatgcc   1800
ccttcagagt gtacatcccc aacaagccct ctaagtacgg catcaagatc ctgatgatgt   1860
gcgacagcgg caccaagtac atgatcaacg gcatgcccta cctcggcaga ggcacccaaa   1920
caaatggcgt gccactgggc gagtactacg tgaaagaact gagcaagcct gtgcacggca   1980
gctgcagaaa catcacctgt gacaactggt ttaccagcat tcccctggcc aagaacctgc   2040
tgcaagaacc ctacaagctg acaatcgtgg gcaccgtgcg gagcaacaag agggaaattc   2100
ccgaggtgct gaagaactct cggagcagac ctgtgggcac cagcatgttc tgcttcgacg   2160
gacctctgac actggtgtcc tacaagccca agcctgccaa gatggtgtac ctgctgagca   2220
gctgtgacga ggacgccagc atcaatgaga gcaccggcaa gccccagatg gtcatgtact   2280
acaaccagac caaaggcggc gtggacaccc tggatcagat gtgcagcgtg atgacctgca   2340
gcagaaagac caacagatgg cccatggctc tgctgtacgg catgatcaat atcgcctgca   2400
tcaacagctt catcatctac agccacaacg tgtccagcaa gggcgagaag gtgcagagcc   2460
ggaagaaatt catgcggaac ctgtacatga gcctgaccag cagcttcatg agaaagcggc   2520
tggaagcccc tacactgaag agatacctgc gggacaacat cagcaacatc ctgcctaaag   2580
aggtgcccgg caccagcgac gatagcacag aggaacccgt gatgaagaag aggacctact   2640
gcacctactg tcccagcaag atccggcgga aggccaacgc cagctgcaaa aagtgcaaga   2700
aagtgatctg ccgcgagcac aacatcgata tgtgccagag ctgcttctga tgagatgcat   2760
tcgaagcggc cgcgagctca agcttgcaat tccgataact tgtttattgc agcttataat   2820
ggttacaaat aaagcaatag catcacaaat ttcacaaata aagcattttt ttcactgcat   2880
tctagttgtg gtttgtccaa actcatcaat gtatcttatc atgtctggcg ctagcagcac   2940
ctcgcaggag gcctggccgg cctccggatt acttccggtg caggcgtcag ctgcatcttg   3000
ctggccagct cggaggactg tccccgtaac tcccgtccgc tgtgtatcaa cacagctcta   3060
gccaaattgt tgaccgaacg acggggttcg attgtttcat tcctcacatc caacacttga   3120
gtagtacaat gccttgtcta agtgcgcttg ggacccagtc tattttgttt gtgtgcacaa   3180
```

gacgatactc ctcgatcacg caccaagcgc aggctggccc taacgacgtg gtattctcgt 3240
attggagagc cccagattgc ataaggcact catcacctgc gtttatgacg ctggacgcct 3300
gcgtatgttg caggactcct atgatgtcgc ttgcctgatg cgttgttatg tgattgaggt 3360
ttagtacttg gcaatatcat tagatggaac taatacgcgg tctaatcgtt acaggtttcc 3420
gacgattgag aagtatcacc tgattctcgg gagcgacttg taacactact acacttattg 3480
atttggtact cctatgtgtt gctatcttga ctccgtaaat cgccgtgata cactctcttc 3540
gtttctcggc aatctatggc tctaaactat acacaggcat tctaagaata atctgacctg 3600
tccctgtagt actggtaggt tactaccagt acggcgacaa tgtgggagct acggcgtggt 3660
agaaccgggt acagacacag tccctgatcc cgatagtaac actgtgcccg tagcagtgat 3720
aatcattgcg cctcaacctg aggaagataa gggaggcagt atatcgtgct attccctcta 3780
ttctcccaca tgcgtatggc ctgaggtcaa tgttcaggta catgccgtaa tatgaggttt 3840
tacgtagccg atcacgaaaa ggttgctaaa tacttctcgt catatcccag ctcattgttg 3900
ggattatcgc taaacaggct aagttctaat gcccgtgggc atggcctcac gatctatggt 3960
gatacagaca gcccgattta gcaatgcttc agagcacagt ggtaaatatt ggttgatacg 4020
tagaaccatg atcactgctc aattcgtgat gaagttgttc aatataccta gaagccactc 4080
aaggattctc tctgagtcac taatagaggt ggtagagtgt ttggaagccg gttccacaca 4140
gatttagagt gtcacctaat tgccgtttat ctaaggaatt acgacaggag ataccgaagt 4200
aattaggcta ttgcagagat acaggctagg tgaggtggag ggtgtcttgc ggtcttcgtc 4260
cagccgcctt gaaagcgggg tttttttcaa gcatcgctgc gtcattgcgt ggtcgagact 4320
tatgcgccct acgaagttcg tctgaagtag tccaggaaag acctactttg cagttatctt 4380
cgcattccca cactcaccac tacaactact cttccctcaa tttcccggtt agtttcgcta 4440
agctccgacc ttgggttact gtgttgcatc cgactcgctg cggctttcta gtacgctgta 4500
ctgtttcatt cttctgtagg tctggttccg taagtccgaa tttccaggcc gtggtctagt 4560
cctaattatt ttctgtcccg gtagctatat ttagccgagg gtttgtccat ttgcccggcg 4620
tagagcgccg cgtttgcgaa catttgcgcc cgtaatacgt agggacaccg tcgggtaatg 4680
gatggcaaaa gccgaaaacg gcgtcttccg gcgcttggat tcagcgctct tgagccataa 4740
accgcgttgc ttctttggtt aattcgtatt aatgatccta agcgccagct tattcgttaa 4800
gaggcactag gcgcgccgcg gcatgcgatc gccagcatgg ctacgtagat aagtagcatg 4860
gcgggttaat cattaactac aaggaacccc tagtgatgga gttggccact ccctctctgc 4920
gcgctcgctc gctcactgag gccgggcgac caaaggtcgc ccgacgcccg ggctttgccc 4980
gggcggcctc agtgagcgag cgagcgcgca gactagtgtc gacatcggat gccgggaccg 5040
acgagtgcag aggcgtgcaa gcgagcttgg cgtaatcatg gtcatagctg tttcctgtgt 5100
gaaattgtta tccgctcaca attccacaca acatacgagc cggaagcata aagtgtaaag 5160
cctggggtgc ctaatgagtg agctaactca cattaattgc gttgcgctca ctgcccgctt 5220
tccagtcggg aaacctgtcg tgccagctgc attaatgaat cggccaacgc gcggggagag 5280
gcggtttgcg tattgggcgc tcttccgctt cctcgctcac tgactcgctg cgctcggtcg 5340
ttcggctgcg gcgagcggta tcagctcact caaaggcggt aatacggtta tccacagaat 5400
caggggataa cgcaggaaag aacatgtgag caaaaggcca gcaaaaggcc aggaaccgta 5460
aaaaggccgc gttgctggcg tttttccata ggctccgccc ccctgacgag catcacaaaa 5520
atcgacgctc aagtcagagg tggcgaaacc cgacaggact ataaagatac caggcgtttc 5580
cccctggaag ctccctcgtg cgctctcctg ttccgaccct gccgcttacc ggatacctgt 5640
ccgcctttct cccttcggga agcgtggcgc tttctcatag ctcacgctgt aggtatctca 5700
gttcggtgta ggtcgttcgc tccaagctgg gctgtgtgca cgaacccccc gttcagcccg 5760
accgctgcgc cttatccggt aactatcgtc ttgagtccaa cccggtaaga cacgacttat 5820
cgccactggc agcagccact ggtaacagga ttagcagagc gaggtatgta ggcggtgcta 5880
cagagttctt gaagtggtgg cctaactacg gctacactag aagaacagta tttggtatct 5940
gcgctctgct gaagccagtt accttcggaa aaagagttgg tagctcttga tccggcaaac 6000
aaaccaccgc tggtagcggt ggtttttttg tttgcaagca gcagattacg cgcagaaaaa 6060
aaggatctca agaagatcct ttgatctttt ctacggggtc tgacgctcag tggaacgaaa 6120
actcacgtta agggattttg gtcatgagat tatcaaaaag gatcttcacc tagatccttt 6180
taaattaaaa atgaagtttt aaatcaatct aaagtatata tgagtaaact tggtctgaca 6240
gttaccaatg cttaatcagt gaggcaccta tctcagcgat ctgtctattt cgttcatcca 6300
tagttgcctg actccccgtc gtgtagataa ctacgatacg ggagggctta ccatctggcc 6360
ccagtgctgc aatgataccg cgagacccac gctcaccggc tccagattta tcagcaataa 6420
accagccagc cggaagggcc gagcgcagaa gtggtcctgc aactttatcc gcctccatcc 6480
agtctattaa ttgttgccgg gaagctagag taagtagttc gccagttaat agtttgcgca 6540
acgttgttgc cattgctaca ggcatcgtgg tgtcacgctc gtcgtttggt atggcttcat 6600
tcagctccgg ttcccaacga tcaaggcgag ttacatgatc ccccatgttg tgcaaaaaag 6660
cggttagctc cttcggtcct ccgatcgttg tcagaagtaa gttggccgca gtgttatcac 6720
tcatggttat ggcagcactg cataattctc ttactgtcat gccatccgta agatgctttt 6780
ctgtgactgg tgagtactca accaagtcat tctgagaata gtgtatgcgg cgaccgagtt 6840
gctcttgccc ggcgtcaata cgggataata ccgcgccaca tagcagaact ttaaaagtgc 6900
tcatcattgg aaaacgttct tcggggcgaa aactctcaag gatcttaccg ctgttgagat 6960
ccagttcgat gtaacccact cgtgcaccca actgatcttc agcatctttt actttcacca 7020
gcgtttctgg gtgagcaaaa acaggaaggc aaaatgccgc aaaaaaggga ataagggcga 7080
cacggaaatg ttgaatactc atactcttcc tttttcaata ttattgaagc atttatcagg 7140
gttattgtct catgagcgga tacatatttg aatgtattta gaaaaataaa caaatagggg 7200
ttccgcgcac atttccccga aaagtgccac ctgacgtcta agaaaccatt attatcatga 7260
cattaaccta taaaaatagg cgtatcacga ggccctttcg tc 7302

<210> SEQ ID NO 44
<211> LENGTH: 594
<212> TYPE: PRT
<213> ORGANISM: Artificial Sequence
<220> FEATURE:
<223> OTHER INFORMATION: Synthetic Sequence

<400> SEQUENCE: 44

Met Gly Ser Ser Leu Asp Asp Glu His Ile Leu Ser Ala Leu Leu Gln
1 5 10 15

Ser Asp Asp Glu Leu Val Gly Glu Asp Ser Asp Ser Glu Ile Ser Asp
20 25 30

His Val Ser Glu Asp Asp Val Gln Ser Asp Thr Glu Glu Ala Phe Ile
35 40 45

```
Asp Glu Val His Glu Val Gln Pro Thr Ser Ser Gly Ser Glu Ile Leu
    50                  55                  60

Asp Glu Gln Asn Val Ile Glu Gln Pro Gly Ser Ser Leu Ala Ser Asn
65                  70                  75                  80

Arg Ile Leu Thr Leu Pro Gln Arg Thr Ile Arg Gly Lys Asn Lys His
                85                  90                  95

Cys Trp Ser Thr Ser Lys Ser Thr Arg Arg Ser Arg Val Ser Ala Leu
            100                 105                 110

Asn Ile Val Arg Ser Gln Arg Gly Pro Thr Arg Met Cys Arg Asn Ile
        115                 120                 125

Tyr Asp Pro Leu Leu Cys Phe Lys Leu Phe Phe Thr Asp Glu Ile Ile
    130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
        195                 200                 205

Val Ser Val Met Ser Arg Asp Arg Phe Asp Phe Leu Ile Arg Cys Leu
    210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
            260                 265                 270

Gly Phe Arg Gly Arg Cys Pro Phe Arg Met Tyr Ile Pro Asn Lys Pro
        275                 280                 285

Ser Lys Tyr Gly Ile Lys Ile Leu Met Met Cys Asp Ser Gly Tyr Lys
    290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
                325                 330                 335

His Gly Ser Cys Arg Asn Ile Thr Cys Asp Asn Trp Phe Thr Ser Ile
            340                 345                 350

Pro Leu Ala Lys Asn Leu Leu Gln Glu Pro Tyr Lys Leu Thr Ile Val
        355                 360                 365

Gly Thr Val Arg Ser Asn Lys Arg Glu Ile Pro Glu Val Leu Lys Asn
    370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
                405                 410                 415

Leu Ser Ser Cys Asp Glu Asp Ala Ser Ile Asn Glu Ser Thr Gly Lys
            420                 425                 430

Pro Gln Met Val Met Tyr Tyr Asn Gln Thr Lys Gly Gly Val Asp Thr
        435                 440                 445

Leu Asp Gln Met Cys Ser Val Met Thr Cys Ser Arg Lys Thr Asn Arg
    450                 455                 460

Trp Pro Met Ala Leu Leu Tyr Gly Met Ile Asn Ile Ala Cys Ile Asn
```

465 470 475 480

Ser Phe Ile Ile Tyr Ser His Asn Val Ser Ser Lys Gly Glu Lys Val
485 490 495

Gln Ser Arg Lys Lys Phe Met Arg Asn Leu Tyr Met Ser Leu Thr Ser
500 505 510

Ser Phe Met Arg Lys Arg Leu Glu Ala Pro Thr Leu Lys Arg Tyr Leu
515 520 525

Arg Asp Asn Ile Ser Asn Ile Leu Pro Asn Glu Val Pro Gly Thr Ser
530 535 540

Asp Asp Ser Thr Glu Glu Pro Val Met Lys Lys Arg Thr Tyr Cys Thr
545 550 555 560

Tyr Cys Pro Ser Lys Ile Arg Arg Lys Ala Asn Ala Ser Cys Lys Lys
565 570 575

Cys Lys Lys Val Ile Cys Arg Glu His Asn Ile Asp Met Cys Gln Ser
580 585 590

Cys Phe

<210> SEQ ID NO 45
<211> LENGTH: 594
<212> TYPE: PRT
<213> ORGANISM: Artificial Sequence
<220> FEATURE:
<223> OTHER INFORMATION: Synthetic Sequence

<400> SEQUENCE: 45

Met Gly Ser Ser Leu Asp Asp Glu His Ile Leu Ser Ala Leu Leu Gln
1 5 10 15

Ser Asp Asp Glu Leu Val Gly Glu Asp Ser Asp Ser Glu Val Ser Asp
20 25 30

His Val Ser Glu Asp Asp Val Gln Ser Asp Thr Glu Glu Ala Phe Ile
35 40 45

Asp Glu Val His Glu Val Gln Pro Thr Ser Ser Gly Ser Glu Ile Leu
50 55 60

Asp Glu Gln Asn Val Ile Glu Gln Pro Gly Ser Ser Leu Ala Ser Asn
65 70 75 80

Arg Ile Leu Thr Leu Pro Gln Arg Thr Ile Arg Gly Lys Asn Lys His
85 90 95

Cys Trp Ser Thr Ser Lys Ser Thr Arg Arg Ser Arg Val Ser Ala Leu
100 105 110

Asn Ile Val Arg Ser Gln Arg Gly Pro Thr Arg Met Cys Arg Asn Ile
115 120 125

Tyr Asp Pro Leu Leu Cys Phe Lys Leu Phe Phe Thr Asp Glu Ile Ile
130 135 140

Ser Glu Ile Val Lys Trp Thr Asn Ala Glu Ile Ser Leu Lys Arg Arg
145 150 155 160

Glu Ser Met Thr Ser Ala Thr Phe Arg Asp Thr Asn Glu Asp Glu Ile
165 170 175

Tyr Ala Phe Phe Gly Ile Leu Val Met Thr Ala Val Arg Lys Asp Asn
180 185 190

His Met Ser Thr Asp Asp Leu Phe Asp Arg Ser Leu Ser Met Val Tyr
195 200 205

Val Ser Val Met Ser Arg Asp Arg Phe Asp Phe Leu Ile Arg Cys Leu
210 215 220

Arg Met Asp Asp Lys Ser Ile Arg Pro Thr Leu Arg Glu Asn Asp Val
225 230 235 240

```
Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
            260                 265                 270

Gly Phe Arg Gly Arg Cys Pro Phe Arg Val Tyr Ile Pro Asn Lys Pro
        275                 280                 285

Ser Lys Tyr Gly Ile Lys Ile Leu Met Met Cys Asp Ser Gly Thr Lys
    290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
                325                 330                 335

His Gly Ser Cys Arg Asn Ile Thr Cys Asp Asn Trp Phe Thr Ser Ile
            340                 345                 350

Pro Leu Ala Lys Asn Leu Leu Gln Glu Pro Tyr Lys Leu Thr Ile Val
        355                 360                 365

Gly Thr Val Arg Ser Asn Lys Arg Glu Ile Pro Glu Val Leu Lys Asn
    370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
                405                 410                 415

Leu Ser Ser Cys Asp Glu Asp Ala Ser Ile Asn Glu Ser Thr Gly Lys
            420                 425                 430

Pro Gln Met Val Met Tyr Tyr Asn Gln Thr Lys Gly Gly Val Asp Thr
        435                 440                 445

Leu Asp Gln Met Cys Ser Val Met Thr Cys Ser Arg Lys Thr Asn Arg
    450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
                485                 490                 495

Gln Ser Arg Lys Lys Phe Met Arg Asn Leu Tyr Met Ser Leu Thr Ser
            500                 505                 510

Ser Phe Met Arg Lys Arg Leu Glu Ala Pro Thr Leu Lys Arg Tyr Leu
        515                 520                 525

Arg Asp Asn Ile Ser Asn Ile Leu Pro Lys Glu Val Pro Gly Thr Ser
    530                 535                 540

Asp Asp Ser Thr Glu Glu Pro Val Met Lys Lys Arg Thr Tyr Cys Thr
545                 550                 555                 560

Tyr Cys Pro Ser Lys Ile Arg Arg Lys Ala Asn Ala Ser Cys Lys Lys
                565                 570                 575

Cys Lys Lys Val Ile Cys Arg Glu His Asn Ile Asp Met Cys Gln Ser
            580                 585                 590

Cys Phe


<210> SEQ ID NO 46
<211> LENGTH: 593
<212> TYPE: PRT
<213> ORGANISM: Artificial Sequence
<220> FEATURE:
<223> OTHER INFORMATION: Synthetic Sequence

<400> SEQUENCE: 46
```

```
Gly Ser Ser Leu Asp Asp Glu His Ile Leu Ser Ala Leu Leu Gln Ser
1               5                   10                  15

Asp Asp Glu Leu Val Gly Glu Asp Ser Asp Ser Glu Ile Ser Asp His
            20                  25                  30

Val Ser Glu Asp Asp Val Gln Ser Asp Thr Glu Glu Ala Phe Ile Asp
        35                  40                  45

Glu Val His Glu Val Gln Pro Thr Ser Ser Gly Ser Glu Ile Leu Asp
    50                  55                  60

Glu Gln Asn Val Ile Glu Gln Pro Gly Ser Ser Leu Ala Ser Asn Arg
65                  70                  75                  80

Ile Leu Thr Leu Pro Gln Arg Thr Ile Arg Gly Lys Asn Lys His Cys
                85                  90                  95

Trp Ser Thr Ser Lys Ser Thr Arg Arg Ser Arg Val Ser Ala Leu Asn
            100                 105                 110

Ile Val Arg Ser Gln Arg Gly Pro Thr Arg Met Cys Arg Asn Ile Tyr
        115                 120                 125

Asp Pro Leu Leu Cys Phe Lys Leu Phe Phe Thr Asp Glu Ile Ile Ser
    130                 135                 140

Glu Ile Val Lys Trp Thr Asn Ala Glu Ile Ser Leu Lys Arg Arg Glu
145                 150                 155                 160

Ser Met Thr Gly Ala Thr Phe Arg Asp Thr Asn Glu Asp Glu Ile Tyr
                165                 170                 175

Ala Phe Phe Gly Ile Leu Val Met Thr Ala Val Arg Lys Asp Asn His
            180                 185                 190

Met Ser Thr Asp Asp Leu Phe Asp Arg Ser Leu Ser Met Val Tyr Val
        195                 200                 205

Ser Val Met Ser Arg Asp Arg Phe Asp Phe Leu Ile Arg Cys Leu Arg
    210                 215                 220

Met Asp Asp Lys Ser Ile Arg Pro Thr Leu Arg Glu Asn Asp Val Phe
225                 230                 235                 240

Thr Pro Val Arg Lys Ile Trp Asp Leu Phe Ile His Gln Cys Ile Gln
                245                 250                 255

Asn Tyr Thr Pro Gly Ala His Leu Thr Ile Asp Glu Gln Leu Leu Gly
            260                 265                 270

Phe Arg Gly Arg Cys Pro Phe Arg Met Tyr Ile Pro Asn Lys Pro Ser
        275                 280                 285

Lys Tyr Gly Ile Lys Ile Leu Met Met Cys Asp Ser Gly Tyr Lys Tyr
    290                 295                 300

Met Ile Asn Gly Met Pro Tyr Leu Gly Arg Gly Thr Gln Thr Asn Gly
305                 310                 315                 320

Val Pro Leu Gly Glu Tyr Tyr Val Lys Glu Leu Ser Lys Pro Val His
                325                 330                 335

Gly Ser Cys Arg Asn Ile Thr Cys Asp Asn Trp Phe Thr Ser Ile Pro
            340                 345                 350

Leu Ala Lys Asn Leu Leu Gln Glu Pro Tyr Lys Leu Thr Ile Val Gly
        355                 360                 365

Thr Val Arg Ser Asn Lys Arg Glu Ile Pro Glu Val Leu Lys Asn Ser
    370                 375                 380

Arg Ser Arg Pro Val Gly Thr Ser Met Phe Cys Phe Asp Gly Pro Leu
385                 390                 395                 400

Thr Leu Val Ser Tyr Lys Pro Lys Pro Ala Lys Met Val Tyr Leu Leu
                405                 410                 415

Ser Ser Cys Asp Glu Asp Ala Ser Ile Asn Glu Ser Thr Gly Lys Pro
```

```
            420                 425                 430

Gln Met Val Met Tyr Tyr Asn Gln Thr Lys Gly Gly Val Asp Thr Leu
        435                 440                 445

Asp Gln Met Cys Ser Val Met Thr Cys Ser Arg Lys Thr Asn Arg Trp
    450                 455                 460

Pro Met Ala Leu Leu Tyr Gly Met Ile Asn Ile Ala Cys Ile Asn Ser
465                 470                 475                 480

Phe Ile Ile Tyr Ser His Asn Val Ser Ser Lys Gly Glu Lys Val Gln
                485                 490                 495

Ser Arg Lys Lys Phe Met Arg Asn Leu Tyr Met Ser Leu Thr Ser Ser
            500                 505                 510

Phe Met Arg Lys Arg Leu Glu Ala Pro Thr Leu Lys Arg Tyr Leu Arg
        515                 520                 525

Asp Asn Ile Ser Asn Ile Leu Pro Asn Glu Val Pro Gly Thr Ser Asp
    530                 535                 540

Asp Ser Thr Glu Glu Pro Val Met Lys Lys Arg Thr Tyr Cys Thr Tyr
545                 550                 555                 560

Cys Pro Ser Lys Ile Arg Arg Lys Ala Asn Ala Ser Cys Lys Lys Cys
                565                 570                 575

Lys Lys Val Ile Cys Arg Glu His Asn Ile Asp Met Cys Gln Ser Cys
            580                 585                 590

Phe
```

<210> SEQ ID NO 47
<211> LENGTH: 593
<212> TYPE: PRT
<213> ORGANISM: Artificial Sequence
<220> FEATURE:
<223> OTHER INFORMATION: Synthetic Sequence

<400> SEQUENCE: 47

```
Gly Ser Ser Leu Asp Asp Glu His Ile Leu Ser Ala Leu Leu Gln Ser
1               5                   10                  15

Asp Asp Glu Leu Val Gly Glu Asp Ser Asp Ser Glu Val Ser Asp His
            20                  25                  30

Val Ser Glu Asp Asp Val Gln Ser Asp Thr Glu Glu Ala Phe Ile Asp
        35                  40                  45

Glu Val His Glu Val Gln Pro Thr Ser Ser Gly Ser Glu Ile Leu Asp
    50                  55                  60

Glu Gln Asn Val Ile Glu Gln Pro Gly Ser Ser Leu Ala Ser Asn Arg
65                  70                  75                  80

Ile Leu Thr Leu Pro Gln Arg Thr Ile Arg Gly Lys Asn Lys His Cys
                85                  90                  95

Trp Ser Thr Ser Lys Ser Thr Arg Arg Ser Arg Val Ser Ala Leu Asn
            100                 105                 110

Ile Val Arg Ser Gln Arg Gly Pro Thr Arg Met Cys Arg Asn Ile Tyr
        115                 120                 125

Asp Pro Leu Leu Cys Phe Lys Leu Phe Phe Thr Asp Glu Ile Ile Ser
    130                 135                 140

Glu Ile Val Lys Trp Thr Asn Ala Glu Ile Ser Leu Lys Arg Arg Glu
145                 150                 155                 160

Ser Met Thr Ser Ala Thr Phe Arg Asp Thr Asn Glu Asp Glu Ile Tyr
                165                 170                 175

Ala Phe Phe Gly Ile Leu Val Met Thr Ala Val Arg Lys Asp Asn His
            180                 185                 190
```

```
Met Ser Thr Asp Asp Leu Phe Asp Arg Ser Leu Ser Met Val Tyr Val
        195                 200                 205

Ser Val Met Ser Arg Asp Arg Phe Asp Phe Leu Ile Arg Cys Leu Arg
    210                 215                 220

Met Asp Asp Lys Ser Ile Arg Pro Thr Leu Arg Glu Asn Asp Val Phe
225                 230                 235                 240

Thr Pro Val Arg Lys Ile Trp Asp Leu Phe Ile His Gln Cys Ile Gln
                245                 250                 255

Asn Tyr Thr Pro Gly Ala His Leu Thr Ile Asp Glu Gln Leu Leu Gly
            260                 265                 270

Phe Arg Gly Arg Cys Pro Phe Arg Val Tyr Ile Pro Asn Lys Pro Ser
        275                 280                 285

Lys Tyr Gly Ile Lys Ile Leu Met Met Cys Asp Ser Gly Thr Lys Tyr
    290                 295                 300

Met Ile Asn Gly Met Pro Tyr Leu Gly Arg Gly Thr Gln Thr Asn Gly
305                 310                 315                 320

Val Pro Leu Gly Glu Tyr Tyr Val Lys Glu Leu Ser Lys Pro Val His
                325                 330                 335

Gly Ser Cys Arg Asn Ile Thr Cys Asp Asn Trp Phe Thr Ser Ile Pro
            340                 345                 350

Leu Ala Lys Asn Leu Leu Gln Glu Pro Tyr Lys Leu Thr Ile Val Gly
        355                 360                 365

Thr Val Arg Ser Asn Lys Arg Glu Ile Pro Glu Val Leu Lys Asn Ser
    370                 375                 380

Arg Ser Arg Pro Val Gly Thr Ser Met Phe Cys Phe Asp Gly Pro Leu
385                 390                 395                 400

Thr Leu Val Ser Tyr Lys Pro Lys Pro Ala Lys Met Val Tyr Leu Leu
                405                 410                 415

Ser Ser Cys Asp Glu Asp Ala Ser Ile Asn Glu Ser Thr Gly Lys Pro
            420                 425                 430

Gln Met Val Met Tyr Tyr Asn Gln Thr Lys Gly Gly Val Asp Thr Leu
        435                 440                 445

Asp Gln Met Cys Ser Val Met Thr Cys Ser Arg Lys Thr Asn Arg Trp
    450                 455                 460

Pro Met Ala Leu Leu Tyr Gly Met Ile Asn Ile Ala Cys Ile Asn Ser
465                 470                 475                 480

Phe Ile Ile Tyr Ser His Asn Val Ser Ser Lys Gly Glu Lys Val Gln
                485                 490                 495

Ser Arg Lys Lys Phe Met Arg Asn Leu Tyr Met Ser Leu Thr Ser Ser
            500                 505                 510

Phe Met Arg Lys Arg Leu Glu Ala Pro Thr Leu Lys Arg Tyr Leu Arg
        515                 520                 525

Asp Asn Ile Ser Asn Ile Leu Pro Lys Glu Val Pro Gly Thr Ser Asp
    530                 535                 540

Asp Ser Thr Glu Glu Pro Val Met Lys Lys Arg Thr Tyr Cys Thr Tyr
545                 550                 555                 560

Cys Pro Ser Lys Ile Arg Arg Lys Ala Asn Ala Ser Cys Lys Lys Cys
                565                 570                 575

Lys Lys Val Ile Cys Arg Glu His Asn Ile Asp Met Cys Gln Ser Cys
            580                 585                 590

Phe
```

<210> SEQ ID NO 48
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 48

Pro Lys Lys Lys Arg Lys Val
1               5

<210> SEQ ID NO 49
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 49
cccaagaaga agcggaaagt t 21

<210> SEQ ID NO 50
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 50

Gly Gly Gly Gly Ser
1               5

<210> SEQ ID NO 51
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 51
ggcggcggag gcagc 15

<210> SEQ ID NO 52
<211> LENGTH: 605
<212> TYPE: PRT
<213> ORGANISM: Artificial Sequence
<220> FEATURE:
<223> OTHER INFORMATION: Synthetic Sequence

<400> SEQUENCE: 52

Met Ala Pro Lys Lys Lys Arg Lys Val Gly Gly Gly Gly Ser Ser Leu
1               5                   10                  15

Asp Asp Glu His Ile Leu Ser Ala Leu Leu Gln Ser Asp Asp Glu Leu
            20                  25                  30

Val Gly Glu Asp Ser Asp Ser Glu Val Ser Asp His Val Ser Glu Asp
        35                  40                  45

Asp Val Gln Ser Asp Thr Glu Glu Ala Phe Ile Asp Glu Val His Glu
    50                  55                  60

Val Gln Pro Thr Ser Ser Gly Ser Glu Ile Leu Asp Glu Gln Asn Val
65                  70                  75                  80

Ile Glu Gln Pro Gly Ser Ser Leu Ala Ser Asn Arg Ile Leu Thr Leu
                85                  90                  95

Pro Gln Arg Thr Ile Arg Gly Lys Asn Lys His Cys Trp Ser Thr Ser
            100                 105                 110

```
Lys Ser Thr Arg Arg Ser Arg Val Ser Ala Leu Asn Ile Val Arg Ser
        115                 120                 125

Gln Arg Gly Pro Thr Arg Met Cys Arg Asn Ile Tyr Asp Pro Leu Leu
    130                 135                 140

Cys Phe Lys Leu Phe Phe Thr Asp Glu Ile Ile Ser Glu Ile Val Lys
145                 150                 155                 160

Trp Thr Asn Ala Glu Ile Ser Leu Lys Arg Arg Glu Ser Met Thr Ser
                165                 170                 175

Ala Thr Phe Arg Asp Thr Asn Glu Asp Glu Ile Tyr Ala Phe Phe Gly
            180                 185                 190

Ile Leu Val Met Thr Ala Val Arg Lys Asp Asn His Met Ser Thr Asp
        195                 200                 205

Asp Leu Phe Asp Arg Ser Leu Ser Met Val Tyr Val Ser Val Met Ser
    210                 215                 220

Arg Asp Arg Phe Asp Phe Leu Ile Arg Cys Leu Arg Met Asp Asp Lys
225                 230                 235                 240

Ser Ile Arg Pro Thr Leu Arg Glu Asn Asp Val Phe Thr Pro Val Arg
                245                 250                 255

Lys Ile Trp Asp Leu Phe Ile His Gln Cys Ile Gln Asn Tyr Thr Pro
            260                 265                 270

Gly Ala His Leu Thr Ile Asp Glu Gln Leu Leu Gly Phe Arg Gly Arg
        275                 280                 285

Cys Pro Phe Arg Val Tyr Ile Pro Asn Lys Pro Ser Lys Tyr Gly Ile
    290                 295                 300

Lys Ile Leu Met Met Cys Asp Ser Gly Thr Lys Tyr Met Ile Asn Gly
305                 310                 315                 320

Met Pro Tyr Leu Gly Arg Gly Thr Gln Thr Asn Gly Val Pro Leu Gly
                325                 330                 335

Glu Tyr Tyr Val Lys Glu Leu Ser Lys Pro Val His Gly Ser Cys Arg
            340                 345                 350

Asn Ile Thr Cys Asp Asn Trp Phe Thr Ser Ile Pro Leu Ala Lys Asn
        355                 360                 365

Leu Leu Gln Glu Pro Tyr Lys Leu Thr Ile Val Gly Thr Val Arg Ser
    370                 375                 380

Asn Lys Arg Glu Ile Pro Glu Val Leu Lys Asn Ser Arg Ser Arg Pro
385                 390                 395                 400

Val Gly Thr Ser Met Phe Cys Phe Asp Gly Pro Leu Thr Leu Val Ser
                405                 410                 415

Tyr Lys Pro Lys Pro Ala Lys Met Val Tyr Leu Leu Ser Ser Cys Asp
            420                 425                 430

Glu Asp Ala Ser Ile Asn Glu Ser Thr Gly Lys Pro Gln Met Val Met
        435                 440                 445

Tyr Tyr Asn Gln Thr Lys Gly Gly Val Asp Thr Leu Asp Gln Met Cys
    450                 455                 460

Ser Val Met Thr Cys Ser Arg Lys Thr Asn Arg Trp Pro Met Ala Leu
465                 470                 475                 480

Leu Tyr Gly Met Ile Asn Ile Ala Cys Ile Asn Ser Phe Ile Ile Tyr
                485                 490                 495

Ser His Asn Val Ser Ser Lys Gly Glu Lys Val Gln Ser Arg Lys Lys
            500                 505                 510

Phe Met Arg Asn Leu Tyr Met Ser Leu Thr Ser Ser Phe Met Arg Lys
        515                 520                 525
```

```
Arg Leu Glu Ala Pro Thr Leu Lys Arg Tyr Leu Arg Asp Asn Ile Ser
    530                 535                 540

Asn Ile Leu Pro Lys Glu Val Pro Gly Thr Ser Asp Asp Ser Thr Glu
545                 550                 555                 560

Glu Pro Val Met Lys Lys Arg Thr Tyr Cys Thr Tyr Cys Pro Ser Lys
                565                 570                 575

Ile Arg Arg Lys Ala Asn Ala Ser Cys Lys Lys Cys Lys Lys Val Ile
            580                 585                 590

Cys Arg Glu His Asn Ile Asp Met Cys Gln Ser Cys Phe
        595                 600                 605


<210> SEQ ID NO 53
<211> LENGTH: 1815
<212> TYPE: DNA
<213> ORGANISM: Artificial Sequence
<220> FEATURE:
<223> OTHER INFORMATION: Synthetic Sequence

<400> SEQUENCE: 53

atggctccca agaagaagcg gaaagttggc ggcggaggca gcagcctgga tgatgagcat     60

attctgagcg ccctgctgca gagcgacgat gaactcgtgg gcgaagatag cgacagcgag    120

gtgtccgatc acgtgtccga ggatgacgtg cagtccgata ccgaggaagc cttcatcgac    180

gaggtgcacg aagtgcagcc tacaagcagc ggcagcgaga tcctggacga gcagaatgtg    240

atcgagcagc caggatctag cctggccagc aacagaatcc tgacactgcc ccagagaacc    300

atccggggca agaacaagca ctgctggtcc accagcaaga gcaccagacg gtctagagtg    360

tctgccctga acatcgtgcg aagccagagg ggccctacca gaatgtgccg gaacatctac    420

gaccctctgc tgtgcttcaa gctgttcttc accgacgaga tcatctccga gatcgtgaag    480

tggaccaacg ccgagatcag cctgaagcgg agagaatcca tgaccagcgc caccttcaga    540

gacaccaacg aggacgagat ctacgccttc ttcggcatcc tggtcatgac agccgtgcgg    600

aaggacaacc acatgagcac cgacgacctg ttcgaccgca gcctgtctat ggtgtacgtg    660

tccgtgatga gccgggacag attcgacttc ctgatccggt gcctgcggat ggacgacaag    720

tccatcagac ccacactgcg cgagaacgac gtgttcacac ctgtgcggaa gatctgggac    780

ctgttcatcc accagtgcat ccagaactac acccctggcg ctcacctgac catcgacgaa    840

cagctgctgg gcttcagagg cagatgcccc ttcagagtgt acatccccaa caagccctct    900

aagtacggca tcaagatcct gatgatgtgc gacagcggca ccaagtacat gatcaacggc    960

atgccctacc tcggcagagg cacccaaaca aatggcgtgc cactgggcga gtactacgtg   1020

aaagaactga gcaagcctgt gcacggcagc tgcagaaaca tcacctgtga caactggttt   1080

accagcattc ccctggccaa gaacctgctg caagaaccct acaagctgac aatcgtgggc   1140

accgtgcgga gcaacaagag ggaaattccc gaggtgctga agaactctcg gagcagacct   1200

gtgggcacca gcatgttctg cttcgacgga cctctgacac tggtgtccta caagcccaag   1260

cctgccaaga tggtgtacct gctgagcagc tgtgacgagg acgccagcat caatgagagc   1320

accggcaagc cccagatggt catgtactac aaccagacca aaggcggcgt ggacaccctg   1380

gatcagatgt gcagcgtgat gacctgcagc agaaagacca acagatggcc catggctctg   1440

ctgtacggca tgatcaatat cgcctgcatc aacagcttca tcatctacag ccacaacgtg   1500

tccagcaagg gcgagaaggt gcagagccgg aagaaattca tgcggaacct gtacatgagc   1560

ctgaccagca gcttcatgag aaagcggctg gaagccccta cactgaagag atacctgcgg   1620
```

gacaacatca gcaacatcct gcctaaagag gtgcccggca ccagcgacga tagcacagag 1680
gaacccgtga tgaagaagag gacctactgc acctactgtc ccagcaagat ccggcggaag 1740
gccaacgcca gctgcaaaaa gtgcaagaaa gtgatctgcc gcgagcacaa catcgatatg 1800
tgccagagct gcttc 1815

<210> SEQ ID NO 54
<211> LENGTH: 603
<212> TYPE: PRT
<213> ORGANISM: Artificial Sequence
<220> FEATURE:
<223> OTHER INFORMATION: Synthetic Sequence

<400> SEQUENCE: 54

Pro Lys Lys Lys Arg Lys Val Gly Gly Gly Gly Ser Ser Leu Asp Asp
1 5 10 15

Glu His Ile Leu Ser Ala Leu Leu Gln Ser Asp Asp Glu Leu Val Gly
20 25 30

Glu Asp Ser Asp Ser Glu Val Ser Asp His Val Ser Glu Asp Asp Val
35 40 45

Gln Ser Asp Thr Glu Glu Ala Phe Ile Asp Glu Val His Glu Val Gln
50 55 60

Pro Thr Ser Ser Gly Ser Glu Ile Leu Asp Glu Gln Asn Val Ile Glu
65 70 75 80

Gln Pro Gly Ser Ser Leu Ala Ser Asn Arg Ile Leu Thr Leu Pro Gln
85 90 95

Arg Thr Ile Arg Gly Lys Asn Lys His Cys Trp Ser Thr Ser Lys Ser
100 105 110

Thr Arg Arg Ser Arg Val Ser Ala Leu Asn Ile Val Arg Ser Gln Arg
115 120 125

Gly Pro Thr Arg Met Cys Arg Asn Ile Tyr Asp Pro Leu Leu Cys Phe
130 135 140

Lys Leu Phe Phe Thr Asp Glu Ile Ile Ser Glu Ile Val Lys Trp Thr
145 150 155 160

Asn Ala Glu Ile Ser Leu Lys Arg Arg Glu Ser Met Thr Ser Ala Thr
165 170 175

Phe Arg Asp Thr Asn Glu Asp Glu Ile Tyr Ala Phe Phe Gly Ile Leu
180 185 190

Val Met Thr Ala Val Arg Lys Asp Asn His Met Ser Thr Asp Asp Leu
195 200 205

Phe Asp Arg Ser Leu Ser Met Val Tyr Val Ser Val Met Ser Arg Asp
210 215 220

Arg Phe Asp Phe Leu Ile Arg Cys Leu Arg Met Asp Asp Lys Ser Ile
225 230 235 240

Arg Pro Thr Leu Arg Glu Asn Asp Val Phe Thr Pro Val Arg Lys Ile
245 250 255

Trp Asp Leu Phe Ile His Gln Cys Ile Gln Asn Tyr Thr Pro Gly Ala
260 265 270

His Leu Thr Ile Asp Glu Gln Leu Leu Gly Phe Arg Gly Arg Cys Pro
275 280 285

Phe Arg Val Tyr Ile Pro Asn Lys Pro Ser Lys Tyr Gly Ile Lys Ile
290 295 300

Leu Met Met Cys Asp Ser Gly Thr Lys Tyr Met Ile Asn Gly Met Pro
305 310 315 320

Tyr Leu Gly Arg Gly Thr Gln Thr Asn Gly Val Pro Leu Gly Glu Tyr

-continued

```
                325                 330                 335

Tyr Val Lys Glu Leu Ser Lys Pro Val His Gly Ser Cys Arg Asn Ile
            340                 345                 350

Thr Cys Asp Asn Trp Phe Thr Ser Ile Pro Leu Ala Lys Asn Leu Leu
        355                 360                 365

Gln Glu Pro Tyr Lys Leu Thr Ile Val Gly Thr Val Arg Ser Asn Lys
    370                 375                 380

Arg Glu Ile Pro Glu Val Leu Lys Asn Ser Arg Ser Arg Pro Val Gly
385                 390                 395                 400

Thr Ser Met Phe Cys Phe Asp Gly Pro Leu Thr Leu Val Ser Tyr Lys
                405                 410                 415

Pro Lys Pro Ala Lys Met Val Tyr Leu Leu Ser Ser Cys Asp Glu Asp
            420                 425                 430

Ala Ser Ile Asn Glu Ser Thr Gly Lys Pro Gln Met Val Met Tyr Tyr
        435                 440                 445

Asn Gln Thr Lys Gly Gly Val Asp Thr Leu Asp Gln Met Cys Ser Val
    450                 455                 460

Met Thr Cys Ser Arg Lys Thr Asn Arg Trp Pro Met Ala Leu Leu Tyr
465                 470                 475                 480

Gly Met Ile Asn Ile Ala Cys Ile Asn Ser Phe Ile Ile Tyr Ser His
                485                 490                 495

Asn Val Ser Ser Lys Gly Glu Lys Val Gln Ser Arg Lys Lys Phe Met
            500                 505                 510

Arg Asn Leu Tyr Met Ser Leu Thr Ser Ser Phe Met Arg Lys Arg Leu
        515                 520                 525

Glu Ala Pro Thr Leu Lys Arg Tyr Leu Arg Asp Asn Ile Ser Asn Ile
    530                 535                 540

Leu Pro Lys Glu Val Pro Gly Thr Ser Asp Asp Ser Thr Glu Glu Pro
545                 550                 555                 560

Val Met Lys Lys Arg Thr Tyr Cys Thr Tyr Cys Pro Ser Lys Ile Arg
                565                 570                 575

Arg Lys Ala Asn Ala Ser Cys Lys Lys Cys Lys Lys Val Ile Cys Arg
            580                 585                 590

Glu His Asn Ile Asp Met Cys Gln Ser Cys Phe
        595                 600
```

```
<210> SEQ ID NO 55
<211> LENGTH: 1809
<212> TYPE: DNA
<213> ORGANISM: Artificial Sequence
<220> FEATURE:
<223> OTHER INFORMATION: Synthetic Sequence

<400> SEQUENCE: 55

cccaagaaga agcggaaagt tggcggcgga ggcagcagcc tggatgatga gcatattctg      60

agcgccctgc tgcagagcga cgatgaactc gtgggcgaag atagcgacag cgaggtgtcc     120

gatcacgtgt ccgaggatga cgtgcagtcc gataccgagg aagccttcat cgacgaggtg     180

cacgaagtgc agcctacaag cagcggcagc gagatcctgg acgagcagaa tgtgatcgag     240

cagccaggat ctagcctggc cagcaacaga atcctgacac tgccccagag aaccatccgg     300

ggcaagaaca agcactgctg gtccaccagc aagagcacca gacggtctag agtgtctgcc     360

ctgaacatcg tgcgaagcca gaggggccct accagaatgt gccggaacat ctacgaccct     420

ctgctgtgct tcaagctgtt cttcaccgac gagatcatct ccgagatcgt gaagtggacc     480
```

aacgccgaga tcagcctgaa gcggagagaa tccatgacca gcgccacctt cagagacacc 540
aacgaggacg agatctacgc cttcttcggc atcctggtca tgacagccgt gcggaaggac 600
aaccacatga gcaccgacga cctgttcgac cgcagcctgt ctatggtgta cgtgtccgtg 660
atgagccggg acagattcga cttcctgatc cggtgcctgc ggatggacga caagtccatc 720
agacccacac tgcgcgagaa cgacgtgttc acacctgtgc ggaagatctg ggacctgttc 780
atccaccagt gcatccagaa ctacacccct ggcgctcacc tgaccatcga cgaacagctg 840
ctgggcttca gaggcagatg ccccttcaga gtgtacatcc ccaacaagcc ctctaagtac 900
ggcatcaaga tcctgatgat gtgcgacagc ggcaccaagt acatgatcaa cggcatgccc 960
tacctcggca gaggcaccca aacaaatggc gtgccactgg gcgagtacta cgtgaaagaa 1020
ctgagcaagc ctgtgcacgg cagctgcaga aacatcacct gtgacaactg gtttaccagc 1080
attcccctgg ccaagaacct gctgcaagaa ccctacaagc tgacaatcgt gggcaccgtg 1140
cggagcaaca agagggaaat tcccgaggtg ctgaagaact ctcggagcag acctgtgggc 1200
accagcatgt tctgcttcga cggacctctg acactggtgt cctacaagcc caagcctgcc 1260
aagatggtgt acctgctgag cagctgtgac gaggacgcca gcatcaatga gagcaccggc 1320
aagccccaga tggtcatgta ctacaaccag accaaaggcg gcgtggacac cctggatcag 1380
atgtgcagcg tgatgacctg cagcagaaag accaacagat ggcccatggc tctgctgtac 1440
ggcatgatca atatcgcctg catcaacagc ttcatcatct acagccacaa cgtgtccagc 1500
aagggcgaga aggtgcagag ccggaagaaa ttcatgcgga acctgtacat gagcctgacc 1560
agcagcttca tgagaaagcg gctggaagcc cctacactga agagatacct gcgggacaac 1620
atcagcaaca tcctgcctaa agaggtgccc ggcaccagcg acgatagcac agaggaaccc 1680
gtgatgaaga agaggaccta ctgcacctac tgtcccagca agatccggcg gaaggccaac 1740
gccagctgca aaaagtgcaa gaaagtgatc tgccgcgagc acaacatcga tatgtgccag 1800
agctgcttc 1809

<210> SEQ ID NO 56
<211> LENGTH: 340
<212> TYPE: PRT
<213> ORGANISM: Artificial Sequence
<220> FEATURE:
<223> OTHER INFORMATION: Synthetic Sequence

<400> SEQUENCE: 56

Met Gly Lys Ser Lys Glu Ile Ser Gln Asp Leu Arg Lys Lys Ile Val
1 5 10 15

Asp Leu His Lys Ser Gly Ser Ser Leu Gly Ala Ile Ser Lys Arg Leu
20 25 30

Lys Val Pro Arg Ser Ser Val Gln Thr Ile Val Arg Lys Tyr Lys His
35 40 45

His Gly Thr Thr Gln Pro Ser Tyr Arg Ser Gly Arg Arg Arg Val Leu
50 55 60

Ser Pro Arg Asp Glu Arg Thr Leu Val Arg Lys Val Gln Ile Asn Pro
65 70 75 80

Arg Thr Thr Ala Lys Asp Leu Val Lys Met Leu Glu Glu Thr Gly Thr
85 90 95

Lys Val Ser Ile Ser Thr Val Lys Arg Val Leu Tyr Arg His Asn Leu
100 105 110

Lys Gly Arg Ser Ala Arg Lys Lys Pro Leu Leu Gln Asn Arg His Lys
115 120 125

```
Lys Ala Arg Leu Arg Phe Ala Thr Ala His Gly Asp Lys Asp Arg Thr
    130                 135                 140

Phe Trp Arg Asn Val Leu Trp Ser Asp Glu Thr Lys Ile Glu Leu Phe
145                 150                 155                 160

Gly His Asn Asp His Arg Tyr Val Trp Arg Lys Lys Gly Glu Ala Cys
                165                 170                 175

Lys Pro Lys Asn Thr Ile Pro Thr Val Lys His Gly Gly Gly Ser Ile
            180                 185                 190

Met Leu Trp Gly Cys Phe Ala Ala Gly Gly Thr Gly Ala Leu His Lys
        195                 200                 205

Ile Asp Gly Ile Met Arg Lys Glu Asn Tyr Val Asp Ile Leu Lys Gln
    210                 215                 220

His Leu Lys Thr Ser Val Arg Lys Leu Lys Leu Gly Arg Lys Trp Val
225                 230                 235                 240

Phe Gln Met Asp Asn Asp Pro Lys His Thr Ser Lys Val Val Ala Lys
                245                 250                 255

Trp Leu Lys Asp Asn Lys Val Lys Val Leu Glu Trp Pro Ser Gln Ser
            260                 265                 270

Pro Asp Leu Asn Pro Ile Glu Asn Leu Trp Ala Glu Leu Lys Lys Arg
        275                 280                 285

Val Arg Ala Arg Arg Pro Thr Asn Leu Thr Gln Leu His Gln Leu Cys
    290                 295                 300

Gln Glu Glu Trp Ala Lys Ile His Pro Thr Tyr Cys Gly Lys Leu Val
305                 310                 315                 320

Glu Gly Tyr Pro Lys Arg Leu Thr Gln Val Lys Gln Phe Lys Gly Asn
                325                 330                 335

Ala Thr Lys Tyr
            340
```

<210> SEQ ID NO 57
<211> LENGTH: 339
<212> TYPE: PRT
<213> ORGANISM: Artificial Sequence
<220> FEATURE:
<223> OTHER INFORMATION: Synthetic Sequence

<400> SEQUENCE: 57

```
Gly Lys Ser Lys Glu Ile Ser Gln Asp Leu Arg Lys Lys Ile Val Asp
1               5                   10                  15

Leu His Lys Ser Gly Ser Ser Leu Gly Ala Ile Ser Lys Arg Leu Lys
            20                  25                  30

Val Pro Arg Ser Ser Val Gln Thr Ile Val Arg Lys Tyr Lys His His
        35                  40                  45

Gly Thr Thr Gln Pro Ser Tyr Arg Ser Gly Arg Arg Arg Val Leu Ser
    50                  55                  60

Pro Arg Asp Glu Arg Thr Leu Val Arg Lys Val Gln Ile Asn Pro Arg
65                  70                  75                  80

Thr Thr Ala Lys Asp Leu Val Lys Met Leu Glu Glu Thr Gly Thr Lys
                85                  90                  95

Val Ser Ile Ser Thr Val Lys Arg Val Leu Tyr Arg His Asn Leu Lys
            100                 105                 110

Gly Arg Ser Ala Arg Lys Lys Pro Leu Leu Gln Asn Arg His Lys Lys
        115                 120                 125

Ala Arg Leu Arg Phe Ala Thr Ala His Gly Asp Lys Asp Arg Thr Phe
    130                 135                 140
```

Trp Arg Asn Val Leu Trp Ser Asp Glu Thr Lys Ile Glu Leu Phe Gly
145 150 155 160

His Asn Asp His Arg Tyr Val Trp Arg Lys Lys Gly Glu Ala Cys Lys
165 170 175

Pro Lys Asn Thr Ile Pro Thr Val Lys His Gly Gly Gly Ser Ile Met
180 185 190

Leu Trp Gly Cys Phe Ala Ala Gly Gly Thr Gly Ala Leu His Lys Ile
195 200 205

Asp Gly Ile Met Arg Lys Glu Asn Tyr Val Asp Ile Leu Lys Gln His
210 215 220

Leu Lys Thr Ser Val Arg Lys Leu Lys Leu Gly Arg Lys Trp Val Phe
225 230 235 240

Gln Met Asp Asn Asp Pro Lys His Thr Ser Lys Val Val Ala Lys Trp
245 250 255

Leu Lys Asp Asn Lys Val Lys Val Leu Glu Trp Pro Ser Gln Ser Pro
260 265 270

Asp Leu Asn Pro Ile Glu Asn Leu Trp Ala Glu Leu Lys Lys Arg Val
275 280 285

Arg Ala Arg Arg Pro Thr Asn Leu Thr Gln Leu His Gln Leu Cys Gln
290 295 300

Glu Glu Trp Ala Lys Ile His Pro Thr Tyr Cys Gly Lys Leu Val Glu
305 310 315 320

Gly Tyr Pro Lys Arg Leu Thr Gln Val Lys Gln Phe Lys Gly Asn Ala
325 330 335

Thr Lys Tyr

<210> SEQ ID NO 58
<211> LENGTH: 340
<212> TYPE: PRT
<213> ORGANISM: Artificial Sequence
<220> FEATURE:
<223> OTHER INFORMATION: Synthetic Sequence

<400> SEQUENCE: 58

Met Gly Lys Ser Lys Glu Ile Ser Gln Asp Leu Arg Lys Arg Ile Val
1 5 10 15

Asp Leu His Lys Ser Gly Ser Ser Leu Gly Ala Ile Ser Lys Arg Leu
20 25 30

Ala Val Pro Arg Ser Ser Val Gln Thr Ile Val Arg Lys Tyr Lys His
35 40 45

His Gly Thr Thr Gln Pro Ser Tyr Arg Ser Gly Arg Arg Arg Val Leu
50 55 60

Ser Pro Arg Asp Glu Arg Thr Leu Val Arg Lys Val Gln Ile Asn Pro
65 70 75 80

Arg Thr Thr Ala Lys Asp Leu Val Lys Met Leu Glu Glu Thr Gly Thr
85 90 95

Lys Val Ser Ile Ser Thr Val Lys Arg Val Leu Tyr Arg His Asn Leu
100 105 110

Lys Gly His Ser Ala Arg Lys Lys Pro Leu Leu Gln Asn Arg His Lys
115 120 125

Lys Ala Arg Leu Arg Phe Ala Thr Ala His Gly Asp Lys Asp Arg Thr
130 135 140

Phe Trp Arg Asn Val Leu Trp Ser Asp Glu Thr Lys Ile Glu Leu Phe
145 150 155 160

```
Gly His Asn Asp His Arg Tyr Val Trp Arg Lys Lys Gly Glu Ala Cys
                165                 170                 175

Lys Pro Lys Asn Thr Ile Pro Thr Val Lys His Gly Gly Gly Ser Ile
            180                 185                 190

Met Leu Trp Gly Cys Phe Ala Ala Gly Gly Thr Gly Ala Leu His Lys
        195                 200                 205

Ile Asp Gly Ile Met Asp Ala Val Gln Tyr Val Asp Ile Leu Lys Gln
    210                 215                 220

His Leu Lys Thr Ser Val Arg Lys Leu Lys Leu Gly Arg Lys Trp Val
225                 230                 235                 240

Phe Gln His Asp Asn Asp Pro Lys His Thr Ser Lys Val Val Ala Lys
                245                 250                 255

Trp Leu Lys Asp Asn Lys Val Lys Val Leu Glu Trp Pro Ser Gln Ser
            260                 265                 270

Pro Asp Leu Asn Pro Ile Glu Asn Leu Trp Ala Glu Leu Lys Lys Arg
        275                 280                 285

Val Arg Ala Arg Arg Pro Thr Asn Leu Thr Gln Leu His Gln Leu Cys
    290                 295                 300

Gln Glu Glu Trp Ala Lys Ile His Pro Asn Tyr Cys Gly Lys Leu Val
305                 310                 315                 320

Glu Gly Tyr Pro Lys Arg Leu Thr Gln Val Lys Gln Phe Lys Gly Asn
                325                 330                 335

Ala Thr Lys Tyr
            340
```

<210> SEQ ID NO 59
<211> LENGTH: 339
<212> TYPE: PRT
<213> ORGANISM: Artificial Sequence
<220> FEATURE:
<223> OTHER INFORMATION: Synthetic Sequence

<400> SEQUENCE: 59

```
Gly Lys Ser Lys Glu Ile Ser Gln Asp Leu Arg Lys Arg Ile Val Asp
1               5                   10                  15

Leu His Lys Ser Gly Ser Ser Leu Gly Ala Ile Ser Lys Arg Leu Ala
            20                  25                  30

Val Pro Arg Ser Ser Val Gln Thr Ile Val Arg Lys Tyr Lys His His
        35                  40                  45

Gly Thr Thr Gln Pro Ser Tyr Arg Ser Gly Arg Arg Arg Val Leu Ser
    50                  55                  60

Pro Arg Asp Glu Arg Thr Leu Val Arg Lys Val Gln Ile Asn Pro Arg
65                  70                  75                  80

Thr Thr Ala Lys Asp Leu Val Lys Met Leu Glu Glu Thr Gly Thr Lys
                85                  90                  95

Val Ser Ile Ser Thr Val Lys Arg Val Leu Tyr Arg His Asn Leu Lys
            100                 105                 110

Gly His Ser Ala Arg Lys Lys Pro Leu Leu Gln Asn Arg His Lys Lys
        115                 120                 125

Ala Arg Leu Arg Phe Ala Thr Ala His Gly Asp Lys Asp Arg Thr Phe
    130                 135                 140

Trp Arg Asn Val Leu Trp Ser Asp Glu Thr Lys Ile Glu Leu Phe Gly
145                 150                 155                 160

His Asn Asp His Arg Tyr Val Trp Arg Lys Lys Gly Glu Ala Cys Lys
                165                 170                 175
```

```
Pro Lys Asn Thr Ile Pro Thr Val Lys His Gly Gly Gly Ser Ile Met
            180                 185                 190

Leu Trp Gly Cys Phe Ala Ala Gly Gly Thr Gly Ala Leu His Lys Ile
        195                 200                 205

Asp Gly Ile Met Asp Ala Val Gln Tyr Val Asp Ile Leu Lys Gln His
    210                 215                 220

Leu Lys Thr Ser Val Arg Lys Leu Lys Leu Gly Arg Lys Trp Val Phe
225                 230                 235                 240

Gln His Asp Asn Asp Pro Lys His Thr Ser Lys Val Val Ala Lys Trp
                245                 250                 255

Leu Lys Asp Asn Lys Val Lys Val Leu Glu Trp Pro Ser Gln Ser Pro
            260                 265                 270

Asp Leu Asn Pro Ile Glu Asn Leu Trp Ala Glu Leu Lys Lys Arg Val
        275                 280                 285

Arg Ala Arg Arg Pro Thr Asn Leu Thr Gln Leu His Gln Leu Cys Gln
    290                 295                 300

Glu Glu Trp Ala Lys Ile His Pro Asn Tyr Cys Gly Lys Leu Val Glu
305                 310                 315                 320

Gly Tyr Pro Lys Arg Leu Thr Gln Val Lys Gln Phe Lys Gly Asn Ala
                325                 330                 335

Thr Lys Tyr


<210> SEQ ID NO 60
<211> LENGTH: 1496
<212> TYPE: PRT
<213> ORGANISM: Artificial Sequence
<220> FEATURE:
<223> OTHER INFORMATION: Synthetic Sequence

<400> SEQUENCE: 60

Met Ser Lys Glu Gln Leu Leu Ile Gln Arg Ser Ser Ala Ala Glu Arg
1               5                   10                  15

Cys Arg Arg Tyr Arg Gln Lys Met Ser Ala Glu Gln Arg Ala Ser Asp
            20                  25                  30

Leu Glu Arg Arg Arg Arg Leu Gln Gln Asn Val Ser Glu Glu Gln Leu
        35                  40                  45

Leu Glu Lys Arg Arg Ser Glu Ala Glu Lys Gln Arg Arg His Arg Gln
    50                  55                  60

Lys Met Ser Lys Asp Gln Arg Ala Phe Glu Val Glu Arg Arg Arg Trp
65                  70                  75                  80

Arg Arg Gln Asn Met Ser Arg Glu Gln Ser Ser Thr Ser Thr Thr Asn
                85                  90                  95

Thr Gly Arg Asn Cys Leu Leu Ser Lys Asn Gly Val His Glu Asp Ala
            100                 105                 110

Ile Leu Glu His Ser Cys Gly Gly Met Thr Val Arg Cys Glu Phe Cys
        115                 120                 125

Leu Ser Leu Asn Phe Ser Asp Glu Lys Pro Ser Asp Gly Lys Phe Thr
    130                 135                 140

Arg Cys Cys Ser Lys Gly Lys Val Cys Pro Asn Asp Ile His Phe Pro
145                 150                 155                 160

Asp Tyr Pro Ala Tyr Leu Lys Arg Leu Met Thr Asn Glu Asp Ser Asp
                165                 170                 175

Ser Lys Asn Phe Met Glu Asn Ile Arg Ser Ile Asn Ser Ser Phe Ala
            180                 185                 190

Phe Ala Ser Met Gly Ala Asn Ile Ala Ser Pro Ser Gly Tyr Gly Pro
```

```
        195                 200                 205

Tyr Cys Phe Arg Ile His Gly Gln Val Tyr His Arg Thr Gly Thr Leu
    210                 215                 220

His Pro Ser Asp Gly Val Ser Arg Lys Phe Ala Gln Leu Tyr Ile Leu
225                 230                 235                 240

Asp Thr Ala Glu Ala Thr Ser Lys Arg Leu Ala Met Pro Glu Asn Gln
                245                 250                 255

Gly Cys Ser Glu Arg Leu Met Ile Asn Ile Asn Asn Leu Met His Glu
            260                 265                 270

Ile Asn Glu Leu Thr Lys Ser Tyr Lys Met Leu His Glu Val Glu Lys
        275                 280                 285

Glu Ala Gln Ser Glu Ala Ala Ala Lys Gly Ile Ala Pro Thr Glu Val
    290                 295                 300

Thr Met Ala Ile Lys Tyr Asp Arg Asn Ser Asp Pro Gly Arg Tyr Asn
305                 310                 315                 320

Ser Pro Arg Val Thr Glu Val Ala Val Ile Phe Arg Asn Glu Asp Gly
                325                 330                 335

Glu Pro Pro Phe Glu Arg Asp Leu Leu Ile His Cys Lys Pro Asp Pro
            340                 345                 350

Asn Asn Pro Asn Ala Thr Lys Met Lys Gln Ile Ser Ile Leu Phe Pro
        355                 360                 365

Thr Leu Asp Ala Met Thr Tyr Pro Ile Leu Phe Pro His Gly Glu Lys
    370                 375                 380

Gly Trp Gly Thr Asp Ile Ala Leu Arg Leu Arg Asp Asn Ser Val Ile
385                 390                 395                 400

Asp Asn Asn Thr Arg Gln Asn Val Arg Thr Arg Val Thr Gln Met Gln
                405                 410                 415

Tyr Tyr Gly Phe His Leu Ser Val Arg Asp Thr Phe Asn Pro Ile Leu
            420                 425                 430

Asn Ala Gly Lys Leu Thr Gln Gln Phe Ile Val Asp Ser Tyr Ser Lys
        435                 440                 445

Met Glu Ala Asn Arg Ile Asn Phe Ile Lys Ala Asn Gln Ser Lys Leu
    450                 455                 460

Arg Val Glu Lys Tyr Ser Gly Leu Met Asp Tyr Leu Lys Ser Arg Ser
465                 470                 475                 480

Glu Asn Asp Asn Val Pro Ile Gly Lys Met Ile Ile Leu Pro Ser Ser
                485                 490                 495

Phe Glu Gly Ser Pro Arg Asn Met Gln Gln Arg Tyr Gln Asp Ala Met
            500                 505                 510

Ala Ile Val Thr Lys Tyr Gly Lys Pro Asp Leu Phe Ile Thr Met Thr
        515                 520                 525

Cys Asn Pro Lys Trp Ala Asp Ile Thr Asn Asn Leu Gln Arg Trp Gln
    530                 535                 540

Lys Val Glu Asn Arg Pro Asp Leu Val Ala Arg Val Phe Asn Ile Lys
545                 550                 555                 560

Leu Asn Ala Leu Leu Asn Asp Ile Cys Lys Phe His Leu Phe Gly Lys
                565                 570                 575

Val Ile Ala Lys Ile His Val Ile Glu Phe Gln Lys Arg Gly Leu Pro
            580                 585                 590

His Ala His Ile Leu Leu Ile Leu Asp Ser Glu Ser Lys Leu Arg Ser
        595                 600                 605

Glu Asp Asp Ile Asp Arg Ile Val Lys Ala Glu Ile Pro Asp Glu Asp
    610                 615                 620
```

```
Gln Cys Pro Arg Leu Phe Gln Ile Val Lys Ser Asn Met Val His Gly
625                 630                 635                 640

Pro Cys Gly Ile Gln Asn Pro Asn Ser Pro Cys Met Glu Asn Gly Lys
                645                 650                 655

Cys Ser Lys Gly Tyr Pro Lys Glu Phe Gln Asn Ala Thr Ile Gly Asn
            660                 665                 670

Ile Asp Gly Tyr Pro Lys Tyr Lys Arg Arg Ser Gly Ser Thr Met Ser
        675                 680                 685

Ile Gly Asn Lys Val Val Asp Asn Thr Trp Ile Val Pro Tyr Asn Pro
    690                 695                 700

Tyr Leu Cys Leu Lys Tyr Asn Cys His Ile Asn Val Glu Val Cys Ala
705                 710                 715                 720

Ser Ile Lys Ser Val Lys Tyr Leu Phe Lys Tyr Ile Tyr Lys Gly His
                725                 730                 735

Asp Cys Ala Asn Ile Gln Ile Ser Glu Lys Asn Ile Ile Asn His Asp
            740                 745                 750

Glu Val Gln Asp Phe Ile Asp Ser Arg Tyr Val Ser Ala Pro Glu Ala
        755                 760                 765

Val Trp Arg Leu Phe Ala Met Arg Met His Asp Gln Ser His Ala Ile
    770                 775                 780

Thr Arg Leu Ala Ile His Leu Pro Asn Asp Gln Asn Leu Tyr Phe His
785                 790                 795                 800

Thr Asp Asp Phe Ala Glu Val Leu Asp Arg Ala Lys Arg His Asn Ser
                805                 810                 815

Thr Leu Met Ala Trp Phe Leu Leu Asn Arg Glu Asp Ser Asp Ala Arg
            820                 825                 830

Asn Tyr Tyr Tyr Trp Glu Ile Pro Gln His Tyr Val Phe Asn Asn Ser
        835                 840                 845

Leu Trp Thr Lys Arg Arg Lys Gly Gly Asn Lys Val Leu Gly Arg Leu
    850                 855                 860

Phe Thr Val Ser Phe Arg Glu Pro Glu Arg Tyr Tyr Leu Arg Leu Leu
865                 870                 875                 880

Leu Leu His Val Lys Gly Ala Ile Ser Phe Glu Asp Leu Arg Thr Val
                885                 890                 895

Gly Gly Val Thr Tyr Asp Thr Phe His Glu Ala Ala Lys His Arg Gly
            900                 905                 910

Leu Leu Leu Asp Asp Thr Ile Trp Lys Asp Thr Ile Asp Asp Ala Ile
        915                 920                 925

Ile Leu Asn Met Pro Lys Gln Leu Arg Gln Leu Phe Ala Tyr Ile Cys
    930                 935                 940

Val Phe Gly Cys Pro Ser Ala Ala Asp Lys Leu Trp Asp Glu Asn Lys
945                 950                 955                 960

Ser His Phe Ile Glu Asp Phe Cys Trp Lys Leu His Arg Arg Glu Gly
                965                 970                 975

Ala Cys Val Asn Cys Glu Met His Ala Leu Asn Glu Ile Gln Glu Val
            980                 985                 990

Phe Thr Leu His Gly Met Lys Cys  Ser His Phe Lys Leu  Pro Asp Tyr
        995                 1000                1005

Pro Leu  Leu Met Asn Ala Asn  Thr Cys Asp Gln Leu  Tyr Glu Gln
    1010                1015                1020

Gln Gln  Ala Glu Val Leu Ile  Asn Ser Leu Asn Asp  Glu Gln Leu
    1025                1030                1035
```

```
Ala Ala  Phe Gln Thr Ile Thr  Ser Ala Ile Glu Asp  Gln Thr Val
    1040                 1045                 1050

His Pro  Lys Cys Phe Phe Leu  Asp Gly Pro Gly Gly  Ser Gly Lys
    1055                 1060                 1065

Thr Tyr  Leu Tyr Lys Val Leu  Thr His Tyr Ile Arg  Gly Arg Gly
    1070                 1075                 1080

Gly Thr  Val Leu Pro Thr Ala  Ser Thr Gly Ile Ala  Ala Asn Leu
    1085                 1090                 1095

Leu Leu  Gly Gly Arg Thr Phe  His Ser Gln Tyr Lys  Leu Pro Ile
    1100                 1105                 1110

Pro Leu  Asn Glu Thr Ser Ile  Ser Arg Leu Asp Ile  Lys Ser Glu
    1115                 1120                 1125

Val Ala  Lys Thr Ile Lys Lys  Ala Gln Leu Leu Ile  Ile Asp Glu
    1130                 1135                 1140

Cys Thr  Met Ala Ser Ser His  Ala Ile Asn Ala Ile  Asp Arg Leu
    1145                 1150                 1155

Leu Arg  Glu Ile Met Asn Leu  Asn Val Ala Phe Gly  Gly Lys Val
    1160                 1165                 1170

Leu Leu  Leu Gly Gly Asp Phe  Arg Gln Cys Leu Ser  Ile Val Pro
    1175                 1180                 1185

His Ala  Met Arg Ser Ala Ile  Val Gln Thr Ser Leu  Lys Tyr Cys
    1190                 1195                 1200

Asn Val  Trp Gly Cys Phe Arg  Lys Leu Ser Leu Lys  Thr Asn Met
    1205                 1210                 1215

Arg Ser  Glu Asp Ser Ala Tyr  Ser Glu Trp Leu Val  Lys Leu Gly
    1220                 1225                 1230

Asp Gly  Lys Leu Asp Ser Ser  Phe His Leu Gly Met  Asp Ile Ile
    1235                 1240                 1245

Glu Ile  Pro His Glu Met Ile  Cys Asn Gly Ser Ile  Ile Glu Ala
    1250                 1255                 1260

Thr Phe  Gly Asn Ser Ile Ser  Ile Asp Asn Ile Lys  Asn Ile Ser
    1265                 1270                 1275

Lys Arg  Ala Ile Leu Cys Pro  Lys Asn Glu His Val  Gln Lys Leu
    1280                 1285                 1290

Asn Glu  Glu Ile Leu Asp Ile  Leu Asp Gly Asp Phe  His Thr Tyr
    1295                 1300                 1305

Leu Ser  Asp Asp Ser Ile Asp  Ser Thr Asp Asp Ala  Glu Lys Glu
    1310                 1315                 1320

Asn Phe  Pro Ile Glu Phe Leu  Asn Ser Ile Thr Pro  Ser Gly Met
    1325                 1330                 1335

Pro Cys  His Lys Leu Lys Leu  Lys Val Gly Ala Ile  Ile Met Leu
    1340                 1345                 1350

Leu Arg  Asn Leu Asn Ser Lys  Trp Gly Leu Cys Asn  Gly Thr Arg
    1355                 1360                 1365

Phe Ile  Ile Lys Arg Leu Arg  Pro Asn Ile Ile Glu  Ala Glu Val
    1370                 1375                 1380

Leu Thr  Gly Ser Ala Glu Gly  Glu Val Val Leu Ile  Pro Arg Ile
    1385                 1390                 1395

Asp Leu  Ser Pro Ser Asp Thr  Gly Leu Pro Phe Lys  Leu Ile Arg
    1400                 1405                 1410

Arg Gln  Phe Pro Val Met Pro  Ala Phe Ala Met Thr  Ile Asn Lys
    1415                 1420                 1425

Ser Gln  Gly Gln Thr Leu Asp  Arg Val Gly Ile Phe  Leu Pro Glu
```

1430 1435 1440

Pro Val Phe Ala His Gly Gln Leu Tyr Val Ala Phe Ser Arg Val
1445 1450 1455

Arg Arg Ala Cys Asp Val Lys Val Lys Val Val Asn Thr Ser Ser
1460 1465 1470

Gln Gly Lys Leu Val Lys His Ser Glu Ser Val Phe Thr Leu Asn
1475 1480 1485

Val Val Tyr Arg Glu Ile Leu Glu
1490 1495

<210> SEQ ID NO 61
<211> LENGTH: 1495
<212> TYPE: PRT
<213> ORGANISM: Artificial Sequence
<220> FEATURE:
<223> OTHER INFORMATION: Synthetic Sequence

<400> SEQUENCE: 61

Ser Lys Glu Gln Leu Leu Ile Gln Arg Ser Ser Ala Ala Glu Arg Cys
1 5 10 15

Arg Arg Tyr Arg Gln Lys Met Ser Ala Glu Gln Arg Ala Ser Asp Leu
20 25 30

Glu Arg Arg Arg Arg Leu Gln Gln Asn Val Ser Glu Glu Gln Leu Leu
35 40 45

Glu Lys Arg Arg Ser Glu Ala Glu Lys Gln Arg Arg His Arg Gln Lys
50 55 60

Met Ser Lys Asp Gln Arg Ala Phe Glu Val Glu Arg Arg Arg Trp Arg
65 70 75 80

Arg Gln Asn Met Ser Arg Glu Gln Ser Ser Thr Ser Thr Thr Asn Thr
85 90 95

Gly Arg Asn Cys Leu Leu Ser Lys Asn Gly Val His Glu Asp Ala Ile
100 105 110

Leu Glu His Ser Cys Gly Gly Met Thr Val Arg Cys Glu Phe Cys Leu
115 120 125

Ser Leu Asn Phe Ser Asp Glu Lys Pro Ser Asp Gly Lys Phe Thr Arg
130 135 140

Cys Cys Ser Lys Gly Lys Val Cys Pro Asn Asp Ile His Phe Pro Asp
145 150 155 160

Tyr Pro Ala Tyr Leu Lys Arg Leu Met Thr Asn Glu Asp Ser Asp Ser
165 170 175

Lys Asn Phe Met Glu Asn Ile Arg Ser Ile Asn Ser Ser Phe Ala Phe
180 185 190

Ala Ser Met Gly Ala Asn Ile Ala Ser Pro Ser Gly Tyr Gly Pro Tyr
195 200 205

Cys Phe Arg Ile His Gly Gln Val Tyr His Arg Thr Gly Thr Leu His
210 215 220

Pro Ser Asp Gly Val Ser Arg Lys Phe Ala Gln Leu Tyr Ile Leu Asp
225 230 235 240

Thr Ala Glu Ala Thr Ser Lys Arg Leu Ala Met Pro Glu Asn Gln Gly
245 250 255

Cys Ser Glu Arg Leu Met Ile Asn Ile Asn Asn Leu Met His Glu Ile
260 265 270

Asn Glu Leu Thr Lys Ser Tyr Lys Met Leu His Glu Val Glu Lys Glu
275 280 285

Ala Gln Ser Glu Ala Ala Ala Lys Gly Ile Ala Pro Thr Glu Val Thr

```
    290                 295                 300

Met Ala Ile Lys Tyr Asp Arg Asn Ser Asp Pro Gly Arg Tyr Asn Ser
305                 310                 315                 320

Pro Arg Val Thr Glu Val Ala Val Ile Phe Arg Asn Glu Asp Gly Glu
                325                 330                 335

Pro Pro Phe Glu Arg Asp Leu Leu Ile His Cys Lys Pro Asp Pro Asn
            340                 345                 350

Asn Pro Asn Ala Thr Lys Met Lys Gln Ile Ser Ile Leu Phe Pro Thr
        355                 360                 365

Leu Asp Ala Met Thr Tyr Pro Ile Leu Phe Pro His Gly Glu Lys Gly
    370                 375                 380

Trp Gly Thr Asp Ile Ala Leu Arg Leu Arg Asp Asn Ser Val Ile Asp
385                 390                 395                 400

Asn Asn Thr Arg Gln Asn Val Arg Thr Arg Val Thr Gln Met Gln Tyr
                405                 410                 415

Tyr Gly Phe His Leu Ser Val Arg Asp Thr Phe Asn Pro Ile Leu Asn
            420                 425                 430

Ala Gly Lys Leu Thr Gln Gln Phe Ile Val Asp Ser Tyr Ser Lys Met
        435                 440                 445

Glu Ala Asn Arg Ile Asn Phe Ile Lys Ala Asn Gln Ser Lys Leu Arg
    450                 455                 460

Val Glu Lys Tyr Ser Gly Leu Met Asp Tyr Leu Lys Ser Arg Ser Glu
465                 470                 475                 480

Asn Asp Asn Val Pro Ile Gly Lys Met Ile Ile Leu Pro Ser Ser Phe
                485                 490                 495

Glu Gly Ser Pro Arg Asn Met Gln Gln Arg Tyr Gln Asp Ala Met Ala
            500                 505                 510

Ile Val Thr Lys Tyr Gly Lys Pro Asp Leu Phe Ile Thr Met Thr Cys
        515                 520                 525

Asn Pro Lys Trp Ala Asp Ile Thr Asn Asn Leu Gln Arg Trp Gln Lys
    530                 535                 540

Val Glu Asn Arg Pro Asp Leu Val Ala Arg Val Phe Asn Ile Lys Leu
545                 550                 555                 560

Asn Ala Leu Leu Asn Asp Ile Cys Lys Phe His Leu Phe Gly Lys Val
                565                 570                 575

Ile Ala Lys Ile His Val Ile Glu Phe Gln Lys Arg Gly Leu Pro His
            580                 585                 590

Ala His Ile Leu Leu Ile Leu Asp Ser Glu Ser Lys Leu Arg Ser Glu
        595                 600                 605

Asp Asp Ile Asp Arg Ile Val Lys Ala Glu Ile Pro Asp Glu Asp Gln
    610                 615                 620

Cys Pro Arg Leu Phe Gln Ile Val Lys Ser Asn Met Val His Gly Pro
625                 630                 635                 640

Cys Gly Ile Gln Asn Pro Asn Ser Pro Cys Met Glu Asn Gly Lys Cys
                645                 650                 655

Ser Lys Gly Tyr Pro Lys Glu Phe Gln Asn Ala Thr Ile Gly Asn Ile
            660                 665                 670

Asp Gly Tyr Pro Lys Tyr Lys Arg Arg Ser Gly Ser Thr Met Ser Ile
        675                 680                 685

Gly Asn Lys Val Val Asp Asn Thr Trp Ile Val Pro Tyr Asn Pro Tyr
    690                 695                 700

Leu Cys Leu Lys Tyr Asn Cys His Ile Asn Val Glu Val Cys Ala Ser
705                 710                 715                 720
```

```
Ile Lys Ser Val Lys Tyr Leu Phe Lys Tyr Ile Tyr Lys Gly His Asp
                725                 730                 735

Cys Ala Asn Ile Gln Ile Ser Glu Lys Asn Ile Ile Asn His Asp Glu
            740                 745                 750

Val Gln Asp Phe Ile Asp Ser Arg Tyr Val Ser Ala Pro Glu Ala Val
        755                 760                 765

Trp Arg Leu Phe Ala Met Arg Met His Asp Gln Ser His Ala Ile Thr
    770                 775                 780

Arg Leu Ala Ile His Leu Pro Asn Asp Gln Asn Leu Tyr Phe His Thr
785                 790                 795                 800

Asp Asp Phe Ala Glu Val Leu Asp Arg Ala Lys Arg His Asn Ser Thr
                805                 810                 815

Leu Met Ala Trp Phe Leu Leu Asn Arg Glu Asp Ser Asp Ala Arg Asn
            820                 825                 830

Tyr Tyr Tyr Trp Glu Ile Pro Gln His Tyr Val Phe Asn Asn Ser Leu
        835                 840                 845

Trp Thr Lys Arg Arg Lys Gly Gly Asn Lys Val Leu Gly Arg Leu Phe
    850                 855                 860

Thr Val Ser Phe Arg Glu Pro Glu Arg Tyr Tyr Leu Arg Leu Leu Leu
865                 870                 875                 880

Leu His Val Lys Gly Ala Ile Ser Phe Glu Asp Leu Arg Thr Val Gly
                885                 890                 895

Gly Val Thr Tyr Asp Thr Phe His Glu Ala Ala Lys His Arg Gly Leu
            900                 905                 910

Leu Leu Asp Asp Thr Ile Trp Lys Asp Thr Ile Asp Asp Ala Ile Ile
        915                 920                 925

Leu Asn Met Pro Lys Gln Leu Arg Gln Leu Phe Ala Tyr Ile Cys Val
    930                 935                 940

Phe Gly Cys Pro Ser Ala Ala Asp Lys Leu Trp Asp Glu Asn Lys Ser
945                 950                 955                 960

His Phe Ile Glu Asp Phe Cys Trp Lys Leu His Arg Arg Glu Gly Ala
                965                 970                 975

Cys Val Asn Cys Glu Met His Ala Leu Asn Glu Ile Gln Glu Val Phe
            980                 985                 990

Thr Leu His Gly Met Lys Cys Ser  His Phe Lys Leu Pro  Asp Tyr Pro
        995                 1000                1005

Leu Leu  Met Asn Ala Asn Thr  Cys Asp Gln Leu Tyr  Glu Gln Gln
    1010                1015                1020

Gln Ala  Glu Val Leu Ile Asn  Ser Leu Asn Asp Glu  Gln Leu Ala
    1025                1030                1035

Ala Phe  Gln Thr Ile Thr Ser  Ala Ile Glu Asp Gln  Thr Val His
    1040                1045                1050

Pro Lys  Cys Phe Phe Leu Asp  Gly Pro Gly Gly Ser  Gly Lys Thr
    1055                1060                1065

Tyr Leu  Tyr Lys Val Leu Thr  His Tyr Ile Arg Gly  Arg Gly Gly
    1070                1075                1080

Thr Val  Leu Pro Thr Ala Ser  Thr Gly Ile Ala Ala  Asn Leu Leu
    1085                1090                1095

Leu Gly  Gly Arg Thr Phe His  Ser Gln Tyr Lys Leu  Pro Ile Pro
    1100                1105                1110

Leu Asn  Glu Thr Ser Ile Ser  Arg Leu Asp Ile Lys  Ser Glu Val
    1115                1120                1125
```

```
Ala Lys  Thr Ile Lys Lys Ala  Gln Leu Leu Ile Ile  Asp Glu Cys
    1130                 1135                 1140

Thr Met  Ala Ser Ser His Ala  Ile Asn Ala Ile Asp  Arg Leu Leu
    1145                 1150                 1155

Arg Glu  Ile Met Asn Leu Asn  Val Ala Phe Gly Gly  Lys Val Leu
    1160                 1165                 1170

Leu Leu  Gly Gly Asp Phe Arg  Gln Cys Leu Ser Ile  Val Pro His
    1175                 1180                 1185

Ala Met  Arg Ser Ala Ile Val  Gln Thr Ser Leu Lys  Tyr Cys Asn
    1190                 1195                 1200

Val Trp  Gly Cys Phe Arg Lys  Leu Ser Leu Lys Thr  Asn Met Arg
    1205                 1210                 1215

Ser Glu  Asp Ser Ala Tyr Ser  Glu Trp Leu Val Lys  Leu Gly Asp
    1220                 1225                 1230

Gly Lys  Leu Asp Ser Ser Phe  His Leu Gly Met Asp  Ile Ile Glu
    1235                 1240                 1245

Ile Pro  His Glu Met Ile Cys  Asn Gly Ser Ile Ile  Glu Ala Thr
    1250                 1255                 1260

Phe Gly  Asn Ser Ile Ser Ile  Asp Asn Ile Lys Asn  Ile Ser Lys
    1265                 1270                 1275

Arg Ala  Ile Leu Cys Pro Lys  Asn Glu His Val Gln  Lys Leu Asn
    1280                 1285                 1290

Glu Glu  Ile Leu Asp Ile Leu  Asp Gly Asp Phe His  Thr Tyr Leu
    1295                 1300                 1305

Ser Asp  Asp Ser Ile Asp Ser  Thr Asp Asp Ala Glu  Lys Glu Asn
    1310                 1315                 1320

Phe Pro  Ile Glu Phe Leu Asn  Ser Ile Thr Pro Ser  Gly Met Pro
    1325                 1330                 1335

Cys His  Lys Leu Lys Leu Lys  Val Gly Ala Ile Ile  Met Leu Leu
    1340                 1345                 1350

Arg Asn  Leu Asn Ser Lys Trp  Gly Leu Cys Asn Gly  Thr Arg Phe
    1355                 1360                 1365

Ile Ile  Lys Arg Leu Arg Pro  Asn Ile Ile Glu Ala  Glu Val Leu
    1370                 1375                 1380

Thr Gly  Ser Ala Glu Gly Glu  Val Val Leu Ile Pro  Arg Ile Asp
    1385                 1390                 1395

Leu Ser  Pro Ser Asp Thr Gly  Leu Pro Phe Lys Leu  Ile Arg Arg
    1400                 1405                 1410

Gln Phe  Pro Val Met Pro Ala  Phe Ala Met Thr Ile  Asn Lys Ser
    1415                 1420                 1425

Gln Gly  Gln Thr Leu Asp Arg  Val Gly Ile Phe Leu  Pro Glu Pro
    1430                 1435                 1440

Val Phe  Ala His Gly Gln Leu  Tyr Val Ala Phe Ser  Arg Val Arg
    1445                 1450                 1455

Arg Ala  Cys Asp Val Lys Val  Lys Val Val Asn Thr  Ser Ser Gln
    1460                 1465                 1470

Gly Lys  Leu Val Lys His Ser  Glu Ser Val Phe Thr  Leu Asn Val
    1475                 1480                 1485

Val Tyr  Arg Glu Ile Leu Glu
    1490                 1495
```

<210> SEQ ID NO 62
<211> LENGTH: 649
<212> TYPE: PRT

<213> ORGANISM: Artificial Sequence
<220> FEATURE:
<223> OTHER INFORMATION: Synthetic Sequence

<400> SEQUENCE: 62

Met Glu Glu Val Cys Asp Ser Ser Ala Ala Ala Ser Ser Thr Val Gln
1 5 10 15

Asn Gln Pro Gln Asp Gln Glu His Pro Trp Pro Tyr Leu Arg Glu Phe
20 25 30

Phe Ser Leu Ser Gly Val Asn Lys Asp Ser Phe Lys Met Lys Cys Val
35 40 45

Leu Cys Leu Pro Leu Asn Lys Glu Ile Ser Ala Phe Lys Ser Ser Pro
50 55 60

Ser Asn Leu Arg Lys His Ile Glu Arg Met His Pro Asn Tyr Leu Lys
65 70 75 80

Asn Tyr Ser Lys Leu Thr Ala Gln Lys Arg Lys Ile Gly Thr Ser Thr
85 90 95

His Ala Ser Ser Ser Lys Gln Leu Lys Val Asp Ser Val Phe Pro Val
100 105 110

Lys His Val Ser Pro Val Thr Val Asn Lys Ala Ile Leu Arg Tyr Ile
115 120 125

Ile Gln Gly Leu His Pro Phe Ser Thr Val Asp Leu Pro Ser Phe Lys
130 135 140

Glu Leu Ile Ser Thr Leu Gln Pro Gly Ile Ser Val Ile Thr Arg Pro
145 150 155 160

Thr Leu Arg Ser Lys Ile Ala Glu Ala Ala Leu Ile Met Lys Gln Lys
165 170 175

Val Thr Ala Ala Met Ser Glu Val Glu Trp Ile Ala Thr Thr Thr Asp
180 185 190

Cys Trp Thr Ala Arg Arg Lys Ser Phe Ile Gly Val Thr Ala His Trp
195 200 205

Ile Asn Pro Gly Ser Leu Glu Arg His Ser Ala Ala Leu Ala Cys Lys
210 215 220

Arg Leu Met Gly Ser His Thr Phe Glu Val Leu Ala Ser Ala Met Asn
225 230 235 240

Asp Ile His Ser Glu Tyr Glu Ile Arg Asp Lys Val Val Cys Thr Thr
245 250 255

Thr Asp Ser Gly Ser Asn Phe Met Lys Ala Phe Arg Val Phe Gly Val
260 265 270

Glu Asn Asn Asp Ile Glu Thr Glu Ala Arg Arg Cys Glu Ser Asp Asp
275 280 285

Thr Asp Ser Glu Gly Cys Gly Glu Gly Ser Asp Gly Val Glu Phe Gln
290 295 300

Asp Ala Ser Arg Val Leu Asp Gln Asp Asp Gly Phe Glu Phe Gln Leu
305 310 315 320

Pro Lys His Gln Lys Cys Ala Cys His Leu Leu Asn Leu Val Ser Ser
325 330 335

Val Asp Ala Gln Lys Ala Leu Ser Asn Glu His Tyr Lys Lys Leu Tyr
340 345 350

Arg Ser Val Phe Gly Lys Cys Gln Ala Leu Trp Asn Lys Ser Ser Arg
355 360 365

Ser Ala Leu Ala Ala Glu Ala Val Glu Ser Glu Ser Arg Leu Gln Leu
370 375 380

Leu Arg Pro Asn Gln Thr Arg Trp Asn Ser Thr Phe Met Ala Val Asp 385 390 395 400

Arg Ile Leu Gln Ile Cys Lys Glu Ala Gly Glu Gly Ala Leu Arg Asn
405 410 415

Ile Cys Thr Ser Leu Glu Val Pro Met Phe Asn Pro Ala Glu Met Leu
420 425 430

Phe Leu Thr Glu Trp Ala Asn Thr Met Arg Pro Val Ala Lys Val Leu
435 440 445

Asp Ile Leu Gln Ala Glu Thr Asn Thr Gln Leu Gly Trp Leu Leu Pro
450 455 460

Ser Val His Gln Leu Ser Leu Lys Leu Gln Arg Leu His His Ser Leu
465 470 475 480

Arg Tyr Cys Asp Pro Leu Val Asp Ala Leu Gln Gln Gly Ile Gln Thr
485 490 495

Arg Phe Lys His Met Phe Glu Asp Pro Glu Ile Ile Ala Ala Ala Ile
500 505 510

Leu Leu Pro Lys Phe Arg Thr Ser Trp Thr Asn Asp Glu Thr Ile Ile
515 520 525

Lys Arg Gly Met Asp Tyr Ile Arg Val His Leu Glu Pro Leu Asp His
530 535 540

Lys Lys Glu Leu Ala Asn Ser Ser Ser Asp Asp Glu Asp Phe Phe Ala
545 550 555 560

Ser Leu Lys Pro Thr Thr His Glu Ala Ser Lys Glu Leu Asp Gly Tyr
565 570 575

Leu Ala Cys Val Ser Asp Thr Arg Glu Ser Leu Leu Thr Phe Pro Ala
580 585 590

Ile Cys Ser Leu Ser Ile Lys Thr Asn Thr Pro Leu Pro Ala Ser Ala
595 600 605

Ala Cys Glu Arg Leu Phe Ser Thr Ala Gly Leu Leu Phe Ser Pro Lys
610 615 620

Arg Ala Arg Leu Asp Thr Asn Asn Phe Glu Asn Gln Leu Leu Leu Lys
625 630 635 640

Leu Asn Leu Arg Phe Tyr Asn Phe Glu
645

<210> SEQ ID NO 63
<211> LENGTH: 648
<212> TYPE: PRT
<213> ORGANISM: Artificial Sequence
<220> FEATURE:
<223> OTHER INFORMATION: Synthetic Sequence

<400> SEQUENCE: 63

Glu Glu Val Cys Asp Ser Ser Ala Ala Ala Ser Ser Thr Val Gln Asn
1 5 10 15

Gln Pro Gln Asp Gln Glu His Pro Trp Pro Tyr Leu Arg Glu Phe Phe
20 25 30

Ser Leu Ser Gly Val Asn Lys Asp Ser Phe Lys Met Lys Cys Val Leu
35 40 45

Cys Leu Pro Leu Asn Lys Glu Ile Ser Ala Phe Lys Ser Ser Pro Ser
50 55 60

Asn Leu Arg Lys His Ile Glu Arg Met His Pro Asn Tyr Leu Lys Asn
65 70 75 80

Tyr Ser Lys Leu Thr Ala Gln Lys Arg Lys Ile Gly Thr Ser Thr His
85 90 95

Ala Ser Ser Ser Lys Gln Leu Lys Val Asp Ser Val Phe Pro Val Lys

```
            100                 105                 110

His Val Ser Pro Val Thr Val Asn Lys Ala Ile Leu Arg Tyr Ile Ile
        115                 120                 125

Gln Gly Leu His Pro Phe Ser Thr Val Asp Leu Pro Ser Phe Lys Glu
    130                 135                 140

Leu Ile Ser Thr Leu Gln Pro Gly Ile Ser Val Ile Thr Arg Pro Thr
145                 150                 155                 160

Leu Arg Ser Lys Ile Ala Glu Ala Ala Leu Ile Met Lys Gln Lys Val
                165                 170                 175

Thr Ala Ala Met Ser Glu Val Glu Trp Ile Ala Thr Thr Thr Asp Cys
            180                 185                 190

Trp Thr Ala Arg Arg Lys Ser Phe Ile Gly Val Thr Ala His Trp Ile
        195                 200                 205

Asn Pro Gly Ser Leu Glu Arg His Ser Ala Ala Leu Ala Cys Lys Arg
    210                 215                 220

Leu Met Gly Ser His Thr Phe Glu Val Leu Ala Ser Ala Met Asn Asp
225                 230                 235                 240

Ile His Ser Glu Tyr Glu Ile Arg Asp Lys Val Val Cys Thr Thr Thr
                245                 250                 255

Asp Ser Gly Ser Asn Phe Met Lys Ala Phe Arg Val Phe Gly Val Glu
            260                 265                 270

Asn Asn Asp Ile Glu Thr Glu Ala Arg Arg Cys Glu Ser Asp Asp Thr
        275                 280                 285

Asp Ser Glu Gly Cys Gly Glu Gly Ser Asp Gly Val Glu Phe Gln Asp
    290                 295                 300

Ala Ser Arg Val Leu Asp Gln Asp Asp Gly Phe Glu Phe Gln Leu Pro
305                 310                 315                 320

Lys His Gln Lys Cys Ala Cys His Leu Leu Asn Leu Val Ser Ser Val
                325                 330                 335

Asp Ala Gln Lys Ala Leu Ser Asn Glu His Tyr Lys Lys Leu Tyr Arg
            340                 345                 350

Ser Val Phe Gly Lys Cys Gln Ala Leu Trp Asn Lys Ser Ser Arg Ser
        355                 360                 365

Ala Leu Ala Ala Glu Ala Val Glu Ser Glu Ser Arg Leu Gln Leu Leu
    370                 375                 380

Arg Pro Asn Gln Thr Arg Trp Asn Ser Thr Phe Met Ala Val Asp Arg
385                 390                 395                 400

Ile Leu Gln Ile Cys Lys Glu Ala Gly Glu Gly Ala Leu Arg Asn Ile
                405                 410                 415

Cys Thr Ser Leu Glu Val Pro Met Phe Asn Pro Ala Glu Met Leu Phe
            420                 425                 430

Leu Thr Glu Trp Ala Asn Thr Met Arg Pro Val Ala Lys Val Leu Asp
        435                 440                 445

Ile Leu Gln Ala Glu Thr Asn Thr Gln Leu Gly Trp Leu Leu Pro Ser
    450                 455                 460

Val His Gln Leu Ser Leu Lys Leu Gln Arg Leu His His Ser Leu Arg
465                 470                 475                 480

Tyr Cys Asp Pro Leu Val Asp Ala Leu Gln Gln Gly Ile Gln Thr Arg
                485                 490                 495

Phe Lys His Met Phe Glu Asp Pro Glu Ile Ile Ala Ala Ala Ile Leu
            500                 505                 510

Leu Pro Lys Phe Arg Thr Ser Trp Thr Asn Asp Glu Thr Ile Ile Lys
        515                 520                 525
```

Arg Gly Met Asp Tyr Ile Arg Val His Leu Glu Pro Leu Asp His Lys
    530                 535                 540

Lys Glu Leu Ala Asn Ser Ser Ser Asp Asp Glu Asp Phe Phe Ala Ser
545                 550                 555                 560

Leu Lys Pro Thr Thr His Glu Ala Ser Lys Glu Leu Asp Gly Tyr Leu
                565                 570                 575

Ala Cys Val Ser Asp Thr Arg Glu Ser Leu Leu Thr Phe Pro Ala Ile
            580                 585                 590

Cys Ser Leu Ser Ile Lys Thr Asn Thr Pro Leu Pro Ala Ser Ala Ala
        595                 600                 605

Cys Glu Arg Leu Phe Ser Thr Ala Gly Leu Leu Phe Ser Pro Lys Arg
    610                 615                 620

Ala Arg Leu Asp Thr Asn Asn Phe Glu Asn Gln Leu Leu Leu Lys Leu
625                 630                 635                 640

Asn Leu Arg Phe Tyr Asn Phe Glu
                645

<210> SEQ ID NO 64
<211> LENGTH: 636
<212> TYPE: PRT
<213> ORGANISM: Artificial Sequence
<220> FEATURE:
<223> OTHER INFORMATION: Synthetic Sequence

<400> SEQUENCE: 64

Met Met Leu Asn Trp Leu Lys Ser Gly Lys Leu Glu Ser Gln Ser Gln
1               5                   10                  15

Glu Gln Ser Ser Cys Tyr Leu Glu Asn Ser Asn Cys Leu Pro Pro Thr
            20                  25                  30

Leu Asp Ser Thr Asp Ile Ile Gly Glu Glu Asn Lys Ala Gly Thr Thr
        35                  40                  45

Ser Arg Lys Lys Arg Lys Tyr Asp Glu Asp Tyr Leu Asn Phe Gly Phe
    50                  55                  60

Thr Trp Thr Gly Asp Lys Asp Glu Pro Asn Gly Leu Cys Val Ile Cys
65                  70                  75                  80

Glu Gln Val Val Asn Asn Ser Ser Leu Asn Pro Ala Lys Leu Lys Arg
                85                  90                  95

His Leu Asp Thr Lys His Pro Thr Leu Lys Gly Lys Ser Glu Tyr Phe
            100                 105                 110

Lys Arg Lys Cys Asn Glu Leu Asn Gln Lys Lys His Thr Phe Glu Arg
        115                 120                 125

Tyr Val Arg Asp Asp Asn Lys Asn Leu Leu Lys Ala Ser Tyr Leu Val
    130                 135                 140

Ser Leu Arg Ile Ala Lys Gln Gly Glu Ala Tyr Thr Ile Ala Glu Lys
145                 150                 155                 160

Leu Ile Lys Pro Cys Thr Lys Asp Leu Thr Thr Cys Val Phe Gly Glu
                165                 170                 175

Lys Phe Ala Ser Lys Val Asp Leu Val Pro Leu Ser Asp Thr Thr Ile
            180                 185                 190

Ser Arg Arg Ile Glu Asp Met Ser Tyr Phe Cys Glu Ala Val Leu Val
        195                 200                 205

Asn Arg Leu Glu Asn Ala Lys Cys Gly Phe Thr Leu Gln Met Asp Glu
    210                 215                 220

Ser Thr Asp Val Ala Gly Leu Ala Ile Leu Leu Val Phe Val Arg Tyr
225                 230                 235                 240

```
Ile His Glu Ser Ser Phe Glu Glu Asp Met Leu Phe Cys Lys Ala Leu
                245                 250                 255

Pro Thr Gln Thr Thr Gly Glu Glu Ile Phe Asn Leu Leu Asn Ala Tyr
            260                 265                 270

Phe Glu Lys His Ser Ile Pro Trp Asn Leu Cys Tyr His Ile Cys Thr
        275                 280                 285

Asp Gly Ala Lys Ala Met Val Gly Val Ile Lys Gly Val Ile Ala Arg
    290                 295                 300

Ile Lys Lys Leu Val Pro Asp Ile Lys Ala Ser His Cys Cys Leu His
305                 310                 315                 320

Arg His Ala Leu Ala Val Lys Arg Ile Pro Asn Ala Leu His Glu Val
                325                 330                 335

Leu Asn Asp Ala Val Lys Met Ile Asn Phe Ile Lys Ser Arg Pro Leu
            340                 345                 350

Asn Ala Arg Val Phe Ala Leu Leu Cys Asp Asp Leu Gly Ser Leu His
        355                 360                 365

Lys Asn Leu Leu Leu His Thr Glu Val Arg Trp Leu Ser Arg Gly Lys
    370                 375                 380

Val Leu Thr Arg Phe Trp Glu Leu Arg Asp Glu Ile Arg Ile Phe Phe
385                 390                 395                 400

Asn Glu Arg Glu Phe Ala Gly Lys Leu Asn Asp Thr Ser Trp Leu Gln
                405                 410                 415

Asn Leu Ala Tyr Ile Ala Asp Ile Phe Ser Tyr Leu Asn Glu Val Asn
            420                 425                 430

Leu Ser Leu Gln Gly Pro Asn Ser Thr Ile Phe Lys Val Asn Ser Arg
        435                 440                 445

Ile Asn Ser Ile Lys Ser Lys Leu Lys Leu Trp Glu Glu Cys Ile Thr
    450                 455                 460

Lys Asn Asn Thr Glu Cys Phe Ala Asn Leu Asn Asp Phe Leu Glu Thr
465                 470                 475                 480

Ser Asn Thr Ala Leu Asp Pro Asn Leu Lys Ser Asn Ile Leu Glu His
                485                 490                 495

Leu Asn Gly Leu Lys Asn Thr Phe Leu Glu Tyr Phe Pro Pro Thr Cys
            500                 505                 510

Asn Asn Ile Ser Trp Val Glu Asn Pro Phe Asn Glu Cys Gly Asn Val
        515                 520                 525

Asp Thr Leu Pro Ile Lys Glu Arg Glu Gln Leu Ile Asp Ile Arg Thr
    530                 535                 540

Asp Thr Thr Leu Lys Ser Ser Phe Val Pro Asp Gly Ile Gly Pro Phe
545                 550                 555                 560

Trp Ile Lys Leu Met Asp Glu Phe Pro Glu Ile Ser Lys Arg Ala Val
                565                 570                 575

Lys Glu Leu Met Pro Phe Val Thr Thr Tyr Leu Cys Glu Lys Ser Phe
            580                 585                 590

Ser Val Tyr Val Ala Thr Lys Thr Lys Tyr Arg Asn Arg Leu Asp Ala
        595                 600                 605

Glu Asp Asp Met Arg Leu Gln Leu Thr Thr Ile His Pro Asp Ile Asp
    610                 615                 620

Asn Leu Cys Asn Asn Lys Gln Ala Gln Lys Ser His
625                 630                 635
```

<210> SEQ ID NO 65
<211> LENGTH: 635

```
<212> TYPE: PRT
<213> ORGANISM: Artificial Sequence
<220> FEATURE:
<223> OTHER INFORMATION: Synthetic Sequence

<400> SEQUENCE: 65

Met Leu Asn Trp Leu Lys Ser Gly Lys Leu Glu Ser Gln Ser Gln Glu
1               5                   10                  15

Gln Ser Ser Cys Tyr Leu Glu Asn Ser Asn Cys Leu Pro Pro Thr Leu
            20                  25                  30

Asp Ser Thr Asp Ile Ile Gly Glu Glu Asn Lys Ala Gly Thr Thr Ser
        35                  40                  45

Arg Lys Lys Arg Lys Tyr Asp Glu Asp Tyr Leu Asn Phe Gly Phe Thr
    50                  55                  60

Trp Thr Gly Asp Lys Asp Glu Pro Asn Gly Leu Cys Val Ile Cys Glu
65                  70                  75                  80

Gln Val Val Asn Asn Ser Ser Leu Asn Pro Ala Lys Leu Lys Arg His
                85                  90                  95

Leu Asp Thr Lys His Pro Thr Leu Lys Gly Lys Ser Glu Tyr Phe Lys
            100                 105                 110

Arg Lys Cys Asn Glu Leu Asn Gln Lys Lys His Thr Phe Glu Arg Tyr
        115                 120                 125

Val Arg Asp Asp Asn Lys Asn Leu Leu Lys Ala Ser Tyr Leu Val Ser
    130                 135                 140

Leu Arg Ile Ala Lys Gln Gly Glu Ala Tyr Thr Ile Ala Glu Lys Leu
145                 150                 155                 160

Ile Lys Pro Cys Thr Lys Asp Leu Thr Thr Cys Val Phe Gly Glu Lys
                165                 170                 175

Phe Ala Ser Lys Val Asp Leu Val Pro Leu Ser Asp Thr Thr Ile Ser
            180                 185                 190

Arg Arg Ile Glu Asp Met Ser Tyr Phe Cys Glu Ala Val Leu Val Asn
        195                 200                 205

Arg Leu Glu Asn Ala Lys Cys Gly Phe Thr Leu Gln Met Asp Glu Ser
    210                 215                 220

Thr Asp Val Ala Gly Leu Ala Ile Leu Leu Val Phe Val Arg Tyr Ile
225                 230                 235                 240

His Glu Ser Ser Phe Glu Glu Asp Met Leu Phe Cys Lys Ala Leu Pro
                245                 250                 255

Thr Gln Thr Thr Gly Glu Glu Ile Phe Asn Leu Leu Asn Ala Tyr Phe
            260                 265                 270

Glu Lys His Ser Ile Pro Trp Asn Leu Cys Tyr His Ile Cys Thr Asp
        275                 280                 285

Gly Ala Lys Ala Met Val Gly Val Ile Lys Gly Val Ile Ala Arg Ile
    290                 295                 300

Lys Lys Leu Val Pro Asp Ile Lys Ala Ser His Cys Cys Leu His Arg
305                 310                 315                 320

His Ala Leu Ala Val Lys Arg Ile Pro Asn Ala Leu His Glu Val Leu
                325                 330                 335

Asn Asp Ala Val Lys Met Ile Asn Phe Ile Lys Ser Arg Pro Leu Asn
            340                 345                 350

Ala Arg Val Phe Ala Leu Leu Cys Asp Asp Leu Gly Ser Leu His Lys
        355                 360                 365

Asn Leu Leu Leu His Thr Glu Val Arg Trp Leu Ser Arg Gly Lys Val
    370                 375                 380
```

```
Leu Thr Arg Phe Trp Glu Leu Arg Asp Glu Ile Arg Ile Phe Phe Asn
385                 390                 395                 400

Glu Arg Glu Phe Ala Gly Lys Leu Asn Asp Thr Ser Trp Leu Gln Asn
                405                 410                 415

Leu Ala Tyr Ile Ala Asp Ile Phe Ser Tyr Leu Asn Glu Val Asn Leu
            420                 425                 430

Ser Leu Gln Gly Pro Asn Ser Thr Ile Phe Lys Val Asn Ser Arg Ile
        435                 440                 445

Asn Ser Ile Lys Ser Lys Leu Lys Leu Trp Glu Glu Cys Ile Thr Lys
    450                 455                 460

Asn Asn Thr Glu Cys Phe Ala Asn Leu Asn Asp Phe Leu Glu Thr Ser
465                 470                 475                 480

Asn Thr Ala Leu Asp Pro Asn Leu Lys Ser Asn Ile Leu Glu His Leu
                485                 490                 495

Asn Gly Leu Lys Asn Thr Phe Leu Glu Tyr Phe Pro Pro Thr Cys Asn
            500                 505                 510

Asn Ile Ser Trp Val Glu Asn Pro Phe Asn Glu Cys Gly Asn Val Asp
        515                 520                 525

Thr Leu Pro Ile Lys Glu Arg Glu Gln Leu Ile Asp Ile Arg Thr Asp
    530                 535                 540

Thr Thr Leu Lys Ser Ser Phe Val Pro Asp Gly Ile Gly Pro Phe Trp
545                 550                 555                 560

Ile Lys Leu Met Asp Glu Phe Pro Glu Ile Ser Lys Arg Ala Val Lys
                565                 570                 575

Glu Leu Met Pro Phe Val Thr Thr Tyr Leu Cys Glu Lys Ser Phe Ser
            580                 585                 590

Val Tyr Val Ala Thr Lys Thr Lys Tyr Arg Asn Arg Leu Asp Ala Glu
        595                 600                 605

Asp Asp Met Arg Leu Gln Leu Thr Thr Ile His Pro Asp Ile Asp Asn
    610                 615                 620

Leu Cys Asn Asn Lys Gln Ala Gln Lys Ser His
625                 630                 635
```

<210> SEQ ID NO 66
<211> LENGTH: 1866
<212> TYPE: DNA
<213> ORGANISM: Artificial Sequence
<220> FEATURE:
<223> OTHER INFORMATION: Synthetic Sequence

<400> SEQUENCE: 66

```
atgccggggt tttacgagat tgtgattaag gtccccagcg accttgacga gcatctgccc     60

ggcatttctg acagctttgt gaactgggtg gccgagaagg aatgggagtt gccgccagat    120

tctgacatgg atctgaatct gattgagcag gcacccctga ccgtggccga gaagctgcag    180

cgcgactttc tgacggaatg gcgccgtgtg agtaaggccc cggaggctct tttctttgtg    240

caatttgaga agggagagag ctacttccac atgcacgtgc tcgtggaaac caccggggtg    300

aaatccatgg ttttgggacg tttcctgagt cagattcgcg aaaaactgat tcagagaatt    360

taccgcggga tcgagccgac tttgccaaac tggttcgcgg tcacaaagac cagaaatggc    420

gccggaggcg ggaacaaggt ggtggatgag tgctacatcc ccaattactt gctccccaaa    480

acccagcctg agctccagtg ggcgtggact aatatggaac agtatttaag cgcctgtttg    540

aatctcacgg agcgtaaacg gttggtggcg cagcatctga cgcacgtgtc gcagacgcag    600

gagcagaaca aagagaatca gaatcccaat tctgatgcgc cggtgatcag atcaaaaact    660
```

tcagccaggt acatggagct ggtcgggtgg ctcgtggaca aggggattac ctcggagaag 720
cagtggatcc aggaggacca ggcctcatac atctccttca atgcggcctc caactcgcgg 780
tcccaaatca aggctgcctt ggacaatgcg ggaaagatta tgagcctgac taaaaccgcc 840
cccgactacc tggtgggcca gcagcccgtg gaggacattt ccagcaatcg gatttataaa 900
attttggaac taaacgggta cgatccccaa tatgcggctt ccgtctttct gggatgggcc 960
acgaaaaagt tcggcaagag gaacaccatc tggctgtttg ggcctgcaac taccgggaag 1020
accaacatcg cggaggccat agcccacact gtgcccttct acgggtgcgt aaactggacc 1080
aatgagaact ttcccttcaa cgactgtgtc gacaagatgg tgatctggtg ggaggagggg 1140
aagatgaccg ccaaggtcgt ggagtcggcc aaagccattc tcggaggaag caaggtgcgc 1200
gtggaccaga aatgcaagtc ctcggcccag atagacccga ctcccgtgat cgtcacctcc 1260
aacaccaaca tgtgcgccgt gattgacggg aactcaacga ccttcgaaca ccagcagccg 1320
ttgcaagacc ggatgttcaa atttgaactc acccgccgtc tggatcatga ctttgggaag 1380
gtcaccaagc aggaagtcaa agactttttc cggtgggcaa aggatcacgt ggttgaggtg 1440
gagcatgaat tctacgtcaa aaagggtgga gccaagaaaa gacccgcccc cagtgacgca 1500
gatataagtg agcccaaacg ggtgcgcgag tcagttgcgc agccatcgac gtcagacgcg 1560
gaagcttcga tcaactacgc agacaggtac caaaacaaat gttctcgtca cgtgggcatg 1620
aatctgatgc tgtttccctg cagacaatgc gagagaatga atcagaattc aaatatctgc 1680
ttcactcacg gacagaaaga ctgtttagag tgctttcccg tgtcagaatc tcaacccgtt 1740
tctgtcgtca aaaaggcgta tcagaaactg tgctacattc atcatatcat gggaaaggtg 1800
ccagacgctt gcactgcctg cgatctggtc aatgtggatt tggatgactg catctttgaa 1860
caataa 1866

<210> SEQ ID NO 67
<211> LENGTH: 2214
<212> TYPE: DNA
<213> ORGANISM: Artificial Sequence
<220> FEATURE:
<223> OTHER INFORMATION: Synthetic Sequence

<400> SEQUENCE: 67
atggctgccg atggttatct tccagattgg ctcgaggaca ctctctctga aggaataaga 60
cagtggtgga agctcaaacc tggcccacca ccaccaaagc ccgcagagcg gcataaggac 120
gacagcaggg gtcttgtgct tccgggttac aaatacctcg gacccggcaa cggactcgac 180
aagggggagc ccgtcaacgc ggcggacgca gcggccctcg agcacgacaa ggcctacgac 240
cagcagctca aagcgggtga caatccgtac ctgcggtata accacgccga cgccgagttt 300
caggagcgtc tgcaagaaga tacgtctttt gggggcaacc tcgggcgagc agtcttccag 360
gccaagaagc gggttctcga acctctcggt ctggttgagg aacctgttaa gacggctccg 420
ggaaaaaaga ggccggtaga gcactctcct gtggagccag actcctcctc gggaaccgga 480
aaggcgggcc agcagcctgc gaggaagcga ctcaactttg gtcagactgg agacaccgac 540
tccgccgctg acccccagcc tctcggagaa ccaccagcag ccccctctgg tctgggaact 600
ggtacaatgg ctgcaggcgg tggcgctcca atggcagaca ataacgaagg cgccgacgga 660
gtgggtaatg cctcgggaaa ttggcattgc gattccacat ggctgggcga cagagtcatc 720
accaccagca cccgcacctg ggccttgccc acctacaata accacctcta caagcaaatc 780

```
tccagtgctt caacgggggc cagcaacgac aaccactact tcggctacag cacccccctgg    840

gggtactttg acttcaaccg cttccactgc cacttctcac cacgtgactg gcaaagactc    900

atcaacaaca actggggatt ccggcccaag agactcaact tcaagctctt caacatccag    960

gtcaaggagg tcacgcagaa tgaaggcacc aagaccatcg ccaataacct taccagcacg   1020

gttcaggtgt ttactgactc ggagtaccag ctgccgtacg ttctcggctc tgcccaccag   1080

ggctgcctgc ctccgttccc ggcggacgtg ttcatgattc cgcagtacgg ctacctaacg   1140

ctcaacaatg gcagccaggc gatgggtcgc tcgtccttct actgcctgga gtactttccg   1200

tcgcagatgc tgagaaccgg caacaacttc cagtttactt acaccttcga ggacgtgcct   1260

ttccacagca gctacgctca cagccagagt ttggatcgct tgatgaatcc tcttattgat   1320

cagtatctgt actacctgaa cagaacgcaa ggaacaacct ctggaacaac caaccaatca   1380

cggctgcttt ttagccaggc tgggcctcag tctatgtctt tgcaggccag aaattggcta   1440

cctgggccct gctaccggca acagagactt tcaaagactg ctaacgacaa caacaacagt   1500

aactttcctt ggacagcggc cagcaaatat catctcaatg gccgcgactc gctggtgaat   1560

ccaggaccag ctatggccag tcacaaggac gatgaagaaa aatttttccc tatgcacggc   1620

aatctaatat ttggcaaaga agggacaacg gcaagtaacg cagaattaga taatgtaatg   1680

attacggatg aagaagagat tcgtaccacc aatcctgtgg caacagagca gtatggaact   1740

gtggcaaata acttgcagag ctcaaataca gctcccacga ctagaactgt caatgatcag   1800

ggggccttac ctggcatggt gtggcaagat cgtgacgtgt accttcaagg acctatctgg   1860

gcaaagattc ctcacacgga tggacacttt catccttctc ctctgatggg cggctttggc   1920

ctgaaacatc ctccgcctca gatcctgatc aagaacacgc ctgtacctgc ggatcctcca   1980

acggccttca acaaggacaa gctgaactct ttcatcaccc agtattctac tggccaagtc   2040

agcgtggaga tcgagtggga gctgcagaag gaaaacagca agcgctggaa ccccgagatc   2100

cagtacacct ccaactacta caaatctaca agtgtggact ttgctgttaa tacagaaggc   2160

gtgtactctg aaccccgccc cattggcacc cgttacctca cccgtaatct gtaa         2214
```

<210> SEQ ID NO 68
<211> LENGTH: 5336
<212> TYPE: DNA
<213> ORGANISM: Artificial Sequence
<220> FEATURE:
<223> OTHER INFORMATION: Synthetic Sequence

<400> SEQUENCE: 68

```
ggtacccaac tccatgctta acagtcccca ggtacagccc accctgcgtc gcaaccagga     60

acagctctac agcttcctgg agcgccactc gccctacttc cgcagccaca gtgcgcagat    120

taggagcgcc acttcttttt gtcacttgaa aaacatgtaa aaataatgta ctaggagaca    180

ctttcaataa aggcaaatgt ttttatttgt acactctcgg gtgattattt accccccacc    240

cttgccgtct gcgccgttta aaaatcaaag ggttctgcc gcgcatcgct atgcgccact    300

ggcagggaca cgttgcgata ctggtgttta gtgctccact taaactcagg cacaaccatc    360

cgcggcagct cggtgaagtt ttcactccac aggctgcgca ccatcaccaa cgcgtttagc    420

aggtcgggcg ccgatatctt gaagtcgcag ttggggcctc cgccctgcgc gcgcgagttg    480

cgatacacag ggttgcagca ctggaacact atcagcgccg ggtggtgcac gctggccagc    540

acgctcttgt cggagatcag atccgcgtcc aggtcctccg cgttgctcag ggcgaacgga    600

gtcaactttg gtagctgcct tcccaaaaag ggtgcatgcc caggctttga gttgcactcg    660
```

```
caccgtagtg gcatcagaag gtgaccgtgc ccggtctggg cgttaggata cagcgcctgc    720
atgaaagcct tgatctgctt aaaagccacc tgagcctttg cgccttcaga gaagaacatg    780
ccgcaagact tgccggaaaa ctgattggcc ggacaggccg cgtcatgcac gcagcacctt    840
gcgtcggtgt tggagatctg caccacattt cggccccacc ggttcttcac gatcttggcc    900
ttgctagact gctccttcag cgcgcgctgc ccgttttcgc tcgtcacatc catttcaatc    960
acgtgctcct tatttatcat aatgctcccg tgtagacact taagctcgcc ttcgatctca   1020
gcgcagcggt gcagccacaa cgcgcagccc gtgggctcgt ggtgcttgta ggttacctct   1080
gcaaacgact gcaggtacgc ctgcaggaat cgccccatca tcgtcacaaa ggtcttgttg   1140
ctggtgaagg tcagctgcaa cccgcggtgc tcctcgttta gccaggtctt gcatacggcc   1200
gccagagctt ccacttggtc aggcagtagc ttgaagtttg cctttagatc gttatccacg   1260
tggtacttgt ccatcaacgc gcgcgcagcc tccatgccct tctcccacgc agacacgatc   1320
ggcaggctca gcgggtttat caccgtgctt tcactttccg cttcactgga ctcttccttt   1380
tcctcttgcg tccgcatacc ccgcgccact gggtcgtctt cattcagccg ccgcaccgtg   1440
cgcttacctc ccttgccgtg cttgattagc accggtgggt tgctgaaacc caccatttgt   1500
agcgccacat cttctctttc ttcctcgctg tccacgatca cctctgggga tggcgggcgc   1560
tcgggcttgg gagaggggcg cttctttttc tttttggacg caatggccaa atccgccgtc   1620
gaggtcgatg gccgcgggct gggtgtgcgc ggcaccagcg catcttgtga cgagtcttct   1680
tcgtcctcgg actcgagacg ccgcctcagc cgcttttttg ggggcgcgcg gggaggcggc   1740
ggcgacggcg acggggacga cacgtcctcc atggttggtg gacgtcgcgc cgcaccgcgt   1800
ccgcgctcgg gggtggtttc gcgctgctcc tcttcccgac tggccatttc cttctcctat   1860
aggcagaaaa agatcatgga gtcagtcgag aaggaggaca gcctaaccgc cccctttgag   1920
ttcgccacca ccgcctccac cgatgccgcc aacgcgccta ccaccttccc cgtcgaggca   1980
cccccgcttg aggaggagga agtgattatc gagcaggacc caggttttgt aagcgaagac   2040
gacgaggatc gctcagtacc aacagaggat aaaaagcaag accaggacga cgcagaggca   2100
aacgaggaac aagtcgggcg gggggaccaa aggcatggcg actacctaga tgtgggagac   2160
gacgtgctgt tgaagcatct gcagcgccag tgcgccatta tctgcgacgc gttgcaagag   2220
cgcagcgatg tgcccctcgc catagcggat gtcagccttg cctacgaacg ccacctgttc   2280
tcaccgcgcg taccccccaa acgccaagaa aacggcacat gcgagcccaa cccgcgcctc   2340
aacttctacc ccgtatttgc cgtgccagag gtgcttgcca cctatcacat ctttttccaa   2400
aactgcaaga taccccatc ctgccgtgcc aaccgcagcc gagcggacaa gcagctggcc    2460
ttgcggcagg gcgctgtcat acctgatatc gcctcgctcg acgaagtgcc aaaaatcttt   2520
gagggtcttg gacgcgacga gaaacgcgcg gcaaacgctc tgcaacaaga aaacagcgaa   2580
aatgaaagtc actgtggagt gctggtggaa cttgagggtg acaacgcgcg cctagccgtg   2640
ctgaaacgca gcatcgaggt cacccacttt gcctacccgg cacttaacct accccccaag   2700
gttatgagca cagtcatgag cgagctgatc gtgcgccgtg cacgacccct ggagagggat   2760
gcaaacttgc aagaacaaac cgaggagggc ctacccgcag ttggcgatga gcagctggcg   2820
cgctggcttg agacgcgcga gcctgccgac ttggaggagc gacgcaagct aatgatggcc   2880
gcagtgcttg ttaccgtgga gcttgagtgc atgcagcggt tctttgctga cccggagatg   2940
cagcgcaagc tagaggaaac gttgcactac acctttcgcc agggctacgt gcgccaggcc   3000
```

tgcaaaattt ccaacgtgga gctctgcaac ctggtctcct accttggaat tttgcacgaa 3060
aaccgcctcg ggcaaaacgt gcttcattcc acgctcaagg gcgaggcgcg ccgcgactac 3120
gtccgcgact gcgtttactt atttctgtgc tacacctggc aaacggccat gggcgtgtgg 3180
cagcaatgcc tggaggagcg caacctaaag gagctgcaga agctgctaaa gcaaaacttg 3240
aaggacctat ggacggcctt caacgagcgc tccgtggccg cgcacctggc ggacattatc 3300
ttccccgaac gcctgcttaa aaccctgcaa cagggtctgc cagacttcac cagtcaaagc 3360
atgttgcaaa actttaggaa ctttatccta gagcgttcag gaattctgcc cgccacctgc 3420
tgtgcgcttc ctagcgactt tgtgcccatt aagtaccgtg aatgccctcc gccgctttgg 3480
ggtcactgct accttctgca gctagccaac taccttgcct accactccga catcatggaa 3540
gacgtgagcg gtgacggcct actggagtgt cactgtcgct gcaacctatg caccccgcac 3600
cgctccctgg tctgcaattc gcaactgctt agcgaaagtc aaattatcgg tacctttgag 3660
ctgcagggtc cctcgcctga cgaaaagtcc gcggctccgg ggttgaaact cactccgggg 3720
ctgtggacgt cggcttacct tcgcaaattt gtacctgagg actaccacgc ccacgagatt 3780
aggttctacg aagaccaatc ccgcccgcca aatgcggagc ttaccgcctg cgtcattacc 3840
cagggccaca tccttggcca attgcaagcc atcaacaaag cccgccaaga gtttctgcta 3900
cgaaagggac ggggggttta cctggacccc cagtccggcg aggagctcaa cccaatcccc 3960
ccgccgccgc agccctatca gcagccgcgg gcccttgctt cccaggatgg cacccaaaaa 4020
gaagctgcag ctgccgccgc cgccacccac ggacgaggag gaatactggg acagtcaggc 4080
agaggaggtt ttggacgagg aggaggagat gatggaagac tgggacagcc tagacgaagc 4140
ttccgaggcc gaagaggtgt cagacgaaac accgtcaccc tcggtcgcat tcccctcgcc 4200
ggcgccccag aaattggcaa ccgttcccag catcgctaca acctccgctc ctcaggcgcc 4260
gccggcactg cctgttcgcc gacccaaccg tagatgggac accactggaa ccagggccgg 4320
taagtctaag cagccgccgc cgttagccca agagcaacaa cagcgccaag gctaccgctc 4380
gtggcgcggg cacaagaacg ccatagttgc ttgcttgcaa gactgtgggg gcaacatctc 4440
cttcgcccgc cgctttcttc tctaccatca cggcgtggcc ttcccccgta acatcctgca 4500
ttactaccgt catctctaca gcccctactg caccggcggc agcggcagcg gcagcaacag 4560
cagcggtcac acagaagcaa aggcgaccgg atagcaagac tctgacaaag cccaagaaat 4620
ccacagcggc ggcagcagca ggaggaggag cgctgcgtct ggcgcccaac gaacccgtat 4680
cgacccgcga gcttagaaat aggatttttc ccactctgta tgctatattt caacaaagca 4740
ggggccaaga acaagagctg aaaataaaaa acaggtctct gcgctccctc acccgcagct 4800
gcctgtatca caaaagcgaa gatcagcttc ggcgcacgct ggaagacgcg gaggctctct 4860
tcagcaaata ctgcgcgctg actcttaagg actagtttcg cgccctttct caaatttaag 4920
cgcgaaaact acgtcatctc cagcggccac acccggcgcc agcacctgtc gtcagcgcca 4980
ttatgagcaa ggaaattccc acgccctaca tgtggagtta ccagccacaa atgggacttg 5040
cggctggagc tgcccaagac tactcaaccc gaataaacta catgagcgcg ggaccccaca 5100
tgatatcccg ggtcaacgga atccgcgccc accgaaaccg aattctcctc gaacaggcgg 5160
ctattaccac cacacctcgt aataacctta atccccgtag ttggcccgct gccctggtgt 5220
accaggaaag tcccgctccc accactgtgg tacttcccag agacgcccag gccgaagttc 5280
agatgactaa ctcaggggcg cagcttgcgg gcggctttcg tcacagggtg cggtcg 5336

<210> SEQ ID NO 69
<211> LENGTH: 3944
<212> TYPE: DNA
<213> ORGANISM: Artificial Sequence
<220> FEATURE:
<223> OTHER INFORMATION: Synthetic Sequence

<400> SEQUENCE: 69
cccgggcgtt ttagggcgga gtaacttgca tgtattggga attgtagttt ttttaaaatg 60
ggaagtgacg tatcgtggga aaacggaagt gaagatttga ggaagttgtg ggtttttttgg 120 ctttcgtttc tgggcgtagg ttcgcgtgcg gttttctggg tgttttttgt ggactttaac 180
cgttacgtca tttttttagtc ctatatatac tcgctctgta cttggccctt tttacactgt 240
gactgattga gctggtgccg tgtcgagtgg tgttttttaa taggtttttt tactggtaag 300
gctgactgtt atggctgccg ctgtggaagc gctgtatgtt gttctggagc gggagggtgc 360
tattttgcct aggcaggagg gtttttcagg tgtttatgtg tttttctctc ctattaattt 420
tgttatacct cctatggggg ctgtaatgtt gtctctacgc ctgcgggtat gtattccccc 480
gggctatttc ggtcgctttt tagcactgac cgatgttaac caacctgatg tgtttaccga 540
gtcttacatt atgactccgg acatgaccga ggaactgtcg gtggtgcttt ttaatcacgg 600
tgaccagttt ttttacggtc acgccggcat ggccgtagtc cgtcttatgc ttataagggt 660
tgtttttcct gttgtaagac aggcttctaa tgtttaaatg tttttttttt tgttatttta 720
ttttgtgttt aatgcaggaa cccgcagaca tgtttgagag aaaaatggtg tctttttctg 780
tggtggttcc ggaacttacc tgcctttatc tgcatgagca tgactacgat gtgcttgctt 840
ttttgcgcga ggctttgcct gatttttga gcagcacctt gcattttata tcgccgccca 900
tgcaacaagc ttacataggg gctacgctgg ttagcatagc tccgagtatg cgtgtcataa 960
tcagtgtggg ttcttttgtc atggttcctg gcggggaagt ggccgcgctg gtccgtgcag 1020
acctgcacga ttatgttcag ctggccctgc gaagggacct acgggatcgc ggtatttttg 1080
ttaatgttcc gcttttgaat cttatacagg tctgtgagga acctgaattt ttgcaatcat 1140
gattcgctgc ttgaggctga aggtggaggg cgctctggag cagattttta caatggccgg 1200
acttaatatt cgggatttgc ttagagacat attgataagg tggcgagatg aaaattattt 1260
gggcatggtt gaaggtgctg gaatgtttat agaggagatt caccctgaag ggtttagcct 1320
ttacgtccac ttggacgtga gggcagtttg ccttttggaa gccattgtgc aacatcttac 1380
aaatgccatt atctgttctt tggctgtaga gtttgaccac gccaccggag gggagcgcgt 1440
tcacttaata gatcttcatt ttgaggtttt ggataatctt ttggaataaa aaaaaaaaaa 1500
catggttctt ccagctcttc ccgctcctcc cgtgtgtgac tcgcagaacg aatgtgtagg 1560
ttggctgggt gtggcttatt ctgcggtggt ggatgttatc agggcagcgg cgcatgaagg 1620
agtttacata gaacccgaag ccagggggcg cctggatgct ttgagagagt ggatatacta 1680
caactactac acagagcgag ctaagcgacg agaccggaga cgcagatctg tttgtcacgc 1740
ccgcacctgg ttttgcttca ggaaatatga ctacgtccgg cgttccattt ggcatgacac 1800
tacgaccaac acgatctcgg ttgtctcggc gcactccgta cagtagggat cgcctacctc 1860
cttttgagac agagacccgc gctaccatac tggaggatca tccgctgctg cccgaatgta 1920
acactttgac aatgcacaac gtgagttacg tgcgaggtct tccctgcagt gtgggattta 1980
cgctgattca ggaatgggtt gttccctggg atatggttct gacgcgggag gagcttgtaa 2040
tcctgaggaa gtgtatgcac gtgtgcctgt gttgtgccaa cattgatatc atgacgagca 2100

```
tgatgatcca tggttacgag tcctgggctc tccactgtca ttgttccagt cccggttccc   2160

tgcagtgcat agccggcggg caggttttgg ccagctggtt taggatggtg gtggatggcg   2220

ccatgtttaa tcagaggttt atatggtacc gggaggtggt gaattacaac atgccaaaag   2280

aggtaatgtt tatgtccagc gtgtttatga ggggtcgcca cttaatctac ctgcgcttgt   2340

ggtatgatgg ccacgtgggt tctgtggtcc ccgccatgag ctttggatac agcgccttgc   2400

actgtgggat tttgaacaat attgtggtgc tgtgctgcag ttactgtgct gatttaagtg   2460

agatcagggt gcgctgctgt gcccggagga caaggcgtct catgctgcgg gcggtgcgaa   2520

tcatcgctga ggagaccact gccatgttgt attcctgcag gacggagcgg cggcggcagc   2580

agtttattcg cgcgctgctg cagcaccacc gccctatcct gatgcacgat tatgactcta   2640

cccccatgta ggcgtggact tccccttcgc cgcccgttga gcaaccgcaa gttggacagc   2700

agcctgtggc tcagcagctg gacagcgaca tgaacttaag cgagctgccc ggggagttta   2760

ttaatatcac tgatgagcgt ttggctcgac aggaaaccgt gtggaatata acacctaaga   2820

atatgtctgt tacccatgat atgatgcttt ttaaggccag ccggggagaa aggactgtgt   2880

actctgtgtg ttgggaggga ggtggcaggt tgaatactag ggttctgtga gtttgattaa   2940

ggtacggtga tcaatataag ctatgtggtg gtggggctat actactgaat gaaaaatgac   3000

ttgaaatttt ctgcaattga aaaataaaca cgttgaaaca taacatgcaa caggttcacg   3060

attctttatt cctgggcaat gtaggagaag gtgtaagagt tggtagcaaa agtttcagtg   3120

gtgtattttc cactttccca ggaccatgta aaagacatag agtaagtgct tacctcgcta   3180

gtttctgtgg attcactaga atcgatgtag gatgttgccc ctcctgacgc ggtaggagaa   3240

ggggagggtg ccctgcatgt ctgccgctgc tcttgctctt gccgctgctg aggagggggg   3300

cgcatctgcc gcagcaccgg atgcatctgg gaaaagcaaa aaaggggctc gtccctgttt   3360

ccggaggaat ttgcaagcgg ggtcttgcat gacggggagg caaacccccg ttcgccgcag   3420

tccggccggc ccgagactcg aaccgggggt cctgcgactc aacccttgga aaataaccct   3480

ccggctacag ggagcgagcc acttaatgct ttcgctttcc agcctaaccg cttacgccgc   3540

gcgcggccag tggccaaaaa agctagcgca gcagccgccg cgcctggaag gaagccaaaa   3600

ggagcgctcc cccgttgtct gacgtcgcac acctgggttc gacacgcggg cggtaaccgc   3660

atggatcacg gcggacggcc ggatccgggg ttcgaacccc ggtcgtccgc catgataccc   3720

ttgcgaattt atccaccaga ccacggaaga gtgcccgctt acaggctctc cttttgcacg   3780

gtctagagcg tcaacgactg cgcacgcctc accggccaga gcgtcccgac catggagcac   3840

tttttgccgc tgcgcaacat ctggaaccgc gtccgcgact ttccgcgcgc ctccaccacc   3900

gccgccggca tcacctggat gtccaggtac atctacggat tacg                    3944
```

```
<210> SEQ ID NO 70
<211> LENGTH: 1866
<212> TYPE: DNA
<213> ORGANISM: Artificial Sequence
<220> FEATURE:
<223> OTHER INFORMATION: Synthetic Sequence

<400> SEQUENCE: 70

atgccggggt tttacgagat tgtgattaag gtccccagcg accttgacga gcatctgccc     60

ggcatttctg acagctttgt gaactgggtg gccgagaagg aatgggagtt gccgccagat    120

tctgacatgg atctgaatct gattgagcag gcacccctga ccgtggccga gaagctgcag    180

cgcgactttc tgacggaatg gcgccgtgtg agtaaggccc cggaggccct tttctttgtg    240
```

```
caatttgaga agggagagag ctacttccac atgcacgtgc tcgtggaaac caccggggtg    300
aaatccatgg ttttgggacg tttcctgagt cagattcgcg aaaaactgat tcagagaatt    360
taccgcggga tcgagccgac tttgccaaac tggttcgcgg tcacaaagac cagaaatggc    420
gccggaggcg ggaacaaggt ggtggatgag tgctacatcc ccaattactt gctccccaaa    480
acccagcctg agctccagtg ggcgtggact aatatggaac agtatttaag cgcctgtttg    540
aatctcacgg agcgtaaacg gttggtggcg cagcatctga cgcacgtgtc gcagacgcag    600
gagcagaaca aagagaatca gaatcccaat tctgatgcgc cggtgatcag atcaaaaact    660
tcagccaggt acatggagct ggtcgggtgg ctcgtggaca aggggattac ctcggagaag    720
cagtggatcc aggaggacca ggcctcatac atctccttca atgcggcctc caactcgcgg    780
tcccaaatca aggctgcctt ggacaatgcg ggaaagatta tgagcctgac taaaaccgcc    840
cccgactacc tggtgggcca gcagcccgtg gaggacattt ccagcaatcg gatttataaa    900
attttggaac taaacgggta cgatccccaa tatgcggctt ccgtctttct gggatgggcc    960
acgaaaaagt tcggcaagag gaacaccatc tggctgtttg ggcctgcaac taccgggaag   1020
accaacatcg cggaggccat agcccacact gtgcccttct acgggtgcgt aaactggacc   1080
aatgagaact ttcccttcaa cgactgtgtc gacaagatgg tgatctggtg ggaggagggg   1140
aagatgaccg ccaaggtcgt ggagtcggcc aaagccattc tcggaggaag caaggtgcgc   1200
gtggaccaga aatgcaagtc ctcggcccag atagacccga ctcccgtgat cgtcacctcc   1260
aacaccaaca tgtgcgccgt gattgacggg aactcaacga ccttcgaaca ccagcagccg   1320
ttgcaagacc ggatgttcaa atttgaactc acccgccgtc tggatcatga ctttgggaag   1380
gtcaccaagc aggaagtcaa agactttttc cggtgggcaa aggatcacgt ggttgaggtg   1440
gagcatgaat tctacgtcaa aaagggtgga gccaagaaaa gacccgcccc cagtgacgca   1500
gatataagtg agcccaaacg ggtgcgcgag tcagttgcgc agccatcgac gtcagacgcg   1560
gaagcttcga tcaactacgc agacaggtac caaaacaaat gttctcgtca cgtgggcatg   1620
aatctgatgc tgtttccctg cagacaatgc gagagaatga atcagaattc aaatatctgc   1680
ttcactcacg gacagaaaga ctgtttagag tgctttcccg tgtcagaatc tcaacccgtt   1740
tctgtcgtca aaaaggcgta tcagaaactg tgctacattc atcatatcat gggaaaggtg   1800
ccagacgctt gcactgcctg cgatctggtc aatgtggatt tggatgactg catctttgaa   1860
caataa                                                              1866
```

<210> SEQ ID NO 71
<211> LENGTH: 2208
<212> TYPE: DNA
<213> ORGANISM: Artificial Sequence
<220> FEATURE:
<223> OTHER INFORMATION: Synthetic Sequence

<400> SEQUENCE: 71

```
atggctgccg atggttatct tccagattgg ctcgaggaca ctctctctga aggaataaga     60
cagtggtgga agctcaaacc tggcccacca ccaccaaagc ccgcagagcg gcataaggac    120
gacagcaggg gtcttgtgct tcctgggtac aagtacctcg gacccttcaa cggactcgac    180
aagggagagc cggtcaacga ggcagacgcc gcggccctcg agcacgacaa agcctacgac    240
cggcagctcg acagcggaga caacccgtac ctcaagtaca accacgccga cgcggagttt    300
caggagcgcc ttaaagaaga tacgtctttt gggggcaacc tcggacgagc agtcttccag    360
```

gcgaaaaaga gggttcttga acctctgggc ctggttgagg aacctgttaa gacggctccg 420
ggaaaaaaga ggccggtaga gcactctcct gtggagccag actcctcctc gggaaccggc 480
aagacaggcc agcagcccgc taaaaagaga ctcaattttg gtcagactgg cgactcagag 540
tcagtcccag accctcaacc tctcggagaa ccaccagcag ccccctctgg tctgggaact 600
aatacgatgg ctacaggcag tggcgcacca atggcagaca ataacgaggg tgccgatgga 660
gtgggtaatt cctcaggaaa ttggcattgc gattcccaat ggctgggcga cagagtcatc 720
accaccagca cccgaacctg ggccctgccc acctacaaca accatctcta caagcaaatc 780
tccagccaat caggagcttc aaacgacaac cactactttg gctacagcac cccttggggg 840
tattttgact ttaacagatt ccactgccac ttctcaccac gtgactggca gcgactcatt 900
aacaacaact ggggattccg gcccaagaaa ctcagcttca agctcttcaa catccaagtt 960
aaagaggtca cgcagaacga tggcacgacg actattgcca ataaccttac cagcacggtt 1020
caagtgttta ctgactcgga gtaccagctc ccgtacgtcc tcggctcggc gcatcaagga 1080
tgcctcccgc cgttcccagc agacgtcttc atggtgccac agtatggata cctcaccctg 1140
aacaacggga gtcaggcagt aggacgctct tcattttact gcctggagta ctttccttct 1200
cagatgctgc gtaccggaaa caactttacc ttcagctaca cttttgagga cgttcctttc 1260
cacagcagct acgctcacag ccagagtctg gaccgtctca tgaatcctct catcgaccag 1320
tacctgtatt acttgagcag aacaaacact ccaagtggaa ccaccacgca gtcaaggctt 1380
cagttttctc aggccggagc gagtgacatt cgggaccagt ctaggaactg gcttcctgga 1440
ccctgttacc gccagcagcg agtatcaaag acatctgcgg ataacaacaa cagtgaatac 1500
tcgtgggctg gagctaccaa gtaccacctc aatggcagag actctctggt gaatccgggc 1560
ccggccatgg caagccacaa ggacgatgaa gaaaagtttt ttcctcagag cggggttctc 1620
atctttggga agcaaggctc agagaaaaca aatgtggaca ttgaaaaggt catgattaca 1680
gacgaagagg aaatcaggac aaccaatccc gtggctacgg agcagtatgg ttctgtatct 1740
accaacctcc agagaggcaa cagacaagca gctaccgcag atgtcgacac acaaggcgtt 1800
cttccaggca tggtatggca ggacagagat gtgtaccttc agggacccat ctgggcaaag 1860
attccacaca cggacggaca ttttcacccc tctcccctca tgggtggatt cggacttaaa 1920
caccctcctc cacagattct catcaagaac accccggtac ctgcgaatcc ttcgaccacc 1980
ttcagtgcgg caaagtttgc ttccttcatc acacagtact caacgggaca ggtcagcgtg 2040
gagatcgagt gggagctgca gaaggaaaac agcaaacgct ggaatcccga aattcagtac 2100
acttccaact acaacaagtc tgttaatgtg gactttactg tggacactaa tggcgtgtat 2160
tcagagcctc gccccattgg caccagatac ctgactcgta atctgtaa 2208

<210> SEQ ID NO 72
<211> LENGTH: 16
<212> TYPE: DNA
<213> ORGANISM: Artificial Sequence
<220> FEATURE:
<223> OTHER INFORMATION: Synthetic Sequence

<400> SEQUENCE: 72
atgatttaaa tcaggt 16

<210> SEQ ID NO 73
<211> LENGTH: 141
<212> TYPE: DNA
<213> ORGANISM: Artificial Sequence
<220> FEATURE:
<223> OTHER INFORMATION: Synthetic Sequence

<400> SEQUENCE: 73
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc t 141

<210> SEQ ID NO 74
<211> LENGTH: 255
<212> TYPE: DNA
<213> ORGANISM: Artificial Sequence
<220> FEATURE:
<223> OTHER INFORMATION: Synthetic Sequence

<400> SEQUENCE: 74
tgtttgctgc ttgcaatgtt tgcccatttt agggtggaca caggacgctg tggtttctga 60
gccagggggc gactcagatc ccagccagtg gacttagccc ctgtttgctc ctccgataac 120
tggggtgacc ttggttaata ttcaccagca gcctcccccg ttgcccctct ggatccactg 180
cttaaatacg gacgaggaca gggccctgtc tcctcagctt caggcaccac cactgacctg 240
ggacagtgaa tcgca 255

<210> SEQ ID NO 75
<211> LENGTH: 122
<212> TYPE: DNA
<213> ORGANISM: Artificial Sequence
<220> FEATURE:
<223> OTHER INFORMATION: Synthetic Sequence

<400> SEQUENCE: 75
aacttgttta ttgcagctta taatggttac aaataaagca atagcatcac aaatttcaca 60
aataaagcat ttttttcact gcattctagt tgtggtttgt ccaaactcat caatgtatct 120
ta 122

<210> SEQ ID NO 76
<211> LENGTH: 1906
<212> TYPE: DNA
<213> ORGANISM: Artificial Sequence
<220> FEATURE:
<223> OTHER INFORMATION: Synthetic Sequence

<400> SEQUENCE: 76
cctcgcagga ggcctggccg gcctccggat tacttccggt gcaggcgtca gctgcatctt 60
gctggccagc tcggaggact gtccccgtaa ctcccgtccg ctgtgtatca acacagctct 120
agccaaattg ttgaccgaac gacggggttc gattgtatca ttcctcacat ccaacacttg 180
agtagtacaa tgccttgtct aagtgcgctt gggacccagt ctattttgtt tgtgtgcaca 240
agacgatact cctcgatcac gtaccaagcg caggctggcc ctaacgacgt ggtattctcg 300
tattggtgtg ccccagattg cataaggcac tcatcacctg cgtttatgac gctggacgcc 360
tgcgtatgtt gcaggactcc tatgatgtcg ctagcctgat gcgttgttat gtgattgagg 420
tttagtactt ggcaatatca ttagatggaa ctaatacgcg gtctaatcgt tacaggtttc 480
cgacgattga gaagtatcac ctgattctcg ggagcgactt gtaactctac tacacttatt 540
gatttggtac tcctatgtgt tgctatcttg actccgtaaa tcgccgtgat acactctctt 600
cgtttctcgg caatctatgg ctctaaacta tacacaggca ttctaagaat aatctgacct 660
gtccctgtag tactggtagg ttactaccag tacggcgaca atgtgggagc tacggcgtgg 720
tagaaccggg tacagacaca gtccctgatc ccgatagtaa cactgtgccc gtagcagtga 780
taatcattgc gcctcaacct gaggaagata agggaggcag tatatcgtgc tattccctct 840
attctcccac atgcgtatgg cctgaggtca atgatcaggt acatgccgta atatgaggtt 900
ttacgtagcc gatcacgaaa aggttgctaa atacttctcg tcatatccca gctcattgtt 960
gggattatcg ctaaacaggc taagttctaa tgcccgtggg catggcctca cgatctatgg 1020
tgaaacagac agcccgattt agcaatgcta cagagcacag tggttaatat tggttgatac 1080
gtagaaccat gatcactgct caattcgtga tgaagttgtt caatatacct agaagccact 1140
caaggattct ctctgtgtca ctaatagagg tggtagagtg tttggaagcc ggttccacac 1200
agatttagag tgtcacctaa ttgccgttta tctaaggaat tacgacagga gattccgaag 1260
taattaggct attgcagaga tacaggctag gtgaggtgga gggtgtcttg cggtcttcgt 1320
ccagccgcct tgaaagcggg gttttttca agcatcgctg cgtcattgcg tggtcgagac 1380
ttatgcgccc tacgaagttc gtctgaagta gtccaggaaa gacctacttt gcagttatct 1440
tcgcattccc acactcacca ctacaactac tcttccctca atttcccggt tagtttcgct 1500
aagctccgac cttgggttac tgtgttgcat ccgactcgct gcggctttct agtacgctgt 1560
actgtttcat tcttctgtag gtctggttcc gtaagtccga atttccaggc cgtggtctag 1620
tcctaattat tttctgtccc ggtagctata tttagccgag ggtttgtcca tttgcccggc 1680
gtagagcgcc gcgtttgcga acatttgcgc ccgtaatacg tagggacacc gtcgggtaat 1740
ggatggcaaa agccgaaaac ggcgtcttcc ggcgcttgga ttcagcgctc ttgagccata 1800
aaccgcgttg cttctttggt taattcgtat taatgatcct aagcgccagc ttattcgtta 1860
agaggcacta ggcgcgccgc ggcatgcgat cgccagcatg gctacg 1906

<210> SEQ ID NO 77
<211> LENGTH: 141
<212> TYPE: DNA
<213> ORGANISM: Artificial Sequence
<220> FEATURE:
<223> OTHER INFORMATION: Synthetic Sequence

<400> SEQUENCE: 77
aggaacccct agtgatggag ttggccactc cctctctgcg cgctcgctcg ctcactgagg 60
ccgggcgacc aaaggtcgcc cgacgcccgg gctttgcccg ggcggcctca gtgagcgagc 120
gagcgcgcag ctgcctgcag g 141

<210> SEQ ID NO 78
<211> LENGTH: 4651
<212> TYPE: DNA
<213> ORGANISM: Artificial Sequence
<220> FEATURE:
<223> OTHER INFORMATION: Synthetic Sequence

<400> SEQUENCE: 78
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc tatcgatggc gcgcctccag atatcataca ctcgagcaac 180
tttgtataga aaagttggcg cgtgtttgct gcttgcaatg tttgcccatt ttagggtgga 240
cacaggacgc tgtggtttct gagccagggg gcgactcaga tcccagccag tggacttagc 300
ccctgtttgc tcctccgata actggggtga ccttggttaa tattcaccag cagcctcccc 360

```
cgttgcccct ctggatccac tgcttaaata cggacgagga cagggccctg tctcctcagc    420
ttcaggcacc accactgacc tgggacagtg aatcgcaaga attcacgcgt caattgctcg    480
aggccaccat ggctcccaag aagaagcgga aagttggcgg cggaggcagc agcctggatg    540
atgagcatat tctgagcgcc ctgctgcaga gcgacgatga actcgtgggc gaagatagcg    600
acagcgaggt gtccgatcac gtgtccgagg atgacgtgca gtccgatacc gaggaagcct    660
tcatcgacga ggtgcacgaa gtgcagccta caagcagcgg cagcgagatc ctggacgagc    720
agaatgtgat cgagcagcca ggatctagcc tggccagcaa cagaatcctg acactgcccc    780
agagaaccat ccggggcaag aacaagcact gctggtccac cagcaagagc accagacggt    840
ctagagtgtc tgccctgaac atcgtgcgaa gccagagggg ccctaccaga atgtgccgga    900
acatctacga ccctctgctg tgcttcaagc tgttcttcac cgacgagatc atctccgaga    960
tcgtgaagtg gaccaacgcc gagatcagcc tgaagcggag agaatccatg accagcgcca   1020
ccttcagaga caccaacgag gacgagatct acgccttctt cggcatcctg gtcatgacag   1080
ccgtgcggaa ggacaaccac atgagcaccg acgacctgtt cgaccgcagc ctgtctatgg   1140
tgtacgtgtc cgtgatgagc cgggacagat tcgacttcct gatccggtgc ctgcggatgg   1200
acgacaagtc catcagaccc acactgcgcg agaacgacgt gttcacacct gtgcggaaga   1260
tctgggacct gttcatccac cagtgcatcc agaactacac ccctggcgct cacctgacca   1320
tcgacgaaca gctgctgggc ttcagaggca gatgcccctt cagagtgtac atccccaaca   1380
agccctctaa gtacggcatc aagatcctga tgatgtgcga cagcggcacc aagtacatga   1440
tcaacggcat gccctacctc ggcagaggca cccaaacaaa tggcgtgcca ctgggcgagt   1500
actacgtgaa agaactgagc aagcctgtgc acggcagctg cagaaacatc acctgtgaca   1560
actggtttac cagcattccc ctggccaaga acctgctgca agaaccctac aagctgacaa   1620
tcgtgggcac cgtgcggagc aacaagaggg aaattcccga ggtgctgaag aactctcgga   1680
gcagacctgt gggcaccagc atgttctgct tcgacggacc tctgacactg gtgtcctaca   1740
agcccaagcc tgccaagatg gtgtacctgc tgagcagctg tgacgaggac gccagcatca   1800
atgagagcac cggcaagccc cagatggtca tgtactacaa ccagaccaaa ggcggcgtgg   1860
acaccctgga tcagatgtgc agcgtgatga cctgcagcag aaagaccaac agatggccca   1920
tggctctgct gtacggcatg atcaatatcg cctgcatcaa cagcttcatc atctacagcc   1980
acaacgtgtc cagcaagggc gagaaggtgc agagccggaa gaaattcatg cggaacctgt   2040
acatgagcct gaccagcagc ttcatgagaa agcggctgga agcccctaca ctgaagagat   2100
acctgcggga caacatcagc aacatcctgc ctaaagaggt gcccggcacc agcgacgata   2160
gcacagagga acccgtgatg aagaagagga cctactgcac ctactgtccc agcaagatcc   2220
ggcggaaggc caacgccagc tgcaaaaagt gcaagaaagt gatctgccgc gagcacaaca   2280
tcgatatgtg ccagagctgc ttctgatgag atgcattcga agcggccgcg agctcaagct   2340
tgcaattccg ataacttgtt tattgcagct tataatggtt acaaataaag caatagcatc   2400
acaaatttca caaataaagc atttttttca ctgcattcta gttgtggttt gtccaaactc   2460
atcaatgtat cttatcatgt ctggcgctag cagcacaagt ttgtacaaaa aagcaggctc   2520
ctcgcaggag gcctggccgg cctccggatt acttccggtg caggcgtcag ctgcatcttg   2580
ctggccagct cggaggactg tccccgtaac tcccgtccgc tgtgtatcaa cacagctcta   2640
gccaaattgt tgaccgaacg acggggttcg attgtatcat tcctcacatc caacacttga   2700
```

gtagtacaat gccttgtcta agtgcgcttg ggacccagtc tattttgttt gtgtgcacaa 2760
gacgatactc ctcgatcacg taccaagcgc aggctggccc taacgacgtg gtattctcgt 2820
attggtgtgc cccagattgc ataaggcact catcacctgc gtttatgacg ctggacgcct 2880
gcgtatgttg caggactcct atgatgtcgc tagcctgatg cgttgttatg tgattgaggt 2940
ttagtacttg gcaatatcat tagatggaac taatacgcgg tctaatcgtt acaggtttcc 3000
gacgattgag aagtatcacc tgattctcgg gagcgacttg taactctact acacttattg 3060
atttggtact cctatgtgtt gctatcttga ctccgtaaat cgccgtgata cactctcttc 3120
gtttctcggc aatctatggc tctaaactat acacaggcat tctaagaata atctgacctg 3180
tccctgtagt actggtaggt tactaccagt acggcgacaa tgtgggagct acggcgtggt 3240
agaaccgggt acagacacag tccctgatcc cgatagtaac actgtgcccg tagcagtgat 3300
aatcattgcg cctcaacctg aggaagataa gggaggcagt atatcgtgct attccctcta 3360
ttctcccaca tgcgtatggc ctgaggtcaa tgatcaggta catgccgtaa tatgaggttt 3420
tacgtagccg atcacgaaaa ggttgctaaa tacttctcgt catatcccag ctcattgttg 3480
ggattatcgc taaacaggct aagttctaat gcccgtgggc atggcctcac gatctatggt 3540
gaaacagaca gcccgattta gcaatgctac agagcacagt ggttaatatt ggttgatacg 3600
tagaaccatg atcactgctc aattcgtgat gaagttgttc aatataccta gaagccactc 3660
aaggattctc tctgtgtcac taatagaggt ggtagagtgt ttggaagccg gttccacaca 3720
gatttagagt gtcacctaat tgccgtttat ctaaggaatt acgacaggag attccgaagt 3780
aattaggcta ttgcagagat acaggctagg tgaggtggag ggtgtcttgc ggtcttcgtc 3840
cagccgcctt gaaagcgggg tttttttcaa gcatcgctgc gtcattgcgt ggtcgagact 3900
tatgcgccct acgaagttcg tctgaagtag tccaggaaag acctactttg cagttatctt 3960
cgcattccca cactcaccac tacaactact cttccctcaa tttcccggtt agtttcgcta 4020
agctccgacc ttgggttact gtgttgcatc cgactcgctg cggctttcta gtacgctgta 4080
ctgtttcatt cttctgtagg tctggttccg taagtccgaa tttccaggcc gtggtctagt 4140
cctaattatt ttctgtcccg gtagctatat ttagccgagg gtttgtccat ttgcccggcg 4200
tagagcgccg cgtttgcgaa catttgcgcc cgtaatacgt agggacaccg tcgggtaatg 4260
gatggcaaaa gccgaaaacg gcgtcttccg gcgcttggat tcagcgctct tgagccataa 4320
accgcgttgc ttctttggtt aattcgtatt aatgatccta agcgccagct tattcgttaa 4380
gaggcactag gcgcgccgcg gcatgcgatc gccagcatgg ctacgaccca gctttcttgt 4440
acaaagtggt gatggccggc cgcttcgagt taattaatcc aaccggttac cgcctaggat 4500
cgatagatct aggaacccct agtgatggag ttggccactc cctctctgcg cgctcgctcg 4560
ctcactgagg ccgggcgacc aaaggtcgcc cgacgcccgg gctttgcccg ggcggcctca 4620
gtgagcgagc gagcgcgcag ctgcctgcag g 4651

<210> SEQ ID NO 79
<211> LENGTH: 238
<212> TYPE: DNA
<213> ORGANISM: Artificial Sequence
<220> FEATURE:
<223> OTHER INFORMATION: Synthetic Sequence

<400> SEQUENCE: 79
ccctagaaag ataatcatat tgtgacgtac gttaaagata atcatgcgta aaattgacgc 60
atgtgtttta tcggtctgta tatcgaggtt tatttattaa tttgaataga tattaagttt 120

-continued

```
tattatattt acacttacat actaataata aattcaacaa acaatttatt tatgtttatt    180

tatttattaa aaaaaaacaa aaactcaaaa tttcttctat aaagtaacaa aactttta      238


<210> SEQ ID NO 80
<211> LENGTH: 309
<212> TYPE: DNA
<213> ORGANISM: Artificial Sequence
<220> FEATURE:
<223> OTHER INFORMATION: Synthetic Sequence

<400> SEQUENCE: 80

gatatctata acaagaaaat atatatataa taagttatca cgtaagtaga acatgaaata     60

acaatataat tatcgtatga gttaaatctt aaaagtcacg taaaagataa tcatgcgtca    120

ttttgactca cgcggtcgtt atagttcaaa atcagtgaca cttaccgcat tgacaagcac    180

gcctcacggg agctccaagc ggcgactgag atgtcctaaa tgcacagcga cggattcgcg    240

ctatttagaa agagagagca atatttcaag aatgcatgcg tcaattttac gcagactatc    300

tttctaggg                                                            309
```

COMPOSITIONS AND METHODS FOR THE TREATMENT OF HEMOPHILIA

RELATED APPLICATIONS

This application is a U.S. National Phase application, filed under 35 U.S.C. § 371, of International Application No. PCT/US2022/018976, filed Mar. 4, 2022, which claims priority to, and the benefit of, U.S. Provisional Application No. 63/156,657, filed on Mar. 4, 2021, the contents of each of which are incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on Aug. 29, 2023, is named "POTH-068_NO1US_SeqList.txt" and is about 277,977 bytes in size.

BACKGROUND

Hemophilia is an inherited genetic disorder that impairs blood clotting in a subject. This impairment in blood clotting means that subjects with hemophilia bleed for longer time periods following an injury, more easily bruise, and suffer from an increased risk of bleeding inside the joints or in the brain. Hemophilia is most typically inherited from a subject's parents through an X chromosome which carries a nonfunctional gene.

The two most prevalent forms of Hemophilia are Hemophilia A and Hemophilia B. Hemophilia A is characterized by reduced levels of clotting Factor VIII (FVIII) and Hemophilia B is characterized by reduced levels of clotting Factor IX (FIX). Other forms of Hemophilia include Hemophilia C, which is characterized by reduced levels of Factor XI (FXI), and Parahemophilia, which is characterized by reduced levels of Factor V (FV).

Currently there are no cures for hemophilia, and treatment is limited to the administration of clotting factors. Thus, there is a long-felt need in the art for compositions and methods directed to the treatment of hemophilia. The present disclosure addresses this need and provides compositions and methods for gene therapy for Hemophilia, more specifically, Hemophilia A and Hemophilia B.

Previous attempts at developing gene therapies for the treatment of hemophilia, have suffered from the inability to produce long-term expression of the delivered transgene in the target tissues. The compositions and methods of the present disclosure provide a solution to this long felt-need in the art by providing transposon/transposase-based AAV vectors that yield long-term expression of the delivered transgene in targeted tissues.

SUMMARY

The present disclosure relates to compositions and methods for the treatment of hemophilia in a subject in need thereof.

The present disclosure provides compositions comprising adeno-associated virus (AAV) piggyBac transposon polynucleotides.

In some aspects an AAV piggyBac transposon polynucleotide can comprise at least one AAV inverted terminal repeat (ITR) sequence. In some aspects, an AAV piggyBac transposon polynucleotide can comprise at least one piggyBac ITR sequence. In some aspects, an AAV piggyBac transposon polynucleotide can comprise at least one insulator sequence. In some aspects an AAV piggyBac transposon polynucleotide can comprise at least one promoter sequence. In some aspects, an AAV piggyBac transposon polynucleotide can comprise at least one transgene sequence. In some aspects, an AAV piggyBac transposon polynucleotide can comprise at least one polyA sequence. In some aspects, an AAV piggyBac transposon polynucleotide can comprise at least one self-cleaving peptide sequence. In some aspects, an AAV piggyBac transposon polynucleotide can comprise at least one DNA spacer sequence. In some aspects, an AAV piggyBac transposon polynucleotide can comprise at least one nucleic acid sequence.

An AAV piggyBac transposon polynucleotide can comprise a first AAV ITR sequence, a first piggyBac ITR sequence, a first insulator sequence, a second insulator sequence, a second piggyBac ITR sequence, and a second AAV ITR sequence.

In some aspects, an AAV piggyBac transposon polynucleotide can comprise in the 5' to 3' direction a first AAV ITR sequence, a first piggyBac ITR sequence, a first insulator sequence, a second insulator sequence, a second piggyBac ITR sequence, and a second AAV ITR sequence.

The present disclosure provides AAV vectors comprising the AAV piggyBac transposon polynucleotides of the present disclosure.

The present disclosure provides methods of treating hemophilia in a subject comprising administering the AAV vectors of the present disclosure to the subject.

Any of the aspects and/or embodiments described herein can be combined with any other aspect and/or embodiment described herein.

Unless otherwise defined, all technical and scientific terms used herein have the same meaning as commonly understood by one of ordinary skill in the art to which this disclosure belongs. In the Specification, the singular forms also include the plural unless the context clearly dictates otherwise; as examples, the terms "a," "an," and "the" are understood to be singular or plural and the term "or" is understood to be inclusive. By way of example, "an element" means one or more element. Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Although methods and materials similar or equivalent to those described herein can be used in the practice or testing of the present disclosure, suitable methods and materials are described below. All publications, patent applications, patents, and other references mentioned herein are incorporated by reference in their entirety. The references cited herein are not admitted to be prior art to the claimed invention. In the case of conflict, the present Specification, including definitions, will control. In addition, the materials, methods, and examples are illustrative only and are not intended to be limiting. Other features and advantages of the disclosure will be apparent from the following detailed description and claim.

BRIEF DESCRIPTION OF THE DRAWINGS

The above and further features will be more clearly appreciated from the following detailed description when taken in conjunction with the accompanying drawings.

DETAILED DESCRIPTION

Figure 1:
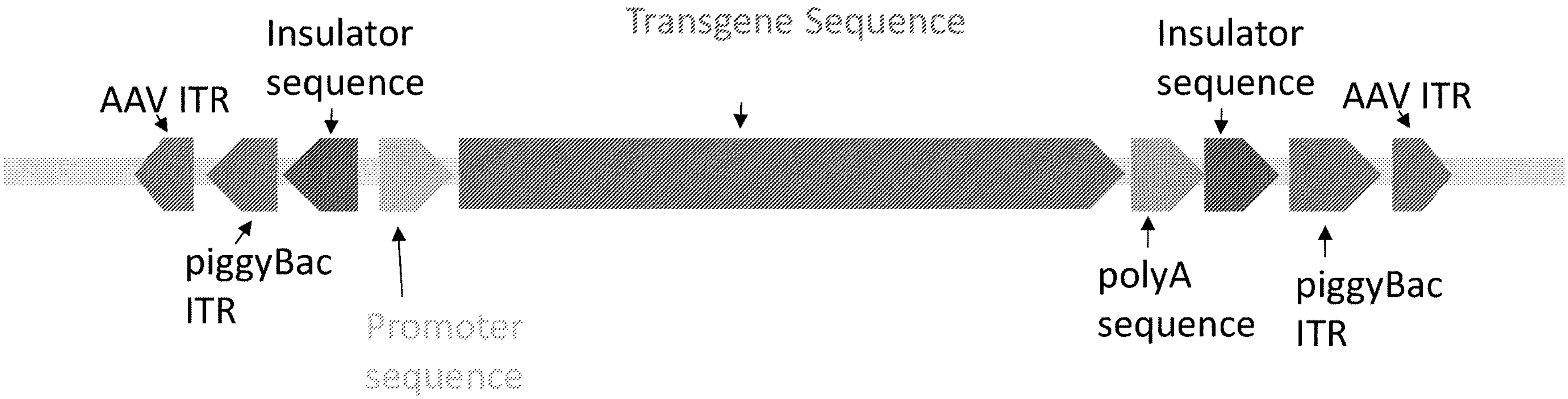
FIG. 1 is a schematic of an exemplary AAV piggyBac transposon polynucleotide of the present disclosure.

The present disclosure provides for compositions and methods for the treatment of hemophilia. The compositions and methods are described in further detail herein.

Compositions of Disclosure

Adeno-Associated Virus (AAV) piggyBac Transposon Polynucleotides

The present disclosure provides compositions comprising adeno-associated virus (AAV) piggyBac transposon polynucleotides.

In some aspects an AAV piggyBac transposon polynucleotide can comprise at least one AAV inverted terminal repeat (ITR) sequence. In some aspects, an AAV piggyBac transposon polynucleotide can comprise at least one piggyBac ITR sequence. In some aspects, an AAV piggyBac transposon polynucleotide can comprise at least one insulator sequence. In some aspects an AAV piggyBac transposon polynucleotide can comprise at least one promoter sequence. In some aspects, an AAV piggyBac transposon polynucleotide can comprise at least one transgene sequence. In some aspects, an AAV piggyBac transposon polynucleotide can comprise at least one polyA sequence. In some aspects, an AAV piggyBac transposon polynucleotide can comprise at least one self-cleaving peptide sequence. In some aspects, an AAV piggyBac transposon polynucleotide can comprise at least one DNA spacer sequence. In some aspects, an AAV piggyBac transposon polynucleotide can comprise at least one nucleic acid sequence.

An AAV piggyBac transposon polynucleotide can comprise a first AAV ITR sequence, a first piggyBac ITR sequence, a first insulator sequence, a second insulator sequence, a second piggyBac ITR sequence, and a second AAV ITR sequence.

In some aspects, an AAV piggyBac transposon polynucleotide can comprise in the 5' to 3' direction a first AAV ITR sequence, a first piggyBac ITR sequence, a first insulator sequence, a second insulator sequence, a second piggyBac ITR sequence, and a second AAV ITR sequence.

In some aspects, an AAV piggyBac transposon polynucleotide can comprise a first AAV ITR sequence, followed by a first piggyBac ITR sequence, followed by a first insulator sequence, followed by a second insulator sequence, followed by a second piggyBac ITR sequence, and followed by a second AAV ITR sequence.

An AAV piggyBac transposon polynucleotide can comprise a first AAV ITR sequence, a first piggyBac ITR sequence, a first insulator sequence, a second insulator sequence, a second piggyBac ITR sequence, and a second AAV ITR sequence, wherein between the first insulator sequence and the second insulator sequence there is any combination of at least one promoter sequence, at least one transgene sequence, at least one self-cleaving peptide sequence, and at least one polyA sequence.

In some aspects, an AAV piggyBac transposon polynucleotide can comprise in the 5' to 3' direction a first AAV ITR sequence, a first piggyBac ITR sequence, a first insulator sequence, a second insulator sequence, a second piggyBac ITR sequence, and a second AAV ITR sequence, wherein between the first insulator sequence and the second insulator sequence there is any combination of at least one promoter sequence, at least one transgene sequence, at least one self-cleaving peptide sequence, and at least one polyA sequence.

In some aspects, an AAV piggyBac transposon polynucleotide can comprise a first AAV ITR sequence, followed by a first piggyBac ITR sequence, followed by a first insulator sequence, followed by a second insulator sequence, followed by a second piggyBac ITR sequence, and followed by a second AAV ITR sequence, wherein between the first insulator sequence and the second insulator sequence there is any combination of at least one promoter sequence, at least one transgene sequence, at least one self-cleaving peptide sequence, and at least one polyA sequence.

An AAV piggyBac transposon polynucleotide can comprise a first AAV ITR sequence, a first piggyBac ITR sequence, a first insulator sequence, at least one promoter sequence, at least one transgene sequence, a polyA sequence, a second insulator sequence, a second piggyBac ITR sequence, and a second AAV ITR sequence.

In some aspects, an AAV piggyBac transposon polynucleotide can comprise in the 5' to 3' direction a first AAV ITR sequence, a first piggyBac ITR sequence, a first insulator sequence, at least one promoter sequence, at least one transgene sequence, a polyA sequence, a second insulator sequence, a second piggyBac ITR sequence, and a second AAV ITR sequence.

In some aspects, an AAV piggyBac transposon polynucleotide can comprise a first AAV ITR sequence, followed by a first piggyBac ITR sequence, followed by a first insulator sequence, followed by at least one promoter sequence, followed by at least one transgene sequence, followed by a polyA sequence, followed by a second insulator sequence, followed by a second piggyBac ITR sequence, and followed by a second AAV ITR sequence.

A schematic of the preceding piggyBac transposon polynucleotide is shown in FIG. 1.

In a non-limiting example of the preceding AAV piggyBac transposon polynucleotides, the at least one promoter sequence can comprise an ApoEhAAT promoter sequence and the at least one transgene sequence can comprise a nucleic acid sequence that encodes for a Factor VIII (FVIII) polypeptide. This non-limiting example of an AAV piggyBac transposon polynucleotide is shown in FIG. 1.

In a non-limiting example of the preceding AAV piggyBac transposon polynucleotides, the at least one promoter sequence can comprise an TTR promoter sequence and the at least one transgene sequence can comprise a nucleic acid sequence that encodes for a FVIII polypeptide. This non-limiting example of an AAV piggyBac transposon polynucleotide is shown in FIG. 1.

In a non-limiting example of the preceding AAV piggyBac transposon polynucleotides, the at least one promoter sequence can comprise an HLP promoter sequence and the at least one transgene sequence can comprise a nucleic acid sequence that encodes for a FVIII polypeptide. This non-limiting example of an AAV piggyBac transposon polynucleotide is shown in FIG. 1.

In a non-limiting example of the preceding AAV piggyBac transposon polynucleotides, the at least one promoter sequence can comprise an TTRm promoter sequence and the at least one transgene sequence can comprise a nucleic acid sequence that encodes for a FVIII polypeptide. This non-limiting example of an AAV piggyBac transposon polynucleotide is shown in FIG. 1.

In a non-limiting example of the preceding AAV piggyBac transposon polynucleotides, the at least one promoter sequence can comprise an TTRm promoter sequence and the at least one transgene sequence can comprise a nucleic acid sequence that encodes for a Factor IX (FIX) polypeptide. This non-limiting example of an AAV piggyBac transposon polynucleotide is shown in FIG. 1.

In a non-limiting example of the preceding AAV piggyBac transposon polynucleotides, the at least one promoter sequence can comprise an HLP promoter sequence and the at least one transgene sequence can comprise a nucleic acid sequence that encodes for a FIX polypeptide. This non-limiting example of an AAV piggyBac transposon polynucleotide is shown in FIG. 1.

An AAV piggyBac transposon polynucleotide can comprise a first AAV ITR sequence, a first piggyBac ITR sequence, a first insulator sequence, at least one promoter sequence, at least one transgene sequence, a polyA sequence, a second insulator sequence, a second piggyBac ITR sequence, at least one DNA spacer sequence and a second AAV ITR sequence.

In some aspects, an AAV piggyBac transposon polynucleotide can comprise in the 5' to 3' direction a first AAV ITR sequence, a first piggyBac ITR sequence, a first insulator sequence, at least one promoter sequence, at least one transgene sequence, a polyA sequence, a second insulator sequence, a second piggyBac ITR sequence, at least one DNA spacer sequence and a second AAV ITR sequence.

Figure 2A:
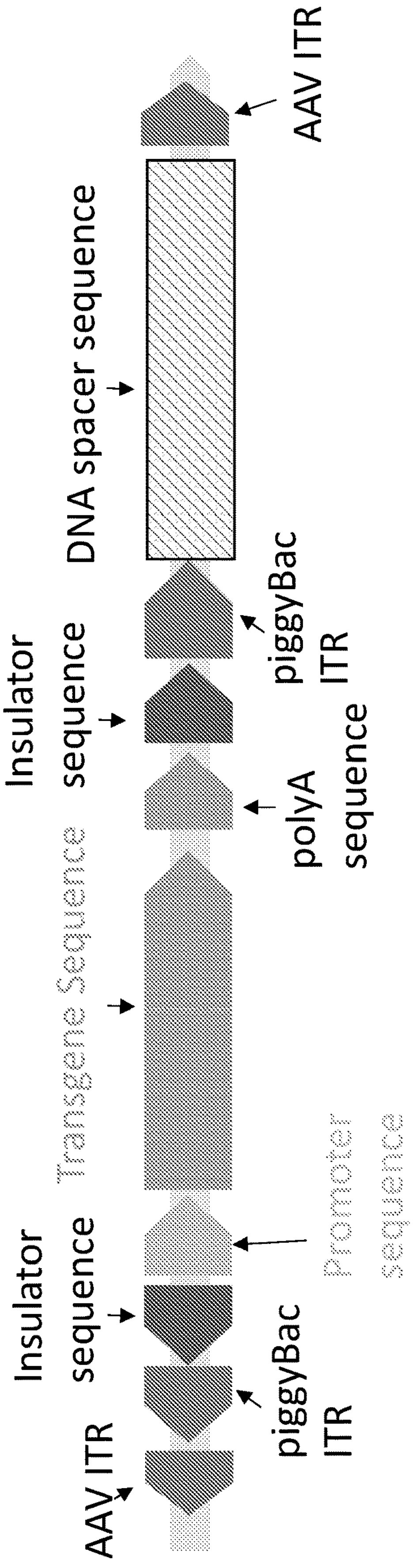
FIG. 2A is a schematic of an exemplary AAV piggyBac transposon polynucleotide of the present disclosure.
Figure 2B:
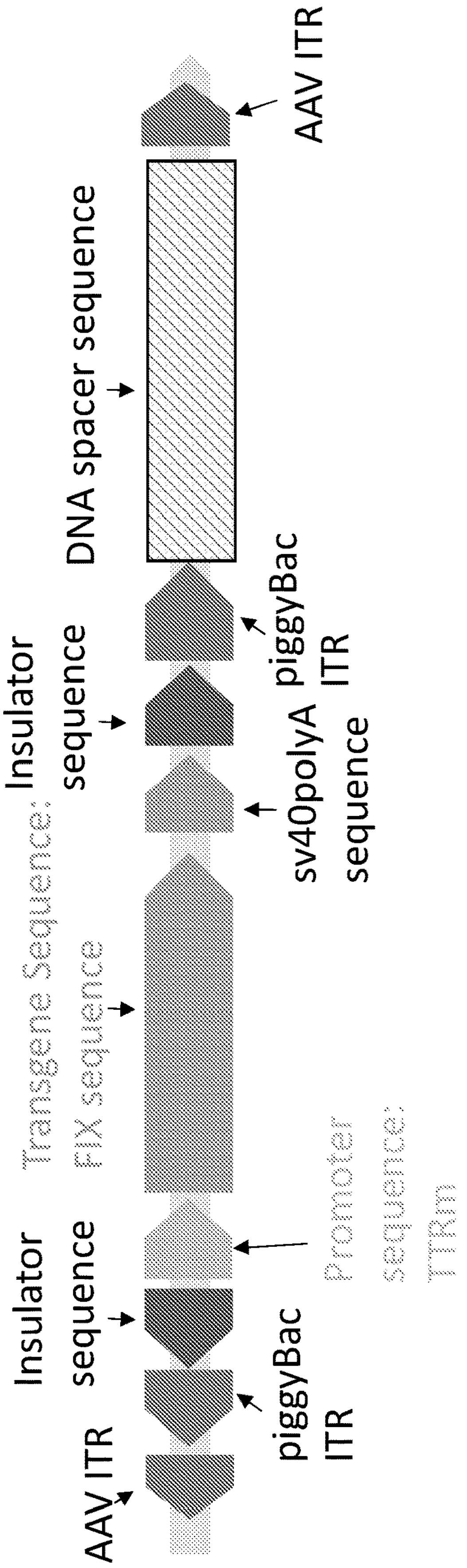
FIG. 2B is a schematic of an exemplary AAV piggyBac transposon polynucleotide of the present disclosure.

In some aspects, an AAV piggyBac transposon polynucleotide can comprise a first AAV ITR sequence, followed by a first piggyBac ITR sequence, followed by a first insulator sequence, followed by at least one promoter sequence, followed by at least one transgene sequence, followed by a polyA sequence, followed by a second insulator sequence, followed by a second piggyBac ITR sequence, followed by at least one DNA spacer sequence and followed by a second AAV ITR sequence. A schematic of the preceding AAV piggyBac transposon polynucleotide is shown in FIG. 2A In a non-limiting example of the preceding AAV piggyBac transposon polynucleotides, the at least one promoter sequence can comprise a TTRm promoter sequence and the at least one transgene sequence can comprise a nucleic acid sequence that encodes for a FIX polypeptide. This non-limiting example of an AAV piggyBac transposon polynucleotide is shown in FIG. 2B.

In some aspects, an AAV piggyBac transposon polynucleotide can comprise in between a second piggyBac ITR sequence and a second AAV ITR sequence, at least one DNA spacer sequence.

An AAV piggyBac transposon polynucleotide can comprise a first AAV ITR sequence, a first piggyBac ITR sequence, a first insulator sequence, at least one promoter sequence, at least one transgene sequence, a polyA sequence, a second insulator sequence, a second piggyBac ITR sequence, a second AAV ITR sequence and at least one DNA spacer sequence.

In some aspects, an AAV piggyBac transposon polynucleotide can comprise in the 5' to 3' direction a first AAV ITR sequence, a first piggyBac ITR sequence, a first insulator sequence, at least one promoter sequence, at least one transgene sequence, a polyA sequence, a second insulator sequence, a second piggyBac ITR sequence, a second AAV ITR sequence and at least one DNA spacer sequence.

In some aspects, an AAV piggyBac transposon polynucleotide can comprise a first AAV ITR sequence, followed by a first piggyBac ITR sequence, followed by a first insulator sequence, followed by at least one promoter sequence, followed by at least one transgene sequence, followed by a polyA sequence, followed by a second insulator sequence, followed by a second piggyBac ITR sequence, followed by a second AAV ITR sequence and followed by at least one DNA spacer sequence.

Figure 2C:
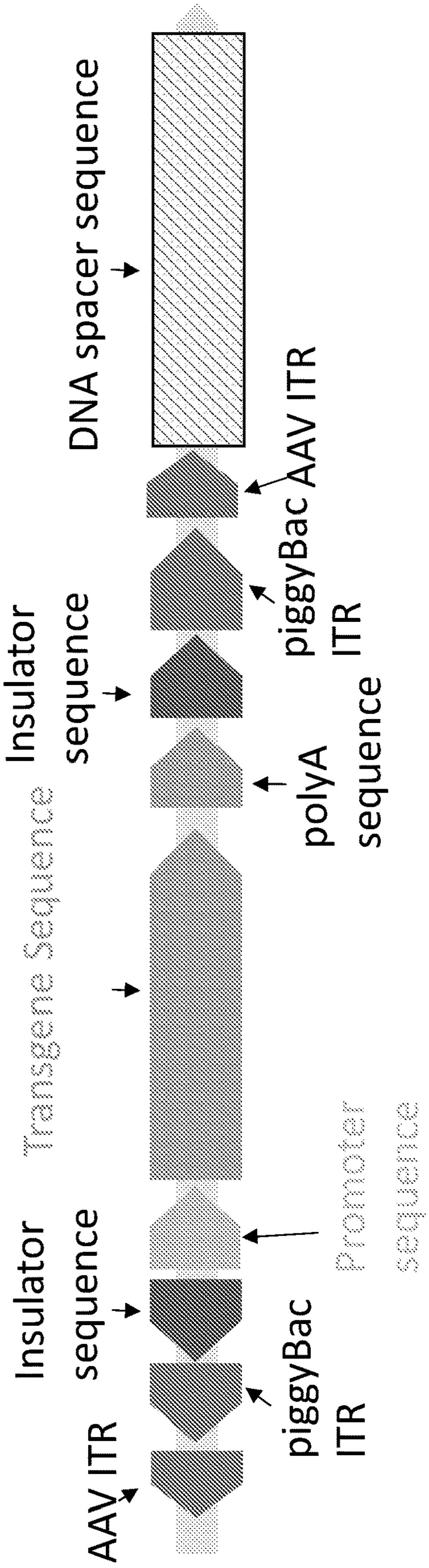
FIG. 2C is a schematic of an exemplary AAV piggyBac transposon polynucleotide of the present disclosure.

A schematic of the preceding AAV piggyBac transposon polynucleotide is shown in FIG. 2C.

An AAV piggyBac transposon polynucleotide can comprise a first AAV ITR sequence, a first piggyBac ITR sequence, a first insulator sequence, at least one promoter sequence, a first transgene sequence, at least one self-cleaving peptide sequence, an at least second transgene sequence, a polyA sequence, a second insulator sequence, a second piggyBac ITR sequence, and a second AAV ITR sequence.

In some aspects, an AAV piggyBac transposon polynucleotide can comprise in the 5' to 3' direction a first AAV ITR sequence, a first piggyBac ITR sequence, a first insulator sequence, at least one promoter sequence, a first transgene sequence, at least one self-cleaving peptide sequence, an at least second transgene sequence, a polyA sequence, a second insulator sequence, a second piggyBac ITR sequence, and a second AAV ITR sequence.

In some aspects, an AAV piggyBac transposon polynucleotide can comprise a first AAV ITR sequence, followed by a first piggyBac ITR sequence, followed by a first insulator sequence, followed by at least one promoter sequence, followed by a first transgene sequence, followed by at least one self-cleaving peptide sequence, followed by an at least second transgene sequence, followed by a polyA sequence, followed by a second insulator sequence, followed by a second piggyBac ITR sequence, and followed by a second AAV ITR sequence.

Figure 4:
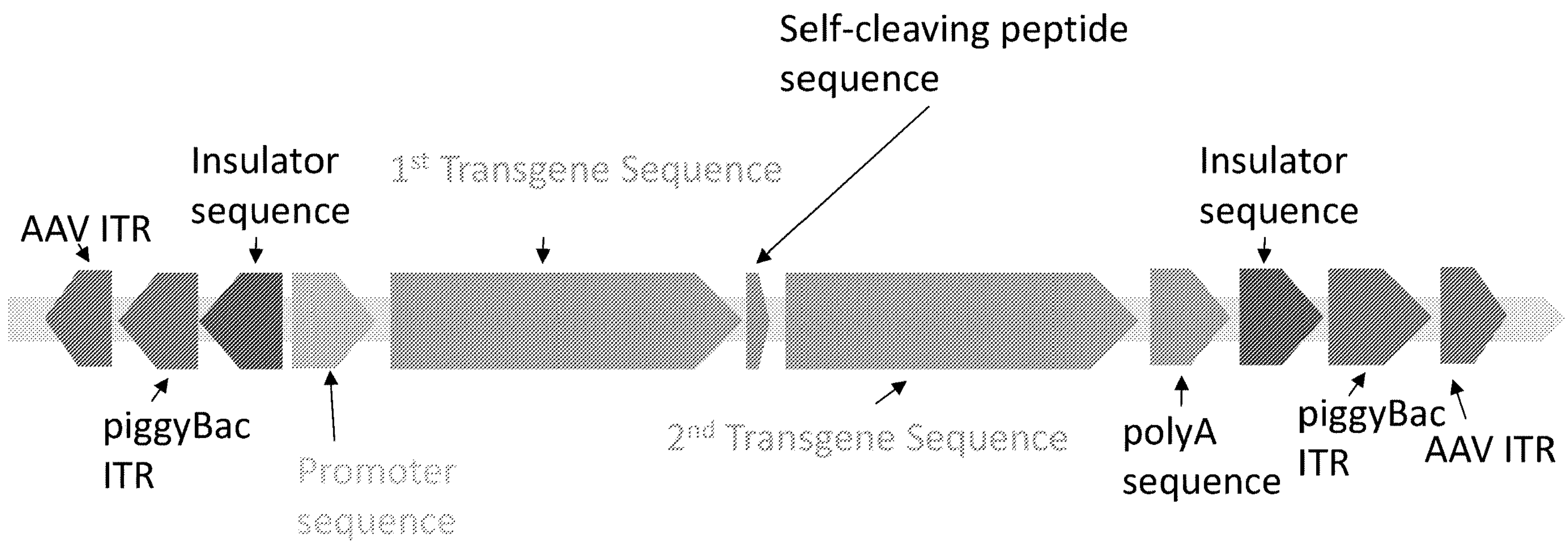
FIG. 4 is a schematic of an exemplary AAV piggyBac transposon polynucleotide of the present disclosure.

A schematic of the preceding AAV piggyBac transposon polynucleotide is shown in FIG. 4.

In another non-limiting example of the preceding AAV piggyBac transposon polynucleotides the at least one promoter sequence can comprise an HLP promoter sequence, the first transgene sequence can comprise a nucleic acid sequence that encodes for FVIII polypeptide, the at least one self-cleaving peptide sequence can comprise that encodes for a T2A peptide and the at least second transgene sequence can comprise a luciferase sequence (e.g. NanoLuc). This non-limiting example of an AAV piggyBac transposon polynucleotide is shown in FIG. 4.

In another non-limiting example of the preceding AAV piggyBac transposon polynucleotides the at least one promoter sequence can comprise an TTRm promoter sequence, the first transgene sequence can comprise a nucleic acid sequence that encodes for FVIII polypeptide, the at least one self-cleaving peptide sequence can comprise that encodes for a T2A peptide and the at least second transgene sequence can comprise a luciferase sequence (e.g. NanoLuc). This non-limiting example of an AAV piggyBac transposon polynucleotide is shown in FIG. 4.

In another non-limiting example of the preceding AAV piggyBac transposon polynucleotides the at least one promoter sequence can comprise an HLP promoter sequence, the first transgene sequence can comprise a nucleic acid sequence that encodes for FIX polypeptide, the at least one self-cleaving peptide sequence can comprise that encodes for a T2A peptide and the at least second transgene sequence can comprise a luciferase sequence (e.g. NanoLuc). This non-limiting example of an AAV piggyBac transposon polynucleotide is shown in FIG. 4.

In another non-limiting example of the preceding AAV piggyBac transposon polynucleotides the at least one promoter sequence can comprise an TTRm promoter sequence, the first transgene sequence can comprise a nucleic acid sequence that encodes for FIX polypeptide, the at least one self-cleaving peptide sequence can comprise that encodes for a T2A peptide and the at least second transgene sequence can comprise a luciferase sequence (e.g. NanoLuc). This non-limiting example of an AAV piggyBac transposon polynucleotide is shown in FIG. 4.

In another non-limiting example of the preceding AAV piggyBac transposon polynucleotides the at least one promoter sequence can comprise an TTRm promoter sequence, the first transgene sequence can comprise a nucleic acid sequence that encodes for FIX polypeptide, the at least one self-cleaving peptide sequence can comprise that encodes for a GSG-T2A peptide and the at least second transgene sequence can comprise a luciferase sequence (e.g. NanoLuc). This non-limiting example of an AAV piggyBac transposon polynucleotide is shown in FIG. 4.

An AAV piggyBac transposon polynucleotide can comprise a first AAV ITR sequence, a first piggyBac ITR sequence, a first insulator sequence, a first promoter sequence, a first transgene sequence, at least a second promoter sequence, an at least second transgene sequence, a polyA sequence, a second insulator sequence, a second piggyBac ITR sequence, and a second AAV ITR sequence.

An AAV piggyBac transposon polynucleotide can comprise in the 5' to 3' direction a first AAV ITR sequence, a first piggyBac ITR sequence, a first insulator sequence, a first promoter sequence, a first transgene sequence, an at least a second promoter sequence, an at least second transgene sequence, a polyA sequence, a second insulator sequence, a second piggyBac ITR sequence, and a second AAV ITR sequence.

An AAV piggyBac transposon polynucleotide can comprise a first AAV ITR sequence, followed by a first piggyBac ITR sequence, followed by a first insulator sequence, followed by a first promoter sequence, followed by a first transgene sequence, followed by an at least a second promoter sequence, followed by an at least second transgene sequence, followed by a polyA sequence, followed by a second insulator sequence, followed by a second piggyBac ITR sequence and followed by a second AAV ITR sequence.

In some aspects, an AAV piggyBac transposon polynucleotide can comprise more than one transgene sequence. In some aspects wherein the AAV piggyBac transposon polynucleotide comprises more than one transgene sequence, individual transgene sequences can be separated by a self-cleaving peptide sequence. In some aspects wherein the AAV piggyBac transposon polynucleotide comprises more than one self-cleaving peptide sequence, the self-cleaving peptide sequences can be the same or can be different.

In some aspects, an AAV piggyBac transposon polynucleotide can comprise more than one transgene sequence. In some aspects wherein the AAV piggyBac transposon polynucleotide comprises more than one transgene sequence, the AAV piggyBac transposon may comprise multiple copies of a nucleic acid sequence that encodes for the same polypeptide.

In some aspects, an AAV piggyBac transposon polynucleotide can comprise more than one promoter sequence. In some aspects wherein the AAV piggyBac transposon polynucleotide comprises more than one promoter sequence, the promoter sequences can be the same or the promoter sequences can be different.

In some aspects, an AAV piggyBac transposon polynucleotide can comprise a first AAV ITR sequence, a first piggyBac ITR sequence, a first insulator sequence, at least one promoter sequence, a first transgene sequence, a first self-cleaving peptide sequence, a second transgene sequence, an at least second self-cleaving peptide sequence, at least a third transgene sequence, a polyA sequence, a second insulator sequence and a second AAV ITR sequence.

In some aspects, an AAV piggyBac transposon polynucleotide can comprise in the 5' to 3' direction a first AAV ITR sequence, a first piggyBac ITR sequence, a first insulator sequence, at least one promoter sequence, a first transgene sequence, a first self-cleaving peptide sequence, a second transgene sequence, an at least second self-cleaving peptide sequence, at least a third transgene sequence, a polyA sequence, a second insulator sequence and a second AAV ITR sequence.

In some aspects, an AAV piggyBac transposon polynucleotide can comprise a first AAV ITR sequence, followed by a first piggyBac ITR sequence, followed by a first insulator sequence, followed by at least one promoter sequence, followed by a first transgene sequence, followed by a first self-cleaving peptide sequence, followed by a second transgene sequence, followed by an at least second self-cleaving peptide sequence, followed by at least a third transgene sequence, followed by a polyA sequence, followed by a second insulator sequence and followed by a second AAV ITR sequence.

In some aspects, an AAV piggyBac transposon polynucleotide can comprise a first AAV ITR sequence, a first piggyBac ITR sequence, a first insulator sequence, at least one promoter sequence, a first transgene sequence, a first self-cleaving peptide sequence, a second transgene sequence, an at least second self-cleaving peptide sequence, at least a third transgene sequence, a polyA sequence, a second insulator sequence, a second piggyBac ITR sequence and a second AAV ITR sequence.

In some aspects, an AAV piggyBac transposon polynucleotide can comprise in the 5' to 3' direction a first AAV ITR sequence, a first piggyBac ITR sequence, a first insulator sequence, at least one promoter sequence, a first transgene sequence, a first self-cleaving peptide sequence, a second transgene sequence, an at least second self-cleaving peptide sequence, at least a third transgene sequence, a polyA sequence, a second insulator sequence, a second piggyBac ITR sequence and a second AAV ITR sequence.

In some aspects, an AAV piggyBac transposon polynucleotide can comprise a first AAV ITR sequence, followed by a first piggyBac ITR sequence, followed by a first insulator sequence, followed by at least one promoter sequence, followed by a first transgene sequence, followed by a first self-cleaving peptide sequence, followed by a second transgene sequence, followed by an at least second self-cleaving peptide sequence, followed by at least a third transgene sequence, followed by a polyA sequence, followed by a second insulator sequence, followed by a second piggyBac ITR sequence and followed by a second AAV ITR sequence An AAV piggyBac transposon polynucleotide can comprise a first nucleic acid sequence, a first piggyBac ITR sequence, a first insulator sequence, a second insulator sequence, a second piggyBac ITR sequence, and a second nucleic acid sequence.

In some aspects, an AAV piggyBac transposon polynucleotide can comprise in the 5' to 3' direction a first nucleic acid sequence, a first piggyBac ITR sequence, a first insulator sequence, a second insulator sequence, a second piggyBac ITR sequence, and a second nucleic acid sequence.

In some aspects, an AAV piggyBac transposon polynucleotide can comprise a first nucleic acid sequence, followed by a first piggyBac ITR sequence, followed by a first insulator sequence, followed by a second insulator sequence, followed by a second piggyBac ITR sequence, and followed by a second nucleic acid sequence.

An AAV piggyBac transposon polynucleotide can comprise a first nucleic acid sequence, a first piggyBac ITR sequence, a first insulator sequence, a second insulator sequence, a second piggyBac ITR sequence, and a second nucleic acid sequence, wherein between the first insulator sequence and the second insulator sequence there is any combination of at least one promoter sequence, at least one transgene sequence, at least one self-cleaving peptide sequence, and at least one polyA sequence.

In some aspects, an AAV piggyBac transposon polynucleotide can comprise in the 5' to 3' direction a first nucleic acid sequence, a first piggyBac ITR sequence, a first insulator sequence, a second insulator sequence, a second piggyBac ITR sequence, and a second nucleic acid sequence, wherein between the first insulator sequence and the second insulator sequence there is any combination of at least one promoter sequence, at least one transgene sequence, at least one self-cleaving peptide sequence, and at least one polyA sequence.

In some aspects, an AAV piggyBac transposon polynucleotide can comprise a first nucleic acid sequence, followed by a first piggyBac ITR sequence, followed by a first insulator sequence, followed by a second insulator sequence, followed by a second piggyBac ITR sequence, and followed by a second nucleic acid sequence, wherein between the first insulator sequence and the second insulator sequence there is any combination of at least one promoter sequence, at least one transgene sequence, at least one self-cleaving peptide sequence, and at least one polyA sequence.

An AAV piggyBac transposon polynucleotide can comprise a first nucleic acid sequence, a first piggyBac ITR sequence, a first insulator sequence, at least one promoter sequence, at least one transgene sequence, a polyA sequence, a second insulator sequence, a second piggyBac ITR sequence, and a second nucleic acid sequence.

In some aspects, an AAV piggyBac transposon polynucleotide can comprise in the 5' to 3' direction a first nucleic acid sequence, a first piggyBac ITR sequence, a first insulator sequence, at least one promoter sequence, at least one transgene sequence, a polyA sequence, a second insulator sequence, a second piggyBac ITR sequence, and a second nucleic acid sequence.

In some aspects, an AAV piggyBac transposon polynucleotide can comprise a first nucleic acid sequence, followed by a first piggyBac ITR sequence, followed by a first insulator sequence, followed by at least one promoter sequence, followed by at least one transgene sequence, followed by a polyA sequence, followed by a second insulator sequence, followed by a second piggyBac ITR sequence, and followed by a second nucleic acid sequence.

An AAV piggyBac transposon polynucleotide can comprise a first nucleic acid sequence, a first piggyBac ITR sequence, a first insulator sequence, at least one promoter sequence, at least one transgene sequence, a polyA sequence, a second insulator sequence, a second piggyBac ITR sequence, at least one DNA spacer sequence and a second nucleic acid sequence.

In some aspects, an AAV piggyBac transposon polynucleotide can comprise in the 5' to 3' direction a first nucleic acid sequence, a first piggyBac ITR sequence, a first insulator sequence, at least one promoter sequence, at least one transgene sequence, a polyA sequence, a second insulator sequence, a second piggyBac ITR sequence, at least one DNA spacer sequence and a second nucleic acid sequence.

In some aspects, an AAV piggyBac transposon polynucleotide can comprise a first nucleic acid sequence, followed by a first piggyBac ITR sequence, followed by a first insulator sequence, followed by at least one promoter sequence, followed by at least one transgene sequence, followed by a polyA sequence, followed by a second insulator sequence, followed by a second piggyBac ITR sequence, followed by at least one DNA spacer sequence and followed by a second nucleic acid sequence.

An AAV piggyBac transposon polynucleotide can comprise a first nucleic acid sequence, a first piggyBac ITR sequence, a first insulator sequence, at least one promoter sequence, at least one transgene sequence, a polyA sequence, a second insulator sequence, a second piggyBac ITR sequence, a second nucleic acid sequence and at least one DNA spacer sequence.

In some aspects, an AAV piggyBac transposon polynucleotide can comprise in the 5' to 3' direction a first nucleic acid sequence, a first piggyBac ITR sequence, a first insulator sequence, at least one promoter sequence, at least one transgene sequence, a polyA sequence, a second insulator sequence, a second piggyBac ITR sequence, a second nucleic acid sequence and at least one DNA spacer sequence.

In some aspects, an AAV piggyBac transposon polynucleotide can comprise a first nucleic acid sequence, followed by a first piggyBac ITR sequence, followed by a first insulator sequence, followed by at least one promoter sequence, followed by at least one transgene sequence, followed by a polyA sequence, followed by a second insulator sequence, followed by a second piggyBac ITR sequence, followed by a second nucleic acid sequence and followed by at least one DNA spacer sequence.

An AAV piggyBac transposon polynucleotide can comprise a first nucleic acid sequence, a first piggyBac ITR sequence, a first insulator sequence, at least one promoter sequence, a first transgene sequence, at least one self-cleaving peptide sequence, an at least second transgene sequence, a polyA sequence, a second insulator sequence, a second piggyBac ITR sequence, and a second nucleic acid sequence.

In some aspects, an AAV piggyBac transposon polynucleotide can comprise in the 5' to 3' direction a first nucleic acid sequence, a first piggyBac ITR sequence, a first insulator sequence, at least one promoter sequence, a first transgene sequence, at least one self-cleaving peptide sequence, an at least second transgene sequence, a polyA sequence, a second insulator sequence, a second piggyBac ITR sequence, and a second nucleic acid sequence.

In some aspects, an AAV piggyBac transposon polynucleotide can comprise a first nucleic acid sequence, followed by a first piggyBac ITR sequence, followed by a first insulator sequence, followed by at least one promoter sequence, followed by a first transgene sequence, followed by at least one self-cleaving peptide sequence, followed by an at least second transgene sequence, followed by a polyA sequence, followed by a second insulator sequence, followed by a second piggyBac ITR sequence, and followed by a second nucleic acid sequence.

An AAV piggyBac transposon polynucleotide can comprise a first nucleic acid sequence, a first piggyBac ITR sequence, a first insulator sequence, a first promoter sequence, a first transgene sequence, at least a second promoter sequence, an at least second transgene sequence, a polyA sequence, a second insulator sequence, a second piggyBac ITR sequence, and a second nucleic acid sequence.

An AAV piggyBac transposon polynucleotide can comprise in the 5' to 3' direction a first nucleic acid sequence, a first piggyBac ITR sequence, a first insulator sequence, a first promoter sequence, a first transgene sequence, an at least a second promoter sequence, an at least second transgene sequence, a polyA sequence, a second insulator sequence, a second piggyBac ITR sequence, and a second nucleic acid sequence.

An AAV piggyBac transposon polynucleotide can comprise a first nucleic acid sequence, followed by a first piggyBac ITR sequence, followed by a first insulator sequence, followed by a first promoter sequence, followed by a first transgene sequence, followed by an at least a second promoter sequence, followed by an at least second transgene sequence, followed by a polyA sequence, followed by a second insulator sequence, followed by a second piggyBac ITR sequence and followed by a second nucleic acid sequence.

In some aspects, an AAV piggyBac transposon polynucleotide can comprise a first nucleic acid sequence, a first piggyBac ITR sequence, a first insulator sequence, at least one promoter sequence, a first transgene sequence, a first self-cleaving peptide sequence, a second transgene sequence, an at least second self-cleaving peptide sequence, at least a third transgene sequence, a polyA sequence, a second insulator sequence and a second nucleic acid sequence.

In some aspects, an AAV piggyBac transposon polynucleotide can comprise in the 5' to 3' direction a first nucleic acid sequence, a first piggyBac ITR sequence, a first insulator sequence, at least one promoter sequence, a first transgene sequence, a first self-cleaving peptide sequence, a second transgene sequence, an at least second self-cleaving peptide sequence, at least a third transgene sequence, a polyA sequence, a second insulator sequence and a second nucleic acid sequence.

In some aspects, an AAV piggyBac transposon polynucleotide can comprise a first nucleic acid sequence, followed by a first piggyBac ITR sequence, followed by a first insulator sequence, followed by at least one promoter sequence, followed by a first transgene sequence, followed by a first self-cleaving peptide sequence, followed by a second transgene sequence, followed by an at least second self-cleaving peptide sequence, followed by at least a third transgene sequence, followed by a polyA sequence, followed by a second insulator sequence and followed by a second nucleic acid sequence.

In some aspects, an AAV piggyBac transposon polynucleotide can comprise a first nucleic acid sequence, a first piggyBac ITR sequence, a first insulator sequence, at least one promoter sequence, a first transgene sequence, a first self-cleaving peptide sequence, a second transgene sequence, an at least second self-cleaving peptide sequence, at least a third transgene sequence, a polyA sequence, a second insulator sequence, a second piggyBac ITR sequence and a second nucleic acid sequence.

In some aspects, an AAV piggyBac transposon polynucleotide can comprise in the 5' to 3' direction a first nucleic acid sequence, a first piggyBac ITR sequence, a first insulator sequence, at least one promoter sequence, a first transgene sequence, a first self-cleaving peptide sequence, a second transgene sequence, an at least second self-cleaving peptide sequence, at least a third transgene sequence, a polyA sequence, a second insulator sequence, a second piggyBac ITR sequence and a second nucleic acid sequence.

In some aspects, an AAV piggyBac transposon polynucleotide can comprise a first nucleic acid sequence, followed by a first piggyBac ITR sequence, followed by a first insulator sequence, followed by at least one promoter sequence, followed by a first transgene sequence, followed by a first self-cleaving peptide sequence, followed by a second transgene sequence, followed by an at least second self-cleaving peptide sequence, followed by at least a third transgene sequence, followed by a polyA sequence, followed by a second insulator sequence, followed by a second piggyBac ITR sequence and followed by a second nucleic acid sequence.

The present disclosure further provides polynucleotide molecules comprising the same structure as the AAV piggyBac transposon polynucleotides described above except without the first AAV ITR sequence and the second AAV ITR sequence.

AAV ITR Sequences

In some aspects, an AAV ITR sequence can comprise any AAV ITR sequence known in the art. In some aspects, an AAV ITR sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to any one of the sequences put forth in SEQ ID NOs: 1, 2, 17 and 18.

In some aspects, a first AAV ITR sequence can comprise consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 1 and a second AAV ITR sequence can comprise consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 2.

In some aspects, a first AAV ITR sequence can comprise consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 17 and a second AAV ITR sequence can comprise consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 18.

First and Second Nucleic Acid Sequences

In some aspects, a first nucleic acid sequence or a second nucleic acid sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to any one of the sequences put forth in SEQ ID NOs: 1, 2, 17 and 18.

In some aspects, a first nucleic acid sequence can comprise consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 1 and a second nucleic acid sequence can comprise consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 2.

In some aspects, a first nucleic acid sequence can comprise consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 17 and a second nucleic acid sequence can comprise consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 18.

piggyBac ITR Sequences

In some aspects, a piggyBac ITR sequence can comprise any piggyBac ITR sequence known in the art. In some aspects, a piggyBac ITR sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to any one of the sequences put forth in SEQ ID NOs: 3, 4, 19 and 21.

In some aspects, a piggyBac ITR sequence can comprise any piggyBac ITR sequence known in the art. In some aspects, a piggyBac ITR sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to any one of the sequences put forth in SEQ ID NOs: 1 and 2.

In some aspects, a piggyBac ITR sequence can comprise any piggyBac ITR sequence known in the art. In some aspects, a piggyBac ITR sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to any one of the sequences put forth in SEQ ID NOs: 79 and 80.

In some aspects, a first piggyBac ITR sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 3 and a second piggyBac ITR sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 4.

In some aspects, a first piggyBac ITR sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 19 and a second piggyBac ITR sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 21.

In some aspects, a first piggyBac ITR sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 79 and a second piggyBac ITR sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 80.

In some aspects of the methods of the present disclosure, a piggyBac ITR sequence, such as a first piggyBac ITR sequence and/or a second piggyBac ITR sequence in an AAV piggyBac transposon can comprise, consist essentially of, or consist of a Sleeping Beauty transposon ITR, a Helraiser transposon ITR, a Tol2 transposon ITR, a TcBuster transposon ITR or any combination thereof.

In some aspects, a piggyBac ITR sequence of the present disclosure can be flanked on either or both ends by at least one of the following sequences: 5'-CTAA-3', 5'-TTAG-3', 5'-ATAA-3', 5'-TCAA-3', 5'AGTT-3', 5'-ATTA-3', 5'-GTTA-3', 5'-TTGA-3', 5'-TTTA-3', 5'-TTAC-3', 5'-ACTA-3', 5'-AGGG-3', 5'-CTAG-3', 5'-TGAA-3', 5'-AGGT-3', 5'-ATCA-3', 5'-CTCC-3', 5'-TAAA-3', 5'-TCTC-3', 5'TGAA-3', 5'-AAAT-3', 5'-AATC-3', 5'-ACAA-3', 5'-ACAT-3', 5'-ACTC-3', 5'-AGTG-3', 5'-ATAG-3', 5'-CAAA-3', 5'-CACA-3', 5'-CATA-3', 5'-CCAG-3', 5'-CCCA-3', 5'-CGTA-3', 5'-GTCC-3', 5'-TAAG-3', 5'-TCTA-3', 5'-TGAG-3', 5'-TGTT-3', 5'-TTCA-3'5'-TTCT-3' and 5'-TTTT-3'. In some aspects, a piggyBac ITR sequence can be flanked by 5'-TTAA-3'. Thus, any AAV transposase polynucleotide, AAV piggyBac transposon polynucleotide and/or any liver nanoplasmid of the present disclosure can further comprise any one of: 5'-CTAA-3', 5'-TTAG-3', 5'-ATAA-3', 5'-TCAA-3', 5'AGTT-3', 5'-ATTA-3', 5'-GTTA-3', 5'-TTGA-3', 5'-TTTA-3', 5'-TTAC-3', 5'-ACTA-3', 5'-AGGG-3', 5'-CTAG-3', 5'-TGAA-3', 5'-AGGT-3', 5'-ATCA-3', 5'-CTCC-3', 5'-TAAA-3', 5'-TCTC-3', 5'TGAA-3', 5'-AAAT-3', 5'-AATC-3', 5'-ACAA-3', 5'-ACAT-3', 5'-ACTC-3', 5'-AGTG-3', 5'-ATAG-3', 5'-CAAA-3', 5'-CACA-3', 5'-CATA-3', 5'-CCAG-3', 5'-CCCA-3', 5'-CGTA-3', 5'-GTCC-3', 5'-TAAG-3', 5'-TCTA-3', 5'-TGAG-3', 5'-TGTT-3', 5'-TTCA-3'5'-TTCT-3' and 5'-TTTT-3' flanking a piggyBac ITR sequence.

Insulator Sequences

In some aspects, an insulator sequence can comprise any insulator sequence known in the art. In some aspects, an insulator sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to any one of the sequences put forth in SEQ ID NOs: 5, 6 and 20.

In some aspects, a first insulator sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 5 and a second insulator sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to any SEQ ID NO: 6.

In some aspects, a first insulator sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 5 and a second insulator sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to any SEQ ID NO: 20.

Promoter Sequences

In some aspects, a promoter sequence can comprise any promoter sequence known in the art. In some aspects, a promoter sequence can comprise any liver-specific promoter sequence known in the art.

In some aspects, a promoter sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to any one of the sequences put forth in SEQ ID NOs: 7-12.

In some aspects, a promoter sequence can comprise an ApoEhAAT promoter sequence. An ApoEhAAT promoter sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 7.

In some aspects, a promoter sequence can comprise a TTR promoter sequence. A TTR promoter sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 8. A TTR promoter sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 9.

In some aspects, a promoter sequence can comprise an HLP promoter sequence. An HLP promoter sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 10.

In some aspects, a promoter sequence can comprise a TTRm promoter sequence. A TTRm promoter sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 11. A TTRm promoter sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 12.

Transgene Sequences

In some aspects, a transgene sequence can comprise a nucleic acid sequence that encodes for a Factor VIII (FVIII) polypeptide. In some aspects, a transgene sequence can comprise a nucleic acid sequence that encodes for a FVIII polypeptide, wherein the FVIII polypeptide comprises, consists essentially of or consist of an amino acid sequence at least 65%, 70%, 75%, 80%, 85%, 90%, 95%, 96%, 97%, 98%, 99% or 100% (or any percentage in between) identical to SEQ ID NO: 26. In some aspects, a nucleic acid sequence that encodes for a FVIII polypeptide can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 13.

In some aspects, a transgene sequence can comprise a nucleic acid sequence that encodes for a Factor IX (FIX) polypeptide. In some aspects, a transgene sequence can comprise a nucleic acid sequence that encodes for a FIX polypeptide, wherein the FIX polypeptide comprises, consists essentially of or consist of an amino acid sequence at least 65%, 70%, 75%, 80%, 85%, 90%, 95%, 96%, 97%, 98%, 99% or 100% (or any percentage in between) identical to SEQ ID NO: 27. In some aspects, a nucleic acid sequence that encodes for a FIX polypeptide can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 23.

In some aspects, a transgene sequence can be codon optimized according to methods known in the art.

In some aspects, the nucleic acid sequence encoding a polypeptide (e.g. FVIII, FIX) can be a codon optimized nucleic acid sequence that encodes for the polypeptide. A codon optimized nucleic acid sequence encoding a polypeptide can comprise, consist essentially of, or consist of a nucleic acid sequence that is no more than 65%, 70%, 75%, 80%, 85%, 90%, 95%, 96%, 97%, 98%, 99% (or any percentage in between) identical to the wildtype human nucleic acid sequence encoding the polypeptide.

SEQ ID NOs: 13 and 23 are unique codon optimized nucleic acid sequences that can be included in the polynucleotides, vectors and compositions of the present disclosure.

In some aspects, a codon optimized nucleic acid sequence encoding a polypeptide, such as those put forth in SEQ ID NOs: 13 and 23, can comprise no donor splice sites. In some aspects, a codon optimized nucleic acid sequence encoding a polypeptide can comprise no more than about one, or about two, or about three, or about four, or about five, or about six, or about seven, or about eight, or about nine, or about ten donor splice sites. In some aspects, a codon optimized nucleic acid sequence encoding a polypeptide comprises at least one, or at least two, or at least three, or at least four, or at least five, or at least six, or at least seven, or at least eight, or at least nine, or at least ten fewer donor splice sites as compared to the wildtype human nucleic acid sequence encoding the polypeptide. Without wishing to be bound by theory, the removal of donor splice sites in the codon optimized nucleic acid sequence can unexpectedly and unpredictably increase expression of the polypeptide in vivo, as cryptic splicing is prevented. Moreover, cryptic splicing may vary between different subjects, meaning that the expression level of the polypeptide comprising donor splice sites may unpredictably vary between different subjects.

In some aspects, a codon optimized nucleic acid sequence encoding a polypeptide, such as those put forth in SEQ ID NOs: 13 and 23, can have a GC content that differs from the GC content of the wildtype human nucleic acid sequence encoding the polypeptide. In some aspects, the GC content of a codon optimized nucleic acid sequence encoding a polypeptide is more evenly distributed across the entire nucleic acid sequence, as compared to the wildtype human nucleic acid sequence encoding the polypeptide. Without wishing to be bound by theory, by more evenly distributing the GC content across the entire nucleic acid sequence, the codon optimized nucleic acid sequence exhibits a more uniform melting temperature ("Tm") across the length of the transcript. The uniformity of melting temperature results unexpectedly in increased expression of the codon optimized nucleic acid in a human subject, as transcription and/or translation of the nucleic acid sequence occurs with less stalling of the polymerase and/or ribosome.

In some aspects, the codon optimized nucleic acid sequence encoding a polypeptide, such as those put forth in SEQ ID NOs: 13 and 23, exhibits at least 5%, at least 10%, at least 20%, at least 30%, at least 50%, at least 75%, at least 100%, at least 200%, at least 300%, at least 500%, or at least 1000% increased expression in a human subject relative to a wild-type or non-codon optimized nucleic acid sequence encoding the polypeptide.

In some aspects, an at least one transgene sequence can be operatively linked to at least one promoter sequence present in the same polynucleotide.

polyA Sequences

In some aspects, a polyA sequence can comprise any polyA sequence known in the art. Non-limiting examples of polyA sequences include, but are not limited to, SV40 polyA sequences In some aspects, an insulator sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to any one of the sequences put forth in SEQ ID NOs: 14 and 22.

Self-Cleaving Peptide Sequence

In some aspects, a self-cleaving peptide sequence can comprise any self-cleaving peptide sequence known in the art. In some aspects, a self-cleaving peptide sequence can comprise an 2A self-cleaving peptide sequence known in the art. Non-limiting examples of self-cleaving peptides include a T2A peptide, GSG-T2A peptide, an E2A peptide, a GSG-E2A peptide, an F2A peptide, a GSG-F2A peptide, a P2A peptide, or a GSG-P2A peptide.

In some aspects, a self-cleaving peptide sequence can comprise a nucleic acid sequence that encodes for a T2A peptide. In some aspects, a nucleic acid sequence that encodes for a T2A peptide can comprise, consist essentially of or consist of a nucleic acid sequence at least 65%, 70%, 75%, 80%, 85%, 90%, 95%, 96%, 97%, 98%, 99% or 100% (or any percentage in between) identical to SEQ ID NO: 15.

In some aspects, a self-cleaving peptide sequence can comprise a nucleic acid sequence that encodes for a GSG-T2A peptide. In some aspects, a nucleic acid sequence that encodes for a GSG-T2A peptide can comprise, consist essentially of or consist of a nucleic acid sequence at least 65%, 70%, 75%, 80%, 85%, 90%, 95%, 96%, 97%, 98%, 99% or 100% (or any percentage in between) identical to SEQ ID NO: 24.

DNA Spacer Sequences

In some aspects, a DNA spacer sequence can comprise, consist essentially of or consist of a nucleic acid sequence at least 65%, 70%, 75%, 80%, 85%, 90%, 95%, 96%, 97%, 98%, 99% or 100% (or any percentage in between) identical to SEQ ID NO: 28.

DNA spacer sequences can be located at any position within an AAV piggyBac transposon polynucleotide or an AAV piggyBac transposase polynucleotide.

In some aspects, a AAV piggyBac transposon polynucleotide can comprise, consist essentially of or consist of a nucleic acid sequence at least 65%, 70%, 75%, 80%, 85%, 90%, 95%, 96%, 97%, 98%, 99% or 100% (or any percentage in between) identical to SEQ ID NO: 29.

In some aspects, a AAV piggyBac transposon polynucleotide can comprise, consist essentially of or consist of a nucleic acid sequence at least 65%, 70%, 75%, 80%, 85%, 90%, 95%, 96%, 97%, 98%, 99% or 100% (or any percentage in between) identical to SEQ ID NO: 30.

In some aspects, a AAV piggyBac transposon polynucleotide can comprise, consist essentially of or consist of a nucleic acid sequence at least 65%, 70%, 75%, 80%, 85%, 90%, 95%, 96%, 97%, 98%, 99% or 100% (or any percentage in between) identical to SEQ ID NO: 31.

In some aspects, a AAV piggyBac transposon polynucleotide can comprise, consist essentially of or consist of a nucleic acid sequence at least 65%, 70%, 75%, 80%, 85%, 90%, 95%, 96%, 97%, 98%, 99% or 100% (or any percentage in between) identical to SEQ ID NO: 32.

In some aspects, a AAV piggyBac transposon polynucleotide can comprise, consist essentially of or consist of a nucleic acid sequence at least 65%, 70%, 75%, 80%, 85%, 90%, 95%, 96%, 97%, 98%, 99% or 100% (or any percentage in between) identical to SEQ ID NO: 33.

In some aspects, a AAV piggyBac transposon polynucleotide can comprise, consist essentially of or consist of a nucleic acid sequence at least 65%, 70%, 75%, 80%, 85%, 90%, 95%, 96%, 97%, 98%, 99% or 100% (or any percentage in between) identical to SEQ ID NO: 34.

In some aspects, a AAV piggyBac transposon polynucleotide can comprise, consist essentially of or consist of a nucleic acid sequence at least 65%, 70%, 75%, 80%, 85%, 90%, 95%, 96%, 97%, 98%, 99% or 100% (or any percentage in between) identical to SEQ ID NO: 35.

In some aspects, a AAV piggyBac transposon polynucleotide can comprise, consist essentially of or consist of a nucleic acid sequence at least 65%, 70%, 75%, 80%, 85%, 90%, 95%, 96%, 97%, 98%, 99% or 100% (or any percentage in between) identical to SEQ ID NO: 36.

In some aspects, a AAV piggyBac transposon polynucleotide can comprise, consist essentially of or consist of a nucleic acid sequence at least 65%, 70%, 75%, 80%, 85%, 90%, 95%, 96%, 97%, 98%, 99% or 100% (or any percentage in between) identical to SEQ ID NO: 37.

In some aspects, a AAV piggyBac transposon polynucleotide can comprise, consist essentially of or consist of a nucleic acid sequence at least 65%, 70%, 75%, 80%, 85%, 90%, 95%, 96%, 97%, 98%, 99% or 100% (or any percentage in between) identical to SEQ ID NO: 38.

In some aspects, a AAV piggyBac transposon polynucleotide can comprise, consist essentially of or consist of a nucleic acid sequence at least 65%, 70%, 75%, 80%, 85%, 90%, 95%, 96%, 97%, 98%, 99% or 100% (or any percentage in between) identical to SEQ ID NO: 39.

In some aspects, a AAV piggyBac transposon polynucleotide can comprise, consist essentially of or consist of a nucleic acid sequence at least 65%, 70%, 75%, 80%, 85%, 90%, 95%, 96%, 97%, 98%, 99% or 100% (or any percentage in between) identical to SEQ ID NO: 40.

In some aspects, a AAV piggyBac transposon polynucleotide can comprise, consist essentially of or consist of a nucleic acid sequence at least 65%, 70%, 75%, 80%, 85%, 90%, 95%, 96%, 97%, 98%, 99% or 100% (or any percentage in between) identical to SEQ ID NO: 41.

The present disclosure also provides a polynucleotide can comprising, consisting essentially of or consisting of a nucleic acid sequence at least 65%, 70%, 75%, 80%, 85%, 90%, 95%, 96%, 97%, 98%, 99% or 100% (or any percentage in between) identical to any one of SEQ ID NOs: 29-41.

AAV Transposase Polynucleotides

The present disclosure provides compositions comprising AAV transposase polynucleotides.

In some aspects an AAV transposase polynucleotide can comprise at least one AAV inverted terminal repeat (ITR) sequence. In some aspects an AAV transposase polynucleotide can comprise at least one promoter sequence. In some aspects, an AAV transposase polynucleotide can comprise at least one transposase sequence. In some aspects, an AAV transposon polynucleotide can comprise at least one polyA sequence. In some aspects, an AAV transposon polynucleotide can comprise at least one DNA spacer sequence.

In some aspects, an AAV transposase polynucleotide can comprise a first AAV ITR sequence, at least one promoter sequence, at least one transposase sequence, a polyA sequence and a second AAV ITR sequence.

In some aspects, an AAV transposase polynucleotide can comprise in the 5' to 3' direction a first AAV ITR sequence, at least one promoter sequence, at least one transposase sequence, a polyA sequence and a second AAV ITR sequence.

In some aspects, an AAV transposase polynucleotide can comprise a first AAV ITR sequence, followed by at least one promoter sequence, followed by at least one transposase sequence, followed by a polyA sequence and followed by a second AAV ITR sequence.

In some aspects, an AAV transposase polynucleotide can comprise a first AAV ITR sequence, at least one promoter sequence, at least one transposase sequence, a polyA sequence, at least one DNA spacer sequence and a second AAV ITR sequence.

In some aspects, an AAV transposase polynucleotide can comprise in the 5' to 3' direction a first AAV ITR sequence, at least one promoter sequence, at least one transposase sequence, a polyA sequence, at least one DNA spacer sequence and a second AAV ITR sequence.

In some aspects, an AAV transposase polynucleotide can comprise a first AAV ITR sequence, followed by at least one promoter sequence, followed by at least one transposase sequence, followed by a polyA sequence, followed by at least one DNA spacer sequence and followed by a second AAV ITR sequence.

In a non-limiting example of the preceding AAV transposase polynucleotides, the at least one promoter sequence can comprise a hybrid liver promoter (HLP) and the at least one transposase sequence can comprise a nucleic acid sequence encoding a Super piggyBac™ (SPB) transposase polypeptide. This non-limiting example of an AAV piggyBac transposon polynucleotide is shown in FIG. 3A.

Figure 3A:
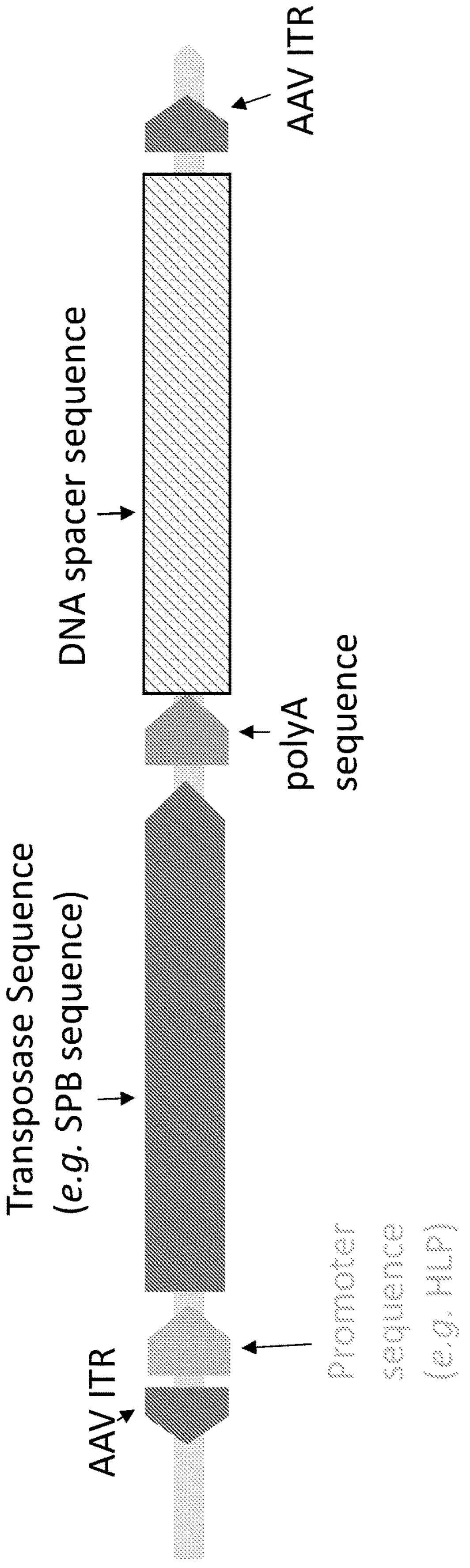
FIG. 3A is a schematic of an exemplary AAV transposase polynucleotide of the present disclosure.

In some aspects, an AAV transposase polynucleotide can comprise, in between a polyA sequence and a second AAV ITR sequence, at least one DNA spacer sequence, as is shown in the non-limiting example presented in FIG. 3A.

In some aspects, an AAV transposase polynucleotide can comprise a first AAV ITR sequence, at least one promoter sequence, at least one transposase sequence, a polyA sequence, a second AAV ITR sequence and at least one DNA spacer sequence.

In some aspects, an AAV transposase polynucleotide can comprise in the 5' to 3' direction a first AAV ITR sequence, at least one promoter sequence, at least one transposase sequence, a polyA sequence, a second AAV ITR sequence and at least one DNA spacer sequence.

In some aspects, an AAV transposase polynucleotide can comprise a first AAV ITR sequence, followed by at least one promoter sequence, followed by at least one transposase sequence, followed by a polyA sequence, followed by a second AAV ITR sequence and followed by at least one DNA spacer sequence.

In a non-limiting example of the preceding AAV transposase polynucleotides, the at least one promoter sequence can comprise a hybrid liver promoter (HLP) and the at least one transposase sequence can comprise a nucleic acid sequence encoding a Super piggyBac™ (SPB) transposase polypeptide. This non-limiting example of an AAV piggyBac transposon polynucleotide is shown in FIG. 3B.

Figure 3B:
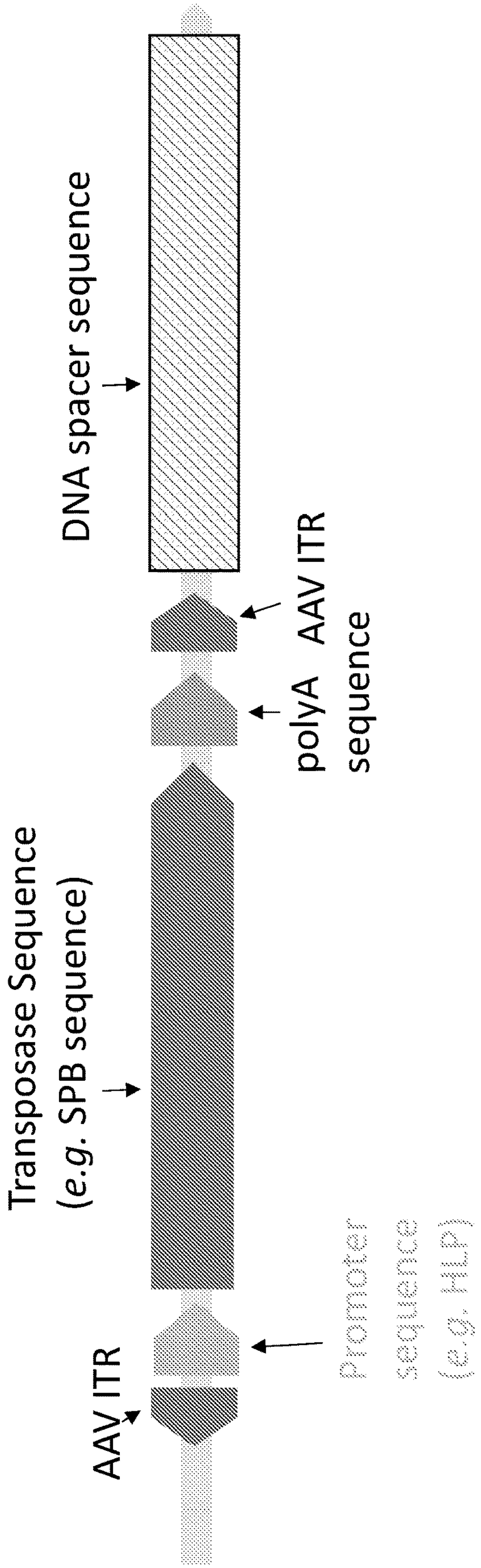
FIG. 3B is a schematic of an exemplary AAV transposase polynucleotide of the present disclosure.

In some aspects, an AAV transposase polynucleotide can comprise, after a second AAV ITR sequence, at least one DNA spacer sequence, as is shown in the non-limiting example presented in FIG. 3B.

In some aspects, an AAV transposase polynucleotide can comprise, consist essentially of or consist of a nucleic acid sequence at least 65%, 70%, 75%, 80%, 85%, 90%, 95%, 96%, 97%, 98%, 99% or 100% (or any percentage in between) identical to the sequence put forth in SEQ ID NO: 42.

In some aspects, an AAV transposase polynucleotide can comprise, consist essentially of or consist of a nucleic acid sequence at least 65%, 70%, 75%, 80%, 85%, 90%, 95%, 96%, 97%, 98%, 99% or 100% (or any percentage in between) identical to the sequence put forth in SEQ ID NO: 43.

Transposase Sequences

In some aspects, a transposase sequence can comprise a nucleic acid sequence that encodes for any transposase polypeptide known in the art. In some aspects, a transposase sequence can comprise a nucleic acid sequence that encodes for a piggyBac™ (PB) transposase polypeptide. In some aspects, a transposase sequence can comprise a nucleic acid sequence that encodes for a piggyBac-like (PBL) transposase polypeptide. In some aspects, a transposase sequence can comprise a nucleic acid sequence that encodes for a Super piggyBac™ (SPB) transposase polypeptide.

Non-limiting examples of PB transposons and PB, PBL and SPB transposases are described in detail in U.S. Pat. Nos. 6,218,182; 6,962,810; 8,399,643 and PCT Publication No. WO 2010/099296.

The PB, PBL and SPB transposases recognize transposon-specific inverted terminal repeat sequences (ITRs) on the ends of the transposon, and inserts the contents between the ITRs at the sequence 5'-TTAA-3' within a chromosomal site (a TTAA target sequence). The target sequence of the PB or PBL transposon can comprise or consist of 5'-CTAA-3', 5'-TTAG-3', 5'-ATAA-3', 5'-TCAA-3', 5'AGTT-3', 5'-ATTA-3', 5'-GTTA-3', 5'-TTGA-3', 5'-TTTA-3', 5'-TTAC-3', 5'-ACTA-3', 5'-AGGG-3', 5'-CTAG-3', 5'-TGAA-3', 5'-AGGT-3', 5'-ATCA-3', 5'-CTCC-3', 5'-TAAA-3', 5'-TCTC-3', 5'TGAA-3', 5'-AAAT-3', 5'-AATC-3', 5'-ACAA-3', 5'-ACAT-3', 5'-ACTC-3', 5'-AGTG-3', 5'-ATAG-3', 5'-CAAA-3', 5'-CACA-3', 5'-CATA-3', 5'-CCAG-3', 5'-CCCA-3', 5'-CGTA-3', 5'-GTCC-3', 5'-TAAG-3', 5'-TCTA-3', 5'-TGAG-3', 5'-TGTT-3', 5'-TTCA-3'5'-TTCT-3' and 5'-TTTT-3'. The PB or PBL transposon system has no payload limit for the genes of interest that can be included between the ITRs.

Exemplary amino acid sequences for one or more PB, PBL and SPB transposases are disclosed in U.S. Pat. Nos. 6,218,185; 6,962,810 and 8,399,643. In a preferred aspect, the PB transposase comprises or consists of an amino acid sequence at least 65%, 70%, 75%, 80%, 85%, 90%, 95%, 96%, 97%, 98%, 99% or 100% (or any percentage in between) identical to SEQ ID NO: 44.

The PB or PBL transposase can comprise or consist of an amino acid sequence having an amino acid substitution at two or more, at three or more or at each of positions 30, 165, 282, and/or 538 of the sequence of SEQ ID NO: 44. The transposase can be a SPB transposase that comprises or consists of the amino acid sequence of the sequence of SEQ ID NO: 44 wherein the amino acid substitution at position 30 can be a substitution of a valine (V) for an isoleucine (I), the amino acid substitution at position 165 can be a substitution of a serine (S) for a glycine (G), the amino acid substitution at position 282 can be a substitution of a valine (V) for a methionine (M), and the amino acid substitution at position 538 can be a substitution of a lysine (K) for an asparagine (N). In a preferred aspect, the SPB transposase comprises or consists of an amino acid sequence at least 65%, 70%, 75%, 80%, 85%, 90%, 95%, 96%, 97%, 98%, 99% or 100% (or any percentage in between) identical to SEQ ID NO: 45.

In certain aspects wherein the transposase comprises the above-described mutations at positions 30, 165, 282 and/or 538, the PB, PBL and SPB transposases can further comprise an amino acid substitution at one or more of positions 3, 46, 82, 103, 119, 125, 177, 180, 185, 187, 200, 207, 209, 226, 235, 240, 241, 243, 258, 296, 298, 311, 315, 319, 327, 328, 340, 421, 436, 456, 470, 486, 503, 552, 570 and 591 of the sequence of SEQ ID NO: 44 or SEQ ID NO: 45 are described in more detail in PCT Publication No. WO 2019/173636 and PCT/US2019/049816.

In a preferred aspect, the PB transposase comprises or consists of an amino acid sequence at least 65%, 70%, 75%, 80%, 85%, 90%, 95%, 96%, 97%, 98%, 99% or 100% (or any percentage in between) identical to SEQ ID NO: 46.

The PB or PBL transposase can comprise or consist of an amino acid sequence having an amino acid substitution at two or more, at three or more or at each of positions 29, 164, 281, and/or 537 of the sequence of SEQ ID NO: 46. The transposase can be a SPB transposase that comprises or consists of the amino acid sequence of the sequence of SEQ ID NO: 46 wherein the amino acid substitution at position 29 can be a substitution of a valine (V) for an isoleucine (I), the amino acid substitution at position 164 can be a substitution of a serine (S) for a glycine (G), the amino acid substitution at position 281 can be a substitution of a valine (V) for a methionine (M), and the amino acid substitution at position 537 can be a substitution of a lysine (K) for an asparagine (N). In a preferred aspect, the SPB transposase comprises or consists of an amino acid sequence at least 65%, 70%, 75%, 80%, 85%, 90%, 95%, 96%, 97%, 98%, 99% or 100% (or any percentage in between) identical to SEQ ID NO: 47.

In certain aspects wherein the transposase comprises the above-described mutations at positions 29, 164, 281, and/or 537, the PB, PBL and SPB transposases can further comprise an amino acid substitution at one or more of positions 2, 45, 81, 102, 118, 124, 176, 179, 184, 186, 199, 206, 208, 225, 234, 239, 240, 242, 257, 295, 297, 310, 314, 318, 326, 327, 339, 420, 435, 455, 469, 485, 502, 551, 569 and 590 of the sequence of SEQ ID NO: 46 or SEQ ID NO: 47 are described in more detail in PCT Publication No. WO 2019/173636 and PCT/US2019/049816.

The PB, PBL or SPB transposases can be isolated or derived from an insect, vertebrate, crustacean or urochordate as described in more detail in PCT Publication No. WO 2019/173636 and PCT/US2019/049816. In preferred aspects, the PB, PBL or SPB transposases is be isolated or derived from the insect *Trichoplusia ni* (GenBank Accession No. AAA87375) or *Bombyx mori* (GenBank Accession No. BAD11135).

A hyperactive PB or PBL transposase is a transposase that is more active than the naturally occurring variant from which it is derived. In a preferred aspect, a hyperactive PB or PBL transposase is isolated or derived from *Bombyx mori* or *Xenopus tropicalis*. Examples of hyperactive PB or PBL transposases are disclosed in U.S. Pat. Nos. 6,218,185; 6,962,810, 8,399,643 and WO 2019/173636. A list of hyperactive amino acid substitutions is disclosed in U.S. Pat. No. 10,041,077.

In some aspects, a PB, PBL or SPB transposase can fused to a nuclear localization signal. Examples of PB, PBL or SPB transposases fused to a nuclear localization signal are disclosed in U.S. Pat. Nos. 6,218,185; 6,962,810, 8,399,643 and WO 2019/173636. A nuclear localization signal can comprise, consist essentially of or consist of a of the amino acid sequence at least 65%, 70%, 75%, 80%, 85%, 90%, 95%, 96%, 97%, 98%, 99% or 100% (or any percentage in between) identical to SEQ ID NO: 48. A nuclear localization signal can be encoded by a nucleic acid sequence that comprises, consists essentially of or consists of the nucleic acid sequence at least 65%, 70%, 75%, 80%, 85%, 90%, 95%, 96%, 97%, 98%, 99% or 100% (or any percentage in between) identical to SEQ ID NO: 49.

In some aspects, a nuclear localization signal can be fused to a PB, PBL or SPB transposase using a G4S linker located between the NLS and the PB, PBL or SPB. A G4S linker can comprise, consist essentially of or consist of an amino acid sequence at least 65%, 70%, 75%, 80%, 85%, 90%, 95%, 96%, 97%, 98%, 99% or 100% (or any percentage in between) identical to SEQ ID NO: 50. A G4S linker can be encoded by a nucleic acid sequence that comprises, consists essentially of or consists of the nucleic acid sequence at least 65%, 70%, 75%, 80%, 85%, 90%, 95%, 96%, 97%, 98%, 99% or 100% (or any percentage in between) identical to SEQ ID NO: 51.

In some aspects, a transposase sequence can comprise a nucleic acid sequence that encodes for a SBP transposase polypeptide fused to an NLS, wherein the SBP transposase polypeptide fused to an NLS comprises, consists essentially of or consist of an amino acid sequence at least 65%, 70%, 75%, 80%, 85%, 90%, 95%, 96%, 97%, 98%, 99% or 100% (or any percentage in between) identical to SEQ ID NO: 52. In some aspects, a nucleic acid sequence that encodes for a SBP transposase polypeptide fused to an NLS can comprise, consist essentially of, or consist of a nucleic acid sequence at least 65%, 70%, 75%, 80%, 85%, 90%, 95%, 96%, 97%, 98%, 99% or 100% (or any percentage in between) identical to any one of the sequences put forth in SEQ ID NOs: 53.

In some aspects, a transposase sequence can comprise a nucleic acid sequence that encodes for a SBP transposase polypeptide fused to an NLS, wherein the SBP transposase polypeptide fused to an NLS comprises, consists essentially of or consist of an amino acid sequence at least 65%, 70%, 75%, 80%, 85%, 90%, 95%, 96%, 97%, 98%, 99% or 100% (or any percentage in between) identical to SEQ ID NO: 54. In some aspects, a nucleic acid sequence that encodes for a SBP transposase polypeptide fused to an NLS can comprise, consist essentially of, or consist of a nucleic acid sequence at least 65%, 70%, 75%, 80%, 85%, 90%, 95%, 96%, 97%, 98%, 99% or 100% (or any percentage in between) identical to any one of the sequences put forth in SEQ ID NOs: 55.

In some aspects, a transposase sequence can comprise a nucleic acid sequence that encodes for a Sleeping Beauty transposase polypeptide (for example as disclosed in U.S. Pat. No. 9,228,180). In some aspects, a transposase sequence can comprise a nucleic acid sequence that encodes for a Hyperactive Sleeping Beauty (SB100X) transposase polypeptide. In some aspects, a Sleeping Beauty transposase comprises or consists of an amino acid sequence at least 65%, 70%, 75%, 80%, 85%, 90%, 95%, 96%, 97%, 98%, 99% or 100% (or any percentage in between) identical to SEQ ID NO: 56 or 57. In a preferred aspect, hyperactive Sleeping Beauty (SB100X) transposase comprises, consists essentially of or consists of an amino acid sequence at least 65%, 70%, 75%, 80%, 85%, 90%, 95%, 96%, 97%, 98%, 99% or 100% (or any percentage in between) identical to SEQ ID NO: 58 or 59.

In some aspects, a transposase sequence can comprise a nucleic acid sequence that encodes for a helitron transposase polypeptide (for example, as disclosed in WO 2019/173636). In some aspects, a Helitron transposase polypeptide comprises, consists essentially of or consists of an amino acid sequence at least 65%, 70%, 75%, 80%, 85%, 90%, 95%, 96%, 97%, 98%, 99% or 100% (or any percentage in between) identical to SEQ ID NO: 60 or 61.

In some aspects, a transposase sequence can comprise a nucleic acid sequence that encodes for a Tol2 transposase polypeptide (for example, as disclosed in WO 2019/173636). In some aspects, a Tol2 transposase polypeptide comprises, consists essentially of or consists of an amino acid sequence at least 65%, 70%, 75%, 80%, 85%, 90%, 95%, 96%, 97%, 98%, 99% or 100% (or any percentage in between) identical to SEQ ID NO: 62 or 63.

In some aspects, a transposase sequence can comprise a nucleic acid sequence that encodes for a TcBuster transposase polypeptide (for example, as disclosed in WO 2019/173636) or a mutant TcBuster transposase polypeptide (as described in more detail in PCT Publication No. WO 2019/173636 and PCT/US2019/049816). In some aspects, a TcBuster transposase polypeptide comprises, consists essentially of or consists of an amino acid sequence at least 65%, 70%, 75%, 80%, 85%, 90%, 95%, 96%, 97%, 98%, 99% or 100% (or any percentage in between) identical to SEQ ID NO: 64 or 65. The polynucleotide encoding a TcBuster transposase can comprise or consist of a naturally occurring nucleic acid sequence or a non-naturally occurring nucleic acid sequence.

In some aspects of the present disclosure, a transgene sequence can comprise a luciferase sequence.

In some aspects, a luciferase sequence can comprise a nucleic acid sequence that encodes for a nanoluciferase (nLuc) polypeptide. In some aspects, a nucleic acid sequence that encodes for an nLuc polypeptide can comprise, consist essentially of, or consist of a nucleic acid sequence at least 65%, 70%, 75%, 80%, 85%, 90%, 95%, 96%, 97%, 98%, 99% or 100% (or any percentage in between) identical to any one of the sequences put forth in SEQ ID NOs: 16 and 25.

Vectors of the Present Disclosure

The present disclosure provides compositions comprising a vector, wherein the vector comprises at least one adeno-associated virus (AAV) piggyBac transposon polynucleotide. A vector comprising at least one adeno-associated virus (AAV) piggyBac transposon polynucleotide is herein referred to as an “AAV piggyBac transposon vector”.

The present disclosure provides compositions comprising a vector, wherein the vector comprises at least one AAV transposase polynucleotide. A vector comprising at least one AAV transposase polynucleotide is herein referred to as an “AAV transposase vector”.

A vector of the present disclose can be a viral vector or a recombinant vector. Viral vectors can comprise a sequence isolated or derived from a retrovirus, a lentivirus, an adenovirus, an adeno-associated virus or any combination thereof. The viral vector may comprise a sequence isolated or derived from an adeno-associated virus (AAV). The viral vector may comprise a recombinant AAV (rAAV).

Exemplary adeno-associated viruses and recombinant adeno-associated viruses include, but are not limited to all serotypes (e.g., AAV1, AAV2, AAV3, AAV4, AAV5, AAV6, AAV7, AAV8, AAV9, AAV10 and AAV11). Exemplary adeno-associated viruses and recombinant adeno-associated viruses include, but are not limited to, self-complementary AAV (scAAV) and AAV hybrids containing the genome of one serotype and the capsid of another serotype (e.g., AAV2/5, AAV-DJ and AAV-DJ8). Exemplary adeno-associated viruses and recombinant adeno-associated viruses include, but are not limited to, rAAV-LK03, AAV-KP-1 (also referred to as AAV-KP1; described in detail in Kerun et al. JCI Insight, 2019; 4(22):e131610) and AAV-NP59 (described in detail in Paulk et al. Molecular Therapy, 2018; 26(1): 289-303).

The present disclosure provides a composition comprising a plurality of AAV-KP-1 particles comprising at least one adeno-associated virus (AAV) piggyBac transposon polynucleotide. The present disclosure provides a composition comprising a plurality of AAV-KP-1 particles comprising at least one AAV transposase polynucleotide. The present disclosure provides a composition comprising a plurality of AAV-KP-1 particles comprising at least one adeno-associated virus (AAV) piggyBac transposon polynucleotide and a plurality of AAV-KP-1 particles comprising at least one AAV transposase polynucleotide.

The present disclosure provides a composition comprising a plurality of AAV-NP59 particles comprising at least one adeno-associated virus (AAV) piggyBac transposon polynucleotide. The present disclosure provides a composition comprising a plurality of AAV-NP59 particles comprising at least one AAV transposase polynucleotide. The present disclosure provides a composition comprising a plurality of AAV-NP59 particles comprising at least one adeno-associated virus (AAV) piggyBac transposon polynucleotide and a plurality of AAV-NP59 particles comprising at least one AAV transposase polynucleotide.

The viral vectors and viral particles of the present disclosure can be produced using standard methods known in the art.

In some aspects, AAV-KP-1 particles of the present disclosure can be produced using a KP-1 capsid vector, wherein the KP-1 capsid vector comprises at least one of the nucleic acid sequences of SEQ ID NO: 66 and SEQ ID NO: 67. In some aspects, AAV-KP-1 particles of the present disclosure can be produced using an AAV vector packaging plasmid, wherein the AAV vector packaging plasmid comprises at least of the nucleic acid sequences of SEQ ID NO: 68 and SEQ ID NO: 69

In some aspects, AAV-NP59 particles of the present disclosure can be produced using a NP-59 capsid vector, wherein the NP-59 capsid vector comprises at least one of the nucleic acid sequences of SEQ ID NO: 70, SEQ ID NO: 71 and SEQ ID NO: 72. In some aspects, AAV-NP59 particles of the present disclosure can be produced using an AAV vector packaging plasmid, wherein the AAV vector packaging plasmid comprises at least of the nucleic acid sequences of SEQ ID NO: 68 and SEQ ID NO: 69.

The cell delivery compositions (e.g., polynucleotides, vectors) disclosed herein can comprise a nucleic acid encoding a therapeutic protein or therapeutic agent. Examples of therapeutic proteins include those disclosed in PCT Publication No. WO 2019/173636 and PCT/US2019/049816. Therapeutic proteins can also include, but are not limited to, any one of polypeptides described herein as part of transgene sequences (e.g. FVIII, FIX, etc.)

Formulations, Dosages and Modes of Administration

The present disclosure provides formulations, dosages and methods for administration of the compositions described herein.

The disclosed compositions and pharmaceutical compositions can further comprise at least one of any suitable auxiliary, such as, but not limited to, diluent, binder, stabilizer, buffers, salts, lipophilic solvents, preservative, adjuvant or the like. Pharmaceutically acceptable auxiliaries are preferred. Non-limiting examples of, and methods of preparing such sterile solutions are well known in the art, such as, but limited to, Gennaro, Ed., Remington's Pharmaceutical Sciences, 18th Edition, Mack Publishing Co. (Easton, Pa.) 1990 and in the “Physician's Desk Reference”, 52nd ed., Medical Economics (Montvale, N.J.) 1998. Pharmaceutically acceptable carriers can be routinely selected that are suitable for the mode of administration, solubility and/or stability of the protein scaffold, fragment or variant composition as well known in the art or as described herein.

Non-limiting examples of pharmaceutical excipients and additives suitable for use include proteins, peptides, amino acids, lipids, and carbohydrates (e.g., sugars, including monosaccharides, di-, tri-, tetra-, and oligosaccharides; derivatized sugars, such as alditols, aldonic acids, esterified sugars and the like; and polysaccharides or sugar polymers), which can be present singly or in combination, comprising alone or in combination 1-99.99% by weight or volume. Non-limiting examples of protein excipients include serum albumin, such as human serum albumin (HSA), recombinant human albumin (rHA), gelatin, casein, and the like. Representative amino acid/protein components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. One preferred amino acid is glycine.

Non-limiting examples of carbohydrate excipients suitable for use include monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), myoinositol and the like. Preferably, the carbohydrate excipients are mannitol, trehalose, and/or raffinose.

The compositions can also include a buffer or a pH-adjusting agent; typically, the buffer is a salt prepared from an organic acid or base. Representative buffers include organic acid salts, such as salts of citric acid, ascorbic acid, gluconic acid, carbonic acid, tartaric acid, succinic acid, acetic acid, or phthalic acid; Tris, tromethamine hydrochloride, or phosphate buffers. Preferred buffers are organic acid salts, such as citrate.

Additionally, the disclosed compositions can include polymeric excipients/additives, such as polyvinylpyrrolidones, ficolls (a polymeric sugar), dextrates (e.g., cyclodextrins, such as 2-hydroxypropyl-β-cyclodextrin), polyethylene glycols, flavoring agents, antimicrobial agents, sweeteners, antioxidants, antistatic agents, surfactants (e.g., polysorbates, such as "TWEEN 20" and "TWEEN 80"), lipids (e.g., phospholipids, fatty acids), steroids (e.g., cholesterol), and chelating agents (e.g., EDTA).

Many known and developed modes can be used for administering therapeutically effective amounts of the compositions or pharmaceutical compositions disclosed herein. Non-limiting examples of modes of administration include bolus, buccal, infusion, intrarticular, intrabronchial, intraabdominal, intracapsular, intracartilaginous, intracavitary, intracelial, intracerebellar, intracerebroventricular, intracolic, intracervical, intragastric, intrahepatic, intralesional, intramuscular, intramyocardial, intranasal, intraocular, intraosseous, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intratumoral, intravenous, intravesical, oral, parenteral, rectal, sublingual, subcutaneous, transdermal or vaginal means.

A composition of the disclosure can be prepared for use for parenteral (subcutaneous, intramuscular or intravenous) or any other administration particularly in the form of liquid solutions or suspensions; for use in vaginal or rectal administration particularly in semisolid forms, such as, but not limited to, creams and suppositories; for buccal, or sublingual administration, such as, but not limited to, in the form of tablets or capsules; or intranasally, such as, but not limited to, the form of powders, nasal drops or aerosols or certain agents; or transdermally, such as not limited to a gel, ointment, lotion, suspension or patch delivery system with chemical enhancers such as dimethyl sulfoxide to either modify the skin structure or to increase the drug concentration in the transdermal patch (Junginger, et al. In "Drug Permeation Enhancement;" Hsieh, D. S., Eds., pp. 59-90 (Marcel Dekker, Inc. New York 1994), or with oxidizing agents that enable the application of formulations containing proteins and peptides onto the skin (WO 98/53847), or applications of electric fields to create transient transport pathways, such as electroporation, or to increase the mobility of charged drugs through the skin, such as iontophoresis, or application of ultrasound, such as sonophoresis (U.S. Pat. Nos. 4,309,989 and 4,767,402) (the above publications and patents being entirely incorporated herein by reference).

For parenteral administration, any composition disclosed herein can be formulated as a solution, suspension, emulsion, particle, powder, or lyophilized powder in association, or separately provided, with a pharmaceutically acceptable parenteral vehicle. Formulations for parenteral administration can contain as common excipients sterile water or saline, polyalkylene glycols, such as polyethylene glycol, oils of vegetable origin, hydrogenated naphthalenes and the like. Aqueous or oily suspensions for injection can be prepared by using an appropriate emulsifier or humidifier and a suspending agent, according to known methods.

Agents for injection can be a non-toxic, non-orally administrable diluting agent, such as aqueous solution, a sterile injectable solution or suspension in a solvent. As the usable vehicle or solvent, water, Ringer's solution, isotonic saline, etc. are allowed; as an ordinary solvent or suspending solvent, sterile involatile oil can be used. For these purposes, any kind of involatile oil and fatty acid can be used, including natural or synthetic or semisynthetic fatty oils or fatty acids; natural or synthetic or semisynthtetic mono- or di- or tri-glycerides. Parental administration is known in the art and includes, but is not limited to, conventional means of injections, a gas pressured needle-less injection device as described in U.S. Pat. No. 5,851,198, and a laser perforator device as described in U.S. Pat. No. 5,839,446.

Formulations for oral administration rely on the co-administration of adjuvants (e.g., resorcinols and nonionic surfactants, such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation. Formulations for delivery of hydrophilic agents including proteins and protein scaffolds and a combination of at least two surfactants intended for oral, buccal, mucosal, nasal, pulmonary, vaginal trans-membrane, or rectal administration are described in U.S. Pat. No. 6,309,663. The active constituent compound of the solid-type dosage form for oral administration can be mixed with at least one additive, including sucrose, lactose, cellulose, mannitol, trehalose, raffinose, maltitol, dextran, starches, agar, arginates, chitins, chitosans, pectins, gum tragacanth, gum arabic, gelatin, collagen, casein, albumin, synthetic or semisynthetic polymer, and glyceride. These dosage forms can also contain other type(s) of additives, e.g., inactive diluting agent, lubricant, such as magnesium stearate, paraben, preserving agent, such as sorbic acid, ascorbic acid, .alpha.-tocopherol, antioxidant such as cysteine, disintegrator, binder, thickener, buffering agent, sweetening agent, flavoring agent, perfuming agent, etc.

Tablets and pills can be further processed into enteric-coated preparations. The liquid preparations for oral administration include emulsion, syrup, elixir, suspension and solution preparations allowable for medical use. These preparations can contain inactive diluting agents ordinarily used in said field, e.g., water. Liposomes have also been described as drug delivery systems for insulin and heparin (U.S. Pat. No. 4,239,754). More recently, microspheres of artificial polymers of mixed amino acids (proteinoids) have been used to deliver pharmaceuticals (U.S. Pat. No. 4,925,673). Furthermore, carrier compounds described in U.S. Pat. Nos. 5,879,681 and 5,871,753 and used to deliver biologically active agents orally are known in the art.

For pulmonary administration, preferably, a composition or pharmaceutical composition described herein is delivered in a particle size effective for reaching the lower airways of the lung or sinuses. The composition or pharmaceutical composition can be delivered by any of a variety of inhalation or nasal devices known in the art for administration of a therapeutic agent by inhalation. These devices capable of depositing aerosolized formulations in the sinus cavity or alveoli of a patient include metered dose inhalers, nebulizers (e.g., jet nebulizer, ultrasonic nebulizer), dry powder generators, sprayers, and the like. All such devices can use formulations suitable for the administration for the dispensing of a composition or pharmaceutical composition described herein in an aerosol. Such aerosols can be comprised of either solutions (both aqueous and non-aqueous) or solid particles. Additionally, a spray including a composition or pharmaceutical composition described herein can be produced by forcing a suspension or solution of at least one protein scaffold through a nozzle under pressure. In a metered dose inhaler (MDI), a propellant, a composition or pharmaceutical composition described herein, and any excipients or other additives are contained in a canister as a mixture including a liquefied compressed gas. Actuation of the metering valve releases the mixture as an aerosol, preferably containing particles in the size range of less than about 10 μm, preferably, about 1 μm to about 5 μm, and, most preferably, about 2 μm to about 3 μm. A more detailed description of pulmonary administration, formulations and related devices is disclosed in PCT Publication No. WO 2019/049816.

For absorption through mucosal surfaces, compositions include an emulsion comprising a plurality of submicron particles, a mucoadhesive macromolecule, a bioactive peptide, and an aqueous continuous phase, which promotes absorption through mucosal surfaces by achieving mucoadhesion of the emulsion particles (U.S. Pat. No. 5,514,670). Mucous surfaces suitable for application of the emulsions of the disclosure can include corneal, conjunctival, buccal, sublingual, nasal, vaginal, pulmonary, stomachic, intestinal, and rectal routes of administration. Formulations for vaginal or rectal administration, e.g., suppositories, can contain as excipients, for example, polyalkyleneglycols, vaseline, cocoa butter, and the like. Formulations for intranasal administration can be solid and contain as excipients, for example, lactose or can be aqueous or oily solutions of nasal drops. For buccal administration, excipients include sugars, calcium stearate, magnesium stearate, pregelinatined starch, and the like (U.S. Pat. No. 5,849,695). A more detailed description of mucosal administration and formulations is disclosed in PCT Publication No. WO 2019/049816.

For transdermal administration, a composition or pharmaceutical composition disclosed herein is encapsulated in a delivery device, such as a liposome or polymeric nanoparticles, microparticle, microcapsule, or microspheres (referred to collectively as microparticles unless otherwise stated). A number of suitable devices are known, including microparticles made of synthetic polymers, such as polyhydroxy acids, such as polylactic acid, polyglycolic acid and copolymers thereof, polyorthoesters, polyanhydrides, and polyphosphazenes, and natural polymers, such as collagen, polyamino acids, albumin and other proteins, alginate and other polysaccharides, and combinations thereof (U.S. Pat. No. 5,814,599). A more detailed description of transdermal administration, formulations and suitable devices is disclosed in PCT Publication No. WO 2019/049816.

It can be desirable to deliver the disclosed compounds to the subject over prolonged periods of time, for example, for periods of one week to one year from a single administration. Various slow release, depot or implant dosage forms can be utilized. For example, a dosage form can contain a pharmaceutically acceptable non-toxic salt of the compounds that has a low degree of solubility in body fluids, for example, (a) an acid addition salt with a polybasic acid, such as phosphoric acid, sulfuric acid, citric acid, tartaric acid, tannic acid, pamoic acid, alginic acid, polyglutamic acid, naphthalene mono- or di-sulfonic acids, polygalacturonic acid, and the like; (b) a salt with a polyvalent metal cation, such as zinc, calcium, bismuth, barium, magnesium, aluminum, copper, cobalt, nickel, cadmium and the like, or with an organic cation formed from e.g., N,N'-dibenzyl-ethylenediamine or ethylenediamine; or (c) combinations of (a) and (b), e.g., a zinc tannate salt. Additionally, the disclosed compounds or, preferably, a relatively insoluble salt, such as those just described, can be formulated in a gel, for example, an aluminum monostearate gel with, e.g., sesame oil, suitable for injection. Particularly preferred salts are zinc salts, zinc tannate salts, pamoate salts, and the like. Another type of slow release depot formulation for injection would contain the compound or salt dispersed for encapsulation in a slow degrading, non-toxic, non-antigenic polymer, such as a polylactic acid/polyglycolic acid polymer for example as described in U.S. Pat. No. 3,773,919. The compounds or, preferably, relatively insoluble salts, such as those described above, can also be formulated in cholesterol matrix silastic pellets, particularly for use in animals. Additional slow release, depot or implant formulations, e.g., gas or liquid liposomes, are known in the literature (U.S. Pat. No. 5,770,222 and "Sustained and Controlled Release Drug Delivery Systems", J. R. Robinson ed., Marcel Dekker, Inc., N.Y., 1978).

Suitable dosages are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000); Nursing 2001 Handbook of Drugs, 21st edition, Springhouse Corp., Springhouse, Pa., 2001; Health Professional's Drug Guide 2001, ed., Shannon, Wilson, Stang, Prentice-Hall, Inc, Upper Saddle River, N.J. Preferred doses can optionally include about 0.1-99 and/or 100-500 mg/kg/administration, or any range, value or fraction thereof, or to achieve a serum concentration of about 0.1-5000 μg/ml serum concentration per single or multiple administration, or any range, value or fraction thereof. A preferred dosage range for the compositions or pharmaceutical compositions disclosed herein is from about 1 mg/kg, up to about 3, about 6 or about 12 mg/kg of body weight of the subject.

Alternatively, the dosage administered can vary depending upon known factors, such as the pharmacodynamic characteristics of the particular agent, and its mode and route of administration; age, health, and weight of the recipient; nature and extent of symptoms, kind of concurrent treatment, frequency of treatment, and the effect desired. Usually a dosage of active ingredient can be about 0.1 to 100 milligrams per kilogram of body weight. Ordinarily 0.1 to 50, and preferably, 0.1 to 10 milligrams per kilogram per administration or in sustained release form is effective to obtain desired results.

As a non-limiting example, treatment of humans or animals can be provided as a one-time or periodic dosage of the compositions or pharmaceutical compositions disclosed herein about 0.1 to 100 mg/kg or any range, value or fraction thereof per day, on at least one of day 1-40, or, alternatively or additionally, at least one of week 1-52, or, alternatively or additionally, at least one of 1-20 years, or any combination thereof, using single, infusion or repeated doses.

Dosage forms suitable for internal administration generally contain from about 0.001 milligram to about 500 milligrams of active ingredient per unit or container. In these pharmaceutical compositions the active ingredient will ordinarily be present in an amount of about 0.5-99.999% by weight based on the total weight of the composition.

An effective amount can comprise an amount of about 0.001 to about 500 mg/kg per single (e.g., bolus), multiple or continuous administration, or to achieve a serum concentration of 0.01-5000 μg/ml serum concentration per single, multiple, or continuous administration, or any effective range or value therein, as done and determined using known methods, as described herein or known in the relevant arts.

In aspects where the compositions to be administered to a subject in need thereof are modified cells as disclosed herein, the cells can be administered between about $1\times10^3$ and $1\times10^{15}$ cells; about $1\times10^4$ and $1\times10^{12}$ cells; about $1\times10^5$ and $1\times10^{10}$ cells; about $1\times10^6$ and $1\times10^9$ cells; about $1\times10^6$ and $1\times10^8$ cells; about $1\times10^6$ and $1\times10^7$ cells; or about $1\times10^6$ and $25\times10^6$ cells. In one aspect the cells are administered between about $5\times10^6$ and $25\times10^6$ cells.

A more detailed description of pharmaceutically acceptable excipients, formulations, dosages and methods of administration of the disclosed compositions and pharmaceutical compositions is disclosed in PCT Publication No. WO 2019/049816.

Methods of Using the Compositions of the Disclosure

The present disclosure provides the use of a disclosed composition or pharmaceutical composition for the treatment of a disease or disorder in a cell, tissue, organ, animal, or subject, as known in the art or as described herein, using the disclosed compositions and pharmaceutical compositions, e.g., administering or contacting the cell, tissue, organ, animal, or subject with a therapeutic effective amount of the composition or pharmaceutical composition. In one aspect, the subject is a mammal. Preferably, the subject is human. The terms “subject” and “patient” are used interchangeably herein.

The disclosure provides a method for treating hemophilia in a subject in need thereof comprising administering to the subject at least one therapeutically effective amount of at least one composition of the present disclosure.

The present disclosure provides at least one composition of the present disclosure for the use in the treatment of hemophilia in a subject, wherein the at least one composition is for administration to the subject in at least one therapeutically effective amount.

The present disclosure provides the use of at least one composition of the present disclosure for the manufacture of a medicament for the treatment of hemophilia in a subject, wherein the at least one composition is for administration to the subject in at least one therapeutically effective amount.

In some aspects of the preceding methods and uses, the at least one composition of the present disclosure can comprise at least one AAV piggyBac transposon vector of the present disclosure.

Accordingly, the disclosure provides a method for treating hemophilia in a subject in need thereof comprising administering to the subject at least one therapeutically effective amount of at least one AAV piggyBac transposon vector of the present disclosure.

The present disclosure provides at least one AAV piggyBac transposon vector of the present disclosure for the use in the treatment of hemophilia in a subject, wherein the at least one AAV piggyBac transposon vector is for administration to the subject in at least one therapeutically effective amount.

The present disclosure provides the use of at least one AAV piggyBac transposon vector of the present disclosure for the manufacture of a medicament for the treatment of hemophilia in a subject, wherein the at least one AAV piggyBac transposon vector is for administration to the subject in at least one therapeutically effective amount.

In some aspects of the preceding methods and uses, the at least one composition of the present disclosure can comprise at least one AAV transposase vector of the present disclosure.

Accordingly, the disclosure provides a method for treating hemophilia in a subject in need thereof comprising administering to the subject at least one therapeutically effective amount of at least one AAV transposase vector of the present disclosure.

The present disclosure provides at least one AAV transposase vector of the present disclosure for the use in the treatment of hemophilia in a subject, wherein the at least one AAV transposase vector is for administration to the subject in at least one therapeutically effective amount.

The present disclosure provides the use of at least one AAV transposase vector of the present disclosure for the manufacture of a medicament for the treatment of hemophilia in a subject, wherein the at least one AAV transposase vector is for administration to the subject in at least one therapeutically effective amount.

The present disclosure provides methods of treating hemophilia in a subject, the methods comprising administering to the subject: a) at least one therapeutically effective amount of a composition comprising a nucleic acid molecule comprising a transposon, wherein the transposon comprises a nucleotide sequence encoding at least one therapeutic protein; and b) at least one therapeutically effective amount of a composition comprising a nucleic acid molecule comprising a nucleotide sequence encoding at least one transposase.

In some aspects of the preceding method, a composition comprising a nucleic acid molecule comprising a transposon can be any AAV piggyBac transposon vector described herein.

In some aspects of the preceding method, a composition comprising a nucleic acid molecule comprising a nucleotide sequence encoding at least one transposase can be any AAV transposase vector of the present disclosure.

Accordingly, the present disclosure provides methods of treating hemophilia in a subject, the methods comprising administering to the subject: a) at least one therapeutically effective amount of at least one AAV piggyBac transposon vector of the present disclosure; and b) at least one therapeutically effective amount of at least one AAV transposase vector of the present disclosure.

Accordingly the present disclosure provides a combination of at least one AAV piggyBac transposon vector of the present disclosure and at least one AAV transposase vector of the present disclosure for use in in the treatment of hemophilia in a subject, wherein the at least one AAV piggyBac transposon vector is for administration to the subject in at least one therapeutically effective amount, and wherein the at least one AAV transposase vector is for administration to the subject in at least one therapeutically effective amount.

Accordingly the present disclosure provides the use of a combination of at least one AAV piggyBac transposon vector of the present disclosure and at least one AAV transposase vector of the present disclosure in the manufacture of a medicament for the treatment of hemophilia in a subject, wherein the at least one AAV piggyBac transposon vector is for administration to the subject in at least one therapeutically effective amount, and wherein the at least one AAV transposase vector is for administration to the subject in at least one therapeutically effective amount.

In some aspects, the hemophilia can be hemophilia A. In some aspects, the hemophilia can be hemophilia B. In some aspects, the hemophilia can be hemophilia C. In some aspects, the hemophilia can be Parahemophilia.

In some aspects of the preceding methods, a composition comprising a nucleic acid molecule comprising a transposon, wherein the transposon comprises a nucleotide sequence encoding at least one therapeutic protein and a composition comprising a nucleic acid molecule comprising a nucleotide sequence encoding at least one transposase can be administered concurrently. In some aspects, a composition comprising a nucleic acid molecule comprising a transposon, wherein the transposon comprises a nucleotide sequence encoding at least one therapeutic protein and a composition comprising a nucleic acid molecule comprising a nucleotide sequence encoding at least one transposase can be administered sequentially. In some aspects, a composition comprising a nucleic acid molecule comprising a transposon, wherein the transposon comprises a nucleotide sequence encoding at least one therapeutic protein and a composition comprising a nucleic acid molecule comprising a nucleotide sequence encoding at least one transposase can be administered in temporal proximity.

As used herein, the term "temporal proximity" refers to that administration of one therapeutic composition (e.g., a composition comprising a transposon) occurs within a time period before or after the administration of another therapeutic composition (e.g., a composition comprising a transposase), such that the therapeutic effect of the one therapeutic agent overlaps with the therapeutic effect of the other therapeutic agent. In some embodiments, the therapeutic effect of the one therapeutic agent completely overlaps with the therapeutic effect of the other therapeutic agent. In some embodiments, "temporal proximity" means that administration of one therapeutic agent occurs within a time period before or after the administration of another therapeutic agent, such that there is a synergistic effect between the one therapeutic agent and the other therapeutic agent. "Temporal proximity" may vary according to various factors, including but not limited to, the age, gender, weight, genetic background, medical condition, disease history, and treatment history of the subject to which the therapeutic agents are to be administered; the disease or condition to be treated or ameliorated; the therapeutic outcome to be achieved; the dosage, dosing frequency, and dosing duration of the therapeutic agents; the pharmacokinetics and pharmacodynamics of the therapeutic agents; and the route(s) through which the therapeutic agents are administered. In some embodiments, "temporal proximity" means within 15 minutes, within 30 minutes, within an hour, within two hours, within four hours, within six hours, within eight hours, within 12 hours, within 18 hours, within 24 hours, within 36 hours, within 2 days, within 3 days, within 4 days, within 5 days, within 6 days, within a week, within 2 weeks, within 3 weeks, within 4 weeks, with 6 weeks, or within 8 weeks. In some embodiments, multiple administration of one therapeutic agent can occur in temporal proximity to a single administration of another therapeutic agent. In some embodiments, temporal proximity may change during a treatment cycle or within a dosing regimen.

In some aspects of the treatment methods of the present disclosure, the administration of the at least one composition and/or vector of the present disclosure to a subject can result in the expression of an exogenous protein (e.g. a therapeutic protein, a transposase, etc.) in at least one organ and/or tissue and/or bodily fluid in the subject.

In some aspects, the administration of the at least one composition and/or vector of the present disclosure results in the expression of the exogenous protein in at least about 10%, or at least about 15%, or at least bout 20%, or at least about 25%, or at least about 30%, or at least about 35%, or at least about 40%, or at least about 45%, or at least about 50%, or at least about 55%, or at least about 60%, or at least about 65%, or at least about 70%, or at least about 75%, or at least about 80%, or at least about 85%, or at least about 90%, or at least about 95%, or at least about 99% of the cells in the tissue and/or organ and/or bodily fluid.

In some aspects, the administration of the at least one composition and/or vector of the present disclosure results in the expression of the exogenous protein in at least about 10%, or at least about 15%, or at least bout 20%, or at least about 25%, or at least about 30%, or at least about 35%, or at least about 40%, or at least about 45%, or at least about 50%, or at least about 55%, or at least about 60%, or at least about 65%, or at least about 70%, or at least about 75%, or at least about 80%, or at least about 85%, or at least about 90%, or at least about 95%, or at least about 99% of a specific subset or subsets of cells in the tissue and/or organ and/or bodily fluid.

In some aspects, the administration of the at least one composition and/or vector of the present disclosure results in the expression of the exogenous protein for at least about 1 day, or at least about 2 days, or at least about 3 days, or at least about 4 days, or at least about 5 days, or at least about 6 days, or at least about 7 days, or at least about 8 days, or at least about 9 days, or at least about 10 days in the tissue and/or organ and/or bodily fluid.

In some aspects, the administration of the at least one composition and/or vector of the present disclosure results in the expression of the exogenous protein for at least about 1 day, or at least about 2 days, or at least about 3 days, or at least about 4 days, or at least about 5 days, or at least about 6 days, or at least about 7 days, or at least about 8 days, or at least about 9 days, or at least about 10 days in a specific subset or subsets of cells in the tissue and/or organ and/or bodily fluid.

In some aspects, the administration of the at least one composition and/or vector of the present disclosure results in the expression of the exogenous protein for no more than about 1 day, or no more than about 2 days, or no more than about 3 days, or no more than about 4 days, or no more than about 5 days, or no more than about 6 days, or no more than about 7 days, or no more than about 8 days, or no more than about 9 days, or no more than about 10 days in the tissue and/or organ and/or bodily fluid.

In some aspects, the administration of the at least one composition and/or vector of the present disclosure results in the expression of the exogenous protein for no more than about 1 day, or no more than about 2 days, or no more than about 3 days, or no more than about 4 days, or no more than about 5 days, or no more than about 6 days, or no more than about 7 days, or no more than about 8 days, or no more than about 9 days, or no more than about 10 days in a specific subset or subsets of cells in the tissue and/or organ and/or bodily fluid.

In some aspects, the tissue and/or organ and/or bodily fluid can be the liver. In some aspects, the specific subset or subsets of cells can include, but are not limited to, hepatocytes, a hepatic stellate cells, Kupffer cells, liver sinusoidal endothelial cells or any combination thereof.

In some aspects, the tissue and/or organ and/or bodily fluid can be blood, plasma, serum or any combination thereof.

Any method of the present disclosure can comprise administering an effective amount of any composition or pharmaceutical composition disclosed herein to a cell, tissue, organ, animal or subject in need of such modulation, treatment or therapy. Such a method can optionally further comprise co-administration or combination therapy for treating such diseases or disorders, wherein the administering of any composition or pharmaceutical composition disclosed herein, further comprises administering, before concurrently, and/or after, at least one additional treatment for urea cycle disorders.

Exemplary Embodiments of the Present Disclosure

Embodiment 1a. An adeno-associated virus (AAV) piggyBac transposon polynucleotide comprising in the 5' to 3' direction:

a) a first AAV inverted terminal repeat (ITR) sequence;
b) a first piggyBac ITR sequence;
c) a first insulator sequence;
d) at least one promoter sequence;
e) at least one transgene sequence;
f) a polyA sequence;
g) a second insulator sequence;
h) a second piggyBac ITR sequence; and
i) a second AAV ITR sequence.

Embodiment 1b. An adeno-associated virus (AAV) piggyBac transposon polynucleotide comprising in the 5' to 3' direction:

a) a first nucleic acid sequence;
b) a first piggyBac ITR sequence;
c) a first insulator sequence;
d) at least one promoter sequence;
e) at least one transgene sequence;
f) a polyA sequence;
g) a second insulator sequence;
h) a second piggyBac ITR sequence; and
i) a second nucleic acid sequence.

Embodiment 2. The AAV piggyBac transposon polynucleotide of embodiment 1a or 1b, wherein the AAV piggyBac transposon polynucleotide comprises DNA, cDNA, gDNA, RNA, mRNA or any combination thereof.

Embodiment 3a. The AAV piggyBac transposon polynucleotide of any one of the preceding embodiments, wherein the first and/or the second AAV ITR sequence comprises the nucleic acid sequence of any one of SEQ ID NOs: 1, 2, 17 and 18.

Embodiment 3b. The AAV piggyBac transposon polynucleotide of any one of the preceding embodiments, wherein the first and/or the second nucleic acid sequence comprises the nucleic acid sequence of any one of SEQ ID NOs: 1, 2, 17 and 18.

Embodiment 4a. The AAV piggyBac transposon polynucleotide of any one of the preceding embodiments, wherein the first AAV ITR sequence comprises the nucleic acid sequence of SEQ ID NO: 1 and the second AAV ITR sequence comprises the nucleic acid sequence of SEQ ID NO: 2.

Embodiment 4b. The AAV piggyBac transposon polynucleotide of any one of the preceding embodiments, wherein the first nucleic acid sequence comprises the nucleic acid sequence of SEQ ID NO: 1 and the second nucleic acid sequence comprises the nucleic acid sequence of SEQ ID NO: 2.

Embodiment 5a. The AAV piggyBac transposon polynucleotide of any one of the preceding embodiments, wherein the first AAV ITR sequence comprises the nucleic acid sequence of SEQ ID NO: 17 and the second AAV ITR sequence comprises the nucleic acid sequence of SEQ ID NO: 18.

Embodiment 5b. The AAV piggyBac transposon polynucleotide of any one of the preceding embodiments, wherein the first nucleic acid sequence comprises the nucleic acid sequence of SEQ ID NO: 17 and the second nucleic acid sequence comprises the nucleic acid sequence of SEQ ID NO: 18.

Embodiment 6a. The AAV piggyBac transposon polynucleotide of any one of the preceding embodiments, wherein the first piggyBac ITR sequence and/or the second piggyBac ITR sequence comprises the nucleic acid sequence of any one of SEQ ID NOs: 3, 4, 19 and 21.

Embodiment 6b. The AAV piggyBac transposon polynucleotide of any one of the preceding embodiments, wherein the first piggyBac ITR sequence and/or the second piggyBac ITR sequence comprises the nucleic acid sequence of any one of SEQ ID NOs: 1 and 2.

Embodiment 6c. The AAV piggyBac transposon polynucleotide of any one of the preceding embodiments, wherein the first piggyBac ITR sequence and/or the second piggyBac ITR sequence comprises the nucleic acid sequence of any one of SEQ ID NOs: 79 and 80.

Embodiment 7. The AAV piggyBac transposon polynucleotide of any one of the preceding embodiments, wherein the first piggyBac ITR sequence comprises the nucleic acid sequence of SEQ ID NO: 3 and the second piggyBac ITR comprises the nucleic acid sequence of SEQ ID NO: 4.

Embodiment 8a. The AAV piggyBac transposon polynucleotide of any one of the preceding embodiments, wherein the first piggyBac ITR sequence comprises the nucleic acid sequence of SEQ ID NO: 19 and the second piggyBac ITR comprises the nucleic acid sequence of SEQ ID NO: 21.

Embodiment 8b. The AAV piggyBac transposon polynucleotide of any one of the preceding embodiments, wherein the first piggyBac ITR sequence comprises the nucleic acid sequence of SEQ ID NO: 79 and the second piggyBac ITR comprises the nucleic acid sequence of SEQ ID NO: 80.

Embodiment 9. The AAV piggyBac transposon polynucleotide of any one of the preceding embodiments, wherein the first insulator sequence and/or the second insulator sequence comprises the nucleic acid sequence of any one of SEQ ID NOs: 5, 6 and 20.

Embodiment 10. The AAV piggyBac transposon polynucleotide of any one of the preceding embodiments, wherein the first insulator sequence comprises the nucleic acid sequence of SEQ ID NO: 5 and the second insulator sequence comprises the nucleic acid sequence of SEQ ID NO: 6.

Embodiment 11. The AAV piggyBac transposon polynucleotide of any one of the preceding embodiments, wherein the first insulator sequence comprises the nucleic acid sequence of SEQ ID NO: 5 and the second insulator sequence comprises the nucleic acid sequence of SEQ ID NO: 20.

Embodiment 12. The AAV piggyBac transposon polynucleotide of any one of the preceding embodiments, wherein the at least one promoter sequence comprises the nucleic acid sequence of any one of SEQ IDS NOs: 7-12.

Embodiment 13. The AAV piggyBac transposon polynucleotide of any one of the preceding embodiments, wherein the at least one promoter sequence comprises the nucleic acid sequence of SEQ IDS NO: 7.

Embodiment 14. The AAV piggyBac transposon polynucleotide of any one of the preceding embodiments, wherein the at least one promoter sequence comprises the nucleic acid sequence of SEQ IDS NO: 8.

Embodiment 15. The AAV piggyBac transposon polynucleotide of any one of the preceding embodiments, wherein the at least one promoter sequence comprises the nucleic acid sequence of SEQ IDS NO: 9.

Embodiment 16. The AAV piggyBac transposon polynucleotide of any one of the preceding embodiments, wherein the at least one promoter sequence comprises the nucleic acid sequence of SEQ IDS NO: 10.

Embodiment 17. The AAV piggyBac transposon polynucleotide of any one of the preceding embodiments, wherein the at least one promoter sequence comprises the nucleic acid sequence of SEQ IDS NO: 11.

Embodiment 18. The AAV piggyBac transposon polynucleotide of any one of the preceding embodiments, wherein the at least one promoter sequence comprises the nucleic acid sequence of SEQ IDS NO: 12.

Embodiment 19. The AAV piggyBac transposon polynucleotide of any one of the preceding embodiments, wherein the at least one transgene sequence comprises a nucleic acid sequence encoding a Factor VIII (FVIII) polypeptide.

Embodiment 20. The AAV piggyBac transposon polynucleotide of any one of the preceding embodiments, wherein the FVIII polypeptide comprises the amino acid sequence of SEQ ID NO: 26.

Embodiment 21. The AAV piggyBac transposon polynucleotide of any one of the preceding embodiments, wherein the nucleic acid sequence encoding a FVIII polypeptide comprises the nucleic acid sequence of SEQ ID NO: 13.

Embodiment 22. The AAV piggyBac transposon polynucleotide of any one of the preceding embodiments, wherein the at least one transgene sequence comprises a nucleic acid sequence encoding a Factor IX (FIX) polypeptide.

Embodiment 23. The AAV piggyBac transposon polynucleotide of any one of the preceding embodiments, wherein the FIX polypeptide comprises the amino acid sequence of SEQ ID NO: 27.

Embodiment 24. The AAV piggyBac transposon polynucleotide of any one of the preceding embodiments, wherein the nucleic acid sequence encoding a FIX polypeptide comprises the nucleic acid sequence of SEQ ID NO: 23.

Embodiment 25. The AAV piggyBac transposon polynucleotide of any one of the preceding embodiments, wherein the at least one transgene sequence is operatively linked to the at least one promoter sequence.

Embodiment 26. The AAV piggyBac transposon polynucleotide of any one of the preceding embodiments, wherein the expression of the at least one transgene sequence is controlled by the at least one promoter sequence.

Embodiment 27. The AAV piggyBac transposon polynucleotide of any one of the preceding embodiments, wherein the polyA sequence comprises the nucleic acid sequence of SEQ ID NO: 14.

Embodiment 28. The AAV piggyBac transposon polynucleotide of any one of the preceding embodiments, wherein the polyA sequence comprises the nucleic acid sequence of SEQ ID NO: 22.

Embodiment 29. The AAV piggyBac transposon polynucleotide of any one of the preceding embodiments, wherein the AAV piggyBac transposon polynucleotide further comprises at least a second transgene sequence.

Embodiment 30. The AAV piggyBac transposon polynucleotide of any one of the preceding embodiments, wherein the at least second transgene sequence comprises a luciferase sequence.

Embodiment 31. The AAV piggyBac transposon polynucleotide of any one of the preceding embodiments, wherein the luciferase sequence comprises SEQ ID NO: 16 or 25.

Embodiment 32. The AAV piggyBac transposon polynucleotide of any one of the preceding embodiments, wherein the AAV piggyBac transposon polynucleotide further comprises at least a second promoter sequence.

Embodiment 33. The AAV piggyBac transposon polynucleotide of any one of the preceding embodiments, wherein the at least second promoter sequence is located between the at least one transgene sequence and the at least second transgene sequence.

Embodiment 34. The AAV piggyBac transposon polynucleotide of any one of the preceding embodiments, wherein the AAV piggyBac transposon polynucleotide further comprises at least one self-cleaving peptide sequence, wherein the at least one self-cleaving peptide sequence is a nucleic acid sequence encoding for a T2A peptide, GSG-T2A peptide, an E2A peptide, a GSG-E2A peptide, an F2A peptide, a GSG-F2A peptide, a P2A peptide, or a GSG-P2A peptide.

Embodiment 35. The AAV piggyBac transposon polynucleotide of any one of the preceding embodiments, wherein the at least one self-cleaving peptide sequence is located between the at least one transgene sequence and the at least second transgene sequence.

Embodiment 36. The AAV piggyBac transposon polynucleotide of any one of the preceding embodiments, wherein the AAV piggyBac transposon polynucleotide comprises at least two transgene sequences.

Embodiment 37. The AAV piggyBac transposon polynucleotide of any one of the preceding embodiments, wherein the at least two transgene sequences are the same sequence.

Embodiment 38. The AAV piggyBac transposon polynucleotide of any one of the preceding embodiments, wherein the at least two transgene sequences are different sequences.

Embodiment 39. The AAV piggyBac transposon polynucleotide of any one of the preceding embodiments, further comprising at least one DNA spacer sequence.

Embodiment 40. The AAV piggyBac transposon polynucleotide of any one of the preceding embodiments, wherein the at least one DNA spacer sequence comprises the nucleic acid sequence of SEQ ID NO: 28.

Embodiment 41. The AAV piggyBac transposon polynucleotide of any one of the preceding embodiments, wherein the AAV piggyBac transposon polynucleotide comprises at least two promoter sequences.

Embodiment 42. The AAV piggyBac transposon polynucleotide of any one of the preceding embodiments, wherein the at least two promoter sequences are the same sequence.

Embodiment 43. The AAV piggyBac transposon polynucleotide of any one of the preceding embodiments, wherein the at least two promoter sequences are different sequences.

Embodiment 44a. An AAV piggyBac transposon polynucleotide comprising in the 5' to 3' direction:

a) a first AAV ITR sequence comprising the nucleic acid sequence of SEQ ID NO: 1;
b) a first piggyBac ITR sequence comprising the nucleic acid sequence of SEQ ID NO: 3;
c) a first insulator sequence comprising the nucleic acid sequence of SEQ ID NO: 5;
d) at least one promoter sequence comprising the nucleic acid sequence of SEQ ID NO: 7;
e) at least one transgene sequence comprising the nucleic acid sequence of SEQ ID NO: 13;
f) a polyA sequence comprising the nucleic acid sequence of SEQ ID NO: 14;
g) a second insulator sequence comprising the nucleic acid sequence of SEQ ID NO: 6;
h) a second piggyBac ITR sequence comprising the nucleic acid sequence of SEQ ID NO: 4;
i) a second AAV ITR sequence comprising the nucleic acid sequence of SEQ ID NO: 2.

Embodiment 44b. An AAV piggyBac transposon polynucleotide comprising in the 5' to 3' direction:

a) a first AAV ITR sequence;
b) a first piggyBac ITR sequence comprising the nucleic acid sequence of SEQ ID NO: 3;
c) a first insulator sequence comprising the nucleic acid sequence of SEQ ID NO: 5;
d) at least one promoter sequence comprising the nucleic acid sequence of SEQ ID NO: 7;
e) at least one transgene sequence comprising the nucleic acid sequence of SEQ ID NO: 13;
f) a polyA sequence comprising the nucleic acid sequence of SEQ ID NO: 14;
g) a second insulator sequence comprising the nucleic acid sequence of SEQ ID NO: 6;
h) a second piggyBac ITR sequence comprising the nucleic acid sequence of SEQ ID NO: 4;
i) a second AAV ITR sequence.

Embodiment 44c. An AAV piggyBac transposon polynucleotide comprising in the 5' to 3' direction:

a) a first nucleic acid sequence comprising the nucleic acid sequence of SEQ ID NO: 1;
b) a first piggyBac ITR sequence comprising the nucleic acid sequence of SEQ ID NO: 3;
c) a first insulator sequence comprising the nucleic acid sequence of SEQ ID NO: 5;
d) at least one promoter sequence comprising the nucleic acid sequence of SEQ ID NO: 7;
e) at least one transgene sequence comprising the nucleic acid sequence of SEQ ID NO: 13;
f) a polyA sequence comprising the nucleic acid sequence of SEQ ID NO: 14;
g) a second insulator sequence comprising the nucleic acid sequence of SEQ ID NO: 6;
h) a second piggyBac ITR sequence comprising the nucleic acid sequence of SEQ ID NO: 4;
i) a second nucleic acid sequence comprising the sequence of SEQ ID NO: 2.

Embodiment 44d. An AAV piggyBac transposon polynucleotide comprising in the 5' to 3' direction:

a) a first AAV ITR sequence;
b) a first piggyBac ITR sequence comprising the nucleic acid sequence of SEQ ID NO: 79;
c) a first insulator sequence comprising the nucleic acid sequence of SEQ ID NO: 5;
d) at least one promoter sequence comprising the nucleic acid sequence of SEQ ID NO: 7;
e) at least one transgene sequence comprising the nucleic acid sequence of SEQ ID NO: 13;
f) a polyA sequence comprising the nucleic acid sequence of SEQ ID NO: 14;
g) a second insulator sequence comprising the nucleic acid sequence of SEQ ID NO: 6;
h) a second piggyBac ITR sequence comprising the nucleic acid sequence of SEQ ID NO: 80;
i) a second AAV ITR sequence.

Embodiment 45a. An AAV piggyBac transposon polynucleotide comprising in the 5' to 3' direction:

a) a first AAV ITR sequence comprising the nucleic acid sequence of SEQ ID NO: 1;
b) a first piggyBac ITR sequence comprising the nucleic acid sequence of SEQ ID NO: 3;
c) a first insulator sequence comprising the nucleic acid sequence of SEQ ID NO: 5;
d) at least one promoter sequence comprising the nucleic acid sequence of SEQ ID NO: 8;
e) at least one transgene sequence comprising the nucleic acid sequence of SEQ ID NO: 13;
f) a polyA sequence comprising the nucleic acid sequence of SEQ ID NO: 14;
g) a second insulator sequence comprising the nucleic acid sequence of SEQ ID NO: 6;
h) a second piggyBac ITR sequence comprising the nucleic acid sequence of SEQ ID NO: 4;
i) a second AAV ITR sequence comprising the nucleic acid sequence of SEQ ID NO: 2.

Embodiment 45b. An AAV piggyBac transposon polynucleotide comprising in the 5' to 3' direction:

a) a first AAV ITR sequence;
b) a first piggyBac ITR sequence comprising the nucleic acid sequence of SEQ ID NO: 3;
c) a first insulator sequence comprising the nucleic acid sequence of SEQ ID NO: 5;
d) at least one promoter sequence comprising the nucleic acid sequence of SEQ ID NO: 8;
e) at least one transgene sequence comprising the nucleic acid sequence of SEQ ID NO: 13;
f) a polyA sequence comprising the nucleic acid sequence of SEQ ID NO: 14;
g) a second insulator sequence comprising the nucleic acid sequence of SEQ ID NO: 6;
h) a second piggyBac ITR sequence comprising the nucleic acid sequence of SEQ ID NO: 4;
i) a second AAV ITR sequence.

Embodiment 45c. An AAV piggyBac transposon polynucleotide comprising in the 5' to 3' direction:
- a) a first nucleic acid sequence comprising the nucleic acid sequence of SEQ ID NO: 1;
- b) a first piggyBac ITR sequence comprising the nucleic acid sequence of SEQ ID NO: 3;
- c) a first insulator sequence comprising the nucleic acid sequence of SEQ ID NO: 5;
- d) at least one promoter sequence comprising the nucleic acid sequence of SEQ ID NO: 8;
- e) at least one transgene sequence comprising the nucleic acid sequence of SEQ ID NO: 13;
- f) a polyA sequence comprising the nucleic acid sequence of SEQ ID NO: 14;
- g) a second insulator sequence comprising the nucleic acid sequence of SEQ ID NO: 6;
- h) a second piggyBac ITR sequence comprising the nucleic acid sequence of SEQ ID NO: 4;
- i) a second nucleic acid sequence comprising the nucleic acid sequence of SEQ ID NO: 2.

Embodiment 45d. An AAV piggyBac transposon polynucleotide comprising in the 5' to 3' direction:
- a) a first AAV ITR sequence;
- b) a first piggyBac ITR sequence comprising the nucleic acid sequence of SEQ ID NO: 79;
- c) a first insulator sequence comprising the nucleic acid sequence of SEQ ID NO: 5;
- d) at least one promoter sequence comprising the nucleic acid sequence of SEQ ID NO: 8;
- e) at least one transgene sequence comprising the nucleic acid sequence of SEQ ID NO: 13;
- f) a polyA sequence comprising the nucleic acid sequence of SEQ ID NO: 14;
- g) a second insulator sequence comprising the nucleic acid sequence of SEQ ID NO: 6;
- h) a second piggyBac ITR sequence comprising the nucleic acid sequence of SEQ ID NO: 80;
- i) a second AAV ITR sequence.

Embodiment 46a. An AAV piggyBac transposon polynucleotide comprising in the 5' to 3' direction:
- a) a first AAV ITR sequence comprising the nucleic acid sequence of SEQ ID NO: 1;
- b) a first piggyBac ITR sequence comprising the nucleic acid sequence of SEQ ID NO: 3;
- c) a first insulator sequence comprising the nucleic acid sequence of SEQ ID NO: 5;
- d) at least one promoter sequence comprising the nucleic acid sequence of SEQ ID NO: 9;
- e) at least one transgene sequence comprising the nucleic acid sequence of SEQ ID NO: 13;
- f) a polyA sequence comprising the nucleic acid sequence of SEQ ID NO: 14;
- g) a second insulator sequence comprising the nucleic acid sequence of SEQ ID NO: 6;
- h) a second piggyBac ITR sequence comprising the nucleic acid sequence of SEQ ID NO: 4;
- i) a second AAV ITR sequence comprising the nucleic acid sequence of SEQ ID NO: 2.

Embodiment 46b. An AAV piggyBac transposon polynucleotide comprising in the 5' to 3' direction:
- a) a first AAV ITR sequence;
- b) a first piggyBac ITR sequence comprising the nucleic acid sequence of SEQ ID NO: 3;
- c) a first insulator sequence comprising the nucleic acid sequence of SEQ ID NO: 5;
- d) at least one promoter sequence comprising the nucleic acid sequence of SEQ ID NO: 9;
- e) at least one transgene sequence comprising the nucleic acid sequence of SEQ ID NO: 13;
- f) a polyA sequence comprising the nucleic acid sequence of SEQ ID NO: 14;
- g) a second insulator sequence comprising the nucleic acid sequence of SEQ ID NO: 6;
- h) a second piggyBac ITR sequence comprising the nucleic acid sequence of SEQ ID NO: 4;
- i) a second AAV ITR sequence.

Embodiment 46c. An AAV piggyBac transposon polynucleotide comprising in the 5' to 3' direction:
- a) a first nucleic acid sequence comprising the nucleic acid sequence of SEQ ID NO: 1;
- b) a first piggyBac ITR sequence comprising the nucleic acid sequence of SEQ ID NO: 3;
- c) a first insulator sequence comprising the nucleic acid sequence of SEQ ID NO: 5;
- d) at least one promoter sequence comprising the nucleic acid sequence of SEQ ID NO: 9;
- e) at least one transgene sequence comprising the nucleic acid sequence of SEQ ID NO: 13;
- f) a polyA sequence comprising the nucleic acid sequence of SEQ ID NO: 14;
- g) a second insulator sequence comprising the nucleic acid sequence of SEQ ID NO: 6;
- h) a second piggyBac ITR sequence comprising the nucleic acid sequence of SEQ ID NO: 4;
- i) a second nucleic acid sequence comprising the nucleic acid sequence of SEQ ID NO: 2.

Embodiment 46d. An AAV piggyBac transposon polynucleotide comprising in the 5' to 3' direction:
- a) a first AAV ITR sequence;
- b) a first piggyBac ITR sequence comprising the nucleic acid sequence of SEQ ID NO: 79;
- c) a first insulator sequence comprising the nucleic acid sequence of SEQ ID NO: 5;
- d) at least one promoter sequence comprising the nucleic acid sequence of SEQ ID NO: 9;
- e) at least one transgene sequence comprising the nucleic acid sequence of SEQ ID NO: 13;
- f) a polyA sequence comprising the nucleic acid sequence of SEQ ID NO: 14;
- g) a second insulator sequence comprising the nucleic acid sequence of SEQ ID NO: 6;
- h) a second piggyBac ITR sequence comprising the nucleic acid sequence of SEQ ID NO: 80;
- i) a second AAV ITR sequence.

Embodiment 47a. An AAV piggyBac transposon polynucleotide comprising in the 5' to 3' direction:
- a) a first AAV ITR sequence comprising the nucleic acid sequence of SEQ ID NO: 1;
- b) a first piggyBac ITR sequence comprising the nucleic acid sequence of SEQ ID NO: 3;
- c) a first insulator sequence comprising the nucleic acid sequence of SEQ ID NO: 5;
- d) at least one promoter sequence comprising the nucleic acid sequence of SEQ ID NO: 10;
- e) at least one transgene sequence comprising the nucleic acid sequence of SEQ ID NO: 13;
- f) a polyA sequence comprising the nucleic acid sequence of SEQ ID NO: 14;
- g) a second insulator sequence comprising the nucleic acid sequence of SEQ ID NO: 6;
- h) a second piggyBac ITR sequence comprising the nucleic acid sequence of SEQ ID NO: 4;
- i) a second AAV ITR sequence comprising the nucleic acid sequence of SEQ ID NO: 2.

Embodiment 47b. An AAV piggyBac transposon polynucleotide comprising in the 5' to 3' direction:

a) a first AAV ITR sequence;
b) a first piggyBac ITR sequence comprising the nucleic acid sequence of SEQ ID NO: 3;
c) a first insulator sequence comprising the nucleic acid sequence of SEQ ID NO: 5;
d) at least one promoter sequence comprising the nucleic acid sequence of SEQ ID NO: 10;
e) at least one transgene sequence comprising the nucleic acid sequence of SEQ ID NO: 13;
f) a polyA sequence comprising the nucleic acid sequence of SEQ ID NO: 14;
g) a second insulator sequence comprising the nucleic acid sequence of SEQ ID NO: 6;
h) a second piggyBac ITR sequence comprising the nucleic acid sequence of SEQ ID NO: 4;
i) a second AAV ITR sequence.

Embodiment 47c. An AAV piggyBac transposon polynucleotide comprising in the 5' to 3' direction:

a) a first nucleic acid sequence comprising the nucleic acid sequence of SEQ ID NO: 1;
b) a first piggyBac ITR sequence comprising the nucleic acid sequence of SEQ ID NO: 3;
c) a first insulator sequence comprising the nucleic acid sequence of SEQ ID NO: 5;
d) at least one promoter sequence comprising the nucleic acid sequence of SEQ ID NO: 10;
e) at least one transgene sequence comprising the nucleic acid sequence of SEQ ID NO: 13;
f) a polyA sequence comprising the nucleic acid sequence of SEQ ID NO: 14;
g) a second insulator sequence comprising the nucleic acid sequence of SEQ ID NO: 6;
h) a second piggyBac ITR sequence comprising the nucleic acid sequence of SEQ ID NO: 4;
i) a second nucleic acid sequence comprising the nucleic acid sequence of SEQ ID NO: 2.

Embodiment 47d. An AAV piggyBac transposon polynucleotide comprising in the 5' to 3' direction:

a) a first AAV ITR sequence;
b) a first piggyBac ITR sequence comprising the nucleic acid sequence of SEQ ID NO: 79;
c) a first insulator sequence comprising the nucleic acid sequence of SEQ ID NO: 5;
d) at least one promoter sequence comprising the nucleic acid sequence of SEQ ID NO: 10;
e) at least one transgene sequence comprising the nucleic acid sequence of SEQ ID NO: 13;
f) a polyA sequence comprising the nucleic acid sequence of SEQ ID NO: 14;
g) a second insulator sequence comprising the nucleic acid sequence of SEQ ID NO: 6;
h) a second piggyBac ITR sequence comprising the nucleic acid sequence of SEQ ID NO: 80;
i) a second AAV ITR sequence.

Embodiment 48a. An AAV piggyBac transposon polynucleotide comprising in the 5' to 3' direction:

a) a first AAV ITR sequence comprising the nucleic acid sequence of SEQ ID NO: 1;
b) a first piggyBac ITR sequence comprising the nucleic acid sequence of SEQ ID NO: 3;
c) a first insulator sequence comprising the nucleic acid sequence of SEQ ID NO: 5;
d) at least one promoter sequence comprising the nucleic acid sequence of SEQ ID NO: 11;
e) at least one transgene sequence comprising the nucleic acid sequence of SEQ ID NO: 13;
f) a polyA sequence comprising the nucleic acid sequence of SEQ ID NO: 14;
g) a second insulator sequence comprising the nucleic acid sequence of SEQ ID NO: 6;
h) a second piggyBac ITR sequence comprising the nucleic acid sequence of SEQ ID NO: 4;
i) a second AAV ITR sequence comprising the nucleic acid sequence of SEQ ID NO: 2.

Embodiment 48b. An AAV piggyBac transposon polynucleotide comprising in the 5' to 3' direction:

a) a first AAV ITR sequence;
b) a first piggyBac ITR sequence comprising the nucleic acid sequence of SEQ ID NO: 3;
c) a first insulator sequence comprising the nucleic acid sequence of SEQ ID NO: 5;
d) at least one promoter sequence comprising the nucleic acid sequence of SEQ ID NO: 11;
e) at least one transgene sequence comprising the nucleic acid sequence of SEQ ID NO: 13;
f) a polyA sequence comprising the nucleic acid sequence of SEQ ID NO: 14;
g) a second insulator sequence comprising the nucleic acid sequence of SEQ ID NO: 6;
h) a second piggyBac ITR sequence comprising the nucleic acid sequence of SEQ ID NO: 4;
i) a second AAV ITR sequence.

Embodiment 48c. An AAV piggyBac transposon polynucleotide comprising in the 5' to 3' direction:

a) a first nucleic acid sequence comprising the nucleic acid sequence of SEQ ID NO: 1;
b) a first piggyBac ITR sequence comprising the nucleic acid sequence of SEQ ID NO: 3;
c) a first insulator sequence comprising the nucleic acid sequence of SEQ ID NO: 5;
d) at least one promoter sequence comprising the nucleic acid sequence of SEQ ID NO: 11;
e) at least one transgene sequence comprising the nucleic acid sequence of SEQ ID NO: 13;
f) a polyA sequence comprising the nucleic acid sequence of SEQ ID NO: 14;
g) a second insulator sequence comprising the nucleic acid sequence of SEQ ID NO: 6;
h) a second piggyBac ITR sequence comprising the nucleic acid sequence of SEQ ID NO: 4;
i) a second nucleic sequence comprising the nucleic acid sequence of SEQ ID NO: 2.

Embodiment 48d. An AAV piggyBac transposon polynucleotide comprising in the 5' to 3' direction:

a) a first AAV ITR sequence;
b) a first piggyBac ITR sequence comprising the nucleic acid sequence of SEQ ID NO: 79;
c) a first insulator sequence comprising the nucleic acid sequence of SEQ ID NO: 5;
d) at least one promoter sequence comprising the nucleic acid sequence of SEQ ID NO: 11;
e) at least one transgene sequence comprising the nucleic acid sequence of SEQ ID NO: 13;
f) a polyA sequence comprising the nucleic acid sequence of SEQ ID NO: 14;
g) a second insulator sequence comprising the nucleic acid sequence of SEQ ID NO: 6;
h) a second piggyBac ITR sequence comprising the nucleic acid sequence of SEQ ID NO: 80;
i) a second AAV ITR sequence.

Embodiment 49a. An AAV piggyBac transposon polynucleotide comprising in the 5' to 3' direction:

a) a first AAV ITR sequence comprising the nucleic acid sequence of SEQ ID NO: 1;
b) a first piggyBac ITR sequence comprising the nucleic acid sequence of SEQ ID NO: 3;
c) a first insulator sequence comprising the nucleic acid sequence of SEQ ID NO: 5;
d) at least one promoter sequence comprising the nucleic acid sequence of SEQ ID NO: 10;
e) a first transgene sequence comprising the nucleic acid sequence of SEQ ID NO: 13;
f) at least one self-cleaving peptide sequence comprising the nucleic acid sequence of SEQ ID NO: 15;
g) an at least second transgene sequence comprising the nucleic acid sequence of SEQ ID NO: 16;
h) a polyA sequence comprising the nucleic acid sequence of SEQ ID NO: 14;
i) a second insulator sequence comprising the nucleic acid sequence of SEQ ID NO: 6;
j) a second piggyBac ITR sequence comprising the nucleic acid sequence of SEQ ID NO: 4; and
k) a second AAV ITR sequence comprising the nucleic acid sequence of SEQ ID NO: 2.

Embodiment 49b. An AAV piggyBac transposon polynucleotide comprising in the 5' to 3' direction:

a) a first AAV ITR sequence;
b) a first piggyBac ITR sequence comprising the nucleic acid sequence of SEQ ID NO: 3;
c) a first insulator sequence comprising the nucleic acid sequence of SEQ ID NO: 5;
d) at least one promoter sequence comprising the nucleic acid sequence of SEQ ID NO: 10;
e) a first transgene sequence comprising the nucleic acid sequence of SEQ ID NO: 13;
f) at least one self-cleaving peptide sequence comprising the nucleic acid sequence of SEQ ID NO: 15;
g) an at least second transgene sequence comprising the nucleic acid sequence of SEQ ID NO: 16;
h) a polyA sequence comprising the nucleic acid sequence of SEQ ID NO: 14;
i) a second insulator sequence comprising the nucleic acid sequence of SEQ ID NO: 6;
j) a second piggyBac ITR sequence comprising the nucleic acid sequence of SEQ ID NO: 4; and
k) a second AAV ITR sequence.

Embodiment 49c. An AAV piggyBac transposon polynucleotide comprising in the 5' to 3' direction:

a) a first nucleic acid sequence comprising the nucleic acid sequence of SEQ ID NO: 1;
b) a first piggyBac ITR sequence comprising the nucleic acid sequence of SEQ ID NO: 3;
c) a first insulator sequence comprising the nucleic acid sequence of SEQ ID NO: 5;
d) at least one promoter sequence comprising the nucleic acid sequence of SEQ ID NO: 10;
e) a first transgene sequence comprising the nucleic acid sequence of SEQ ID NO: 13;
f) at least one self-cleaving peptide sequence comprising the nucleic acid sequence of SEQ ID NO: 15;
g) an at least second transgene sequence comprising the nucleic acid sequence of SEQ ID NO: 16;
h) a polyA sequence comprising the nucleic acid sequence of SEQ ID NO: 14;
i) a second insulator sequence comprising the nucleic acid sequence of SEQ ID NO: 6;
j) a second piggyBac ITR sequence comprising the nucleic acid sequence of SEQ ID NO: 4; and
k) a second nucleic acid sequence comprising the nucleic acid sequence of SEQ ID NO: 2.

Embodiment 49d. An AAV piggyBac transposon polynucleotide comprising in the 5' to 3' direction:

a) a first AAV ITR sequence;
b) a first piggyBac ITR sequence comprising the nucleic acid sequence of SEQ ID NO: 79;
c) a first insulator sequence comprising the nucleic acid sequence of SEQ ID NO: 5;
d) at least one promoter sequence comprising the nucleic acid sequence of SEQ ID NO: 10;
e) a first transgene sequence comprising the nucleic acid sequence of SEQ ID NO: 13;
f) at least one self-cleaving peptide sequence comprising the nucleic acid sequence of SEQ ID NO: 15;
g) an at least second transgene sequence comprising the nucleic acid sequence of SEQ ID NO: 16;
h) a polyA sequence comprising the nucleic acid sequence of SEQ ID NO: 14;
i) a second insulator sequence comprising the nucleic acid sequence of SEQ ID NO: 6;
j) a second piggyBac ITR sequence comprising the nucleic acid sequence of SEQ ID NO: 80; and
k) a second AAV ITR sequence.

Embodiment 50a. An AAV piggyBac transposon polynucleotide comprising in the 5' to 3' direction:

a) a first AAV ITR sequence comprising the nucleic acid sequence of SEQ ID NO: 1;
b) a first piggyBac ITR sequence comprising the nucleic acid sequence of SEQ ID NO: 3;
c) a first insulator sequence comprising the nucleic acid sequence of SEQ ID NO: 5;
d) at least one promoter sequence comprising the nucleic acid sequence of SEQ ID NO: 12;
e) a first transgene sequence comprising the nucleic acid sequence of SEQ ID NO: 13;
f) at least one self-cleaving peptide sequence comprising the nucleic acid sequence of SEQ ID NO: 15;
g) an at least second transgene sequence comprising the nucleic acid sequence of SEQ ID NO: 16;
h) a polyA sequence comprising the nucleic acid sequence of SEQ ID NO: 14;
i) a second insulator sequence comprising the nucleic acid sequence of SEQ ID NO: 6;
j) a second piggyBac ITR sequence comprising the nucleic acid sequence of SEQ ID NO: 4; and
k) a second AAV ITR sequence comprising the nucleic acid sequence of SEQ ID NO: 2.

Embodiment 50b. An AAV piggyBac transposon polynucleotide comprising in the 5' to 3' direction:

a) a first AAV ITR sequence;
b) a first piggyBac ITR sequence comprising the nucleic acid sequence of SEQ ID NO: 3;
c) a first insulator sequence comprising the nucleic acid sequence of SEQ ID NO: 5;
d) at least one promoter sequence comprising the nucleic acid sequence of SEQ ID NO: 12;
e) a first transgene sequence comprising the nucleic acid sequence of SEQ ID NO: 13;
f) at least one self-cleaving peptide sequence comprising the nucleic acid sequence of SEQ ID NO: 15;
g) an at least second transgene sequence comprising the nucleic acid sequence of SEQ ID NO: 16;
h) a polyA sequence comprising the nucleic acid sequence of SEQ ID NO: 14;

i) a second insulator sequence comprising the nucleic acid sequence of SEQ ID NO: 6;
j) a second piggyBac ITR sequence comprising the nucleic acid sequence of SEQ ID NO: 4; and
k) a second AAV ITR sequence.

Embodiment 50c. An AAV piggyBac transposon polynucleotide comprising in the 5' to 3' direction:
a) a first nucleic acid sequence comprising the nucleic acid sequence of SEQ ID NO: 1;
b) a first piggyBac ITR sequence comprising the nucleic acid sequence of SEQ ID NO: 3;
c) a first insulator sequence comprising the nucleic acid sequence of SEQ ID NO: 5;
d) at least one promoter sequence comprising the nucleic acid sequence of SEQ ID NO: 12;
e) a first transgene sequence comprising the nucleic acid sequence of SEQ ID NO: 13;
f) at least one self-cleaving peptide sequence comprising the nucleic acid sequence of SEQ ID NO: 15;
g) an at least second transgene sequence comprising the nucleic acid sequence of SEQ ID NO: 16;
h) a polyA sequence comprising the nucleic acid sequence of SEQ ID NO: 14;
i) a second insulator sequence comprising the nucleic acid sequence of SEQ ID NO: 6;
j) a second piggyBac ITR sequence comprising the nucleic acid sequence of SEQ ID NO: 4; and
k) a second nucleic acid sequence comprising the nucleic acid sequence of SEQ ID NO: 2.

Embodiment 50d. An AAV piggyBac transposon polynucleotide comprising in the 5' to 3' direction:
a) a first AAV ITR sequence;
b) a first piggyBac ITR sequence comprising the nucleic acid sequence of SEQ ID NO: 79;
c) a first insulator sequence comprising the nucleic acid sequence of SEQ ID NO: 5;
d) at least one promoter sequence comprising the nucleic acid sequence of SEQ ID NO: 12;
e) a first transgene sequence comprising the nucleic acid sequence of SEQ ID NO: 13;
f) at least one self-cleaving peptide sequence comprising the nucleic acid sequence of SEQ ID NO: 15;
g) an at least second transgene sequence comprising the nucleic acid sequence of SEQ ID NO: 16;
h) a polyA sequence comprising the nucleic acid sequence of SEQ ID NO: 14;
i) a second insulator sequence comprising the nucleic acid sequence of SEQ ID NO: 6;
j) a second piggyBac ITR sequence comprising the nucleic acid sequence of SEQ ID NO: 80; and
k) a second AAV ITR sequence.

Embodiment 51a. An AAV piggyBac transposon polynucleotide comprising in the 5' to 3' direction:
a) a first AAV ITR sequence comprising the nucleic acid sequence of SEQ ID NO: 1;
b) a first piggyBac ITR sequence comprising the nucleic acid sequence of SEQ ID NO: 3;
c) a first insulator sequence comprising the nucleic acid sequence of SEQ ID NO: 5;
d) at least one promoter sequence comprising the nucleic acid sequence of SEQ ID NO: 11;
e) at least one transgene sequence comprising the nucleic acid sequence of SEQ ID NO: 23;
f) a polyA sequence comprising the nucleic acid sequence of SEQ ID NO: 14;
g) a second insulator sequence comprising the nucleic acid sequence of SEQ ID NO: 6;
h) a second piggyBac ITR sequence comprising the nucleic acid sequence of SEQ ID NO: 4;
i) a second AAV ITR sequence comprising the nucleic acid sequence of SEQ ID NO: 2.

Embodiment 51b. An AAV piggyBac transposon polynucleotide comprising in the 5' to 3' direction:
a) a first AAV ITR sequence;
b) a first piggyBac ITR sequence comprising the nucleic acid sequence of SEQ ID NO: 3;
c) a first insulator sequence comprising the nucleic acid sequence of SEQ ID NO: 5;
d) at least one promoter sequence comprising the nucleic acid sequence of SEQ ID NO: 11;
e) at least one transgene sequence comprising the nucleic acid sequence of SEQ ID NO: 23;
f) a polyA sequence comprising the nucleic acid sequence of SEQ ID NO: 14;
g) a second insulator sequence comprising the nucleic acid sequence of SEQ ID NO: 6;
h) a second piggyBac ITR sequence comprising the nucleic acid sequence of SEQ ID NO: 4;
i) a second AAV ITR sequence.

Embodiment 51c. An AAV piggyBac transposon polynucleotide comprising in the 5' to 3' direction:
a) a first nucleic acid sequence comprising the nucleic acid sequence of SEQ ID NO: 1;
b) a first piggyBac ITR sequence comprising the nucleic acid sequence of SEQ ID NO: 3;
c) a first insulator sequence comprising the nucleic acid sequence of SEQ ID NO: 5;
d) at least one promoter sequence comprising the nucleic acid sequence of SEQ ID NO: 11;
e) at least one transgene sequence comprising the nucleic acid sequence of SEQ ID NO: 23;
f) a polyA sequence comprising the nucleic acid sequence of SEQ ID NO: 14;
g) a second insulator sequence comprising the nucleic acid sequence of SEQ ID NO: 6;
h) a second piggyBac ITR sequence comprising the nucleic acid sequence of SEQ ID NO: 4;
i) a second nucleic acid sequence comprising the nucleic acid sequence of SEQ ID NO: 2.

Embodiment 51d. An AAV piggyBac transposon polynucleotide comprising in the 5' to 3' direction:
a) a first AAV ITR sequence;
b) a first piggyBac ITR sequence comprising the nucleic acid sequence of SEQ ID NO: 79;
c) a first insulator sequence comprising the nucleic acid sequence of SEQ ID NO: 5;
d) at least one promoter sequence comprising the nucleic acid sequence of SEQ ID NO: 11;
e) at least one transgene sequence comprising the nucleic acid sequence of SEQ ID NO: 23;
f) a polyA sequence comprising the nucleic acid sequence of SEQ ID NO: 14;
g) a second insulator sequence comprising the nucleic acid sequence of SEQ ID NO: 6;
h) a second piggyBac ITR sequence comprising the nucleic acid sequence of SEQ ID NO: 80;
i) a second AAV ITR sequence.

Embodiment 52a. An AAV piggyBac transposon polynucleotide comprising in the 5' to 3' direction:
a) a first AAV ITR sequence comprising the nucleic acid sequence of SEQ ID NO: 1;
b) a first piggyBac ITR sequence comprising the nucleic acid sequence of SEQ ID NO: 3;

c) a first insulator sequence comprising the nucleic acid sequence of SEQ ID NO: 5;
d) at least one promoter sequence comprising the nucleic acid sequence of SEQ ID NO: 10;
e) at least one transgene sequence comprising the nucleic acid sequence of SEQ ID NO: 23;
f) a polyA sequence comprising the nucleic acid sequence of SEQ ID NO: 14;
g) a second insulator sequence comprising the nucleic acid sequence of SEQ ID NO: 6;
h) a second piggyBac ITR sequence comprising the nucleic acid sequence of SEQ ID NO: 4;
i) a second AAV ITR sequence comprising the nucleic acid sequence of SEQ ID NO: 2.

Embodiment 52b. An AAV piggyBac transposon polynucleotide comprising in the 5' to 3' direction:
a) a first AAV ITR sequence;
b) a first piggyBac ITR sequence comprising the nucleic acid sequence of SEQ ID NO: 3;
c) a first insulator sequence comprising the nucleic acid sequence of SEQ ID NO: 5;
d) at least one promoter sequence comprising the nucleic acid sequence of SEQ ID NO: 10;
e) at least one transgene sequence comprising the nucleic acid sequence of SEQ ID NO: 23;
f) a polyA sequence comprising the nucleic acid sequence of SEQ ID NO: 14;
g) a second insulator sequence comprising the nucleic acid sequence of SEQ ID NO: 6;
h) a second piggyBac ITR sequence comprising the nucleic acid sequence of SEQ ID NO: 4;
i) a second AAV ITR sequence.

Embodiment 52c. An AAV piggyBac transposon polynucleotide comprising in the 5' to 3' direction:
a) a first nucleic acid sequence comprising the nucleic acid sequence of SEQ ID NO: 1;
b) a first piggyBac ITR sequence comprising the nucleic acid sequence of SEQ ID NO: 3;
c) a first insulator sequence comprising the nucleic acid sequence of SEQ ID NO: 5;
d) at least one promoter sequence comprising the nucleic acid sequence of SEQ ID NO: 10;
e) at least one transgene sequence comprising the nucleic acid sequence of SEQ ID NO: 23;
f) a polyA sequence comprising the nucleic acid sequence of SEQ ID NO: 14;
g) a second insulator sequence comprising the nucleic acid sequence of SEQ ID NO: 6;
h) a second piggyBac ITR sequence comprising the nucleic acid sequence of SEQ ID NO: 4;
i) a second nucleic acid sequence comprising the nucleic acid sequence of SEQ ID NO: 2.

Embodiment 52d. An AAV piggyBac transposon polynucleotide comprising in the 5' to 3' direction:
a) a first AAV ITR sequence;
b) a first piggyBac ITR sequence comprising the nucleic acid sequence of SEQ ID NO: 79;
c) a first insulator sequence comprising the nucleic acid sequence of SEQ ID NO: 5;
d) at least one promoter sequence comprising the nucleic acid sequence of SEQ ID NO: 10;
e) at least one transgene sequence comprising the nucleic acid sequence of SEQ ID NO: 23;
f) a polyA sequence comprising the nucleic acid sequence of SEQ ID NO: 14;
g) a second insulator sequence comprising the nucleic acid sequence of SEQ ID NO: 6;
h) a second piggyBac ITR sequence comprising the nucleic acid sequence of SEQ ID NO: 80;
i) a second AAV ITR sequence.

Embodiment 53a. An AAV piggyBac transposon polynucleotide comprising in the 5' to 3' direction:
a) a first AAV ITR sequence comprising the nucleic acid sequence of SEQ ID NO: 1;
b) a first piggyBac ITR sequence comprising the nucleic acid sequence of SEQ ID NO: 3;
c) a first insulator sequence comprising the nucleic acid sequence of SEQ ID NO: 5;
d) at least one promoter sequence comprising the nucleic acid sequence of SEQ ID NO: 10;
e) a first transgene sequence comprising the nucleic acid sequence of SEQ ID NO: 23;
f) at least one self-cleaving peptide sequence comprising the nucleic acid sequence of SEQ ID NO: 15;
g) an at least second transgene sequence comprising the nucleic acid sequence of SEQ ID NO: 16;
h) a polyA sequence comprising the nucleic acid sequence of SEQ ID NO: 14;
i) a second insulator sequence comprising the nucleic acid sequence of SEQ ID NO: 6;
j) a second piggyBac ITR sequence comprising the nucleic acid sequence of SEQ ID NO: 4; and
k) a second AAV ITR sequence comprising the nucleic acid sequence of SEQ ID NO: 2.

Embodiment 53b. An AAV piggyBac transposon polynucleotide comprising in the 5' to 3' direction:
a) a first AAV ITR sequence;
b) a first piggyBac ITR sequence comprising the nucleic acid sequence of SEQ ID NO: 3;
c) a first insulator sequence comprising the nucleic acid sequence of SEQ ID NO: 5;
d) at least one promoter sequence comprising the nucleic acid sequence of SEQ ID NO: 10;
e) a first transgene sequence comprising the nucleic acid sequence of SEQ ID NO: 23;
f) at least one self-cleaving peptide sequence comprising the nucleic acid sequence of SEQ ID NO: 15;
g) an at least second transgene sequence comprising the nucleic acid sequence of SEQ ID NO: 16;
h) a polyA sequence comprising the nucleic acid sequence of SEQ ID NO: 14;
i) a second insulator sequence comprising the nucleic acid sequence of SEQ ID NO: 6;
j) a second piggyBac ITR sequence comprising the nucleic acid sequence of SEQ ID NO: 4; and
k) a second AAV ITR sequence.

Embodiment 53c. An AAV piggyBac transposon polynucleotide comprising in the 5' to 3' direction:
a) a first nucleic acid sequence comprising the nucleic acid sequence of SEQ ID NO: 1;
b) a first piggyBac ITR sequence comprising the nucleic acid sequence of SEQ ID NO: 3;
c) a first insulator sequence comprising the nucleic acid sequence of SEQ ID NO: 5;
d) at least one promoter sequence comprising the nucleic acid sequence of SEQ ID NO: 10;
e) a first transgene sequence comprising the nucleic acid sequence of SEQ ID NO: 23;
f) at least one self-cleaving peptide sequence comprising the nucleic acid sequence of SEQ ID NO: 15;
g) an at least second transgene sequence comprising the nucleic acid sequence of SEQ ID NO: 16;
h) a polyA sequence comprising the nucleic acid sequence of SEQ ID NO: 14;

i) a second insulator sequence comprising the nucleic acid sequence of SEQ ID NO: 6;

j) a second piggyBac ITR sequence comprising the nucleic acid sequence of SEQ ID NO: 4; and k) a second nucleic acid sequence comprising the nucleic acid sequence of SEQ ID NO: 2.

Embodiment 53d. An AAV piggyBac transposon polynucleotide comprising in the 5' to 3' direction:

a) a first AAV ITR sequence;

b) a first piggyBac ITR sequence comprising the nucleic acid sequence of SEQ ID NO: 79;

c) a first insulator sequence comprising the nucleic acid sequence of SEQ ID NO: 5;

d) at least one promoter sequence comprising the nucleic acid sequence of SEQ ID NO: 10;

e) a first transgene sequence comprising the nucleic acid sequence of SEQ ID NO: 23;

f) at least one self-cleaving peptide sequence comprising the nucleic acid sequence of SEQ ID NO: 15;

g) an at least second transgene sequence comprising the nucleic acid sequence of SEQ ID NO: 16;

h) a polyA sequence comprising the nucleic acid sequence of SEQ ID NO: 14;

i) a second insulator sequence comprising the nucleic acid sequence of SEQ ID NO: 6;

j) a second piggyBac ITR sequence comprising the nucleic acid sequence of SEQ ID NO: 80; and k) a second AAV ITR sequence.

Embodiment 54a. An AAV piggyBac transposon polynucleotide comprising in the 5' to 3' direction:

a) a first AAV ITR sequence comprising the nucleic acid sequence of SEQ ID NO: 1;

b) a first piggyBac ITR sequence comprising the nucleic acid sequence of SEQ ID NO: 3;

c) a first insulator sequence comprising the nucleic acid sequence of SEQ ID NO: 5;

d) at least one promoter sequence comprising the nucleic acid sequence of SEQ ID NO: 12;

e) a first transgene sequence comprising the nucleic acid sequence of SEQ ID NO: 23;

f) at least one self-cleaving peptide sequence comprising the nucleic acid sequence of SEQ ID NO: 15;

g) an at least second transgene sequence comprising the nucleic acid sequence of SEQ ID NO: 16;

h) a polyA sequence comprising the nucleic acid sequence of SEQ ID NO: 14;

i) a second insulator sequence comprising the nucleic acid sequence of SEQ ID NO: 6;

j) a second piggyBac ITR sequence comprising the nucleic acid sequence of SEQ ID NO: 4; and k) a second AAV ITR sequence comprising the nucleic acid sequence of SEQ ID NO: 2.

Embodiment 54b. An AAV piggyBac transposon polynucleotide comprising in the 5' to 3' direction:

a) a first AAV ITR sequence;

b) a first piggyBac ITR sequence comprising the nucleic acid sequence of SEQ ID NO: 3;

c) a first insulator sequence comprising the nucleic acid sequence of SEQ ID NO: 5;

d) at least one promoter sequence comprising the nucleic acid sequence of SEQ ID NO: 12;

e) a first transgene sequence comprising the nucleic acid sequence of SEQ ID NO: 23;

f) at least one self-cleaving peptide sequence comprising the nucleic acid sequence of SEQ ID NO: 15;

g) an at least second transgene sequence comprising the nucleic acid sequence of SEQ ID NO: 16;

h) a polyA sequence comprising the nucleic acid sequence of SEQ ID NO: 14;

i) a second insulator sequence comprising the nucleic acid sequence of SEQ ID NO: 6;

j) a second piggyBac ITR sequence comprising the nucleic acid sequence of SEQ ID NO: 4; and k) a second AAV ITR sequence.

Embodiment 54c. An AAV piggyBac transposon polynucleotide comprising in the 5' to 3' direction:

a) a first nucleic acid sequence comprising the nucleic acid sequence of SEQ ID NO: 1;

b) a first piggyBac ITR sequence comprising the nucleic acid sequence of SEQ ID NO: 3;

c) a first insulator sequence comprising the nucleic acid sequence of SEQ ID NO: 5;

d) at least one promoter sequence comprising the nucleic acid sequence of SEQ ID NO: 12;

e) a first transgene sequence comprising the nucleic acid sequence of SEQ ID NO: 23;

f) at least one self-cleaving peptide sequence comprising the nucleic acid sequence of SEQ ID NO: 15;

g) an at least second transgene sequence comprising the nucleic acid sequence of SEQ ID NO: 16;

h) a polyA sequence comprising the nucleic acid sequence of SEQ ID NO: 14;

i) a second insulator sequence comprising the nucleic acid sequence of SEQ ID NO: 6;

j) a second piggyBac ITR sequence comprising the nucleic acid sequence of SEQ ID NO: 4; and k) a second nucleic acid sequence comprising the nucleic acid sequence of SEQ ID NO: 2.

Embodiment 54d. An AAV piggyBac transposon polynucleotide comprising in the 5' to 3' direction:

a) a first AAV ITR sequence;

b) a first piggyBac ITR sequence comprising the nucleic acid sequence of SEQ ID NO: 79;

c) a first insulator sequence comprising the nucleic acid sequence of SEQ ID NO: 5;

d) at least one promoter sequence comprising the nucleic acid sequence of SEQ ID NO: 12;

e) a first transgene sequence comprising the nucleic acid sequence of SEQ ID NO: 23;

f) at least one self-cleaving peptide sequence comprising the nucleic acid sequence of SEQ ID NO: 15;

g) an at least second transgene sequence comprising the nucleic acid sequence of SEQ ID NO: 16;

h) a polyA sequence comprising the nucleic acid sequence of SEQ ID NO: 14;

i) a second insulator sequence comprising the nucleic acid sequence of SEQ ID NO: 6;

j) a second piggyBac ITR sequence comprising the nucleic acid sequence of SEQ ID NO: 80; and k) a second AAV ITR sequence.

Embodiment 55a. An AAV piggyBac transposon polynucleotide comprising in the 5' to 3' direction:

a) a first AAV ITR sequence comprising the nucleic acid sequence of SEQ ID NO: 17;

b) a first piggyBac ITR sequence comprising the nucleic acid sequence of SEQ ID NO: 19;

c) a first insulator sequence comprising the nucleic acid sequence of SEQ ID NO: 5;

d) at least one promoter sequence comprising the nucleic acid sequence of SEQ ID NO: 12;

e) a first transgene sequence comprising the nucleic acid sequence of SEQ ID NO: 23;

f) a polyA sequence comprising the nucleic acid sequence of SEQ ID NO: 22;

g) a second insulator sequence comprising the nucleic acid sequence of SEQ ID NO: 20;

h) a second piggyBac ITR sequence comprising the nucleic acid sequence of SEQ ID NO: 21;

i) a DNA spacer sequence comprising the nucleic acid sequence SEQ ID NO: 28 j) a second AAV ITR sequence comprising the nucleic acid sequence of SEQ ID NO: 18.

Embodiment 55b. An AAV piggyBac transposon polynucleotide comprising in the 5' to 3' direction:

a) a first AAV ITR sequence;

b) a first piggyBac ITR sequence comprising the nucleic acid sequence of SEQ ID NO: 19;

c) a first insulator sequence comprising the nucleic acid sequence of SEQ ID NO: 5;

d) at least one promoter sequence comprising the nucleic acid sequence of SEQ ID NO: 12;

e) a first transgene sequence comprising the nucleic acid sequence of SEQ ID NO: 23;

f) a polyA sequence comprising the nucleic acid sequence of SEQ ID NO: 22;

g) a second insulator sequence comprising the nucleic acid sequence of SEQ ID NO: 20;

h) a second piggyBac ITR sequence comprising the nucleic acid sequence of SEQ ID NO: 21;

i) a DNA spacer sequence comprising the nucleic acid sequence SEQ ID NO: 28 j) a second AAV ITR sequence.

Embodiment 55c. An AAV piggyBac transposon polynucleotide comprising in the 5' to 3' direction:

a) a first nucleic acid sequence comprising the nucleic acid sequence of SEQ ID NO: 17;

b) a first piggyBac ITR sequence comprising the nucleic acid sequence of SEQ ID NO: 19;

c) a first insulator sequence comprising the nucleic acid sequence of SEQ ID NO: 5;

d) at least one promoter sequence comprising the nucleic acid sequence of SEQ ID NO: 12;

e) a first transgene sequence comprising the nucleic acid sequence of SEQ ID NO: 23;

f) a polyA sequence comprising the nucleic acid sequence of SEQ ID NO: 22;

g) a second insulator sequence comprising the nucleic acid sequence of SEQ ID NO: 20;

h) a second piggyBac ITR sequence comprising the nucleic acid sequence of SEQ ID NO: 21;

i) a DNA spacer sequence comprising the nucleic acid sequence SEQ ID NO: 28 j) a second nucleic acid sequence comprising the nucleic acid sequence of SEQ ID NO: 18.

Embodiment 55d. An AAV piggyBac transposon polynucleotide comprising in the 5' to 3' direction:

a) a first AAV ITR sequence;

b) a first piggyBac ITR sequence comprising the nucleic acid sequence of SEQ ID NO: 79;

c) a first insulator sequence comprising the nucleic acid sequence of SEQ ID NO: 5;

d) at least one promoter sequence comprising the nucleic acid sequence of SEQ ID NO: 12;

e) a first transgene sequence comprising the nucleic acid sequence of SEQ ID NO: 23;

f) a polyA sequence comprising the nucleic acid sequence of SEQ ID NO: 22;

g) a second insulator sequence comprising the nucleic acid sequence of SEQ ID NO: 20;

h) a second piggyBac ITR sequence comprising the nucleic acid sequence of SEQ ID NO: 80;

i) a DNA spacer sequence comprising the nucleic acid sequence SEQ ID NO: 28 j) a second AAV ITR sequence.

Embodiment 56a. An AAV piggyBac transposon polynucleotide comprising in the 5' to 3' direction:

a) a first AAV ITR sequence comprising the nucleic acid sequence of SEQ ID NO: 17;

b) a first piggyBac ITR sequence comprising the nucleic acid sequence of SEQ ID NO: 19;

c) a first insulator sequence comprising the nucleic acid sequence of SEQ ID NO: 5;

d) at least one promoter sequence comprising the nucleic acid sequence of SEQ ID NO: 12;

e) a first transgene sequence comprising the nucleic acid sequence of SEQ ID NO: 23;

f) at least one self-cleaving peptide sequence comprising the nucleic acid sequence of SEQ ID NO: 24;

g) an at least second transgene sequence comprising the nucleic acid sequence of SEQ ID NO: 25;

h) a polyA sequence comprising the nucleic acid sequence of SEQ ID NO: 22;

i) a second insulator sequence comprising the nucleic acid sequence of SEQ ID NO: 20;

j) a second piggyBac ITR sequence comprising the nucleic acid sequence of SEQ ID NO: 21; and k) a second AAV ITR sequence comprising the nucleic acid sequence of SEQ ID NO: 18.

Embodiment 56b. An AAV piggyBac transposon polynucleotide comprising in the 5' to 3' direction:

a) a first AAV ITR sequence;

b) a first piggyBac ITR sequence comprising the nucleic acid sequence of SEQ ID NO: 19;

c) a first insulator sequence comprising the nucleic acid sequence of SEQ ID NO: 5;

d) at least one promoter sequence comprising the nucleic acid sequence of SEQ ID NO: 12;

e) a first transgene sequence comprising the nucleic acid sequence of SEQ ID NO: 23;

f) at least one self-cleaving peptide sequence comprising the nucleic acid sequence of SEQ ID NO: 24;

g) an at least second transgene sequence comprising the nucleic acid sequence of SEQ ID NO: 25;

h) a polyA sequence comprising the nucleic acid sequence of SEQ ID NO: 22;

i) a second insulator sequence comprising the nucleic acid sequence of SEQ ID NO: 20;

j) a second piggyBac ITR sequence comprising the nucleic acid sequence of SEQ ID NO: 21; and k) a second AAV ITR sequence.

Embodiment 56c. An AAV piggyBac transposon polynucleotide comprising in the 5' to 3' direction:

a) a first nucleic acid sequence comprising the nucleic acid sequence of SEQ ID NO: 17;

b) a first piggyBac ITR sequence comprising the nucleic acid sequence of SEQ ID NO: 19;

c) a first insulator sequence comprising the nucleic acid sequence of SEQ ID NO: 5;

d) at least one promoter sequence comprising the nucleic acid sequence of SEQ ID NO: 12;

e) a first transgene sequence comprising the nucleic acid sequence of SEQ ID NO: 23;

f) at least one self-cleaving peptide sequence comprising the nucleic acid sequence of SEQ ID NO: 24;

g) an at least second transgene sequence comprising the nucleic acid sequence of SEQ ID NO: 25;

h) a polyA sequence comprising the nucleic acid sequence of SEQ ID NO: 22;

i) a second insulator sequence comprising the nucleic acid sequence of SEQ ID NO: 20;

j) a second piggyBac ITR sequence comprising the nucleic acid sequence of SEQ ID NO: 21; and k) a second nucleic acid sequence comprising the nucleic acid sequence of SEQ ID NO: 18.

Embodiment 56d. An AAV piggyBac transposon polynucleotide comprising in the 5' to 3' direction:

a) a first AAV ITR sequence;

b) a first piggyBac ITR sequence comprising the nucleic acid sequence of SEQ ID NO: 79;

c) a first insulator sequence comprising the nucleic acid sequence of SEQ ID NO: 5;

d) at least one promoter sequence comprising the nucleic acid sequence of SEQ ID NO: 12;

e) a first transgene sequence comprising the nucleic acid sequence of SEQ ID NO: 23;

f) at least one self-cleaving peptide sequence comprising the nucleic acid sequence of SEQ ID NO: 24;

g) an at least second transgene sequence comprising the nucleic acid sequence of SEQ ID NO: 25;

h) a polyA sequence comprising the nucleic acid sequence of SEQ ID NO: 22;

i) a second insulator sequence comprising the nucleic acid sequence of SEQ ID NO: 20;

j) a second piggyBac ITR sequence comprising the nucleic acid sequence of SEQ ID NO: 80; and k) a second AAV ITR sequence.

Embodiment 57. The AAV piggyBac transposon polynucleotide of any one of the preceding embodiments, wherein the AAV piggyBac transposon polynucleotide comprises the nucleic acid sequence of SEQ ID NO: 29.

Embodiment 58. The AAV piggyBac transposon polynucleotide of any one of the preceding embodiments, wherein the AAV piggyBac transposon polynucleotide comprises the nucleic acid sequence of SEQ ID NO: 30.

Embodiment 59. The AAV piggyBac transposon polynucleotide of any one of the preceding embodiments, wherein the AAV piggyBac transposon polynucleotide comprises the nucleic acid sequence of SEQ ID NO: 31.

Embodiment 60. The AAV piggyBac transposon polynucleotide of any one of the preceding embodiments, wherein the AAV piggyBac transposon polynucleotide comprises the nucleic acid sequence of SEQ ID NO: 32.

Embodiment 61. The AAV piggyBac transposon polynucleotide of any one of the preceding embodiments, wherein the AAV piggyBac transposon polynucleotide comprises the nucleic acid sequence of SEQ ID NO: 33.

Embodiment 62. The AAV piggyBac transposon polynucleotide of any one of the preceding embodiments, wherein the AAV piggyBac transposon polynucleotide comprises the nucleic acid sequence of SEQ ID NO: 34.

Embodiment 63. The AAV piggyBac transposon polynucleotide of any one of the preceding embodiments, wherein the AAV piggyBac transposon polynucleotide comprises the nucleic acid sequence of SEQ ID NO: 35.

Embodiment 64. The AAV piggyBac transposon polynucleotide of any one of the preceding embodiments, wherein the AAV piggyBac transposon polynucleotide comprises the nucleic acid sequence of SEQ ID NO: 36.

Embodiment 65. The AAV piggyBac transposon polynucleotide of any one of the preceding embodiments, wherein the AAV piggyBac transposon polynucleotide comprises the nucleic acid sequence of SEQ ID NO: 37.

Embodiment 66. The AAV piggyBac transposon polynucleotide of any one of the preceding embodiments, wherein the AAV piggyBac transposon polynucleotide comprises the nucleic acid sequence of SEQ ID NO: 38.

Embodiment 67. The AAV piggyBac transposon polynucleotide of any one of the preceding embodiments, wherein the AAV piggyBac transposon polynucleotide comprises the nucleic acid sequence of SEQ ID NO: 39.

Embodiment 68. The AAV piggyBac transposon polynucleotide of any one of the preceding embodiments, wherein the AAV piggyBac transposon polynucleotide comprises the nucleic acid sequence of SEQ ID NO: 40.

Embodiment 69. The AAV piggyBac transposon polynucleotide of any one of the preceding embodiments, wherein the AAV piggyBac transposon polynucleotide comprises the nucleic acid sequence of SEQ ID NO: 41.

Embodiment 70. A vector comprising the AAV piggyBac transposon polynucleotide of any one of the preceding embodiments.

Embodiment 71. The vector of any one of the preceding embodiments, wherein the vector is a viral vector.

Embodiment 72. The vector of any one of the preceding embodiments, wherein the viral vector is an adeno-associated virus (AAV) viral vector.

Embodiment 73. The vector of any one of the preceding embodiments, wherein the AAV viral vector is an AAV1, AAV2, AAV3, AAV4, AAV5, AAV6, AAV7, AAV8, AAV9, AAV10 or AAV11 viral vector.

Embodiment 74. The vector of any one of the preceding embodiments, wherein the AAV viral vector is an AAV-KP-1 or AAV-NP59 viral vector, preferably wherein the AAV viral vector is an AAV-KP-1 viral vector.

Embodiment 75. A composition comprising the vector of any one of embodiments 70-74.

Embodiment 76. An AAV transposase polynucleotide comprising in the 5' to 3' direction a first AAV ITR sequence, at least one promoter sequence, at least one transposase sequence, a polyA sequence and a second AAV ITR sequence.

Embodiment 77. An AAV transposase polynucleotide comprising in the 5' to 3' direction:

a) a first AAV ITR sequence comprising the nucleic acid sequence of SEQ ID NO: 73;

b) at least one promoter sequence at least one promoter sequence comprising the nucleic acid sequence of 74;

c) at least one transposase sequence comprising the nucleic acid sequence of SEQ ID NO: 53;

d) a polyA sequence comprising the nucleic acid sequences of SEQ ID NO: 75;

e) at least one DNA spacer sequence comprising the nucleic acid sequences of SEQ ID NO: 76; and f) a second AAV ITR sequence comprising the nucleic acid sequences of SEQ ID NO: 77.

Embodiment 78. The AAV piggyBac transposase polynucleotide of any one of the proceeding Embodiments, wherein the at least one promoter sequence comprises the nucleic acid sequence of SEQ ID NO: 78.

Embodiment 79. A vector comprising the AAV transposase polynucleotide of any one of the preceding embodiments.

Embodiment 80. The vector of any one of the preceding embodiments, wherein the vector is a viral vector.

Embodiment 81. The vector of any one of the preceding embodiments, wherein the viral vector is an adeno-associated virus (AAV) viral vector.

Embodiment 82. The vector of any one of the preceding embodiments, wherein the AAV viral vector is an AAV1, AAV2, AAV3, AAV4, AAV5, AAV6, AAV7, AAV8, AAV9, AAV10 or AAV11 viral vector.

Embodiment 83. The vector of any one of the preceding embodiments, wherein the AAV viral vector is an AAV-KP-1 or AAV-NP59 AAV viral vector, preferably wherein the AAV viral vector is an AAV-KP-1 viral vector.

Embodiment 84. A composition comprising the vector of any one of embodiments 79-83.

Embodiment 85. A composition comprising the vector of any one of embodiments 70-74 and the vector of any one of embodiments 79-83.

Embodiment 86. A method of treating hemophilia in a subject in need thereof comprising administering to the subject at least one therapeutically effective amount of at least one polynucleotide, vector or composition of any one of the preceding embodiments.

Embodiment 87. A method of treating hemophilia in a subject in need thereof comprising administering to a subject:

a) at least one therapeutically effective amount of the AAV piggyBac transposon polynucleotide of any one of the preceding embodiments, or any one of the vectors and/or compositions of the preceding embodiments that comprise an AAV piggyBac transposon polynucleotide; and b) at least one therapeutically effective amount of the AAV piggyBac transposase polynucleotide of any one of the preceding embodiments, or any one of the vectors and/or compositions of the preceding embodiments that comprise an AAV piggyBac transposase polynucleotide.

Embodiment 88. The method of embodiment 86 or 87, wherein the hemophilia is hemophilia A, hemophilia B, hemophilia C, parahemophila or any combination thereof.

Embodiment 89. The method of embodiment 88, wherein the hemophilia is hemophilia A.

Embodiment 90. The method of embodiment 88, wherein the hemophilia is hemophilia B.

Embodiment 91. A polynucleotide comprising in the 5' to 3' direction:

a) a first piggyBac ITR sequence;
b) a first insulator sequence;
c) at least one promoter sequence;
d) at least one transgene sequence;
e) a polyA sequence;
f) a second insulator sequence;
g) a second piggyBac ITR sequence.

Embodiment 92. The polynucleotide of embodiment 91, wherein the polynucleotide comprises DNA, cDNA, gDNA, RNA, mRNA or any combination thereof.

Embodiment 93. The polynucleotide of any one of the preceding embodiments, wherein the first and/or the second nucleic acid sequence comprises the nucleic acid sequence of any one of SEQ ID NOs: 1, 2, 17 and 18.

Embodiment 94. The polynucleotide of any one of the preceding embodiments, wherein the first piggyBac ITR sequence and/or the second piggyBac ITR sequence comprises the nucleic acid sequence of any one of SEQ ID NOs: 3, 4, 19 and 21.

Embodiment 95. The Polynucleotide of any one of the preceding embodiments, wherein the first piggyBac ITR sequence and/or the second piggyBac ITR sequence comprises the nucleic acid sequence of any one of SEQ ID NOs: 1 and 2.

Embodiment 96. The polynucleotide of any one of the preceding embodiments, wherein the first piggyBac ITR sequence and/or the second piggyBac ITR sequence comprises the nucleic acid sequence of any one of SEQ ID NOs: 79 and 80.

Embodiment 97. The polynucleotide of any one of the preceding embodiments, wherein the first piggyBac ITR sequence comprises the nucleic acid sequence of SEQ ID NO: 3 and the second piggyBac ITR comprises the nucleic acid sequence of SEQ ID NO: 4.

Embodiment 98. The polynucleotide of any one of the preceding embodiments, wherein the first piggyBac ITR sequence comprises the nucleic acid sequence of SEQ ID NO: 19 and the second piggyBac ITR comprises the nucleic acid sequence of SEQ ID NO: 21.

Embodiment 99. The polynucleotide of any one of the preceding embodiments, wherein the first piggyBac ITR sequence comprises the nucleic acid sequence of SEQ ID NO: 79 and the second piggyBac ITR comprises the nucleic acid sequence of SEQ ID NO: 80.

Embodiment 100. The polynucleotide of any one of the preceding embodiments, wherein the first insulator sequence and/or the second insulator sequence comprises the nucleic acid sequence of any one of SEQ ID NOs: 5, 6 and 20.

Embodiment 101. The polynucleotide of any one of the preceding embodiments, wherein the first insulator sequence comprises the nucleic acid sequence of SEQ ID NO: 5 and the second insulator sequence comprises the nucleic acid sequence of SEQ ID NO: 6.

Embodiment 102. The polynucleotide of any one of the preceding embodiments, wherein the first insulator sequence comprises the nucleic acid sequence of SEQ ID NO: 5 and the second insulator sequence comprises the nucleic acid sequence of SEQ ID NO: 20.

Embodiment 103. The polynucleotide of any one of the preceding embodiments, wherein the at least one promoter sequence comprises the nucleic acid sequence of any one of SEQ IDS NOs: 7-12.

Embodiment 104. The polynucleotide of any one of the preceding embodiments, wherein the at least one promoter sequence comprises the nucleic acid sequence of SEQ IDS NO: 7.

Embodiment 105. The polynucleotide of any one of the preceding embodiments, wherein the at least one promoter sequence comprises the nucleic acid sequence of SEQ IDS NO: 8.

Embodiment 106. The polynucleotide of any one of the preceding embodiments, wherein the at least one promoter sequence comprises the nucleic acid sequence of SEQ IDS NO: 9.

Embodiment 107. The polynucleotide of any one of the preceding embodiments, wherein the at least one promoter sequence comprises the nucleic acid sequence of SEQ IDS NO: 10.

Embodiment 108. The polynucleotide of any one of the preceding embodiments, wherein the at least one promoter sequence comprises the nucleic acid sequence of SEQ IDS NO: 11.

Embodiment 109. The polynucleotide of any one of the preceding embodiments, wherein the at least one promoter sequence comprises the nucleic acid sequence of SEQ IDS NO: 12.

Embodiment 110. The polynucleotide of any one of the preceding embodiments, wherein the at least one transgene sequence comprises a nucleic acid sequence encoding a Factor VIII (FVIII) polypeptide.

Embodiment 111. The polynucleotide of any one of the preceding embodiments, wherein the FVIII polypeptide comprises the amino acid sequence of SEQ ID NO: 26.

Embodiment 112. The polynucleotide of any one of the preceding embodiments, wherein the nucleic acid sequence encoding a FVIII polypeptide comprises the nucleic acid sequence of SEQ ID NO: 13.

Embodiment 113. The polynucleotide of any one of the preceding embodiments, wherein the at least one transgene sequence comprises a nucleic acid sequence encoding a Factor IX (FIX) polypeptide.

Embodiment 114. The polynucleotide of any one of the preceding embodiments, wherein the FIX polypeptide comprises the amino acid sequence of SEQ ID NO: 27.

Embodiment 115. The polynucleotide of any one of the preceding embodiments, wherein the nucleic acid sequence encoding a FIX polypeptide comprises the nucleic acid sequence of SEQ ID NO: 23.

Embodiment 116. The polynucleotide of any one of the preceding embodiments, wherein the at least one transgene sequence is operatively linked to the at least one promoter sequence.

Embodiment 117. The polynucleotide of any one of the preceding embodiments, wherein the expression of the at least one transgene sequence is controlled by the at least one promoter sequence.

Embodiment 118. The polynucleotide of any one of the preceding embodiments, wherein the polyA sequence comprises the nucleic acid sequence of SEQ ID NO: 14.

Embodiment 119. The polynucleotide of any one of the preceding embodiments, wherein the polyA sequence comprises the nucleic acid sequence of SEQ ID NO: 22.

Embodiment 120. The polynucleotide of any one of the preceding embodiments, wherein the polynucleotide further comprises at least a second transgene sequence.

Embodiment 121. The polynucleotide of any one of the preceding embodiments, wherein the at least second transgene sequence comprises a luciferase sequence.

Embodiment 122. The polynucleotide of any one of the preceding embodiments, wherein the luciferase sequence comprises SEQ ID NO: 16 or 25.

Embodiment 123. The polynucleotide of any one of the preceding embodiments, wherein the polynucleotide further comprises at least a second promoter sequence.

Embodiment 124. The polynucleotide of any one of the preceding embodiments, wherein the at least second promoter sequence is located between the at least one transgene sequence and the at least second transgene sequence.

Embodiment 125. The polynucleotide of any one of the preceding embodiments, wherein the polynucleotide further comprises at least one self-cleaving peptide sequence, wherein the at least one self-cleaving peptide sequence is a nucleic acid sequence encoding for a T2A peptide, GSG-T2A peptide, an E2A peptide, a GSG-E2A peptide, an F2A peptide, a GSG-F2A peptide, a P2A peptide, or a GSG-P2A peptide.

Embodiment 126. The polynucleotide of any one of the preceding embodiments, wherein the at least one self-cleaving peptide sequence is located between the at least one transgene sequence and the at least second transgene sequence.

Embodiment 127. The polynucleotide of any one of the preceding embodiments, wherein the polynucleotide comprises at least two transgene sequences.

Embodiment 128. The polynucleotide of any one of the preceding embodiments, wherein the at least two transgene sequences are the same sequence.

Embodiment 129. The polynucleotide of any one of the preceding embodiments, wherein the at least two transgene sequences are different sequences.

Embodiment 130. The polynucleotide of any one of the preceding embodiments, further comprising at least one DNA spacer sequence.

Embodiment 131. The polynucleotide of any one of the preceding embodiments, wherein the at least one DNA spacer sequence comprises the nucleic acid sequence of SEQ ID NO: 28.

Embodiment 132. The polynucleotide of any one of the preceding embodiments, wherein the polynucleotide comprises at least two promoter sequences.

Embodiment 133. The polynucleotide of any one of the preceding embodiments, wherein the at least two promoter sequences are the same sequence.

Embodiment 134. The polynucleotide of any one of the preceding embodiments, wherein the at least two promoter sequences are different sequences.

Embodiment 135. An polynucleotide comprising in the 5' to 3' direction:

a) a first piggyBac ITR sequence comprising the nucleic acid sequence of SEQ ID NO: 3;
b) a first insulator sequence comprising the nucleic acid sequence of SEQ ID NO: 5;
c) at least one promoter sequence comprising the nucleic acid sequence of SEQ ID NO: 7;
d) at least one transgene sequence comprising the nucleic acid sequence of SEQ ID NO: 13;
e) a polyA sequence comprising the nucleic acid sequence of SEQ ID NO: 14;
f) a second insulator sequence comprising the nucleic acid sequence of SEQ ID NO: 6;
g) a second piggyBac ITR sequence comprising the nucleic acid sequence of SEQ ID NO: 4.

Embodiment 136. A polynucleotide comprising in the 5' to 3' direction:

a) a first piggyBac ITR sequence comprising the nucleic acid sequence of SEQ ID NO: 79;
b) a first insulator sequence comprising the nucleic acid sequence of SEQ ID NO: 5;
c) at least one promoter sequence comprising the nucleic acid sequence of SEQ ID NO: 7;
d) at least one transgene sequence comprising the nucleic acid sequence of SEQ ID NO: 13;
e) a polyA sequence comprising the nucleic acid sequence of SEQ ID NO: 14;
f) a second insulator sequence comprising the nucleic acid sequence of SEQ ID NO: 6;
g) a second piggyBac ITR sequence comprising the nucleic acid sequence of SEQ ID NO: 80.

Embodiment 137. A polynucleotide comprising in the 5' to 3' direction:

a) a first piggyBac ITR sequence comprising the nucleic acid sequence of SEQ ID NO: 3;
b) a first insulator sequence comprising the nucleic acid sequence of SEQ ID NO: 5;
c) at least one promoter sequence comprising the nucleic acid sequence of SEQ ID NO: 8;
d) at least one transgene sequence comprising the nucleic acid sequence of SEQ ID NO: 13;
e) a polyA sequence comprising the nucleic acid sequence of SEQ ID NO: 14;
f) a second insulator sequence comprising the nucleic acid sequence of SEQ ID NO: 6;
g) a second piggyBac ITR sequence comprising the nucleic acid sequence of SEQ ID NO: 4.

Embodiment 138. A polynucleotide comprising in the 5' to 3' direction:

a) a first piggyBac ITR sequence comprising the nucleic acid sequence of SEQ ID NO: 79;
b) a first insulator sequence comprising the nucleic acid sequence of SEQ ID NO: 5;
c) at least one promoter sequence comprising the nucleic acid sequence of SEQ ID NO: 8;
d) at least one transgene sequence comprising the nucleic acid sequence of SEQ ID NO: 13;
e) a polyA sequence comprising the nucleic acid sequence of SEQ ID NO: 14;
f) a second insulator sequence comprising the nucleic acid sequence of SEQ ID NO: 6;
g) a second piggyBac ITR sequence comprising the nucleic acid sequence of SEQ ID NO: 80.

Embodiment 139. A polynucleotide comprising in the 5' to 3' direction:
a) a first piggyBac ITR sequence comprising the nucleic acid sequence of SEQ ID NO: 3;
b) a first insulator sequence comprising the nucleic acid sequence of SEQ ID NO: 5;
c) at least one promoter sequence comprising the nucleic acid sequence of SEQ ID NO: 9;
d) at least one transgene sequence comprising the nucleic acid sequence of SEQ ID NO: 13;
e) a polyA sequence comprising the nucleic acid sequence of SEQ ID NO: 14;
f) a second insulator sequence comprising the nucleic acid sequence of SEQ ID NO: 6;
g) a second piggyBac ITR sequence comprising the nucleic acid sequence of SEQ ID NO: 4.

Embodiment 140. A polynucleotide comprising in the 5' to 3' direction:
a) a first piggyBac ITR sequence comprising the nucleic acid sequence of SEQ ID NO: 79;
b) a first insulator sequence comprising the nucleic acid sequence of SEQ ID NO: 5;
c) at least one promoter sequence comprising the nucleic acid sequence of SEQ ID NO: 9;
d) at least one transgene sequence comprising the nucleic acid sequence of SEQ ID NO: 13;
e) a polyA sequence comprising the nucleic acid sequence of SEQ ID NO: 14;
f) a second insulator sequence comprising the nucleic acid sequence of SEQ ID NO: 6;
g) a second piggyBac ITR sequence comprising the nucleic acid sequence of SEQ ID NO: 80.

Embodiment 141. A polynucleotide comprising in the 5' to 3' direction:
a) a first piggyBac ITR sequence comprising the nucleic acid sequence of SEQ ID NO: 3;
b) a first insulator sequence comprising the nucleic acid sequence of SEQ ID NO: 5;
c) at least one promoter sequence comprising the nucleic acid sequence of SEQ ID NO: 10;
d) at least one transgene sequence comprising the nucleic acid sequence of SEQ ID NO: 13;
e) a polyA sequence comprising the nucleic acid sequence of SEQ ID NO: 14;
f) a second insulator sequence comprising the nucleic acid sequence of SEQ ID NO: 6;
g) a second piggyBac ITR sequence comprising the nucleic acid sequence of SEQ ID NO: 4.

Embodiment 142. A polynucleotide comprising in the 5' to 3' direction:
a) a first piggyBac ITR sequence comprising the nucleic acid sequence of SEQ ID NO: 79;
b) a first insulator sequence comprising the nucleic acid sequence of SEQ ID NO: 5;
c) at least one promoter sequence comprising the nucleic acid sequence of SEQ ID NO: 10;
d) at least one transgene sequence comprising the nucleic acid sequence of SEQ ID NO: 13;
e) a polyA sequence comprising the nucleic acid sequence of SEQ ID NO: 14;
f) a second insulator sequence comprising the nucleic acid sequence of SEQ ID NO: 6;
g) a second piggyBac ITR sequence comprising the nucleic acid sequence of SEQ ID NO: 80.

Embodiment 143. A polynucleotide comprising in the 5' to 3' direction:
a) a first piggyBac ITR sequence comprising the nucleic acid sequence of SEQ ID NO: 3;
b) a first insulator sequence comprising the nucleic acid sequence of SEQ ID NO: 5;
c) at least one promoter sequence comprising the nucleic acid sequence of SEQ ID NO: 11;
d) at least one transgene sequence comprising the nucleic acid sequence of SEQ ID NO: 13;
e) a polyA sequence comprising the nucleic acid sequence of SEQ ID NO: 14;
f) a second insulator sequence comprising the nucleic acid sequence of SEQ ID NO: 6;
g) a second piggyBac ITR sequence comprising the nucleic acid sequence of SEQ ID NO: 4.

Embodiment 144. A polynucleotide comprising in the 5' to 3' direction:
a) a first piggyBac ITR sequence comprising the nucleic acid sequence of SEQ ID NO: 79;
b) a first insulator sequence comprising the nucleic acid sequence of SEQ ID NO: 5;
c) at least one promoter sequence comprising the nucleic acid sequence of SEQ ID NO: 11;
d) at least one transgene sequence comprising the nucleic acid sequence of SEQ ID NO: 13;
e) a polyA sequence comprising the nucleic acid sequence of SEQ ID NO: 14;
f) a second insulator sequence comprising the nucleic acid sequence of SEQ ID NO: 6;
g) a second piggyBac ITR sequence comprising the nucleic acid sequence of SEQ ID NO: 80.

Embodiment 145. A polynucleotide comprising in the 5' to 3' direction:
a) a first piggyBac ITR sequence comprising the nucleic acid sequence of SEQ ID NO: 3;
b) a first insulator sequence comprising the nucleic acid sequence of SEQ ID NO: 5;
c) at least one promoter sequence comprising the nucleic acid sequence of SEQ ID NO: 10;
d) a first transgene sequence comprising the nucleic acid sequence of SEQ ID NO: 13;
e) at least one self-cleaving peptide sequence comprising the nucleic acid sequence of SEQ ID NO: 15;
f) an at least second transgene sequence comprising the nucleic acid sequence of SEQ ID NO: 16;
g) a polyA sequence comprising the nucleic acid sequence of SEQ ID NO: 14;
h) a second insulator sequence comprising the nucleic acid sequence of SEQ ID NO: 6;
i) a second piggyBac ITR sequence comprising the nucleic acid sequence of SEQ ID NO: 4.

Embodiment 146. A polynucleotide comprising in the 5' to 3' direction:

a) a first piggyBac ITR sequence comprising the nucleic acid sequence of SEQ ID NO: 79;
b) a first insulator sequence comprising the nucleic acid sequence of SEQ ID NO: 5;
c) at least one promoter sequence comprising the nucleic acid sequence of SEQ ID NO: 10;
d) a first transgene sequence comprising the nucleic acid sequence of SEQ ID NO: 13;
e) at least one self-cleaving peptide sequence comprising the nucleic acid sequence of SEQ ID NO: 15;
f) an at least second transgene sequence comprising the nucleic acid sequence of SEQ ID NO: 16;
g) a polyA sequence comprising the nucleic acid sequence of SEQ ID NO: 14;
h) a second insulator sequence comprising the nucleic acid sequence of SEQ ID NO: 6;
i) a second piggyBac ITR sequence comprising the nucleic acid sequence of SEQ ID NO: 80.

Embodiment 147. A polynucleotide comprising in the 5' to 3' direction:
a) a first piggyBac ITR sequence comprising the nucleic acid sequence of SEQ ID NO: 3;
b) a first insulator sequence comprising the nucleic acid sequence of SEQ ID NO: 5;
c) at least one promoter sequence comprising the nucleic acid sequence of SEQ ID NO: 12;
d) a first transgene sequence comprising the nucleic acid sequence of SEQ ID NO: 13;
e) at least one self-cleaving peptide sequence comprising the nucleic acid sequence of SEQ ID NO: 15;
f) an at least second transgene sequence comprising the nucleic acid sequence of SEQ ID NO: 16;
g) a polyA sequence comprising the nucleic acid sequence of SEQ ID NO: 14;
h) a second insulator sequence comprising the nucleic acid sequence of SEQ ID NO: 6;
i) a second piggyBac ITR sequence comprising the nucleic acid sequence of SEQ ID NO: 4.

Embodiment 148. A polynucleotide comprising in the 5' to 3' direction:
a) a first piggyBac ITR sequence comprising the nucleic acid sequence of SEQ ID NO: 79;
b) a first insulator sequence comprising the nucleic acid sequence of SEQ ID NO: 5;
c) at least one promoter sequence comprising the nucleic acid sequence of SEQ ID NO: 12;
d) a first transgene sequence comprising the nucleic acid sequence of SEQ ID NO: 13;
e) at least one self-cleaving peptide sequence comprising the nucleic acid sequence of SEQ ID NO: 15;
f) an at least second transgene sequence comprising the nucleic acid sequence of SEQ ID NO: 16;
g) a polyA sequence comprising the nucleic acid sequence of SEQ ID NO: 14;
h) a second insulator sequence comprising the nucleic acid sequence of SEQ ID NO: 6;
i) a second piggyBac ITR sequence comprising the nucleic acid sequence of SEQ ID NO: 80.

Embodiment 149. A polynucleotide comprising in the 5' to 3' direction:
a) a first piggyBac ITR sequence comprising the nucleic acid sequence of SEQ ID NO: 3;
b) a first insulator sequence comprising the nucleic acid sequence of SEQ ID NO: 5;
c) at least one promoter sequence comprising the nucleic acid sequence of SEQ ID NO: 11;
d) at least one transgene sequence comprising the nucleic acid sequence of SEQ ID NO: 23;
e) a polyA sequence comprising the nucleic acid sequence of SEQ ID NO: 14;
f) a second insulator sequence comprising the nucleic acid sequence of SEQ ID NO: 6;
g) a second piggyBac ITR sequence comprising the nucleic acid sequence of SEQ ID NO: 4.

Embodiment 150. A polynucleotide comprising in the 5' to 3' direction:
a) a first piggyBac ITR sequence comprising the nucleic acid sequence of SEQ ID NO: 79;
b) a first insulator sequence comprising the nucleic acid sequence of SEQ ID NO: 5;
c) at least one promoter sequence comprising the nucleic acid sequence of SEQ ID NO: 11;
d) at least one transgene sequence comprising the nucleic acid sequence of SEQ ID NO: 23;
e) a polyA sequence comprising the nucleic acid sequence of SEQ ID NO: 14;
f) a second insulator sequence comprising the nucleic acid sequence of SEQ ID NO: 6;
g) a second piggyBac ITR sequence comprising the nucleic acid sequence of SEQ ID NO: 80.

Embodiment 151. A polynucleotide comprising in the 5' to 3' direction:
a) a first piggyBac ITR sequence comprising the nucleic acid sequence of SEQ ID NO: 3;
b) a first insulator sequence comprising the nucleic acid sequence of SEQ ID NO: 5;
c) at least one promoter sequence comprising the nucleic acid sequence of SEQ ID NO: 10;
d) at least one transgene sequence comprising the nucleic acid sequence of SEQ ID NO: 23;
e) a polyA sequence comprising the nucleic acid sequence of SEQ ID NO: 14;
f) a second insulator sequence comprising the nucleic acid sequence of SEQ ID NO: 6;
g) a second piggyBac ITR sequence comprising the nucleic acid sequence of SEQ ID NO: 4.

Embodiment 152. A polynucleotide comprising in the 5' to 3' direction:
a) a first piggyBac ITR sequence comprising the nucleic acid sequence of SEQ ID NO: 79;
b) a first insulator sequence comprising the nucleic acid sequence of SEQ ID NO: 5;
c) at least one promoter sequence comprising the nucleic acid sequence of SEQ ID NO: 10;
d) at least one transgene sequence comprising the nucleic acid sequence of SEQ ID NO: 23;
e) a polyA sequence comprising the nucleic acid sequence of SEQ ID NO: 14;
f) a second insulator sequence comprising the nucleic acid sequence of SEQ ID NO: 6;
g) a second piggyBac ITR sequence comprising the nucleic acid sequence of SEQ ID NO: 80.

Embodiment 153. A polynucleotide comprising in the 5' to 3' direction:
a) a first piggyBac ITR sequence comprising the nucleic acid sequence of SEQ ID NO: 3;
b) a first insulator sequence comprising the nucleic acid sequence of SEQ ID NO: 5;
c) at least one promoter sequence comprising the nucleic acid sequence of SEQ ID NO: 10;
d) a first transgene sequence comprising the nucleic acid sequence of SEQ ID NO: 23;

e) at least one self-cleaving peptide sequence comprising the nucleic acid sequence of SEQ ID NO: 15;
f) an at least second transgene sequence comprising the nucleic acid sequence of SEQ ID NO: 16;
g) a polyA sequence comprising the nucleic acid sequence of SEQ ID NO: 14;
h) a second insulator sequence comprising the nucleic acid sequence of SEQ ID NO: 6;
i) a second piggyBac ITR sequence comprising the nucleic acid sequence of SEQ ID NO: 4.

Embodiment 154. A polynucleotide comprising in the 5' to 3' direction:
a) a first piggyBac ITR sequence comprising the nucleic acid sequence of SEQ ID NO: 79;
b) a first insulator sequence comprising the nucleic acid sequence of SEQ ID NO: 5;
c) at least one promoter sequence comprising the nucleic acid sequence of SEQ ID NO: 10;
d) a first transgene sequence comprising the nucleic acid sequence of SEQ ID NO: 23;
e) at least one self-cleaving peptide sequence comprising the nucleic acid sequence of SEQ ID NO: 15;
f) an at least second transgene sequence comprising the nucleic acid sequence of SEQ ID NO: 16;
g) a polyA sequence comprising the nucleic acid sequence of SEQ ID NO: 14;
h) a second insulator sequence comprising the nucleic acid sequence of SEQ ID NO: 6;
i) a second piggyBac ITR sequence comprising the nucleic acid sequence of SEQ ID NO: 80.

Embodiment 155. A polynucleotide comprising in the 5' to 3' direction:
a) a first piggyBac ITR sequence comprising the nucleic acid sequence of SEQ ID NO: 3;
b) a first insulator sequence comprising the nucleic acid sequence of SEQ ID NO: 5;
c) at least one promoter sequence comprising the nucleic acid sequence of SEQ ID NO: 12;
d) a first transgene sequence comprising the nucleic acid sequence of SEQ ID NO: 23;
e) at least one self-cleaving peptide sequence comprising the nucleic acid sequence of SEQ ID NO: 15;
f) an at least second transgene sequence comprising the nucleic acid sequence of SEQ ID NO: 16;
g) a polyA sequence comprising the nucleic acid sequence of SEQ ID NO: 14;
h) a second insulator sequence comprising the nucleic acid sequence of SEQ ID NO: 6;
i) a second piggyBac ITR sequence comprising the nucleic acid sequence of SEQ ID NO: 4.

Embodiment 156. A polynucleotide comprising in the 5' to 3' direction:
a) a first piggyBac ITR sequence comprising the nucleic acid sequence of SEQ ID NO: 79;
b) a first insulator sequence comprising the nucleic acid sequence of SEQ ID NO: 5;
c) at least one promoter sequence comprising the nucleic acid sequence of SEQ ID NO: 12;
d) a first transgene sequence comprising the nucleic acid sequence of SEQ ID NO: 23;
e) at least one self-cleaving peptide sequence comprising the nucleic acid sequence of SEQ ID NO: 15;
f) an at least second transgene sequence comprising the nucleic acid sequence of SEQ ID NO: 16;
g) a polyA sequence comprising the nucleic acid sequence of SEQ ID NO: 14;
h) a second insulator sequence comprising the nucleic acid sequence of SEQ ID NO: 6;
i) a second piggyBac ITR sequence comprising the nucleic acid sequence of SEQ ID NO: 80.

Embodiment 157. A polynucleotide comprising in the 5' to 3' direction:
a) a first piggyBac ITR sequence comprising the nucleic acid sequence of SEQ ID NO: 19;
b) a first insulator sequence comprising the nucleic acid sequence of SEQ ID NO: 5;
c) at least one promoter sequence comprising the nucleic acid sequence of SEQ ID NO: 12;
d) a first transgene sequence comprising the nucleic acid sequence of SEQ ID NO: 23;
e) a polyA sequence comprising the nucleic acid sequence of SEQ ID NO: 22;
f) a second insulator sequence comprising the nucleic acid sequence of SEQ ID NO: 20;
g) a second piggyBac ITR sequence comprising the nucleic acid sequence of SEQ ID NO: 21;
h) a DNA spacer sequence comprising the nucleic acid sequence SEQ ID NO: 28.

Embodiment 158. A polynucleotide comprising in the 5' to 3' direction:
a) a first piggyBac ITR sequence comprising the nucleic acid sequence of SEQ ID NO: 79;
b) a first insulator sequence comprising the nucleic acid sequence of SEQ ID NO: 5;
c) at least one promoter sequence comprising the nucleic acid sequence of SEQ ID NO: 12;
d) a first transgene sequence comprising the nucleic acid sequence of SEQ ID NO: 23;
e) a polyA sequence comprising the nucleic acid sequence of SEQ ID NO: 22;
f) a second insulator sequence comprising the nucleic acid sequence of SEQ ID NO: 20;
g) a second piggyBac ITR sequence comprising the nucleic acid sequence of SEQ ID NO: 80;
h) a DNA spacer sequence comprising the nucleic acid sequence SEQ ID NO: 28.

Embodiment 159. A polynucleotide comprising in the 5' to 3' direction:
a) a first piggyBac ITR sequence comprising the nucleic acid sequence of SEQ ID NO: 19;
b) a first insulator sequence comprising the nucleic acid sequence of SEQ ID NO: 5;
c) at least one promoter sequence comprising the nucleic acid sequence of SEQ ID NO: 12;
d) a first transgene sequence comprising the nucleic acid sequence of SEQ ID NO: 23;
e) at least one self-cleaving peptide sequence comprising the nucleic acid sequence of SEQ ID NO: 24;
f) an at least second transgene sequence comprising the nucleic acid sequence of SEQ ID NO: 25;
g) a polyA sequence comprising the nucleic acid sequence of SEQ ID NO: 22;
h) a second insulator sequence comprising the nucleic acid sequence of SEQ ID NO: 20;
i) a second piggyBac ITR sequence comprising the nucleic acid sequence of SEQ ID NO: 21.

Embodiment 160. A polynucleotide comprising in the 5' to 3' direction:
a) a first piggyBac ITR sequence comprising the nucleic acid sequence of SEQ ID NO: 79;
b) a first insulator sequence comprising the nucleic acid sequence of SEQ ID NO: 5;

c) at least one promoter sequence comprising the nucleic acid sequence of SEQ ID NO: 12;
d) a first transgene sequence comprising the nucleic acid sequence of SEQ ID NO: 23;
e) at least one self-cleaving peptide sequence comprising the nucleic acid sequence of SEQ ID NO: 24;
f) an at least second transgene sequence comprising the nucleic acid sequence of SEQ ID NO: 25;
g) a polyA sequence comprising the nucleic acid sequence of SEQ ID NO: 22;
h) a second insulator sequence comprising the nucleic acid sequence of SEQ ID NO: 20;
i) a second piggyBac ITR sequence comprising the nucleic acid sequence of SEQ ID NO: 80.

Embodiment 161. The polynucleotide of any one of the preceding embodiments, wherein the polynucleotide comprises the nucleic acid sequence of SEQ ID NO: 29.

Embodiment 162. The polynucleotide of any one of the preceding embodiments, wherein the polynucleotide comprises the nucleic acid sequence of SEQ ID NO: 30.

Embodiment 163. The polynucleotide of any one of the preceding embodiments, wherein the polynucleotide comprises the nucleic acid sequence of SEQ ID NO: 31.

Embodiment 164. The polynucleotide of any one of the preceding embodiments, wherein the polynucleotide comprises the nucleic acid sequence of SEQ ID NO: 32.

Embodiment 165. The polynucleotide of any one of the preceding embodiments, wherein the polynucleotide comprises the nucleic acid sequence of SEQ ID NO: 33.

Embodiment 166. The polynucleotide of any one of the preceding embodiments, wherein the polynucleotide comprises the nucleic acid sequence of SEQ ID NO: 34.

Embodiment 167. The polynucleotide of any one of the preceding embodiments, wherein the polynucleotide comprises the nucleic acid sequence of SEQ ID NO: 35.

Embodiment 168. The polynucleotide of any one of the preceding embodiments, wherein the polynucleotide comprises the nucleic acid sequence of SEQ ID NO: 36.

Embodiment 169. The polynucleotide of any one of the preceding embodiments, wherein the polynucleotide comprises the nucleic acid sequence of SEQ ID NO: 37.

Embodiment 170. The polynucleotide of any one of the preceding embodiments, wherein the polynucleotide comprises the nucleic acid sequence of SEQ ID NO: 38.

Embodiment 171. The polynucleotide of any one of the preceding embodiments, wherein the polynucleotide comprises the nucleic acid sequence of SEQ ID NO: 39.

Embodiment 172. The polynucleotide of any one of the preceding embodiments, wherein the polynucleotide comprises the nucleic acid sequence of SEQ ID NO: 40.

Embodiment 173. The polynucleotide of any one of the preceding embodiments, wherein the polynucleotide comprises the nucleic acid sequence of SEQ ID NO: 41.

Embodiment 174. A vector comprising the polynucleotide of any one of the preceding embodiments.

Embodiment 175. The vector of any one of the preceding embodiments, wherein the vector is a viral vector.

Embodiment 176. The vector of any one of the preceding embodiments, wherein the viral vector is an adeno-associated virus (AAV) viral vector.

Embodiment 177. The vector of any one of the preceding embodiments, wherein the AAV viral vector is an AAV1, AAV2, AAV3, AAV4, AAV5, AAV6, AAV7, AAV8, AAV9, AAV10 or AAV11 viral vector.

Embodiment 178. The vector of any one of the preceding embodiments, wherein the AAV viral vector is an AAV-KP-1 or AAV-NP59 viral vector, preferably wherein the AAV viral vector is an AAV-KP-1 viral vector.

Embodiment 179. A composition comprising the vector or polynucleotide of any one of the preceding embodiments.

Embodiment 180. A method of treating hemophilia in a subject in need thereof comprising administering to the subject at least one therapeutically effective amount of at least one polynucleotide, vector or composition of any one of the preceding embodiments.

Embodiment 181. The method of embodiment 181, wherein the hemophilia is hemophilia A, hemophilia B, hemophilia C, parahemophila or any combination thereof.

Embodiment 182. The method of embodiment 182, wherein the hemophilia is hemophilia A.

Embodiment 183. The method of embodiment 182, wherein the hemophilia is hemophilia B.

Definitions

Nucleic Acid and Polynucleotide Molecules

Nucleic acid molecules and polynucleotide molecules of the present disclosure can be in the form of RNA, such as mRNA, hnRNA, tRNA or any other form, or in the form of DNA, including, but not limited to, cDNA and genomic DNA obtained by cloning or produced synthetically, or any combinations thereof. The DNA can be triple-stranded, double-stranded or single-stranded, or any combination thereof. Any portion of at least one strand of the DNA or RNA can be the coding strand, also known as the sense strand, or it can be the non-coding strand, also referred to as the anti-sense strand.

Construction of Nucleic Acid and Polynucleotide Molecules

The nucleic acid and polynucleotide molecules of the present disclosure can be made using (a) recombinant methods, (b) synthetic techniques, (c) purification techniques, and/or (d) combinations thereof, as well-known in the art.

The nucleic acid and polynucleotide molecules can conveniently comprise nucleotide sequences in addition to a polynucleotide of the present disclosure. For example, a multi-cloning site comprising one or more endonuclease restriction sites can be inserted into the nucleic acid to aid in isolation of the polynucleotide. Also, translatable sequences can be inserted to aid in the isolation of the translated polynucleotide of the disclosure. For example, a hexa-histidine marker sequence provides a convenient means to purify the proteins of the disclosure. The nucleic acid of the disclosure, excluding the coding sequence, is optionally a vector, adapter, or linker for cloning and/or expression of a polynucleotide of the disclosure.

Additional sequences can be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art.

Recombinant Methods for Constructing Nucleic Acid and Polynucleotide Molecules The nucleic acid and polynucleotide molecules of this disclosure, such as RNA, cDNA, genomic DNA, or any combination thereof, can be obtained from biological sources using any number of cloning methodologies known to those of skill in the art. In some aspects, oligonucleotide probes that selectively hybridize, under stringent conditions, to the polynucleotides of the present disclosure are used to identify the desired sequence in a cDNA or genomic DNA library. The isolation of RNA, and construction of cDNA and genomic libraries are well known to those of ordinary skill in the art.

Nucleic Acid Screening and Isolation Methods

A cDNA or genomic library can be screened using a probe based upon the sequence of a polynucleotide of the disclosure. Probes can be used to hybridize with genomic DNA or cDNA sequences to isolate homologous genes in the same or different organisms. Those of skill in the art will appreciate that various degrees of stringency of hybridization can be employed in the assay; and either the hybridization or the wash medium can be stringent. As the conditions for hybridization become more stringent, there must be a greater degree of complementarity between the probe and the target for duplex formation to occur. The degree of stringency can be controlled by one or more of temperature, ionic strength, pH and the presence of a partially denaturing solvent, such as formamide. For example, the stringency of hybridization is conveniently varied by changing the polarity of the reactant solution through, for example, manipulation of the concentration of formamide within the range of 0% to 50%. The degree of complementarity (sequence identity) required for detectable binding will vary in accordance with the stringency of the hybridization medium and/or wash medium. The degree of complementarity will optimally be 100%, or 70-100%, or any range or value therein. However, it should be understood that minor sequence variations in the probes and primers can be compensated for by reducing the stringency of the hybridization and/or wash medium.

Methods of amplification of RNA or DNA are well known in the art and can be used according to the disclosure without undue experimentation, based on the teaching and guidance presented herein.

Known methods of DNA or RNA amplification include, but are not limited to, polymerase chain reaction (PCR) and related amplification processes (see, e.g., U.S. Pat. Nos. 4,683,195, 4,683,202, 4,800,159, 4,965,188, to Mullis, et al.; 4,795,699 and 4,921,794 to Tabor, et al; U.S. Pat. No. 5,142,033 to Innis; U.S. Pat. No. 5,122,464 to Wilson, et al.; U.S. Pat. No. 5,091,310 to Innis; U.S. Pat. No. 5,066,584 to Gyllensten, et al; U.S. Pat. No. 4,889,818 to Gelfand, et al; U.S. Pat. No. 4,994,370 to Silver, et al; U.S. Pat. No. 4,766,067 to Biswas; U.S. Pat. No. 4,656,134 to Ringold) and RNA mediated amplification that uses anti-sense RNA to the target sequence as a template for double-stranded DNA synthesis (U.S. Pat. No. 5,130,238 to Malek, et al, with the tradename NASBA), the entire contents of which references are incorporated herein by reference.

For instance, polymerase chain reaction (PCR) technology can be used to amplify the sequences of polynucleotides of the disclosure and related genes directly from genomic DNA or cDNA libraries. PCR and other in vitro amplification methods can also be useful, for example, to clone nucleic acid sequences that code for proteins to be expressed, to make nucleic acids to use as probes for detecting the presence of the desired mRNA in samples, for nucleic acid sequencing, or for other purposes. Examples of techniques sufficient to direct persons of skill through in vitro amplification methods are found in U.S. Pat. No. 4,683,202 (1987); and Innis, et al., PCR Protocols A Guide to Methods and Applications, Eds., Academic Press Inc., San Diego, Calif. (1990). Commercially available kits for genomic PCR amplification are known in the art. See, e.g., Advantage-GC Genomic PCR Kit (Clontech). Additionally, e.g., the T4 gene 32 protein (Boehringer Mannheim) can be used to improve yield of long PCR products.

Synthetic Methods for Constructing Nucleic Acids

The nucleic acid and polynucleotide molecules of the disclosure can also be prepared by direct chemical synthesis by known methods. Chemical synthesis generally produces a single-stranded oligonucleotide, which can be converted into double-stranded DNA by hybridization with a complementary sequence, or by polymerization with a DNA polymerase using the single strand as a template. One of skill in the art will recognize that while chemical synthesis of DNA can be limited to sequences of about 100 or more bases, longer sequences can be obtained by the ligation of shorter sequences.

Recombinant Expression Cassettes

The disclosure further provides recombinant expression cassettes comprising a nucleic acid or polynucleotide molecule of the present disclosure. A nucleic acid or polynucleotide of the present disclosure can be used to construct a recombinant expression cassette that can be introduced into at least one desired host cell. A recombinant expression cassette will typically comprise a polynucleotide of the disclosure operably linked to transcriptional initiation regulatory sequences that will direct the transcription of the polynucleotide in the intended host cell. Both heterologous and non-heterologous (i.e., endogenous) promoters can be employed to direct expression of the nucleic acids of the disclosure.

In some aspects, isolated nucleic acids that serve as promoter, enhancer, or other elements can be introduced in the appropriate position (upstream, downstream or in the intron) of a non-heterologous form of a polynucleotide of the disclosure so as to up or down regulate expression of a polynucleotide of the disclosure. For example, endogenous promoters can be altered in vivo or in vitro by mutation, deletion and/or substitution.

Expression Vectors and Host Cells

The disclosure also relates to vectors that include isolated nucleic acid and polynucleotide molecules of the disclosure, host cells that are genetically engineered with the recombinant vectors, and the production of at least polynucleotide by recombinant techniques, as is well known in the art.

The polynucleotides can optionally be joined to a vector containing a selectable marker for propagation in a host. Generally, a plasmid vector is introduced in a precipitate, such as a calcium phosphate precipitate, or in a complex with a charged lipid. If the vector is a virus, it can be packaged in vitro using an appropriate packaging cell line and then transduced into host cells.

The DNA insert should be operatively linked to an appropriate promoter. The expression constructs will further contain sites for transcription initiation, termination and, in the transcribed region, a ribosome binding site for translation. The coding portion of the mature transcripts expressed by the constructs will preferably include a translation initiating at the beginning and a termination codon (e.g., UAA, UGA or UAG) appropriately positioned at the end of the mRNA to be translated, with UAA and UAG preferred for mammalian or eukaryotic cell expression.

Expression vectors will preferably but optionally include at least one selectable marker. Such markers include, e.g., but are not limited to, ampicillin, zeocin (Sh bla gene), puromycin (pac gene), hygromycin B (hygB gene), G418/Geneticin (neo gene), DHFR (encoding Dihydrofolate Reductase and conferring resistance to Methotrexate), mycophenolic acid, or glutamine synthetase (GS, U.S. Pat. Nos. 5,122,464; 5,770,359; 5,827,739), blasticidin (bsd gene), resistance genes for eukaryotic cell culture as well as ampicillin, zeocin (Sh bla gene), puromycin (pac gene), hygromycin B (hygB gene), G418/Geneticin (neo gene), kanamycin, spectinomycin, streptomycin, carbenicillin, bleomycin, erythromycin, polymyxin B, or tetracycline resistance genes for culturing in *E. coli* and other bacteria or prokaryotics (the above patents are entirely incorporated hereby by reference). Appropriate culture mediums and conditions for the above-described host cells are known in the art. Suitable vectors will be readily apparent to the skilled artisan. Introduction of a vector construct into a host cell can be effected by calcium phosphate transfection, DEAE-dextran mediated transfection, cationic lipid-mediated transfection, electroporation, transduction, infection or other known methods.

Expression vectors will preferably but optionally include at least one selectable cell surface marker for isolation of cells modified by the compositions and methods of the disclosure. Selectable cell surface markers of the disclosure comprise surface proteins, glycoproteins, or group of proteins that distinguish a cell or subset of cells from another defined subset of cells. Preferably the selectable cell surface marker distinguishes those cells modified by a composition or method of the disclosure from those cells that are not modified by a composition or method of the disclosure. Such cell surface markers include, e.g., but are not limited to, “cluster of designation” or “classification determinant” proteins (often abbreviated as “CD”) such as a truncated or full length form of CD19, CD271, CD34, CD22, CD20, CD33, CD52, or any combination thereof. Cell surface markers further include the suicide gene marker RQR8 (Philip B et al. Blood. 2014 Aug. 21; 124(8):1277-87).

Expression vectors will preferably but optionally include at least one selectable drug resistance marker for isolation of cells modified by the compositions and methods of the disclosure. Selectable drug resistance markers of the disclosure may comprise wild-type or mutant Neo, DHFR, TYMS, FRANCF, RAD51C, GCS, MDR1, ALDH1, NKX2.2, or any combination thereof.

Those of ordinary skill in the art are knowledgeable in the numerous expression systems available for expression of a nucleic acid or polynucleotide molecule. Alternatively, nucleic acids of the disclosure can be expressed in a host cell by turning on (by manipulation) in a host cell that contains endogenous DNA encoding a nucleic acid or polynucleotide of the present disclosure. Such methods are well known in the art, e.g., as described in U.S. Pat. Nos. 5,580,734, 5,641,670, 5,733,746, and 5,733,761, entirely incorporated herein by reference Illustrative of cell cultures useful for the production of the nucleic acid and polynucleotide molecules of the present disclosure, specified portions or variants thereof, are bacterial, yeast, and mammalian cells as known in the art. Mammalian cell systems often will be in the form of monolayers of cells although mammalian cell suspensions or bioreactors can also be used. A number of suitable host cell lines have been developed in the art, and include the COS-1 (e.g., ATCC CRL 1650), COS-7 (e.g., ATCC CRL-1651), HEK293, BHK21 (e.g., ATCC CRL-10), CHO (e.g., ATCC CRL 1610) and BSC-1 (e.g., ATCC CRL-26) cell lines, Cos-7 cells, CHO cells, hep G2 cells, P3X63Ag8.653, SP2/0-Agl4, 293 cells, HeLa cells and the like, which are readily available from, for example, American Type Culture Collection, Manassas, Va. (www.atcc.org). Preferred host cells include cells of lymphoid origin, such as myeloma and lymphoma cells. Particularly preferred host cells are P3X63Ag8.653 cells (ATCC Accession Number CRL-1580) and SP2/0-Agl4 cells (ATCC Accession Number CRL-1851). In a preferred aspect, the recombinant cell is a P3X63Ab8.653 or an SP2/0-Agl4 cell.

Expression vectors for these cells can include one or more of the following expression control sequences, such as, but not limited to, an origin of replication; a promoter (e.g., late or early SV40 promoters, the CMV promoter (U.S. Pat. Nos. 5,168,062; 5,385,839), an HSV tk promoter, a pgk (phosphoglycerate kinase) promoter, an EF-1 alpha promoter (U.S. Pat. No. 5,266,491), at least one human promoter; an enhancer, and/or processing information sites, such as ribosome binding sites, RNA splice sites, polyadenylation sites (e.g., an SV40 large T Ag poly A addition site), and transcriptional terminator sequences. See, e.g., Ausubel et al., supra; Sambrook, et al., supra. Other cells useful for production of nucleic acids or proteins of the present disclosure are known and/or available, for instance, from the American Type Culture Collection Catalogue of Cell Lines and Hybridomas (www.atcc.org) or other known or commercial sources.

When eukaryotic host cells are employed, polyadenlyation or transcription terminator sequences are typically incorporated into the vector. An example of a terminator sequence is the polyadenlyation sequence from the bovine growth hormone gene. Sequences for accurate splicing of the transcript can also be included. An example of a splicing sequence is the VP1 intron from SV40 (Sprague, et al., J. Virol. 45:773-781 (1983)). Additionally, gene sequences to control replication in the host cell can be incorporated into the vector, as known in the art.

The disclosure provides isolated or substantially purified polynucleotide or protein compositions. An “isolated” or “purified” polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material or culture medium when produced by recombinant techniques, or substantially free of chemical precursors or other chemicals when chemically synthesized. Optimally, an “isolated” polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various aspects, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A protein that is substantially free of cellular material includes preparations of protein having less than about 30%, 20%, 10%, 5%, or 1% (by dry weight) of contaminating protein. When the protein of the disclosure or biologically active portion thereof is recombinantly produced, optimally culture medium represents less than about 30%, 20%, 10%, 5%, or 1% (by dry weight) of chemical precursors or non-protein-of-interest chemicals.

The disclosure provides fragments and variants of the disclosed DNA sequences and proteins encoded by these DNA sequences. As used throughout the disclosure, the term “fragment” refers to a portion of the DNA sequence or a portion of the amino acid sequence and hence protein encoded thereby. Fragments of a DNA sequence comprising coding sequences may encode protein fragments that retain biological activity of the native protein and hence DNA recognition or binding activity to a target DNA sequence as herein described. Alternatively, fragments of a DNA sequence that are useful as hybridization probes generally do not encode proteins that retain biological activity or do not retain promoter activity. Thus, fragments of a DNA sequence may range from at least about 20 nucleotides, about 50 nucleotides, about 100 nucleotides, and up to the full-length polynucleotide of the disclosure.

Nucleic acids or proteins of the disclosure can be constructed by a modular approach including preassembling monomer units and/or repeat units in target vectors that can subsequently be assembled into a final destination vector. Polypeptides of the disclosure may comprise repeat monomers of the disclosure and can be constructed by a modular approach by preassembling repeat units in target vectors that can subsequently be assembled into a final destination vector. The disclosure provides polypeptide produced by this method as well nucleic acid sequences encoding these polypeptides. The disclosure provides host organisms and cells comprising nucleic acid sequences encoding polypeptides produced this modular approach.

The term "comprising" is intended to mean that the compositions and methods include the recited elements, but do not exclude others. "Consisting essentially of" when used to define compositions and methods, shall mean excluding other elements of any essential significance to the combination when used for the intended purpose. Thus, a composition consisting essentially of the elements as defined herein would not exclude trace contaminants or inert carriers. "Consisting of shall mean excluding more than trace elements of other ingredients and substantial method steps. Aspects defined by each of these transition terms are within the scope of this disclosure.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in a eukaryotic cell.

"Gene expression" refers to the conversion of the information, contained in a gene, into a gene product. A gene product can be the direct transcriptional product of a gene (e.g., mRNA, tRNA, rRNA, antisense RNA, ribozyme, shRNA, micro RNA, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" or "regulation" of gene expression refers to a change in the activity of a gene. Modulation of expression can include, but is not limited to, gene activation and gene repression.

The term "operatively linked" or its equivalents (e.g., "linked operatively") means two or more molecules are positioned with respect to each other such that they are capable of interacting to affect a function attributable to one or both molecules or a combination thereof. In some aspects, a transgene sequence, or any other sequence, is said to be operatively linked to a promoter sequence when the promoter sequence controls the expression of the transgene sequence, or any other sequence. In some aspects, a transposase sequence is said to be operatively linked to a promoter sequence when the promoter sequence controls the expression of the transposase sequence.

Non-covalently linked components and methods of making and using non-covalently linked components, are disclosed. The various components may take a variety of different forms as described herein. For example, non-covalently linked (i.e., operatively linked) proteins may be used to allow temporary interactions that avoid one or more problems in the art. The ability of non-covalently linked components, such as proteins, to associate and dissociate enables a functional association only or primarily under circumstances where such association is needed for the desired activity. The linkage may be of duration sufficient to allow the desired effect.

The terms "nucleic acid" or "oligonucleotide" or "polynucleotide" refer to at least two nucleotides covalently linked together. The depiction of a single strand also defines the sequence of the complementary strand. Thus, a nucleic acid may also encompass the complementary strand of a depicted single strand. A nucleic acid of the disclosure also encompasses substantially identical nucleic acids and complements thereof that retain the same structure or encode for the same protein.

Nucleic acids of the disclosure may be single- or double-stranded. Nucleic acids of the disclosure may contain double-stranded sequences even when the majority of the molecule is single-stranded. Nucleic acids of the disclosure may contain single-stranded sequences even when the majority of the molecule is double-stranded. Nucleic acids of the disclosure may include genomic DNA, cDNA, RNA, or a hybrid thereof. Nucleic acids of the disclosure may contain combinations of deoxyribo- and ribo-nucleotides. Nucleic acids of the disclosure may contain combinations of bases including uracil, adenine, thymine, cytosine, guanine, inosine, xanthine hypoxanthine, isocytosine and isoguanine. Nucleic acids of the disclosure may be synthesized to comprise non-natural amino acid modifications. Nucleic acids of the disclosure may be obtained by chemical synthesis methods or by recombinant methods.

Nucleic acids of the disclosure, either their entire sequence, or any portion thereof, may be non-naturally occurring. Nucleic acids of the disclosure may contain one or more mutations, substitutions, deletions, or insertions that do not naturally-occur, rendering the entire nucleic acid sequence non-naturally occurring. Nucleic acids of the disclosure may contain one or more duplicated, inverted or repeated sequences, the resultant sequence of which does not naturally-occur, rendering the entire nucleic acid sequence non-naturally occurring. Nucleic acids of the disclosure may contain modified, artificial, or synthetic nucleotides that do not naturally-occur, rendering the entire nucleic acid sequence non-naturally occurring.

Given the redundancy in the genetic code, a plurality of nucleotide sequences may encode any particular protein. All such nucleotides sequences are contemplated herein.

As used throughout the disclosure, the term "operably linked" refers to the expression of a gene that is under the control of a promoter with which it is spatially connected. A promoter can be positioned 5' (upstream) or 3' (downstream) of a gene under its control. The distance between a promoter and a gene can be approximately the same as the distance between that promoter and the gene it controls in the gene from which the promoter is derived. Variation in the distance between a promoter and a gene can be accommodated without loss of promoter function.

As used throughout the disclosure, the term "promoter" refers to a synthetic or naturally-derived molecule which is capable of conferring, activating or enhancing expression of a nucleic acid in a cell. A promoter can comprise one or more specific transcriptional regulatory sequences to further enhance expression and/or to alter the spatial expression and/or temporal expression of same. A promoter can also comprise distal enhancer or repressor elements, which can be located as much as several thousand base pairs from the start site of transcription. A promoter can be derived from sources including viral, bacterial, fungal, plants, insects, and animals. A promoter can regulate the expression of a gene component constitutively or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, EF-1 Alpha promoter, CAG promoter, SV40 early promoter or SV40 late promoter and the CMV IE promoter.

As used throughout the disclosure, the term "substantially complementary" refers to a first sequence that is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540, or more nucleotides or amino acids, or that the two sequences hybridize under stringent hybridization conditions.

As used throughout the disclosure, the term "substantially identical" refers to a first and second sequence are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540 or more nucleotides or amino acids, or with respect to nucleic acids, if the first sequence is substantially complementary to the complement of the second sequence.

As used throughout the disclosure, the term "variant" when used to describe a nucleic acid, refers to (i) a portion or fragment of a referenced nucleotide sequence; (ii) the complement of a referenced nucleotide sequence or portion thereof, (iii) a nucleic acid that is substantially identical to a referenced nucleic acid or the complement thereof, or (iv) a nucleic acid that hybridizes under stringent conditions to the referenced nucleic acid, complement thereof, or a sequences substantially identical thereto.

As used throughout the disclosure, the term "vector" refers to a nucleic acid sequence containing an origin of replication. A vector can be a viral vector, bacteriophage, bacterial artificial chromosome or yeast artificial chromosome. A vector can be a DNA or RNA vector. A vector can be a self-replicating extrachromosomal vector, and preferably, is a DNA plasmid. A vector may comprise a combination of an amino acid with a DNA sequence, an RNA sequence, or both a DNA and an RNA sequence.

As used throughout the disclosure, the term "variant" when used to describe a peptide or polypeptide, refers to a peptide or polypeptide that differs in amino acid sequence by the insertion, deletion, or conservative substitution of amino acids, but retain at least one biological activity. Variant can also mean a protein with an amino acid sequence that is substantially identical to a referenced protein with an amino acid sequence that retains at least one biological activity.

A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157: 105-132 (1982). The hydropathic index of an amino acid is based on a consideration of its hydrophobicity and charge. Amino acids of similar hydropathic indexes can be substituted and still retain protein function. In an aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference.

Substitution of amino acids having similar hydrophilicity values can result in peptides retaining biological activity, for example immunogenicity. Substitutions can be performed with amino acids having hydrophilicity values within 2 of each other. Both the hyrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

As used herein, "conservative" amino acid substitutions may be defined as set out in Tables A, B, or C below. In some aspects, fusion polypeptides and/or nucleic acids encoding such fusion polypeptides include conservative substitutions have been introduced by modification of polynucleotides encoding polypeptides of the disclosure. Amino acids can be classified according to physical properties and contribution to secondary and tertiary protein structure. A conservative substitution is a substitution of one amino acid for another amino acid that has similar properties. Exemplary conservative substitutions are set out in Table A.

TABLE A

Conservative Substitutions I

| Side chain characteristics | | Amino Acid |
|---|---|---|
| Aliphatic | Non-polar | G A P I L V F |
| | Polar - uncharged | C S T M N Q |
| | Polar - charged | D E K R |
| Aromatic | | H F W Y |
| Other | | N Q D E |

Alternately, conservative amino acids can be grouped as described in Lehninger, (Biochemistry, Second Edition; Worth Publishers, Inc. NY, N.Y. (1975), pp. 71-77) as set forth in Table B.

TABLE B

Conservative Substitutions II

| Side Chain Characteristic | | Amino Acid |
|---|---|---|
| Non-polar (hydrophobic) | Aliphatic: | A L I V P |
| | Aromatic: | F W Y |
| | Sulfur-containing: | M |
| | Borderline: | G Y |
| Uncharged-polar | Hydroxyl: | S T Y |
| | Amides: | N Q |
| | Sulfhydryl: | C |
| | Borderline: | G Y |
| Positively Charged (Basic): | | K R H |
| Negatively Charged (Acidic): | | D E |

Alternately, exemplary conservative substitutions are set out in Table C.

TABLE C

Conservative Substitutions III

| Original Residue | Exemplary Substitution |
|---|---|
| Ala (A) | Val Leu Ile Met |
| Arg (R) | Lys His |
| Asn (N) | Gln |
| Asp (D) | Glu |
| Cys (C) | Ser Thr |
| Gln (Q) | Asn |
| Glu (E) | Asp |
| Gly (G) | Ala Val Leu Pro |
| His (H) | Lys Arg |
| Ile (I) | Leu Val Met Ala Phe |
| Leu (L) | Ile Val Met Ala Phe |
| Lys (K) | Arg His |
| Met (M) | Leu Ile Val Ala |
| Phe (F) | Trp Tyr Ile |
| Pro (P) | Gly Ala Val Leu Ile |
| Ser (S) | Thr |
| Thr (T) | Ser |
| Trp (W) | Tyr Phe Ile |
| Tyr (Y) | Trp Phe Thr Ser |
| Val (V) | Ile Leu Met Ala |

It should be understood that the polypeptides of the disclosure are intended to include polypeptides bearing one or more insertions, deletions, or substitutions, or any combination thereof, of amino acid residues as well as modifications other than insertions, deletions, or substitutions of amino acid residues. Polypeptides or nucleic acids of the disclosure may contain one or more conservative substitution.

As used throughout the disclosure, the term "more than one" of the aforementioned amino acid substitutions refers to 2, 3, 4, 5, 6, 7, 8, 9, 10, 11, 12, 13, 14, 15, 16, 17, 18, 19, or 20 or more of the recited amino acid substitutions. The term "more than one" may refer to 2, 3, 4, or 5 of the recited amino acid substitutions.

Polypeptides and proteins of the disclosure, either their entire sequence, or any portion thereof, may be non-naturally occurring. Polypeptides and proteins of the disclosure may contain one or more mutations, substitutions, deletions, or insertions that do not naturally-occur, rendering the entire amino acid sequence non-naturally occurring. Polypeptides and proteins of the disclosure may contain one or more duplicated, inverted or repeated sequences, the resultant sequence of which does not naturally-occur, rendering the entire amino acid sequence non-naturally occurring. Polypeptides and proteins of the disclosure may contain modified, artificial, or synthetic amino acids that do not naturally-occur, rendering the entire amino acid sequence non-naturally occurring.

As used throughout the disclosure, "sequence identity" may be determined by using the stand-alone executable BLAST engine program for blasting two sequences (bl2seq), which can be retrieved from the National Center for Biotechnology Information (NCBI) ftp site, using the default parameters (Tatusova and Madden, FEMS Microbiol Lett., 1999, 174, 247-250; which is incorporated herein by reference in its entirety). The terms "identical" or "identity" when used in the context of two or more nucleic acids or polypeptide sequences, refer to a specified percentage of residues that are the same over a specified region of each of the sequences. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) can be considered equivalent. Identity can be performed manually or by using a computer sequence algorithm such as BLAST or BLAST 2.0.

As used throughout the disclosure, the term "endogenous" refers to nucleic acid or protein sequence naturally associated with a target gene or a host cell into which it is introduced.

As used throughout the disclosure, the term "exogenous" refers to nucleic acid or protein sequence not naturally associated with a target gene or a host cell into which it is introduced, including non-naturally occurring multiple copies of a naturally occurring nucleic acid, e.g., DNA sequence, or naturally occurring nucleic acid sequence located in a non-naturally occurring genome location.

The disclosure provides methods of introducing a polynucleotide construct comprising a DNA sequence into a host cell. By "introducing" is intended presenting to the cell the polynucleotide construct in such a manner that the construct gains access to the interior of the host cell. The methods of the disclosure do not depend on a particular method for introducing a polynucleotide construct into a host cell, only that the polynucleotide construct gains access to the interior of one cell of the host. Methods for introducing polynucleotide constructs into bacteria, plants, fungi and animals are known in the art including, but not limited to, stable transformation methods, transient transformation methods, and virus-mediated methods.

It is to be understood that the present disclosure also provides pharmaceutical compositions comprising any compound described herein in combination with at least one pharmaceutically acceptable excipient or carrier.

As used herein, the term "pharmaceutical composition" is a formulation containing the compounds of the present disclosure in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this disclosure include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

The terms "effective amount" and "therapeutically effective amount" of an agent or compound are used in the broadest sense to refer to a nontoxic but sufficient amount of an active agent or compound to provide the desired effect or benefit. It is to be understood that, for any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

The term "benefit" is used in the broadest sense and refers to any desirable effect and specifically includes clinical benefit as defined herein. Clinical benefit can be measured by assessing various endpoints, e.g., inhibition, to some extent, of disease progression, including slowing down and complete arrest; reduction in the number of disease episodes and/or symptoms; reduction in lesion size; inhibition (i.e., reduction, slowing down or complete stopping) of disease cell infiltration into adjacent peripheral organs and/or tissues; inhibition (i.e. reduction, slowing down or complete stopping) of disease spread; decrease of auto-immune response, which may, but does not have to, result in the regression or ablation of the disease lesion; relief, to some extent, of one or more symptoms associated with the disorder; increase in the length of disease-free presentation following treatment, e.g., progression-free survival; increased overall survival; higher response rate; and/or decreased mortality at a given point of time following treatment.

As used herein, the term "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

It is to be understood that a pharmaceutical composition of the disclosure is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

It is to be understood that a compound or pharmaceutical composition of the disclosure can be administered to a subject in many of the well-known methods currently used for chemotherapeutic treatment. For example, a compound of the disclosure may be injected into the blood stream or body cavities or taken orally or applied through the skin with patches. The dose chosen should be sufficient to constitute effective treatment but not so high as to cause unacceptable side effects. The state of the disease condition and the health of the patient should preferably be closely monitored during and for a reasonable period after treatment.

As used herein, the term "therapeutically effective amount", refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present disclosure may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Example 1—AAV Viral Vectors of the Present Disclosure for the Treatment of Hemophilia The following is a non-limiting example demonstrating the compositions and methods of the present disclosure can be used to in the treatment of hemophilia, and more specifically hemophilia B.

Three-week old C57BL/6 mice were either left untreated, or were administered one of the following two treatments:

Treatment #1: AAV piggyBac transposon vectors of the present disclosure at $3.75\times10^{13}$ vg/kg Treatment #2: AAV piggyBac transposon vectors of the present disclosure at $2.5\times10^{13}$ vg/kg in combination with AAV transposase vectors of the present disclosure at $1.25\times10^{13}$ vg/kg.

The AAV piggyBac transposon vectors of the present disclosure were AAV viral vector particles comprising an AAV piggyBac transposon polynucleotide of the present disclosure comprising a TTRm promoter sequence and a transgene sequence encoding for a Factor IX polypeptide. The AAV viral vector particles were KP-1 AAV viral vector particles.

The AAV transposase vector of the present disclosure were AAV viral vector particles comprising an AAV transposase polynucleotide of the present disclosure comprising an HLP promoter sequence and a transposase sequence encoding for a Super piggyBac transposase. The AAV viral vector particles were KP-1 AAV viral vector particles.

Three weeks following administration of the treatments, ELISA experiments were performed to determine the amount of human Factor IX polypeptide in the plasma of the mice.

Figure 5:
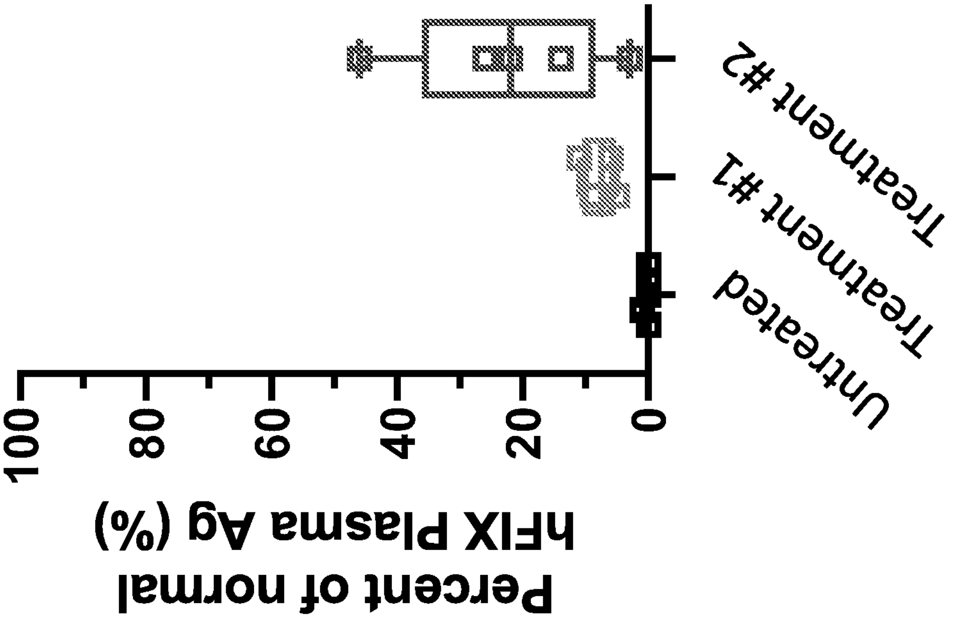
FIG. 5 is a graph showing the levels of human Factor IX protein in mice administered various vectors of the present disclosure.

The results of these ELISA experiments are shown in FIG. 5. FIG. 5 shows that human Factor IX protein levels were observed in the samples at a level corresponding to between about 10-35% of normal human Factor IX following administration of Treatment #2.

Figure 6:
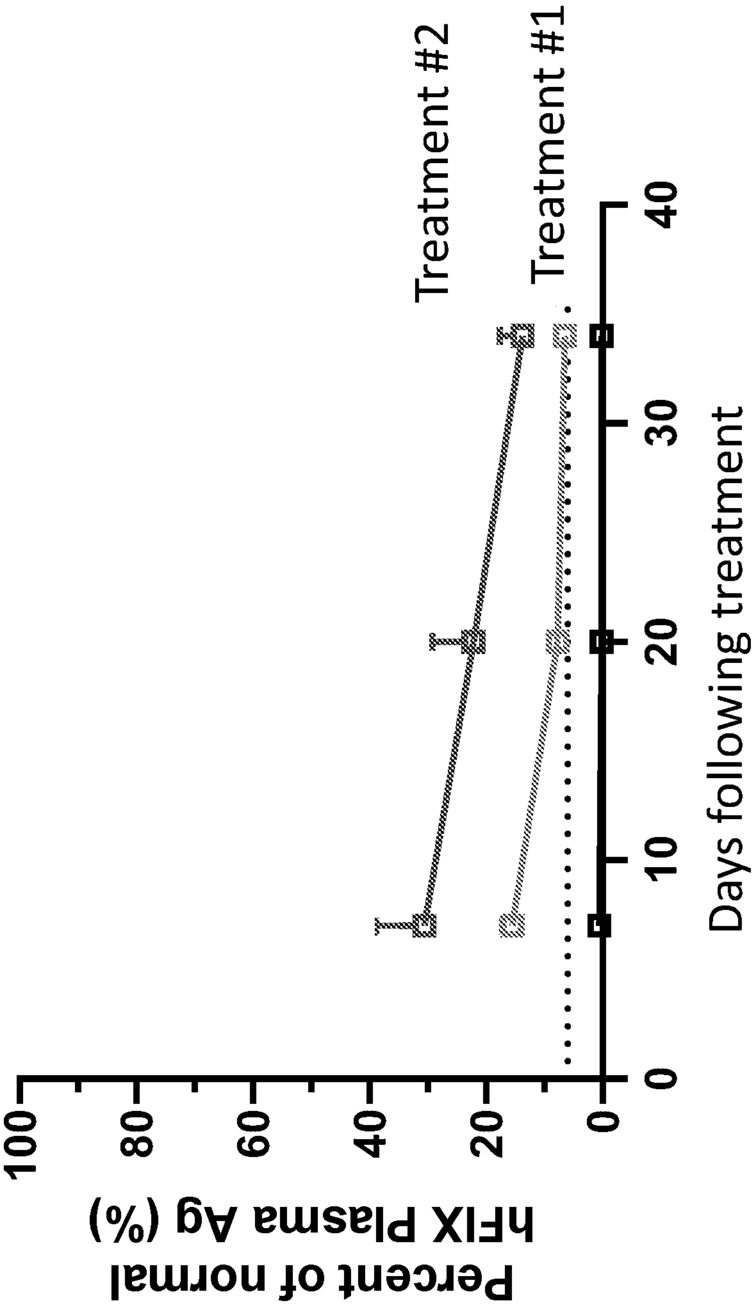
FIG. 6 is a graph showing the levels of human Factor IX protein in mice administered various vectors of the present disclosure.

Additionally, similar ELISA experiments were performed at various time points following administration of the treatment. The results of these ELISA experiments are shown in FIG. 6.

The results presented in this example demonstrate that the AAV piggyBac transposon vectors and AAV transposase vectors of the present disclosure can be used to drive high levels of Factor IX expression in vivo, thereby demonstrating that the composition and methods of the present disclosure can be used to treat hemophilia B.

EQUIVALENTS

The foregoing description has been presented only for the purposes of illustration and is not intended to limit the disclosure to the precise form disclosed. The details of one or more embodiments of the disclosure are set forth in the accompanying description above. Although any methods and materials similar or equivalent to those described herein can be used in the practice or testing of the present disclosure, the preferred methods and materials are now described. Other features, objects, and advantages of the disclosure will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this disclosure belongs. All patents and publications cited in this specification are incorporated by reference.

What is claimed is:

1. An AAV piggyBac transposon polynucleotide comprising in the 5' to 3' direction:

a) a first AAV ITR sequence comprising the nucleic acid sequence of SEQ ID NO: 17;

b) a first piggyBac ITR sequence comprising the nucleic acid sequence of SEQ ID NO: 19;

c) a first insulator sequence comprising the nucleic acid sequence of SEQ ID NO: 5;

d) at least one promoter sequence comprising the nucleic acid sequence of SEQ ID NO: 12;

e) a first transgene sequence comprising the nucleic acid sequence of SEQ ID NO: 23;

f) a polyA sequence comprising the nucleic acid sequence of SEQ ID NO: 22;

g) a second insulator sequence comprising the nucleic acid sequence of SEQ ID NO: 20;

h) a second piggyBac ITR sequence comprising the nucleic acid sequence of SEQ ID NO: 21;

i) a DNA spacer sequence comprising the nucleic acid sequence SEQ ID NO: 28; and j) a second AAV ITR sequence comprising the nucleic acid sequence of SEQ ID NO: 18.

2. The AAV piggyBac transposon polynucleotide of claim 1, wherein the AAV piggyBac transposon polynucleotide comprises the nucleic acid sequence of SEQ ID NO: 40.

3. A vector comprising the AAV piggyBac transposon polynucleotide of claim 1.

4. The vector of claim 3, wherein the vector is a viral vector.

5. The vector of claim 4, wherein the viral vector is an AAV viral vector.

6. A composition comprising the vector of claim 3.

7. A method of treating hemophilia B in a subject in need thereof comprising administering to the subject at least one therapeutically effective dose of the AAV piggyBac transposon polynucleotide of claim 1.

8. A method of treating hemophilia B in a subject in need thereof comprising administering to the subject at least one therapeutically effective dose of the vector of claim 5.

9. An AAV piggyBac transposon polynucleotide comprising in the 5' to 3' direction:

a) a first AAV ITR sequence comprising the nucleic acid sequence of SEQ ID NO: 1;

b) a first piggyBac ITR sequence comprising the nucleic acid sequence of SEQ ID NO: 3;

c) a first insulator sequence comprising the nucleic acid sequence of SEQ ID NO: 5;

d) at least one promoter sequence comprising the nucleic acid sequence of SEQ ID NO: 11;

e) at least one transgene sequence comprising the nucleic acid sequence of SEQ ID NO: 23;

f) a polyA sequence comprising the nucleic acid sequence of SEQ ID NO: 14;

g) a second insulator sequence comprising the nucleic acid sequence of SEQ ID NO: 6;

h) a second piggyBac ITR sequence comprising the nucleic acid sequence of SEQ ID NO: 4; and i) a second AAV ITR sequence comprising the nucleic acid sequence of SEQ ID NO: 2.

10. The AAV piggyBac transposon polynucleotide of claim 9, wherein the AAV piggyBac transposon polynucleotide comprises the nucleic acid sequence of SEQ ID NO: 36.

11. A vector comprising the AAV piggyBac transposon polynucleotide of claim 9.

12. The vector of claim 11, wherein the vector is a viral vector.

13. The vector of claim 12, wherein the viral vector is an AAV viral vector.

14. A method of treating hemophilia B in a subject in need thereof comprising administering to the subject at least one therapeutically effective dose of the AAV piggyBac transposon polynucleotide of claim 9.

15. A method of treating hemophilia B in a subject in need thereof comprising administering to the subject at least one therapeutically effective dose of the vector of claim 13.

* * * * *